United States Patent
Wang et al.

(10) Patent No.: US 11,326,180 B2
(45) Date of Patent: May 10, 2022

(54) BIOLOGICAL CONTROL OF CUCUMBER GREEN MOTTLE MOSAIC VIRUS

(71) Applicant: A&L Canada Laboratories, Inc., London (CA)

(72) Inventors: Keri Wang, London (CA); George Lazarovits, London (CA); Yibin Liu, London (CA); Magda Konopka, London (CA); Greg Patterson, London (CA)

(73) Assignee: A&L CANADA LABORATORIES INC., London (CA)

( * ) Notice: Subject to any disclaimer, the term of this patent is extended or adjusted under 35 U.S.C. 154(b) by 55 days.

(21) Appl. No.: 17/017,992

(22) Filed: Sep. 11, 2020

(65) Prior Publication Data
US 2020/0407745 A1    Dec. 31, 2020

Related U.S. Application Data

(62) Division of application No. 16/558,069, filed on Aug. 31, 2019, now Pat. No. 10,829,780.

(30) Foreign Application Priority Data

Sep. 14, 2018  (CA) ................. CA 3017465

(51) Int. Cl.
    *C12N 15/82*    (2006.01)
    *C12N 7/00*     (2006.01)
(52) U.S. Cl.
    CPC ........... *C12N 15/8283* (2013.01); *C12N 7/00* (2013.01); *C12N 2770/14021* (2013.01)
(58) Field of Classification Search
    CPC .................................................. C12N 15/82
    See application file for complete search history.

(56) References Cited

PUBLICATIONS

Tan et al (1997 Ann. Phytophgathol. Soc. Jpn. 63:470-474) provied in parent Application 165580669 (Year: 1997).*

Slavokhotova et al (2016 American Journal of Plant Sciences 7:724-732) provied in parent Application 165580669 (Year: 2016).*
Ali, Md E., et al., "Molecular analysis of an attenuated strain of Cucumber green mottle mosaic virus using in vitro infectious cDNA clone: pathogenicity and suppression of RNA silencing." J. Plant Biochem. Biotechnol., 2016, 25(1): 79-86.
Chen, B., "Molecular Characterization of Viruses Infecting Greenhouse Vegetables in Ontario." Electronic Thesis and Dissertation Repository, 2016, 4222: 1-91.
Motoyoshi, F., et al., "Control of virus diseases by attenuated virus strains, comparison between attenuated strains of cucumber green mottle mosaic virus and tobacco mosaic virus." Gamma Field Symposia, Institute of Radiation Breeding, 1988, 27: 91-109.
Nishiguchi, M., et al., "Attentuated plant viruses: preventing virus diseases and understanding the molecular mechanism." J Gen Plant Pathol, 2011, 77: 221-229.
Slavokhotova, A.A., et al., "An Attenuated Strain of Cucumber Green Mottle Mosaic Virus as a Biological Control Agent against Pathogenic Viral Strains." American Journal of Plant Sciences, 2016, 7: 724-732.
Tan, S.H., et al., "Molecular Analysis of the Genome of an Attenuated Strain of Cucumber Green Mottle Mosaic Virus." Ann. Phytopathol. Soc Jpn., 1997, 63: 470-474.
Ugaki, M., et al., "The complete nucleotide sequence of cucumber green mottle mosaic virus (SH strain) genomic RNA." Journal of General Virology, 191, 72: 1487-1495.

* cited by examiner

*Primary Examiner* — Brent T Page
(74) *Attorney, Agent, or Firm* — Saliwanchik, Lloyd & Eisenschenk

(57) ABSTRACT

An attenuated strain of cucumber green mottle mosaic virus (CGMMV) is useful to protect cucumber plants from infection with the wild-type infectious CGMMV strain. The genome of the attenuated virus contains at least one mutation or group of mutations selected from c.4969G>A, c.3334C>T, and a group of at least six of the mutations c.315G>A; c.1498A>G; c.1660C>T; c.3430C>T; c.3528A>G; c.4144C>T; c.4248C>T; and c.6228C>T. These mutated genomes encode one or more mutations selected from R163711 in the 186 kDa readthrough replication protein, A1092V in the 129 kDa replication protein and/or the 186 kDa readthrough replication protein, and at least six mutations selected from G86S, E480G, S534F, A1124V, N1157D, P1362L, P1397S in the 129 kDa replication protein and/or the 186 kDa readthrough replication protein, and the A156V mutation in the coat protein.

14 Claims, 6 Drawing Sheets
Specification includes a Sequence Listing.

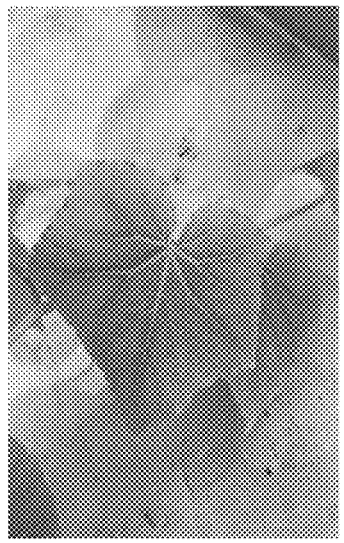
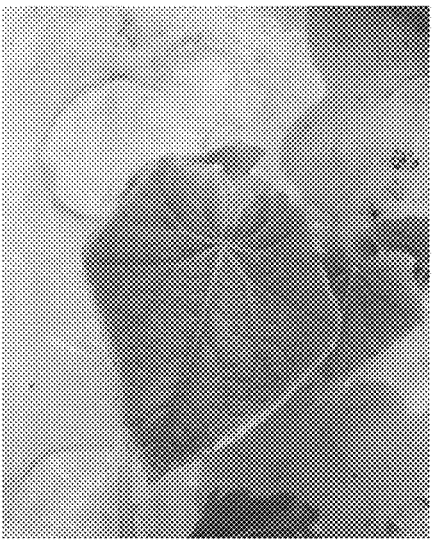
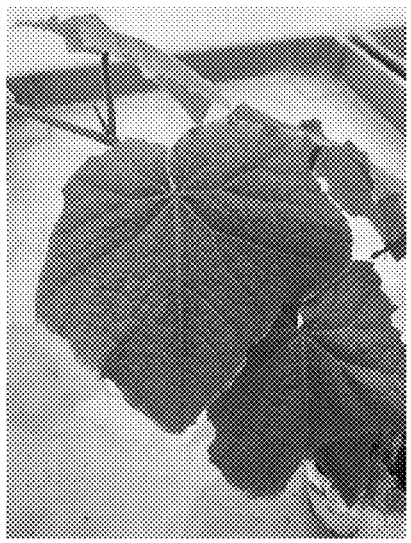
FIG. 4A   FIG. 4B   FIG. 4C
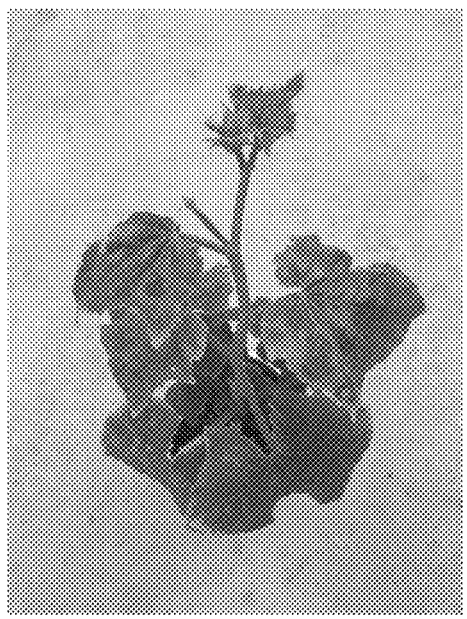
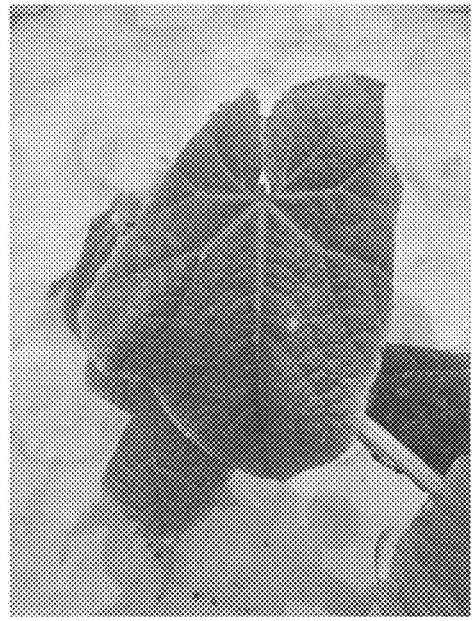
FIG. 4D   FIG. 4E

BIOLOGICAL CONTROL OF CUCUMBER GREEN MOTTLE MOSAIC VIRUS

CROSS REFERENCE TO A RELATED APPLICATION

This application is a division of co-pending U.S. patent application Ser. No. 16/558,069, filed Aug. 31, 2019; which claims priority to Canadian Patent Application No. 3,017,465, filed Sep. 14, 2018, both of which are incorporated herein by reference in their entirety.

The Sequence Listing for this application is labeled "SeqList-31Aug19-ST25.txt", which was created on Sep. 14, 2018, and is 290 KB. The entire content is incorporated herein by reference in its entirety.

FIELD

The present application is directed to attenuated plant viruses. More specifically, the present application provides attenuated strains of cucumber green mottle mosaic virus (CGMMV), compositions thereof, and methods of using such virus strains and compositions for biological control of plant disease.

BACKGROUND

Cucumber green mottle mosaic virus (CGMMV) is a member of the *Tobamovirus* genus in the family Virgaviridae. CGMMV has a 6.4-kb single-stranded, positive-sense RNA genome with a 3' tRNA-like structure instead of a poly(A) tail. The genome contains three open reading frames (ORFs) that encode four defined proteins. The first ORF encodes a 129 kDa protein, including methyltransferase and helicase domains required for RNA replication, and a 186 kDa protein produced by readthrough translation of the ORF, including the methyltransferase and helicase domains and an additional RNA-dependent RNA polymerase (RdRp) domain. The remaining two ORFs encode a movement protein (MP) and a coat protein (CP), respectively.

CGMMV infection causes serious diseases in plants of the family Cucurbitaceae (cucurbits), including cucumber, pumpkin, watermelon, melon, squash, zucchini, gourds, gherkins and others. CGMMV was first reported in 1935 in the UK and is found in Europe, Asia, the Middle East and, since 2013, in Canada and the United States. CGMMV infection is becoming a major limiting factor with regard to production of cucurbits worldwide, and has become an increasing threat to the commercial production of cucumber and other commercially-grown cucurbit crops.

CGMMV is a seed-borne virus and can be transmitted by root-to-root contact and by transfer from contaminated seeds, soil, gardening implements such as pruners and stakes, irrigation water, packing materials, or the clothing or hands of farmers, pickers or other persons handling the plants. The CGMMV virus is extremely stable and can remain infectious under relatively extreme conditions for long periods of time. Therefore, the presence of even a few infected plants in a cucumber greenhouse can eventually lead to the spread of CGMMV infection to the entire crop.

CGMMV is responsible for a wide range of symptoms on leaves and fruits of infected plants, depending on the CGMMV strain, stage of infection and plant species. The induced symptoms include vein clearing and crumpling in young leaves, light green mottling, mosaic patterns, necrotic lesions, fruit distortion or streak, change of sugar accumulation and flavor, and premature degradation of the pulp, making the fruit unmarketable and unfit for consumption. CGMMV infection can result in substantial yield losses up to 100%, although losses of 40-80% are more common in a commercial field or greenhouse production setting, in addition to having a major impact on fruit quality, leading to low market value.

There are no known effective chemical methods for controlling virus diseases of plants, and crop protection relies completely on aspects of sanitation that may include removal of infected plants, using only virus-free seeds and vegetative stocks, using resistant varieties, and controlling transmission by contact with insects, water and humans. Two new techniques that are now being investigated for managing plant virus diseases rely on cross protection by inoculation with attenuated/mild strains and by creating transgenic or engineered resistance based on expression of the viral coat protein of a specific viral pathogen.

Cross protection is an acquired immunity phenomenon which has been demonstrated in a number of systems. The technique makes use of the observation that plants infected with an attenuated virus isolate or strain causing mild or no symptoms can develop tolerance to further infection when challenged by an isolate or strain of the same or a related virus species which causes more severe symptoms. Cross protection is virus specific, occurring only between strains of the same virus or related virus species, and is seen as an acceptable method for crop protection in greenhouse systems as it does not rely on harmful materials or chemicals. This approach was first applied successfully in several countries in the 1970s to protect tomato plants against infection with tobacco mosaic virus. More recently, in 2015, the treatment PMV™-01, which contains a mild isolate of the Chilean strain of pepino mosaic virus (PepMV), has been registered in Europe and commercially used to protect tomato plants from severe losses in quality and yield caused by aggressive infection with PepMV.

In order to develop cross protection, attenuated/mild strains of a plant virus are needed which cause no visible or only very mild symptoms but which prevent infection by strains causing more severe symptoms. Attenuated isolates advantageously have little or no impact on plant symptoms, total yield and fruit quality, and effectively protect against more virulent isolates. The following properties have been proposed as desirable criteria for an attenuated virus strain for use in crop protection:

no symptoms or very mild symptoms are induced in any of the cultivated hosts, and the quality and quantity of the crop products are not reduced;

most host tissues are fully infected systemically;

the attenuated strains are highly stable genetically without mutating into a severe phenotype;

there is no vector transmission to other crops;

the attenuated strains protect against a wide range of viruses and strains; and the quality/quantity control of the inoculum and inoculations are easy and inexpensive.

An attenuated CGMMV strain SH33b is known (Motoyoshi, F., and Nishiguchi, M. 1988. Control of virus diseases by attenuated virus strains: comparison between attenuated strains of cucumber green mottle mosaic virus and tobacco mosaic virus. Gamma Field Symposia, 27: 91-107) which induces no or only mild systematic symptoms in leaves of muskmelon plants when a low concentration of attenuated virus was used to inoculate muskmelon seedlings. However, although this strain was effective in protecting muskmelon plants from outbreaks of severe symptoms, and in eliminating wild-type CGMMV from the greenhouse, inoculation of cotyledons with higher concentrations of the purified virus led to appearance of mosaic symptoms in the upper leaves.

In addition, an attenuated CGMMV strain VIROG-43M is known (Slavokhotova, A. A., et al, *American Journal of Plant Sciences* (2016), 7: 724-732), which showed effectiveness in protecting inoculated cucumber plants from disease symptoms under greenhouse conditions. However, VIROG-43M itself could induce symptoms in inoculated cucumber plants after two months of inoculation. In addition, only 85% of the cucumber plants inoculated with VIROG-43M and challenged with the pathogenic CGMMV strain NC-1 were observed to be symptomless after 3 months of inoculation under laboratory greenhouse conditions.

Recently, it was reported that several attenuated CGMMV strains were obtained from a pathogenic CGMMV strain by multi site-directed mutagenesis, based on sequence comparison of related tobamoviruses (Chen, Bin, "Molecular Characterization of Viruses Infecting Greenhouse Vegetables in Ontario" (2016). *Electronic Thesis and Dissertation Repository*. 4222, University of Western Ontario. Available at https://irlib.uwo.ca/etd/4222). However, the reported mutants could develop visible mosaic symptoms in cucumber plants to various extents, although the symptoms were generally mild compared with those caused by the wild-type strain. Even the best attenuated CGMMV isolates induced symptoms in cucumber plants after 28 days post inoculation.

It is therefore desirable to provide an attenuated strain of CGMMV for protecting plants against infection with CGMMV, and in particular, for protecting plants which are susceptible to infection with CGMMV such as species of the Cucurbitaceae family.

SUMMARY

In one aspect, the present application provides an attenuated strain of cucumber green mottle mosaic virus (CGMMV) comprising a genome, wherein the genome is a polyribonucleotide having a sequence functionally equivalent to a variant of SEQ ID NO:18, the sequence comprising at least one residue or group of residues selected from:
a) A at the position corresponding to position 4969 of SEQ ID NO:18;
b) U at the position corresponding to position 3334 of SEQ ID NO:18; and
c) a group of at least six residues selected from:
A at the position corresponding to position 315 of SEQ ID NO:18;
G at the position corresponding to position 1498 of SEQ ID NO:18;
U at the position corresponding to position 1660 of SEQ ID NO:18;
U at the position corresponding to position 3430 of SEQ ID NO:18;
G at the position corresponding to position 3528 of SEQ ID NO:18;
U at the position corresponding to position 4144 of SEQ ID NO:18;
U at the position corresponding to position 4248 of SEQ ID NO:18; and
U at the position corresponding to position 6228 of SEQ ID NO:18.

In another aspect, the present application provides a polydeoxyribonucleotide having a sequence functionally equivalent to a sequence of a cucumber green mottle mosaic virus (CGMMV) genome, wherein the sequence of the polydeoxyribonucleotide is a variant of SEQ ID NO:18 comprising at least one residue or group of residues selected from:
a) A at the position corresponding to position 4969 of SEQ ID NO:18;
b) Tat the position corresponding to position 3334 of SEQ ID NO:18; and
c) a group of at least six residues selected from:
A at the position corresponding to position 315 of SEQ ID NO:18;
G at the position corresponding to position 1498 of SEQ ID NO:18;
T at the position corresponding to position 1660 of SEQ ID NO:18;
T at the position corresponding to position 3430 of SEQ ID NO:18;
G at the position corresponding to position 3528 of SEQ ID NO:18;
T at the position corresponding to position 4144 of SEQ ID NO:18;
T at the position corresponding to position 4248 of SEQ ID NO:18; and
T at the position corresponding to position 6228 of SEQ ID NO:18.

In at least one embodiment, the polydeoxyribonucleotide is configured for expression in a host cell. In at least one embodiment, the host cell is a microorganism. In at least one embodiment, the host cell is a plant cell.

In another aspect, the present application provides a vector comprising a polydeoxyribonucleotide as described herein. In at least one embodiment, the vector is configured to genetically modify a host cell. In at least one embodiment, the host cell is a microorganism. In at least one embodiment, the host cell is a plant cell.

A further aspect of the present application provides a genetically modified cell comprising a polydeoxyribonucleotide as described herein. In at least one embodiment, the cell is a microorganism. In at least one embodiment, the cell is a plant cell.

Yet another aspect of the present application provides a composition for preventing symptoms associated with infection by wild-type CGMMV in a plant, where the composition comprises an attenuated strain of CGMMV or a genetically modified cell as described herein and an agriculturally acceptable carrier.

In an additional aspect, the present application provides a composition for increasing resistance of a plant to infection by wild-type CGMMV, where the composition comprises an attenuated strain of CGMMV or a genetically modified cell as described herein and an agriculturally acceptable carrier.

Another aspect of the present application provides a method for preventing symptoms associated with infection by wild-type CGMMV in a plant, where the method includes inoculating the plant with an attenuated strain of CGMMV or with a genetically modified cell or with a composition as described herein.

A further aspect of the present application provides a method for increasing resistance of a plant to infection by wild-type CGMMV, where the method includes inoculating the plant with an attenuated strain of CGMMV or with a genetically modified cell or with a composition as described herein.

In a further aspect, the present application provides a genetically modified plant comprising a genome which comprises a polydeoxyribonucleotide as described herein. In at least one embodiment, the plant is a cucurbit. In at least one embodiment, the plant is a cucumber plant.

BRIEF DESCRIPTION OF THE DRAWINGS

Further features of the present invention will become apparent from the following written description and the accompanying figures, in which:

FIG. 4A is a photograph showing leaves of a cucumber plant inoculated with an attenuated CGMMV strain according to the present invention (ONBM), then challenged with a wild-type CGMMV and grown under laboratory conditions;

FIG. 4B is a photograph showing leaves of a cucumber plant inoculated with another attenuated CGMMV strain according to the present invention (ONBM-2), then challenged with a wild-type CGMMV and grown under the laboratory conditions of FIG. 4A;

FIG. 4C is a photograph showing leaves of a cucumber plant inoculated with yet another attenuated CGMMV strain according to the present invention (ONBM-3), then challenged with a wild-type CGMMV and grown under the laboratory conditions of FIG. 4A;

FIG. 4D is a photograph showing leaves of a cucumber plant infected with wild-type CGMMV and grown under the laboratory conditions of FIG. 4A;

FIG. 4E is a photograph showing leaves of a healthy cucumber plant without CGMMV infection grown as a control under the laboratory conditions of FIG. 4A;

DETAILED DESCRIPTION

Figure 1A:
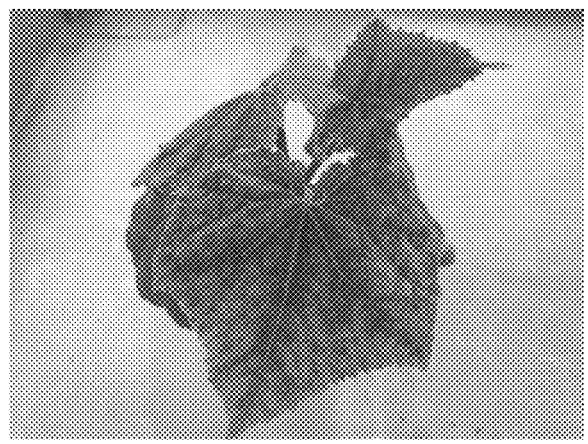
FIG. 1A is a photograph showing leaves of a cucumber plant grown for two weeks after inoculation with a clone of a wild-type cucumber green mottle mosaic virus (CGMMV) Ontario strain.

The present application provides an attenuated strain of the cucumber green mottle mosaic virus (CGMMV). In at least one embodiment, the attenuated CGMMV strain may be useful for protecting one or more plants against the deleterious effects of infection by a wild-type strain of CGMMV. In at least one embodiment, plants which may be protected against infection by wild-type CGMMV include but are not limited to any plant susceptible to infection by CGMMV, including but not limited to plants of the family Cucurbitaceae (cucurbits), including but not limited to varieties of cucumber (*Cucumis sativus*), pumpkin, watermelon, melon, squash, zucchini, gourds, gherkins and others well known in the art. In at least one embodiment, curcubits such as cucumber plants inoculated with at least one embodiment of the attenuated CGMMV strain may not show significant visible symptoms for a period of up to two months or longer after inoculation with the attenuated CGMMV strain.

In at least one embodiment, the attenuated strain of CGMMV has a genome which is a polyribonucleotide having a sequence which is functionally equivalent to a variant of SEQ ID NO:18 including one or more variations thereof.

In at least one embodiment, the polyribonucleotide has a sequence including A at the position corresponding to position 4969 of SEQ ID NO:18.

In at least one embodiment, the polyribonucleotide has a sequence including U at the position corresponding to position 3334 of SEQ ID NO:18.

In at least one embodiment, the polyribonucleotide has a sequence including A at the position corresponding to position 4969 of SEQ ID NO:18 and U at the position corresponding to position 3334 of SEQ ID NO:18.

In at least one embodiment, the polyribonucleotide has a sequence including at least six of the following residues:
A at the position corresponding to position 315 of SEQ ID NO:18;
G at the position corresponding to position 1498 of SEQ ID NO:18;
U at the position corresponding to position 1660 of SEQ ID NO:18;
U at the position corresponding to position 3430 of SEQ ID NO:18;
G at the position corresponding to position 3528 of SEQ ID NO:18;
U at the position corresponding to position 4144 of SEQ ID NO:18;
U at the position corresponding to position 4248 of SEQ ID NO:18; and
U at the position corresponding to position 6228 of SEQ ID NO:18.

In at least one such embodiment, the polyribonucleotide sequence also includes one or both of:
U at the position corresponding to position 3334 of SEQ ID NO:18; and
A at the position corresponding to position 4969 of SEQ ID NO:18.

In at least one embodiment, the polyribonucleotide has a sequence including the following residues:
A at the position corresponding to position 315 of SEQ ID NO:18;
G at the position corresponding to position 1498 of SEQ ID NO:18;
U at the position corresponding to position 1660 of SEQ ID NO:18;
U at the position corresponding to position 3430 of SEQ ID NO:18;
G at the position corresponding to position 3528 of SEQ ID NO:18;
U at the position corresponding to position 4144 of SEQ ID NO:18;
U at the position corresponding to position 4248 of SEQ ID NO:18; and
U at the position corresponding to position 6228 of SEQ ID NO:18.

In at least one such embodiment, the polyribonucleotide sequence also includes one or both of:
U at the position corresponding to position 3334 of SEQ ID NO:18; and
A at the position corresponding to position 4969 of SEQ ID NO:18.

As used herein, the term "polynucleotide" is intended to mean a polymeric molecule comprising two or more nucleosides linked through covalent bonds to phosphate groups, such that the 5'-hydroxyl group of a nucleoside and the 3'-hydroxyl group of an adjacent nucleoside are both covalently bonded to the same phosphate group. As understood in the art, when covalently linked together to form the polynucleotide molecule, each individual nucleoside unit is also known as a "residue". As used herein, the term "nucleoside" is intended to mean a molecule in which a sugar moiety selected from ribose and deoxyribose is bonded to a purine or pyrimidine base moiety selected from adenine (A), guanine (G), cytosine (C), thymine (T) or uracil (U). A polynucleotide includes polynucleotides of any length, including but not limited to dinucleotides, trinucleotides, tetranucleotides, oligonucleotides and nucleic acids.

When the sugar moiety is ribose, the base is selected from A, G, C and U, and the nucleoside is referred to as a ribonucleoside. A polynucleotide comprising two or more such ribonucleosides is referred to as a polyribonucleotide or ribonucleic acid (RNA). When the sugar moiety is deoxyribose, the base is selected from A, G, C and T, and the nucleoside is referred to as a deoxyribonucleoside. A polynucleotide comprising two or more such deoxyribonucleosides is referred to as a polydeoxyribonucleotide or deoxyribonucleic acid (DNA).

In at least one embodiment, the attenuated strains can be obtained by mutation of wild type CGMMV to introduce one or more variations or mutations into the genome sequence of the wild type CGMMV. As used herein interchangeably with respect to a polynucleotide sequence, the term "variation" or "mutation" is intended to refer to a difference in the polynucleotide sequence with respect to a reference polynucleotide sequence. Variations or mutations can include substitution of one or more nucleotide residues with different nucleotide residues, insertion of additional nucleotide residues or deletion of nucleotide residues. A variation or mutation may or may not alter the open reading frame(s) of the polynucleotide or the amino acid sequence of any protein(s) encoded by the polynucleotide. In at least one embodiment, the variation or mutation is a naturally occurring variation or mutation arising without artificial intervention. In at least one embodiment, the variation or mutation is introduced intentionally by methods well known in the art, including but not limited to random mutagenesis or directed mutagenesis.

An RNA virus such as CGMMV, including but not limited to attenuated strains thereof, contains an RNA genome, in which the genetic information of the virus is stored in the form of RNA. As will be understood by a person of skill in the art, it is possible to express viral proteins encoded by such an RNA genome in a host cell which expresses genetic information from DNA by preparing a complementary DNA (cDNA) molecule carrying the same genetic information as is encoded by the RNA genome, and transforming the host cell with the cDNA such that the transformed host cell can express viral proteins encoded by the cDNA. In at least one embodiment, the virus can be assembled and/or replicated within the transformed host cell.

Therefore, another aspect of the present invention provides a polydeoxyribonucleotide having a sequence functionally equivalent to a sequence of a cucumber green mottle mosaic virus (CGMMV) genome, wherein the polydeoxyribonucleotide sequence comprises a variant of SEQ ID NO:18 including one or more variations from SEQ ID NO:18.

In at least one embodiment, the polydeoxyribonucleotide sequence comprises a sequence wherein the one or more variations from SEQ ID NO:18 include A at the position corresponding to position 4969 of SEQ ID NO:18.

In at least one embodiment, the polydeoxyribonucleotide sequence comprises a sequence wherein the one or more variations from SEQ ID NO:18 include T at the position corresponding to position 3334 of SEQ ID NO:18.

In at least one embodiment, the polydeoxyribonucleotide sequence comprises a sequence wherein the one or more variations from SEQ ID NO:18 include A at the position corresponding to position 4969 of SEQ ID NO:18 and T at the position corresponding to position 3334 of SEQ ID NO:18.

In at least one embodiment, the polydeoxyribonucleotide sequence comprises a sequence wherein the one or more variations from SEQ ID NO:18 include at least six of the following residues:
A at the position corresponding to position 315 of SEQ ID NO:18;
G at the position corresponding to position 1498 of SEQ ID NO:18;
T at the position corresponding to position 1660 of SEQ ID NO:18;
T at the position corresponding to position 3430 of SEQ ID NO:18;
G at the position corresponding to position 3528 of SEQ ID NO:18;
T at the position corresponding to position 4144 of SEQ ID NO:18;
T at the position corresponding to position 4248 of SEQ ID NO:18; and
T at the position corresponding to position 6228 of SEQ ID NO:18.

In at least one such embodiment, the one or more variations from SEQ ID NO:18 further include one or both of:
T at the position corresponding to position 3334 of SEQ ID NO:18; and
A at the position corresponding to position 4969 of SEQ ID NO:18.

In at least one embodiment, the polydeoxyribonucleotide sequence comprises a sequence wherein the one or more variations from SEQ ID NO:18 include the following residues:
A at the position corresponding to position 315 of SEQ ID NO:18;
G at the position corresponding to position 1498 of SEQ ID NO:18;
T at the position corresponding to position 1660 of SEQ ID NO:18;
T at the position corresponding to position 3430 of SEQ ID NO:18;
G at the position corresponding to position 3528 of SEQ ID NO:18;
T at the position corresponding to position 4144 of SEQ ID NO:18;
T at the position corresponding to position 4248 of SEQ ID NO:18; and
T at the position corresponding to position 6228 of SEQ ID NO:18.

In at least one such embodiment, the one or more variations from SEQ ID NO:18 further include one or both of:
T at the position corresponding to position 3334 of SEQ ID NO:18; and
A at the position corresponding to position 4969 of SEQ ID NO:18.

As used herein with reference to a polynucleotide sequence, the term "functionally equivalent to" is intended to mean that the polynucleotide sequence contains the same genetic information, including but not limited to coding information, as the genetic information contained in the reference polynucleotide sequence. In at least one embodiment, a functionally equivalent polynucleotide sequence will encode the same protein or proteins as are encoded by the reference polynucleotide sequence. In at least one embodiment, a given position in the polynucleotide sequence will bear a base equivalent to the base borne by the corresponding position of the reference polynucleotide sequence. As used herein with reference to bases in functionally equivalent polynucleotide sequences, the term "equivalent" is intended to mean that the bases are either identical or provide the same coding information. Thus, the base T (which is found in polydeoxyribonucleotides) and the base U (which is found in polyribonucleotides) are considered herein to be equivalent to each other. In other words, when a polydeoxyribonucleotide sequence is functionally equivalent to a polyribonucleotide sequence, positions in the polydeoxyribonucleotide sequence which bear the base T are considered to correspond to positions in the polyribonucleotide sequence which bear the base U.

In at least one embodiment, the sequence of the polydeoxyribonucleotide is selected from SEQ ID NO:42, SEQ ID NO:45, SEQ ID NO:48, SEQ ID NO:53, SEQ ID NO:58, SEQ ID NO:60, and variants thereof which include at least one residue or group of residues selected from:
a) A at the position corresponding to position 4969 of SEQ ID NO:18;
b) T at the position corresponding to position 3334 of SEQ ID NO:18; and
c) a group of at least six residues selected from:
A at the position corresponding to position 315 of SEQ ID NO:18;
G at the position corresponding to position 1498 of SEQ ID NO:18;
T at the position corresponding to position 1660 of SEQ ID NO:18;
T at the position corresponding to position 3430 of SEQ ID NO:18;
G at the position corresponding to position 3528 of SEQ ID NO:18;
T at the position corresponding to position 4144 of SEQ ID NO:18;
T at the position corresponding to position 4248 of SEQ ID NO:18; and
T at the position corresponding to position 6228 of SEQ ID NO:18.

In at least one embodiment, the sequence of the variant can have at least 89%, at least 90%, at least 95%, at least 99% or at least 99.9% identity to a sequence selected from SEQ ID NO:42, SEQ ID NO:45, SEQ ID NO:48, SEQ ID NO:53, SEQ ID NO:58 or SEQ ID NO:60, wherein the variant sequence comprises at least one residue or group of residues selected from:
a) A at the position corresponding to position 4969 of SEQ ID NO:18;
b) T at the position corresponding to position 3334 of SEQ ID NO:18; and
c) a group of at least six residues selected from:
A at the position corresponding to position 315 of SEQ ID NO:18;
G at the position corresponding to position 1498 of SEQ ID NO:18;
T at the position corresponding to position 1660 of SEQ ID NO:18;
T at the position corresponding to position 3430 of SEQ ID NO:18;
G at the position corresponding to position 3528 of SEQ ID NO:18;
T at the position corresponding to position 4144 of SEQ ID NO:18;
T at the position corresponding to position 4248 of SEQ ID NO:18; and
T at the position corresponding to position 6228 of SEQ ID NO:18.

In at least one embodiment, the sequence of the polydeoxyribonucleotide is selected from SEQ ID NO:42, SEQ ID NO:45, SEQ ID NO:48, SEQ ID NO:53, SEQ ID NO:58, SEQ ID NO:60, and variants thereof which encode one or more of the proteins encoded by the polydeoxyribonucleotide having the sequence selected from SEQ ID NO:42, SEQ ID NO:45, SEQ ID NO:48, SEQ ID NO:53, SEQ ID NO:58 and SEQ ID NO:60.

As used herein, the term "variant" when used in reference to a polynucleotide is intended to refer to a polynucleotide which differs in its nucleotide sequence from the sequence of a reference polynucleotide to which the variant is being compared by one or more nucleotide residues. The differences between the sequence of the variant and the sequence of the reference polynucleotide, also referred to herein as variations or mutations, can include substitution of one or more nucleotide residues with different nucleotide residues, insertion of additional nucleotide residues or deletion of nucleotide residues. In certain embodiments, a variant can differ from a reference polynucleotide by substitution of one or more nucleotide residues with replacement nucleotide residues which do not alter the open reading frame(s) of the polynucleotide or the amino acid sequence of any protein(s) encoded by the polynucleotide.

As used herein, the term "variant" when used in reference to a polypeptide is intended to refer to a polypeptide which differs in its amino acid sequence from the sequence of a reference polypeptide to which the variant is being compared by one or more amino acid residues. The differences between the sequence of the variant and the sequence of the reference polypeptide can include substitution of one or more amino acid residues with different amino acid residues, insertion of additional amino acid residues or deletion of amino acid residues. In certain embodiments, a variant can differ from a reference polypeptide by conservative substitution of one or more amino acid residues with replacement amino acid residues which may have similar properties, including but not limited to charge, size and hydrophilicity, to the amino acid residues which the new residues replace. In certain embodiments, variants may completely or partially retain one or more biological functions of the reference polypeptide. In certain embodiments, variants may not retain one or more biological functions of the reference polypeptide.

As used herein, the term "percent identity" or "% identity" when used in reference to the sequence of a polypeptide or a polynucleotide is intended to mean the percentage of the total number of amino acid or nucleotide residues, respectively, in the sequence which are identical to those at the corresponding position of a reference polypeptide or polynucleotide sequence. In at least one embodiment, when the length of the variant sequence and the length of the reference sequence are not identical, percent identity can be calculated based on the total number of residues in the variant sequence or based on the total number or residues in the reference sequence. Percent identity can be measured by various local or global sequence alignment algorithms well known in the art, including but not limited to the Smith-Waterman algorithm and the Needleman-Wunsch algorithm. Tools using these or other suitable algorithms include but are not limited to BLAST (Basic Local Alignment Search Tool) and other such tools well known in the art.

In at least one embodiment, a variant polynucleotide sequence can hybridize to a polyribonucleotide or polydeoxyribonucleotide as described herein under at least moderately stringent conditions. By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrid, is determined by the melting temperature ($T_m$), which in sodium-containing buffers is a function of the sodium ion concentration ([Na$^+$]) and temperature ($T_m$=81.5° C.−16.6 (Log$_{10}$, [Na$^+$])+0.41(%(G+C)−600/l), where % G+C is the percentage of cytosine and guanine nucleotides in the nucleic acid and 1 is the length of the nucleic acid in base pairs, or similar equation). Accordingly, the parameters in the wash conditions that determine hybrid stability are sodium ion concentration and temperature. In order to identify molecules that are similar, but not identical, to a known nucleic acid molecule, a 1% mismatch may be assumed to result in about a 1° C. decrease in $T_m$. For example, if nucleic acid molecules are sought that have a >95% identity, the final wash temperature may be reduced by about 5° C. Based on these considerations those skilled in the art will be able to readily select appropriate hybridization conditions.

In some embodiments, stringent hybridization conditions are selected. By way of example the following conditions may be employed to achieve stringent hybridization: hybridization at 5× sodium chloride/sodium citrate (SSC)/5×Denhardt's solution/1.0% sodium dodecylsulfate (SDS) at $T_m$−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

In at least one embodiment, the polyribonucleotide CGMMV genome and the functionally equivalent polydeoxyribonucleotide can each encode one or more viral proteins including but not limited to a 129 kDa protein including methyltransferase and helicase domains required for RNA replication, a 186 kDa protein including the methyltransferase and helicase domains and an additional RNA-dependent RNA polymerase (RdRp) domain, a movement protein (MP) and a coat protein (CP).

In at least one embodiment, the 129 kDa protein has an amino acid sequence comprising valine (V, Val) at the position corresponding to position 1092 of SEQ ID NO:63.

In at least one embodiment, the 129 kDa protein sequence includes at least two residues selected from:
  serine (S, Ser) at the position corresponding to position 86 of SEQ ID NO:63;
  glycine (G, Gly) at the position corresponding to position 480 of SEQ ID NO:63;
  phenylalanine (F, Phe) at the position corresponding to position 534 of SEQ ID NO:63; and
  valine (V, Val) at the position corresponding to position 1124 of SEQ ID NO:63.

In at least one such embodiment, the 129 kDa protein sequence further includes valine (V, Val) at the position corresponding to position 1092 of SEQ ID NO:63.

In at least one embodiment, the 129 kDa protein sequence includes at least three residues selected from:
  serine (S, Ser) at the position corresponding to position 86 of SEQ ID NO:63;

glycine (G, Gly) at the position corresponding to position 480 of SEQ ID NO:63;
phenylalanine (F, Phe) at the position corresponding to position 534 of SEQ ID NO:63; and
valine (V, Val) at the position corresponding to position 1124 of SEQ ID NO:63.

In at least one such embodiment, the 129 kDa protein sequence further includes valine (V, Val) at the position corresponding to position 1092 of SEQ ID NO:63.

In at least one embodiment, the 129 kDa protein sequence includes the residues:
serine (S, Ser) at the position corresponding to position 86 of SEQ ID NO:63;
glycine (G, Gly) at the position corresponding to position 480 of SEQ ID NO:63;
phenylalanine (F, Phe) at the position corresponding to position 534 of SEQ ID NO:63; and
valine (V, Val) at the position corresponding to position 1124 of SEQ ID NO:63.

In at least one such embodiment, the 129 kDa protein sequence further includes valine (V, Val) at the position corresponding to position 1092 of SEQ ID NO:63.

In at least one embodiment, the sequence of the 129 kDa protein is selected from SEQ ID NO:43, SEQ ID NO:46, SEQ ID NO:49, SEQ ID NO:54, SEQ ID NO:61 and variants thereof which include valine (V, Val) at the position corresponding to position 1092 of SEQ ID NO:63.

In at least one embodiment, the sequence of the 129 kDa protein is selected from SEQ ID NO:43, SEQ ID NO:46, SEQ ID NO:49, SEQ ID NO:54, SEQ ID NO:61 and variants thereof which include at least two residues selected from:
serine (S, Ser) at the position corresponding to position 86 of SEQ ID NO:63;
glycine (G, Gly) at the position corresponding to position 480 of SEQ ID NO:63;
phenylalanine (F, Phe) at the position corresponding to position 534 of SEQ ID NO:63; and
valine (V, Val) at the position corresponding to position 1124 of SEQ ID NO:63.

In at least one such embodiment, the variants of the 129 kDa protein sequence further include valine (V, Val) at the position corresponding to position 1092 of SEQ ID NO:63.

In at least one embodiment, the sequence of the 129 kDa protein is selected from SEQ ID NO:43, SEQ ID NO:46, SEQ ID NO:49, SEQ ID NO:54, SEQ ID NO:61 and variants thereof which include at least three residues selected from:
serine (S, Ser) at the position corresponding to position 86 of SEQ ID NO:63;
glycine (G, Gly) at the position corresponding to position 480 of SEQ ID NO:63;
phenylalanine (F, Phe) at the position corresponding to position 534 of SEQ ID NO:63; and
valine (V, Val) at the position corresponding to position 1124 of SEQ ID NO:63.

In at least one such embodiment, the variants of the 129 kDa protein sequence further include valine (V, Val) at the position corresponding to position 1092 of SEQ ID NO:63.

In at least one embodiment, the sequence of the 129 kDa protein is selected from SEQ ID NO:43, SEQ ID NO:46, SEQ ID NO:49, SEQ ID NO:54, SEQ ID NO:61 and variants thereof which include the residues:
serine (S, Ser) at the position corresponding to position 86 of SEQ ID NO:63;
glycine (G, Gly) at the position corresponding to position 480 of SEQ ID NO:63;
phenylalanine (F, Phe) at the position corresponding to position 534 of SEQ ID NO:63; and
valine (V, Val) at the position corresponding to position 1124 of SEQ ID NO:63.

In at least one such embodiment, the variants of the 129 kDa protein sequence further include valine (V, Val) at the position corresponding to position 1092 of SEQ ID NO:63.

In at least one embodiment, the 186 kDa protein has an amino acid sequence comprising histidine (H, His) at the position corresponding to position 1637 of SEQ ID NO:64.

In at least one embodiment, the 186 kDa protein sequence includes valine (V, Val) at the position corresponding to position 1092 of SEQ ID NO:64.

In at least one embodiment, the 186 kDa protein sequence includes histidine (H, His) at the position corresponding to position 1637 of SEQ ID NO:64 and valine (V, Val) at the position corresponding to position 1092 of SEQ ID NO:64.

In at least one embodiment, the 186 kDa protein sequence includes at least five residues selected from:
serine (S, Ser) at the position corresponding to position 86 of SEQ ID NO:64;
glycine (G, Gly) at the position corresponding to position 480 of SEQ ID NO:64;
phenylalanine (F, Phe) at the position corresponding to position 534 of SEQ ID NO:64;
valine (V, Val) at the position corresponding to position 1124 of SEQ ID NO:64;
aspartic acid (D, Asp) at the position corresponding to position 1157 of SEQ ID NO:64;
leucine (L, Leu) at the position corresponding to position 1362 of SEQ ID NO:64; and
serine (S, Ser) at the position corresponding to position 1397 of SEQ ID NO:64.

In at least one such embodiment, the 186 kDa protein sequence further includes one or both of:
valine (V, Val) at the position corresponding to position 1092 of SEQ ID NO:64; and
histidine (H, His) at the position corresponding to position 1637 of SEQ ID NO:64.

In at least one embodiment, the 186 kDa protein sequence includes at least six residues selected from:
serine (S, Ser) at the position corresponding to position 86 of SEQ ID NO:64;
glycine (G, Gly) at the position corresponding to position 480 of SEQ ID NO:64;
phenylalanine (F, Phe) at the position corresponding to position 534 of SEQ ID NO:64;
valine (V, Val) at the position corresponding to position 1124 of SEQ ID NO:64;
aspartic acid (D, Asp) at the position corresponding to position 1157 of SEQ ID NO:64;
leucine (L, Leu) at the position corresponding to position 1362 of SEQ ID NO:64; and
serine (S, Ser) at the position corresponding to position 1397 of SEQ ID NO:64.

In at least one such embodiment, the 186 kDa protein sequence further includes one or both of:
valine (V, Val) at the position corresponding to position 1092 of SEQ ID NO:64; and
histidine (H, His) at the position corresponding to position 1637 of SEQ ID NO:64.

In at least one embodiment, the 186 kDa protein sequence includes the residues:
serine (S, Ser) at the position corresponding to position 86 of SEQ ID NO:64;
glycine (G, Gly) at the position corresponding to position 480 of SEQ ID NO:64;

phenylalanine (F, Phe) at the position corresponding to position 534 of SEQ ID NO:64;
valine (V, Val) at the position corresponding to position 1124 of SEQ ID NO:64;
aspartic acid (D, Asp) at the position corresponding to position 1157 of SEQ ID NO:64;
leucine (L, Leu) at the position corresponding to position 1362 of SEQ ID NO:64; and
serine (S, Ser) at the position corresponding to position 1397 of SEQ ID NO:64.

In at least one such embodiment, the 186 kDa protein sequence further includes one or both of:
valine (V, Val) at the position corresponding to position 1092 of SEQ ID NO:64; and
histidine (H, His) at the position corresponding to position 1637 of SEQ ID NO:64.

In at least one embodiment, the sequence of the 186 kDa protein is selected from SEQ ID NO:44, SEQ ID NO:47, SEQ ID NO:50, SEQ ID NO:55, SEQ ID NO:59, SEQ ID NO:62 and variants thereof which include histidine (H, His) at the position corresponding to position 1637 of SEQ ID NO:64.

In at least one embodiment, the sequence of the 186 kDa protein is selected from SEQ ID NO:44, SEQ ID NO:47, SEQ ID NO:50, SEQ ID NO:55, SEQ ID NO:59, SEQ ID NO:62 and variants thereof which include valine (V, Val) at the position corresponding to position 1092 of SEQ ID NO:64.

In at least one embodiment, the sequence of the 186 kDa protein is selected from SEQ ID NO:44, SEQ ID NO:47, SEQ ID NO:50, SEQ ID NO:55, SEQ ID NO:59, SEQ ID NO:62 and variants thereof which include histidine (H, His) at the position corresponding to position 1637 of SEQ ID NO:64 and valine (V, Val) at the position corresponding to position 1092 of SEQ ID NO:64.

In at least one embodiment, the sequence of the 186 kDa protein is selected from SEQ ID NO:44, SEQ ID NO:47, SEQ ID NO:50, SEQ ID NO:55, SEQ ID NO:59, SEQ ID NO:62 and variants thereof which include at least five residues selected from:
serine (S, Ser) at the position corresponding to position 86 of SEQ ID NO:64;
glycine (G, Gly) at the position corresponding to position 480 of SEQ ID NO:64;
phenylalanine (F, Phe) at the position corresponding to position 534 of SEQ ID NO:64;
valine (V, Val) at the position corresponding to position 1124 of SEQ ID NO:64;
aspartic acid (D, Asp) at the position corresponding to position 1157 of SEQ ID NO:64;
leucine (L, Leu) at the position corresponding to position 1362 of SEQ ID NO:64; and
serine (S, Ser) at the position corresponding to position 1397 of SEQ ID NO:64.

In at least one embodiment, the variants of the 186 kDa protein sequence further include one or both of:
valine (V, Val) at the position corresponding to position 1092 of SEQ ID NO:64; and
histidine (H, His) at the position corresponding to position 1637 of SEQ ID NO:64.

In at least one embodiment, the sequence of the 186 kDa protein is selected from SEQ ID NO:44, SEQ ID NO:47, SEQ ID NO:50, SEQ ID NO:55, SEQ ID NO:59, SEQ ID NO:62 and variants thereof which include at least six residues selected from:
serine (S, Ser) at the position corresponding to position 86 of SEQ ID NO:64;
glycine (G, Gly) at the position corresponding to position 480 of SEQ ID NO:64;
phenylalanine (F, Phe) at the position corresponding to position 534 of SEQ ID NO:64;
valine (V, Val) at the position corresponding to position 1124 of SEQ ID NO:64;
aspartic acid (D, Asp) at the position corresponding to position 1157 of SEQ ID NO:64;
leucine (L, Leu) at the position corresponding to position 1362 of SEQ ID NO:64; and
serine (S, Ser) at the position corresponding to position 1397 of SEQ ID NO:64.

In at least one embodiment, the variants of the 186 kDa protein sequence further include one or both of:
valine (V, Val) at the position corresponding to position 1092 of SEQ ID NO:64; and
histidine (H, His) at the position corresponding to position 1637 of SEQ ID NO:64.

In at least one embodiment, the sequence of the 186 kDa protein is selected from SEQ ID NO:44, SEQ ID NO:47, SEQ ID NO:50, SEQ ID NO:55, SEQ ID NO:59, SEQ ID NO:62 and variants thereof which include the residues:
serine (S, Ser) at the position corresponding to position 86 of SEQ ID NO:64;
glycine (G, Gly) at the position corresponding to position 480 of SEQ ID NO:64;
phenylalanine (F, Phe) at the position corresponding to position 534 of SEQ ID NO:64;
valine (V, Val) at the position corresponding to position 1124 of SEQ ID NO:64;
aspartic acid (D, Asp) at the position corresponding to position 1157 of SEQ ID NO:64;
leucine (L, Leu) at the position corresponding to position 1362 of SEQ ID NO:64; and
serine (S, Ser) at the position corresponding to position 1397 of SEQ ID NO:64.

In at least one embodiment, the variants of the 186 kDa protein sequence further include one or both of:
valine (V, Val) at the position corresponding to position 1092 of SEQ ID NO:64; and
histidine (H, His) at the position corresponding to position 1637 of SEQ ID NO:64.

Because the 186 kDa protein is encoded by an open reading frame in the CGMMV genome which includes the open reading frame for the 129 kDa protein, it will be clear to the person of skill in the art that a polyribonucleotide or a polydeoxyribonucleotide as described herein which encodes a 186 kDa protein as described herein will also encode a 129 kDa protein as described herein.

In at least one embodiment, the coat protein has an amino acid sequence comprising valine (V, Val) at the position corresponding to position 156 of SEQ ID NO:65. In at least one embodiment, the sequence of the coat protein is selected from SEQ ID NO:32 and variants thereof comprising valine (V, Val) at the position corresponding to position 156 of SEQ ID NO:65.

As will be understood in the art, the degeneracy of the genetic code allows for some amino acids to be encoded by more than one codon or group of three nucleoside residues. Therefore, it is contemplated that the sequences of the present polyribonucleotide or polydeoxyribonucleotide can also include mutations other than those specifically described herein such that the polyribonucleotide or polydeoxyribonucleotide will encode proteins having amino acid sequences as described herein.

In at least one embodiment, the polydeoxyribonucleotide is configured for expression in a host cell so as to permit expression of viral proteins and/or assembly and/or replication of infectious virus in the host cell, as will be understood by those skilled in the art, who will be capable of configuring the polydeoxyribonucleotide for expression in such a host cell without undue experimentation in light of the teaching herein. In at least one embodiment, the host cell is a microorganism. In at least one embodiment, the host cell is a plant cell.

In another aspect, the present application provides a vector comprising a polydeoxyribonucleotide as described herein. In at least one embodiment, the vector is configured for use to genetically modify a cell. Thus, a further aspect of the present application provides a genetically modified cell comprising a polydeoxyribonucleotide as described herein. In at least one embodiment, the cell is a microorganism. In at least one embodiment, the cell is a plant cell. Those skilled in the art would be aware of methods for preparing such vectors and using them to genetically modify such cells.

Another aspect of the present application provides a composition for preventing symptoms associated with infection by wild-type CGMMV in a plant, where the composition comprises an attenuated strain of CGMMV or a genetically modified cell as described herein and an agriculturally acceptable carrier. In at least one embodiment, the composition comprises two or more attenuated strains of CGMMV or genetically modified cells as described herein.

As used herein, the term "carrier" is intended to refer to a diluent, adjuvant, excipient, or vehicle with which an attenuated strain of CGMMV or a genetically modified cell can be applied or administered to a plant or crop. As used herein, the term "agriculturally acceptable" is intended to refer to carriers and compositions containing such carriers that are tolerable and do not typically produce untoward reactions to a plant or crop being treated with such carriers and compositions, or to a worker applying such carriers and compositions to a plant or crop under normal agricultural conditions. Preferably, as used herein, the term "agriculturally acceptable" means approved by a regulatory agency of the federal or a state government for use in agricultural applications. Such agriculturally acceptable carriers are well known in the art.

In an additional aspect, the present application provides a composition for increasing resistance of a plant to infection by wild-type CGMMV, where the composition comprises an attenuated strain of CGMMV or a genetically modified cell as described herein and an agriculturally acceptable carrier. In at least one embodiment, the composition comprises two or more attenuated strains of CGMMV or genetically modified cells as described herein.

Another aspect of the present application provides a method for preventing symptoms associated with infection by wild-type CGMMV in a plant, where the method includes inoculating the plant with an attenuated strain of CGMMV or with a genetically modified cell as described herein. Methods of inoculating plants with viruses, including but not limited to attenuated strains thereof, and/or with cells, including but not limited to microorganisms, genetically modified to express such viruses or associated viral proteins, and/or with compositions thereof are well known in the art, and well within the capability of the skilled person in light of the teaching of the present application.

A further aspect of the present application provides a method for increasing resistance of a plant to infection by wild-type CGMMV, where the method includes inoculating the plant with an attenuated strain of CGMMV or with a genetically modified cell as described herein.

In a further aspect, the present application provides a genetically modified plant comprising a genome which comprises a polydeoxyribonucleotide as described herein. It is contemplated that such a genetically modified plant may have increased resistance to infection by wild type strains of CGMMV. In at least one embodiment, the plant is a cucurbit. In at least one embodiment, the plant is a cucumber plant.

As used herein, the terms "about" or "approximately" as applied to a numerical value or range of values are intended to mean that the recited values can vary within an acceptable degree of error for the quantity measured given the nature or precision of the measurements, such that the variation is considered in the art as equivalent to the recited values and provides the same function or result. For example, the degree of error can be indicated by the number of significant figures provided for the measurement, as is understood in the art, and includes but is not limited to a variation of ±1 in the most precise significant figure reported for the measurement. Typical exemplary degrees of error are within 20 percent (%), preferably within 10%, and more preferably within 5% of a given value or range of values. Alternatively, and particularly in biological systems, the terms "about" and "approximately" can mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

As used herein, the term "substantially" refers to the complete or nearly complete extent or degree of an action, characteristic, property, state, structure, item, or result. For example, an object that is "substantially" in a given position including but not limited to vertical, horizontal, or adjacent to or aligned with another object, would mean that the object is either completely in that position or nearly completely in that position. The exact allowable degree of deviation from absolute completeness may in some cases depend on the specific context. However, generally speaking, the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. For example, a composition that is "substantially free of" an ingredient or element would either completely lack that ingredient or element, or so nearly completely lack that ingredient or element that the effect would be the same as if it completely lacked that ingredient or element. In other words, a composition that is "substantially free of" an ingredient or element may still actually contain such item as long as there is no measurable or significant effect thereof.

EXAMPLES

Other features of the present invention will become apparent from the following non-limiting examples which illustrate, by way of example, the principles of the invention.

Example 1: Cucumber Green Mottle Mosaic Virus (CGMMV) Ontario Strain

Isolation, Cloning and Sequencing of a Wild-Type Ontario Strain

Cucumber green mottle mosaic virus (CGMMV) Ontario strain (also referred to herein as the "wild-type" strain) was extracted from cucumber plants showing green mottle and mosaic symptoms collected from a commercial greenhouse in Ontario. cDNA was synthesized from the CGMMV RNA genome using Agilent AccuScript™ High-Fidelity Reverse Transcriptase (Agilent) and an oligonucleotide primer having the sequence CGGCTCGAGCCCGTTTCGTCCTT-TAGGGACTCGTCAGTGTACTGA-TATAAGTACA-GACTGGGCCCCTACCCGGGGAAAGGGGGGATT (SEQ ID NO:1). The full-length genome of CGMMV Ontario strain was amplified from cDNA by polymerase chain reaction (PCR) using Q5™ High-fidelity 2× Master Mix (New England Biolabs) and the primers GTTTTAAT-TTTTAAAAT-TAAACAAACAACAACAACAACAACAAAC (SEQ ID NO:2) and CCCCGGCTCGAGCCCGTTTCGTCCTT-TAGGGACTCGT (SEQ ID NO:3). The PCR product was digested with XhoI and cloned into a binary vector pKW8 between the StuI and XhoI sites in 10-beta *Escherichia coli* (New England Biolabs) by electroporation. The whole cDNA genome was sequenced using primers which were designed based on analysis of genome sequences published in GenBank for other CGMMV strains. The sequences of the primers are listed in Table 1 below.

TABLE 1

Primers used to sequence the cDNA genome of CGMMV wild-type Ontario strain

| Primer sequence (5' to 3') | Sequence identifier |
| --- | --- |
| CGTACCTCCTGAATGCATCTATC | SEQ ID NO: 4 |
| CGGTAACTATACGCAGCACTT | SEQ ID NO: 5 |
| CAGTTTAGGGTCGATGGTGATG | SEQ ID NO: 6 |
| CAAGGCCTTAGTGTGGAAGAA | SEQ ID NO: 7 |
| CTCGCTTCCGGTGATGATTT | SEQ ID NO: 8 |
| GTCGGAACCTCGATGACTTTAC | SEQ ID NO: 9 |
| GTGACGATACCACTCGCATAAT | SEQ ID NO: 10 |
| CTGATGGTCCATACGGGATTAC | SEQ ID NO: 11 |
| GGCCTTAACTAGGCACACTAAG | SEQ ID NO: 12 |
| CCGGGTCTTCTTGAGAATCTTG | SEQ ID NO: 13 |
| TGGCTTGGATGTGGTCTATG | SEQ ID NO: 14 |
| GGTCGATAAGTTGCTCCCTAAC | SEQ ID NO: 15 |
| TAGTCGAGTCTGTCGTCTCTTC | SEQ ID NO: 16 |
| CCTGTGTTGAGGCCTATCTTC | SEQ ID NO: 17 |

The full-length cDNA genome sequence of CGMMV Ontario strain is shown below.

(SEQ ID NO: 18)
GTTTTAATTTTTAAAATTAAACAAACAACAACAACAACAAACAATTT

AAAACAACAATGGCAAACATTAATGAACAAATCAACAACCAACGCGACGC

CGCGGCCAGCGGGAGAAACAATCTCGTTAGCCAATTGGCGTCAAAAAGGG

TGTATGACGAGGCTGTTCGCTCGTTGGATCATCAAGACAGACGCCCAAAA

ATGAACTTTTCTCGTGTGGTCAGCACAGAGCACACCAGGCTTGTAACTGA

TGCGTATCCGGAGTTTTCGATTAGCTTTACCGCCACCAAGAACTCTGTAC

ACTCCCTTGCGGGTGGTCTGAGGCTCCTTGAACTGGAATATATGATGATG

CAAGTGCCCTACGGCTCACCTTGTTATGATATCGGCGGTAACTATACGCA

GCACTTGTTCAAAGGTAGATCATATGTGCATTGCTGCAATCCGTGCCTGG

ATCTTAAAGATGTTGCGAGGAACGTGATGTATAACGATATGGTCACACAA

CATGTACGAGGCACAAGGGATCTGGCGGGTGCAGACCTCTTCCAACTTT

TCAGATAGATGCATTCAGGAGGTACGATAATTCTCCCTGTGCGGTCACCT

GTTCAGACGTTTTCCAAGAGTGTTCCTATGATTTTGGGAGCGGTAGGGAT

AATCATGCAGTCTCGCTGCATTCAATCTACGATATCCCTTATTCTTCGAT

CGGACCTGCTCTTCATAGGAAGAACGTGCGAGTTTGTTATGCAGCCTTTC

ACTTCTCGGAGGCATTGCTTTTAGGTTCACCTGTAGGTAATTTAAATAGT

ATTGGGGCTCAGTTTAGGGTCGATGGTGATGATGTGCATTTTCTTTTTAG

TGAAGAGTCTACTTTGCATTATACTCATAGTTTAGAAAATATCAAATTAA

TTGTGATGCGTACTTATTTTCCTGCTGATGATAGGTACGTGTATATTAAG

GAGTTTATGGTCAAGCGTGTGGATACTTTCTTCTTTAGGTTGGTCAGAGC

AGACACACATATGCTTCATAAATCTGTGGGGCACTATTCAAAATCGAAAT

CTGAGTACTTTGCGCTGAATACCCCTCCGATCTTCCAAGACAAAGCCACG

TTTTCTGTGTGGTTTCCTGAGGCGAAGCGTAAGGTGTTGATACCCAAGTT

TGAACTTTCAAGATTCCTTTCTGGGAATGTGAAAATCTCTAGGATGCTTG

TCGATGCTGATTTCGTCCATACCATTATTAATCACATTAGCACGTATGAT

AATAAGGCCTTAGTGTGGAAGAATGTTCAGTCCTTTGTGGAATCTATACG

CTCAAGAGTAATTGTAAACGGAGTTTCGGTGAAATCTGAATGGAACGTAC

CGGTTGATCAGCTCACTGATATCTCGTTCTCGATATTCCTTCTCGTGAAG

GTTAGGAAGGTACAGATCGAGTTAATGTCTGATAAAGTTGTAATCGAGGC

GAGGGGCTTGCTCCGGAGGTTCGCAGACAGTCTTAAATCCGCCGTAGAAG

GACTAGGTGATTGCGTCTATGATGCTCTAGTTCAAACCGGCTGGTTTGAT

ACCTCTAGCGACGAACTGAAAGTTTTGCTACCTGAACCGTTTATGACCTT

TTCGGATTATCTTGAAGGGATGTACGAGGCAGATGCAAAGATCGAGAGAG

AGAGTGTCTCTGAGTTGCTCGCTTCCGGTGACGATTGTTCAAGAAAATC

GATGAGATAAGAAACAATTACAGTGGAGTCGAATTTGATGTAGAGAAATT

CCAGGAATTTTGCAAGGAACTGAATGTTAATCCTATGCTAATTGGCCATG

TTATCGAAGCTATTTTTTCGCAGAAAGCTGGGGTGACAGTAACGGGTCTG

GGTACCCTCTCTCCTGAGATGGGTGCTTCTGTTGCGTTATCCAATACCTC

TGTAGATACATGTGAAGATATGGATGTAACTGAAGATATGGAGGATATAG

TGTTGATGGCGGACAAGAGTCATTCTTACATGTCCCCAGAAATGGCGAGA

TGGGCTGATGTAAAATACGACAACAATAAAGGGGGCCTGGTCGAATACAA

AGTCGGAACCTCGATGACTTTACCTGCCACCTGGGCAGAGAAGGGTAAGG

CTGTCTTACCGTTGTCGGGGATCTGTGTGAGGAAACCCCAATTTTCGAAG

CCGCTTGATGAGGAAGACGACTTGAGGTTATCAAACATGAATTTCTTTAA

GGTGAGCGATCTGAAGTTGAAGAAAACTATCACTCCAGTTGTTTACACTG

GGACCATTCGAGAGAGGCAAATGAAGAATTATATTGATTACTTATCGGCC
TCTCTTGGTTCTACGCTGGGTAATCTGGAGAGAATTGTGCGGAGTGATTG
GAACGGTACCGAGGAGAGTATGCAAACGTTCGGGTTGTATGACTGCGAAA
AGTGCAAGTGGTTACTGTTACCAGCCGAAAAGAAGCACGCATGGGCTGTG
GTTCTGGCAAGTGATGATACCACTCGCATAATCTTCCTCTCATATGACGA
ATCTGGTTCTCCCATAATTGATAAGAGAAACTGGAAGCGATTTGCTGTTT
GCTCTGAGACCAAAGTCTATAGCGTAATTCGTAGTTTAGAGGTACTAAAT
AAGGAAGCAATAGTCGACCCCGGGGTTCATATAACATTAGTTGACGGAGT
GCCGGGTTGTGGAAAGACCGCCGAAATTATAGCGAGGGTCAATTGGAAAA
CCGATCTAGTATTGACTCCCGGGAGGGAGGCGGCTGCTATGATTAGGCGG
AGGGCCTGCGCCCTGCACAAGTCACCTGTGGCAACCAGTGACAACGTTAG
AACTTTCGATTCTTTTGTGATGAATAAGAAAATCTTCAAGTTTGACGCTG
TCTATGTTGACGAGGGTCTGATGGTCCATACGGGTTTACTTAATTTTGCG
TTGAAGATCTCAGGTTGTAAAAGGCCTTCGTCTTTGGTGATGCTAAGCA
AATCCCGTTTATAAACAGAGTCATGAATTTTGATTATCCTAAGGAGTTAA
GAACTTTAATAGTCGATAATGTAGAGCGTAGGTATGTTACCCATAGGTGT
CCTAGAGATGTCACTAGTTTTCTTAATACTATTTACAAAGCCGCTGTCGC
TACTACTAGTCCGGTTGTACATTCTGTGAAGGCGATTAAAGTGTCAGGGG
CCGGTATTCTGAGGCCCGAGTTGACGAAGATCAAAGGAAAGATAATAACG
TTTACTCAATCTGATAAGCAGTCCTTGATCAAGAGTGGGTACAATGACGT
GAACACTGTGCATGAAATTCAGGGAGAAACCTTTGAAGAGACGGCGGTTG
TGCGTGCCACCCCGACTCCGATAGGTTTAATTGCCCGTGATTCACCACAT
GTACTAGTGGCCTTAACGAGGCACACTAAGGCAATGGTGTATTATACTGT
TGTGTTCGATGCAGTTACAAGTATAATAGCGGATGTGGAAAAGGTCGACC
AGTCGATCTTGACTATGTTGCTACCACTGTGCCTACCAAATAGCAATTA
ATGCAGAACTCACTGTATGTCCATCGTAATATTTTCCTCCCTGTTAGTAA
AACGGGGTTTTATACAGACATGCAGGAGTTCTATGATAGATGCCTTCCTG
GGAATTCCTTCGTGCTGAATGATTTCGATGCCGTAACCATGCGGTTGAGG
GACAACGAATTTAACCTACAACCTTGTAGGCTAACCTTAAGTAATTTAGA
TCCAGTACCCGCTTTGGTTAAGAGTGAAGCGCAGAATTTTCTGATTCCCG
TTTTGCGTACGGCCTGTGAAAGGCCGCGCATTCCAGGTCTCCTTGAAAAT
CTTGTAGCTATGATAAAGAGGAATATGAATACTCCTGATCTAGCTGGGAC
TGTGGATATAACTAATATGTCGATTTCTATAGTAGATAACTTCTTTTCTT
CTTTTGTTAGAGACGAGGTTTTGCTTGATCATTTAGATTGTGTTAGGGCT
AGTTCCATTCAAAGTTTTTCTGATTGGTTTTCGTGTCAGCCAACCTCGGC
GGTTGGTCAATTAGCTAATTTCAATTTCATAGATTTGCCTGCCTTTGATA
CTTATATGCACATGATTAAGCGGCAGCCCAAGAGTCGGTTGGATACTTCG
ATTCAGTCTGAATATCCGGCCTTGCAAACTATTGTTTATCACCCTAAAGT
GGTAAATGCAGTTTTCGGTCCGGTTTTTAAGTATTTGACCACCAAGTTTC
TTAGCATGGTAGATAGTTCTAAGTTTTTCTTTTACACTAGGAAAAAACCA
GAAGATCTGCAGGAATTTTTCTCAGATCTCTCTTCCCATTCTGATTATGA

GATTCTTGAGCTGGATGTTTCTAAATATGACAAGTCACAATCCGATTTCC
ATTTCTCTATTGAGATGGCAATTTGGGAAAAATTGGGGCTGGACGATATT
TTGGCTTGGATGTGGTCTATGGGTCACAAGAGAACTATACTGCAAGATTT
CCAAGCCGGGATAAAGACGCTCATTTACTATCAACGGAAGTCTGGTGATG
TAACTACTTTCATAGGTAATACCTTTATTATCGCAGCGTGTGTAGCTAGT
ATGTTGCCGTTAGACAAGTGTTTTAAAGCTAGTTTTTGTGGTGATGATTC
GCTGATCTACCTTCCTAAGGGTTTGGAGTATCCTGATATACAGGCTACTG
CCAACTTGGTTTGGAATTTTGAGGCGAAACTTTTCCGAAAGAAGTATGGT
TACTTCTGTGGGAAGTATATAATTCACCATGCCAACGGCTGTATTGTTTA
CCCTGACCCTTTAAAATTAATTAGTAAATTAGGTAATAAGAGTCTTGTAG
GGTATGAGCATGTTGAGGAGTTTCGTATATCTCTCCTCGACGTCGCTCAT
AGTTTGTTTAATGGTGCTTATTTCCATTTACTCGACGATGCAATCCACGA
ATTATTTCCTAACGCTGGGGGTTGCAGTTTTGTAATTAATTGTTTGTGCA
AGTATTTGAGTGATAAGCGCCTTTTCCGTAGTCTTTATATAGATGTCTCT
AAGTAAGGTGTCGGTCGAGAACTCATTGAAACCCGAGAAGTTTGTTAAAA
TCTCTTGGGTCGATAAGTTGCTCCCTAACTATTTTCCATTCTTAAGTAT
TTATCTATAACTGACTTTAGCGTAGTTAAAGCTCAGAGCTATGAATCCCT
CGTGCCTGTCAAGTTGTTGCGTGGTGTTGATCTTACAAAACACCTTTATG
TCACATTGTTGGGCGTTGTGGTTTCTGGTGTATGGAACGTACCGGAATCC
TGTAGGGGTGGTGCTACTGTTGCTCTGGTTGACACAAGGATGCATTCTGT
TGCAGAGGGAACTATATGCAAATTTTCAGCTCCCGCCACCGTCCGCGAAT
TCTCTGTTAGGTTCATACCTAACTATTCTGTCGTGGCTGCGGATGCCCTT
CGCGATCCTTGGTCTTTATTTGTGAGACTCTCTAATGTAGGGATTAAAGA
TGGTTTCCATCCTTTGACCTTAGAGGTCGCTTGTTTAGTCGCTACAACTA
ACTCTATTATCAAAAAGGGTCTTAGAGCTTCTGTAGTCGAGTCTGTCGTC
TCTTCCGATCAGTCCATTGTCCTAGATTCTTTATCCGAGAAAGTTGAACC
TTTCTTTGATAAAGTTCCTATTTCGGCGGCTGTGATGGCAAGAGACCCCA
GTTATAGGTCTAGGTCGCAGTCTGTCGGTGGTCGTGGTAAGCGGCATTCT
AAACCTCCAAATCGGAGGTTGGACTCTGCTTCTGAAGAGTCCAGTTCTGT
TTCTTTCGAAGATGGCTTACAATCCGATCACACCTAGCAAACTTATTGCG
TTTAGTGCTTCTTATGTTCCCGTCAGGACTTTACTTAATTTTCTAGTTGC
TTCACAAGGTACCGCCTTCCAGACTCAAGCGGGAAGAGATTCTTTCCGCG
AGTCCCTGTCTGCGTTACCCTCGTCTGTCGTAGATATTAATTCTAGGTTC
CCAAATGCGGGTTTTTACGCTTTCCTCAACGGTCCTGTGTTGAGGCCTAT
CTTCGTTTCGCTTCTTAGCTCTACGGATACGCGTAATAGGGTCATTGAGG
TTGTAGATCCTAGCAATCCTACGACTGCTGAGTCGCTTAACGCTGTAAAG
CGTACTGATGACGCATCTACGGCCGCTAGGGCTGAAATAGATAAATTTAAT
AGAGTCTATTTCTAAGGGTTTTGATGTTTATGATAGGGCTTCATTTGAAG
CCGCGTTTTCGGTAGTCTGGTCAGAGGCTACCACCTCGAAAGCTTAGCTT
CGAGGGTCTTCTGATGGTGGTGCACACCAAAGTGCATAGTGCTTTCCCGT

```
TCACTTAAATCGAACGGTTTGCTCATTGGTTTGCGGAAACCTCTCACGTG

TGGCGTTGAAGTTCTATGGGCAGTAATTCTGCAAGGGGTTCGAATCCCC

CCTTTCCCCGGGTAGGGCCCA.
```

The 129 kDa protein encoded by the wild type CGMMV Ontario strain has the following sequence.

```
                                        (SEQ ID NO: 63)
MANINEQINNQRDAAASGRNNLVSQLASKRVYDEAVRSLDHQDRRPKMNF

SRVVSTEHTRLVTDAYPEFSISFTATKNSVHSLAGGLRLLELEYMMMQVP

YGSPCYDIGGNYTQHLFKGRSYVHCCNPCLDLKDVARNVMYNDMVTQHVQ

RHKGSGGCRPLPTFQIDAFRRYDNSPCAVTCSDVFQECSYDFGSGRDNHA

VSLHSIYDIPYSSIGPALHRKNVRVCYAAFHFSEALLLGSPVGNLNSIGA

QFRVDGDDVHFLFSEESTLHYTHSLENIKLIVMRTYFPADDRYVYIKEFM

VKRVDTFFFRLVRADTHMLHKSVGHYSKSKSEYFALNIPPIFQDKATFSV

WFPEAKRKVLIPKFELSRFLSGNVKISRMLVDADFVHTIINHISTYDNKA

LVWKNVQSFVESIRSRVIVNGVSVKSEWNVPVDQLTDISFSIFLLVKVRK

VQIELMSDKVVIEARGURRFADSLKSAVEGLGDCVYDALVQTGWFDTSSD

ELKVLLPEPFMTFSDYLEGMYEADAKIERESVSELLASGDDLFKKIDEIR

NNYSGVEFDVEKFQEFCKELNVNPMLIGHVIEAIFSQKAGVTVTGLGTLS

PEMGASVALSNTSVDTCEDMDVTEDMEDIVLMADKSHSYMSPEMARWADV

KYDNNKGGLVEYKVGTSMTLPATWAEKGKAVLPLSGICVRKPQFSKPLDE

EDDDLRLSNMNFFKVSDLKLKKTITPVVYTGTIREROMKNYIDYLSASLGS

TLGNLERIVRSDWNGTEESMQTFGLYDCEKCKWLLLPAEKKHAWAVVLAS

DDTTRIIFLSYDESGSPIIDKRNWKRFAVCSETKVYSVIRSLEVLNKEAI

VDPGVHITLVDGVPGCGKTAEIIARVNWKTDLVLTPGREAAAMIRRRACA

LHKSPVATSDNVRTFDSFVMNKKIFKFDAVYVDEGLMVHTGLLNFALKIS

GCKKAFVFGDAKQIPFINRVMNFDYPKELRTLIVDNVERRYVTHRCPRDV

TSFLNTIYKAAVATTSPVVHSVKAIKVSGAGILRPELTKIKGKIITFTQS

DKQSLIKSGYNDVNTVHEIQGETFEETAVVRATPTPIGLIARDSPHVLVA

LTRHTKAMVYYTVVEDAVTSIIADVEKVDQSILTMFATTVPTK.
```

The 186 kDa protein encoded by the wild type CGMMV Ontario strain has the following sequence.

```
                                        (SEQ ID NO: 64)
MANINEQINNQRDAAASGRNNLVSQLASKRVYDEAVRSLDHQDRRPKMNF

SRVVSTEHTRLVTDAYPEFSISFTATKNSVHSLAGGLRLLELEYMMMQVP

YGSPCYDIGGNYTQHLFKGRSYVHCCNPCLDLKDVARNVMYNDMVTQHVQ

RHKGSGGCRPLPTFQIDAFRRYDNSPCAVTCSDVFQECSYDFGSGRDNHA

VSLHSIYDIPYSSIGPALHRKNVRVCYAAFHFSEALLLGSPVGNLNSIGA

QFRVDGDDVHFLFSEESTLHYTHSLENIKLIVMRTYFPADDRYVYIKEFM

VKRVDTFFFRLVRADTHMLHKSVGHYSKSKSEYFALNTPPIFQDKATFSV

WFPEAKRKVLIPKFELSRFLSGNVKISRMLVDADFVHTIINHISTYDNKA

LVWKNVQSFVESIRSRVIVNGVSVKSEWNVPVDQLTDISFSIFLLVKVRK

VQIELMSDKVVIEARGLLRRFADSLKSAVEGLGDCVYDALVQTGWFDTSS

DELKVLLPEPFMTFSDYLEGMYEADAKIERESVSELLASGDDLFKKIDEI

RNNYSGVEFDVEKFQEFCKELNVNPMLIGHVIEAIFSQKAGVTVTGLGTL

SPEMGASVALSNTSVDTCEDMDVTEDMEDIVLMADKSHSYMSPEMARWAD

VKYDNNKGGLVEYKVGTSMTLPATWAEKGKAVLPLSGICVRKPQFSKPLD

EEDDLRLSNMNFFKVSDLKLKKTITPVVYTGTIREROMKNYIDYLSASLG

STLGNLERIVRSDWNGTEESMQTFGLYDCEKCKWLLLPAEKKHAWAVVLA

SDDTTRIIFLSYDESGSPIIDKRNWKRFAVCSETKVYSVIRSLEVLNKEA

IVDPGVHITLVDGVPGCGKTAEIIARVNWKTDLVLTPGREAAAMIRRRAC

ALHKSPVATSDNVRTFDSFVMNKKIFKFDAVYVDEGLMVHTGLLNFALKI

SGCKKAFVFGDAKQIPFINRVMNFDYPKELRTLIVDNVERRYVTHRCPRD

VTSFLNTIYKAAVATTSPVVHSVKAIKVSGAGILRPELTKIKGKIITFTQ

SDKQSLIKSGYNDVNTVHEIQGETFEETAVVRATPTPIGLIARDSPHVLV

ALTRHTKAMVYYTVVFDAVTSIIADVEKVDQSILTMFATTVPTKXQLMQN

SLYVHRNIFLPVSKTGFYTDMQEFYDRCLPGNSFVLNDFDAVTMRLRDNE

FNLQPCRLTLSNLDPVPALVKSEAQNFLIPVLRTACERPRIPGLLENLVA

MIKRNMNTPDLAGTVDITNMSISIVDNFFSSFVRDEVLLDHLDCVRASSI

QSFSDWFSCQPTSAVGQLANFNFIDLPAFDTYMHMIKRQPKSRLDTSIQS

EYPALQTIVYHPKVVNAVFGPVFKYLTTKFLSMVDSSKFFFYTRKKPEDL

QEFFSDLSSHSDYEILELDVSKYDKSQSDFHFSIEMAIWEKLGLDDILAW

MWSMGHKRTILQDFQAGIKTLIYYQRKSGDVTTFIGNTFIIAACVASMLP

LDKCFKASFCGDDSLIYLPKGLEYPDIQATANLVWNFEAKLFRKKYGYFC

GKYIIHHANGCIVYPDPLKLISKLGNKSLVGYEHVEEFRISLLDVAHSLF

NGAYFHLLDDAIHELFPNAGGCSFVINCLCKYLSDKRLFRSLYIDVSK.
```

The coat protein encoded by the wild type CGMMV Ontario strain has the following sequence.

```
                                        (SEQ ID NO: 65)
MAYNPITPSKLIAFSASYVPVRTLLNFLVASQGTAFQTQAGRDSFRESLS

ALPSSVVDINSRFPNAGFYAFLNGPVLRPIFVSLLSSTDTRNRVIEVVDP

SNPTTAESLNAVKRTDDASTAARAEIDNLIESISKGFDVYDRASFEAAFS

VVWSEATTSKA.
```

Infection of Cucumber Plants with the Wild-Type Ontario Strain

The CGMMV Ontario strain clone was transformed into *Agrobacterium tumefaciens* strain EHA105 by electroporation. The *Agrobacterium* transformants were selected on LB medium plates containing 50 μg/ml of kanamycin and 20 μg/ml of rifampicin. After confirmation by colony PCR, the *Agrobacterium* transformants carrying CGMMV Ontario strain were cultured overnight at 30° C. with shaking at 200 rpm in LB medium (lysogeny broth, also known as Luria-Bertani medium) containing 50 μg/ml of kanamycin and 20 μg/ml of rifampicin. The overnight culture was used to inoculate fresh LB medium containing 50 μg/ml of kanamycin, 20 μg/ml of rifampicin, 10 mM MES (2-(N-morpholino) ethanesulfonic acid), and 200 μM acetosyringone (3',5'-dimethoxy-4'-hydroxyacetophenone) and the culture was incubated with shaking at 30° C. until the optical density at 600 nm ($OD_{600}$) reached between 0.5 and 1.0.

Bacterial cells were harvested by centrifugation at 4000 g for 10 minutes and resuspended in the same volume of *Agrobacterium* induction buffer (10 mM MES, 200 µM acetosyringone). The suspended cells were incubated at room temperature with gentle shaking (50 rpm) for 3-4 hours. The *Agrobacterium* cells were inoculated into the cotyledon of 1-2 week-old cucumber plants by leaf infiltration using a 1 ml needleless syringe. After incubation for a further two weeks under laboratory greenhouse conditions (16 h daylight at 22° C., 8 h darkness at 20° C.), cucumber plant leaves were sampled and tested for the presence of CGMMV by ELISA using a commercial ELISA kit for detecting CGMMV (Agdia) and following the manufacturer's directions. The results shown in Table 2 demonstrated that the clone of CGMMV Ontario strain was fully infectious.

TABLE 2

ELISA results of cucumber plants inoculated with the CGMMV clone and wild-type CGMMV isolate after 2 weeks inoculation.

| | Optical Density at 405 nm | | | | |
| --- | --- | --- | --- | --- | --- |
| Treatment | Plant 1 | Plant 2 | Plant 3 | Plant 4 | Plant 5 |
| CGMMV Clone | 1.419 | 1.401 | 1.348 | 1.463 | 1.378 |
| Wild-type CGMMV isolate | 1.609 | 1.734 | 1.169 | 1.457 | 1.357 |
| Negative | −0.01 | 0.003 | −0.002 | 0.002 | −0.001 |

Figure 1B:
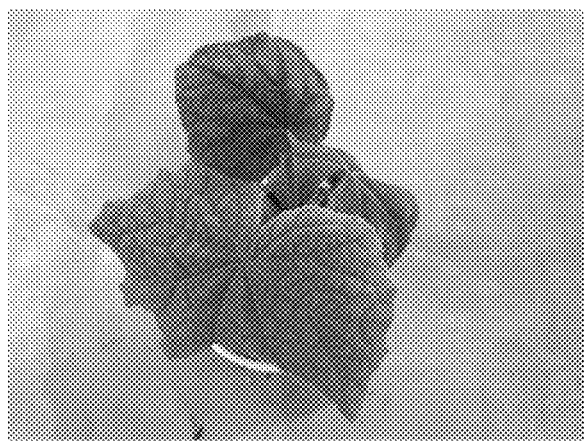
FIG. 1B is a photograph showing leaves of a cucumber plant grown for two weeks after inoculation with a wild-type CGMMV Ontario strain isolate.
Figure 1C:
FIG. 1C is a photograph showing leaves of a cucumber plant grown for two weeks in the absence of CGMMV (negative control)

In addition, as seen in FIGS. 1A to C, the CGMMV Ontario strain clone expressed in *Agrobacterium tumefaciens* produced similar symptoms in infected leaves (FIG. 1A) as those produced by infection with the wild-type CGMMV Ontario strain isolate (FIG. 1B). FIG. 1C shows uninfected leaves as a negative control.

Example 2: Attenuated CGMMV Strains

Mutant CGMMV Ontario strain ONB

Directed mutation of the cDNA genome of the cloned CGMMV Ontario strain (Example 1) was carried out to introduce mutations (c.1498A>G; c.3430C>T; c.3528A>G; c.4248C>T; and c.6228C>T) corresponding to those observed in the attenuated SH33b strain of CGMMV (Tan et al, *Ann. Phytopathol. Soc. Jpn* (1997), 63(6): 470-474). These mutations resulted in amino acid substitutions in the encoded viral proteins (E480G and A1124V in the 129 kDa protein; E480G, A1124V, N1157D, and P1397S in the 186 kDa protein; and A156V in the coat protein).

Mutations were introduced using the QuikChange™ Lightning Multi Site-Directed Mutagenesis kit (Agilent Technologies), following the manufacturer's instructions, and using the mutagenic primers listed in Table 3. Nucleotide residues indicated in bold indicate sites of mutation. The resulting mutant CGMMV strain was designated Ontario strain ONB.

TABLE 3

Primers used to produce mutant CGMMV Ontario strain ONB

| Primer sequence (5' to 3') | Sequence Identifier |
| --- | --- |
| TCTTAAATCCGCCGTAGGAGGACTAGGTGATTGCG | SEQ ID NO: 19 |
| CGCAATCACCTAGTCCTCCTACGGCGGATTTAAGA | SEQ ID NO: 20 |
| TCGATGCAGTTACAAGTATAATAGTGGATGTGGAAAAGGTCG | SEQ ID NO: 21 |
| CGACCTTTTCCACATCCACTATTATACTTGTAACTGCATCGA | SEQ ID NO: 22 |
| CTCACTGTATGTCCATCGTGATATTTTCCTCCCTGTTAG | SEQ ID NO: 23 |
| CTAACAGGGAGGAAAATATCACGATGGACATACAGTGAG | SEQ ID NO: 24 |
| TCTAAGTTTTCTTTTACACTAGGAAAAAATCAGAAGATCTGCAGGA | SEQ ID NO: 25 |
| TCCTGCAGATCTTCTGATTTTTTCCTAGTGTAAAAGAAAAACTTAGA | SEQ ID NO: 26 |
| GTAGTCTGGTCAGAGGTTACCACCTCGAAAGCT | SEQ ID NO: 27 |
| AGCTTTCGAGGTGGTAACCTCTGACCAGACTAC | SEQ ID NO: 28 |

The cDNA genome sequence of CGMMV strain ONB is shown below.

(SEQ ID NO: 29)
GTTTTAATTTTTAAAATTAAACAAACAACAACAACAACAAACAATTT

AAAACAACAATGGCAAACATTAATGAACAAATCAACAACCAACGCGACGC

CGCGGCCAGCGGGAGAAACAATCTCGTTAGCCAATTGGCGTCAAAAAGGG

TGTATGACGAGGCTGTTCGCTCGTTGGATCATCAAGACAGACGCCCAAAA

ATGAACTTTTCTCGTGTGGTCAGCACAGAGCACACCAGGCTTGTAACTGA

TGCGTATCCGGAGTTTTCGATTAGCTTTACCGCCACCAAGAACTCTGTAC

ACTCCCTTGCGGGTGGTCTGAGGCTCCTTGAACTGGAATATATGATGATG

CAAGTGCCCTACGGCTCACCTTGTTATGATATCGGCGGTAACTATACGCA

GCACTTGTTCAAAGGTAGATCATATGTGCATTGCTGCAATCCGTGCCTGG

ATCTTAAAGATGTTGCGAGGAACGTGATGTATAACGATATGGTCACACAA

CATGTACAGAGGCACAAGGGATCTGGCGGGTGCAGACCTCTTCCAACTTT

TCAGATAGATGCATTCAGGAGGTACGATAATTCTCCCTGTGCGGTCACCT

GTTCAGACGTTTTCCAAGAGTGTTCCTATGATTTTGGGAGCGGTAGGGAT

AATCATGCAGTCTCGCTGCATTCAATCTACGATATCCCTTATTCTTCGAT

CGGACCTGCTCTTCATAGGAAGAACGTGCGAGTTTGTTATGCAGCCTTTC

ACTTCTCGGAGGCATTGCTTTTAGGTTCACCTGTAGGTAATTTAAATAGT

ATTGGGGCTCAGTTTAGGGTCGATGGTGATGATGTGCATTTTCTTTTTAG

TGAAGAGTCTACTTTGCATTATACTCATAGTTTAGAAAATATCAAATTAA

TTGTGATGCGTACTTATTTTCCTGCTGATGATAGGTACGTGTATATTAAG

GAGTTTATGGTCAAGCGTGTGGATACATTCTTCTTTAGGTTGGTCAGAGC

```
AGACACACATATGCTTCATAAATCTGTGGGGCACTATTCAAAATCGAAAT
CTGAGTACTTTGCGCTAATACCCCTCCGATCTTCCAAGACAAAGCCACG
TTTTCTGTGTGGTTTCCTGAGGCGAAGCGTAAGGTGTTGATACCCAAGTT
TGAACTTTCAAGATTCCTTTCTGGGAATGTGAAAATCTCTAGGATGCTTG
TCGATGCTGATTTCGTCCATACCATTATTAATCACATTAGCACGTATGAT
AATAAGGCCTTAGTGTGGAAGAATGTTCAGTCCTTTGTGGAATCTATACG
CTCAAGAGTAATTGTAAACGGAGTTTCGGTGAAATCTGAATGGAACGTAC
CGGTTGATCAGCTCACTGATATCTCGTTCTCGATATTCCTTCTCGTGAAG
GTTAGGAAGGTACAGATCGAGTTAATGTCTGATAAAGTTGTAATCGAGGC
GAGGGGCTTGCTCCGGAGGTTCGCAGACAGTCTTAAATCCGCCGTAGGAG
GACTAGGTGATTGCGTCTATGATGCTCTAGTTCAAACCGGCTGGTTTGAT
ACCTCTAGCGACAACTGAAAGTTTTGCTACCTGAACCGTTTATGACCTT
TTCGGATTATCTTGAAGGGATGTACGAGGCAGATGCAAAGATCGAGAGAG
AGAGTGTCTCTGAGTTGCTCGCTTCCGGTGACGATTTGTTCAAGAAAATC
GATGAGATAAGAAACAATTACAGTGGAGTCGAATTTGATGTAGAGAAATT
CCAGGAATTTTGCAAGGAACTGAATGTTAATCCTATGCTAATTGGCCATG
TTATCGAAGCTATTTTTTCGCAGAAAGCTGGGGTGACAGTAACGGGTCTG
GGTACCCTCTCCTGAGATGGGTGCTTCTGTTGCGTTATCCAATACCTC
TGTAGATACATGTGAAGATATGGATGTAACTGAAGATATGGAGGATATAG
TGTTGATGGCGGACAAGAGTCATTCTTACATGTCCCCAGAAATGGCGAGA
TGGGCTGATGTAAAATACGACAACAATAAAGGGGCCTGGTCGAATACAA
AGTCGGAACCTCGATGACTTTACCTGCCACCTGGGCAGAGAAGGGTAAGG
CTGTCTTACCGTTGTCGGGATCTGTGTGAGGAAACCCCAATTTTCGAAG
CCGCTTGATGAGGAAGACGACTTGAGGTTATCAAACATGAATTTCTTTAA
GGTGAGCGATCTGAAGTTGAAGAAAACTATCACTCCAGTTGTTTACACTG
GGACCATTCGAGAGAGGCAAATGAAGAATTATATTGATTACTTATCGGCC
TCTCTTGGTTCTACGCTGGGTAATCTGGAGAGAATTGTGCGGAGTGATTG
GAACGGTACCGAGGAGAGTATGCAAACGTTCGGGTTGTATGACTGCGAAA
AGTGCAAGTGGTTACTGTTACCAGCCGAAAAGAAGCACGCATGGGCTGTG
GTTCTGGCAAGTGATGATACCACTCGCATAATCTTCCTCTCATATGACGA
ATCTGGTTCTCCCATAATTGATAAGAGAAACTGGAAGCGATTTGCTGTTT
GCTCTGAGACCAAAGTCTATAGCGTAATTCGTAGTTTAGAGGTACTAAAT
AAGGAAGCAATAGTCGACCCCGGGGTTCATATAACATTAGTTGACGGAGT
GCCGGGTTGTGGAAAGACCGCCGAAATTATAGCGAGGGTCAATTGGAAAA
CCGATCTAGTATTGACTCCCGGGAGGGAGGCGGCTGCTATGATTAGGCGG
AGGGCCTGCGCCCTGCACAAGTCACCTGTGGCAACCAGTGACAACGTTAG
AACTTTCGATTCTTTTGTGATGAATAAGAAAATCTTCAAGTTTGACGCTG
TCTATGTTGACGAGGGTCTGATGGTCCATACGGGTTTACTTAATTTTGCG
TTGAAGATCTCAGGTTGTAAAAAGGCCTTCGTCTTTGGTGATGCTAAGCA
AATCCCGTTTATAAACAGAGTCATGAATTTTGATTATCCTAAGGAGTTAA
GAACTTTAATAGTCGATAATGTAGAGCGTAGGTATGTTACCCATAGGTGT
CCTAGAGATGTCACTAGTTTTCTTAATACTATTTACAAAGCCGCTGTCGC
TACTACTAGTCCGGTTGTACATTCTGTGAAGGCGATTAAAGTGTCAGGGG
CCGGTATTCTGAGGCCCGAGTTGACGAAGATCAAAGGAAAGATAATAACG
TTTACTCAATCTGATAAGCAGTCCTTGATCAAGAGTGGGTACAATGACGT
GAACACTGTGCATGAAATTCAGGGAGAAACCTTTGAAGAGACGGCGGTTG
TGCGTGCCACCCCGACTCCGATAGGTTTAATTGCCCGTGATTCACCACAT
GTACTAGTGGCCTTAACGAGGCACACTAAGGCAATGGTGTATTATACTGT
TGTGTTCGATGCAGTTACAAGTATAATAGTGGATGTGGAAAAGGTCGACC
AGTCGATCTTGACTATGTTTGCTACCACTGTGCCTACCAAATAGCAATTA
ATGCAGAACTCACTGTATGTCCATCGTGATATTTTCCTCCCTGTTAGTAA
AACGGGGTTTTATACAGACATGCAGGAGTTCTATGATAGATGCCTTCCTG
GGAATTCCTTCGTGCTGAATGATTTCGATGCCGTAACCATGCGGTTGAGG
GACAACGAATTTAACCTACAACCTTGTAGGCTAACCTTAAGTAATTTAGA
TCCAGTACCCGCTTTGGTTAAGAGTGAAGCGCAGAATTTCTGATTCCCG
TTTTGCGTACGGCCTGTGAAAGGCCGCGCATTCCAGGTCTCCTTGAAAAT
CTTGTAGCTATGATAAAGAGGAATATGAATACTCCTGATCTAGCTGGGAC
TGTGGATATAACTAATATGTCGATTTCTATAGTAGATAACTTCTTTTCTT
CTTTTGTTAGAGACGAGGTTTTGCTTGATCATTTAGATTGTGTTAGGGCT
AGTTCCATTCAAAGTTTTTCTGATTGGTTTTCGTGTCAGCCAACCTCGGC
GGTTGGTCAATTAGCTAATTTCAATTTCATAGATTTGCCTGCCTTTGATA
CTTATATGCACATGATTAAGCGGCAGCCCAAGAGTCGGTTGGATACTTCG
ATTCAGTCTGAATATCCGGCCTTGCAAACTATTGTTTATCACCCTAAAGT
GGTAAATGCAGTTTTCGGTCCGGTTTTTAAGTATTTGACCACCAAGTTTC
TTAGCATGGTAGATAGTTCTAAGTTTTTCTTTTACACTAGGAAAAAATCA
GAAGATCTGCAGGAATTTTTCTCAGATCTCTCTTCCCATTCTGATTATGA
GATTCTTGAGCTGGATGTTTCTAAATATGACAAGTCACAATCCGATTTCC
ATTTCTCTATTGAGATGGCAATTTGGGAAAAATTGGGCTGGACGATATT
TTGGCTTGGATGTGGTCTATGGGTCACAAGAGAACTATACTGCAAGATTT
CCAAGCCGGGATAAAGACGCTCATTTACTATCAACGGAAGTCTGGTGATG
TAACTACTTTCATAGGTAATACCTTTATTATCGCAGCGTGTGTAGCTAGT
ATGTTGCCGTTAGACAAGTGTTTTAAAGCTAGTTTTTGTGGTGATGATTC
GCTGATCTACCTTCCTAAGGGTTTGGAGTATCCTGATATACAGGCTACTG
CCAACTTGGTTTGGAATTTTGAGGCGAAACTTTTCCGAAAGAAGTATGGT
TACTTCTGTGGGAAGTATATAATTCACCATGCCAACGGCTGTATTGTTTA
CCCTGACCCTTTAAAATTAATTAGTAAATTAGGTAATAAGAGTCTTGTAG
GGTATGAGCATGTTGAGGAGTTTCGTATATCTCCTCGACGTCGCTCAT
AGTTTGTTTAATGGTGCTTATTTCCATTTACTCGACGATGCAATCCACGA
ATTATTTCCTAACGCTGGGGGTTGCAGTTTTGTAATTAATTGTTTGTGCA
AGTATTTGAGTGATAAGCGCCTTTTCCGTAGTCTTTATATAGATGTCTCT
AAGTAAGGTGTCGGTCGAGAACTCATTGAAACCCGAGAAGTTTGTTAAAA
```

```
TCTCTTGGGTCGATAAGTTGCTCCCTAACTATTTTTCCATTCTTAAGTAT

TTATCTATAACTGACTTTAGCGTAGTTAAAGCTCAGAGCTATGAATCCCT

CGTGCCTGTCAAGTTGTTGCGTGGTGTTGATCTTACAAAACACCTTTATG

TCACATTGTTGGGCGTTGTGGTTTCTGGTGTATGGAACGTACCGGAATCC

TGTAGGGGTGGTGCTACTGTTGCTCTGGTTGACACAAGGATGCATTCTGT

TGCAGAGGGAACTATATGCAAATTTTCAGCTCCCGCCACCGTCCGCGAAT

TCTCTGTTAGGTTCATACCTAACTATTCTGTCGTGGCTGCGGATGCCCTT

CGCGATCCTTGGTCTTTATTTGTGAGACTCTCTAATGTAGGGATTAAAGA

TGGTITCCATCCITTGACCTTAGAGGTCGCTTGTTTAGTCGCTACAACTA

ACTCTATTATCAAAAGGGTCTTAGAGCTTCTGTAGTCGAGTCTGTCGTC

TCTTCCGATCAGTCCATTGTCCTAGATTCTTTATCCGAGAAAGTTGAACC

TTTCTTTGATAAAGTTCCTATTTCGGCGGCTGTGATGGCAAGAGACCCCA

GTTATAGGTCTAGGTCGCAGTCTGTCGGTGGTCGTGGTAAGCGGCATTCT

AAACCTCCAAATCGGAGGTTGGACTCTGCTTCTGAAGAGTCCAGTICTGT

TTCTTTCGAAGATGGCTTACAATCCGATCACACCTAGCAAACTTATTGCG

TTTAGTGCTTCTTATGTTCCCGTCAGGACTTTACTTAATTTTCTAGTTGC

TTCACAAGGTACCGCCTTCCAGACTCAAGCGGGAAGAGATTCTTTCCGCG

AGTCCCTGTCTGCGTTACCCTCGTCTGTCGTAGATATTAATTCTAGGTTC

CCAAATGCGGGTTTTTACGCTTTCCTCAACGGTCCTGTGTTGAGGCCTAT

CTTCGTTTCGCTTCTTAGCTCTACGGATACGCGTAATAGGGTCATTGAGG

TTGTAGATCCTAGCAATCCTACGACTGCTGAGTCGCTTAACGCTGTAAAG

CGTACTGATGACGCATCTACGCCGCTAGGGCTGAAATAGATAATTTAAT

AGAGTCTATTTCTAAGGGTTTTGATGTTTATGATAGGGCTTCATTTGAAG

CCGCGTTTTCGGTAGTCTGGTCAGAGGTTACCACCTCGAAAGCTTAGCTT

CGAGGGTCTTCTGATGGTGGTGCACACCAAAGTGCATAGTGCTTTCCCGT

TCACTTAAATCGAACGGTTTGCTCATTGGTTTGCGGAAACCTCTCACGTG

TGGCGTTGAAGTTTCTATGGGCAGTAATTCTGCAAGGGGTTCGAATCCCC

CCTTTCCCCGGGTAGGGCCCA.
```

The 129 kDa protein encoded by CGMMV strain ONB has the following sequence.

```
                                      (SEQ ID NO: 30)
MANINEQINNQRDAAASGRNNLVSQLASKRVYDEAVRSLDHQDRRPKMNF

SRVVSTEHTRLVTDAYPEFSISFTATKNSVHSLAGGLRLLELEYMMMQVP

YGSPCYDIGGNYTQHLFKGRSYVHCCNPCLDLKDVARNVMYNDMVTQHVQ

RHKGSGGCRPLPTFQIDAFRRYDNSPCAVTCSDVFQECSYDFGSGRDNHA

VSLHSIYDIPYSSIGPALHRKNVRVCYAAFHFSEALLLGSPVGNLNSIGA

QFRVDGDDVHFLFSEESTLHYTHSLENIKLIVMRTYFPADDRYVYIKEFM

VKRVDTFFFRLVRADTHMLHKSVGHYSKSKSEYFALNTPPIFQDKATFSV

WFPEAKRKVLIPKFELSRFLSGNVKISRMLVDADFVHTIINHISTYDNKA

LVWKNVQSFVESIRSRVIVNGVSVKSEWNVPVDQLTDISFSIFLLVKVRK

VQIELMSDKVVIEARGLLRREADSLKSAVGGLGDCVYDALVQTGWFDTSS

DELKVLLPEPFMTFSDYLEGMYEADAKIERESVSELLASGDDLEKKIDEI

RNNYSGVEFDVEKFQEFCKELNVNPMLIGHVIEAIFSQKAGVTVTGLGTL

SPEMGASVALSNTSVDTCEDMDVTEDMEDIVLMADKSHSYMSPEMARWAD

VKYDNNKGGLVEYKVGTSMTLPATWAEKGKAVLPLSGICVRKPQFSKPLD

EEDDLRLSNMNFFKVSDLKLKICTITPVVYTGTIRERQMKNYIDYLSASL

GSTLGNLERIVRSDWNGTEESMQTEGLYDCEKCKWLLLPAEKKHAWAVVL

ASDDTTRIIELSYDESGSPIIDKRNWKRFAVCSETKVYSVIRSLEVLNKE

AIVDPGVHITLVDGVPGCGKTAEIIARVNWKTDLVLTPGREAAAMIRRRA

CALHKSPVATSDNVRTEDSFVMNKKIFKFDAVYVDEGLMVHTGLLNFALK

ISGCKKAFVFGDAKQIPFINRVMNFDYPKELRTLIVDNVERRYVTHRCPR

DVTSFLNTIYKAAVATTSPVVHSVKAIKVSGAGILRPELTKIKGKIITFT

QSDKQSLIKSGYNDVNTVHEIQGETFEETAVVRATPTPIGLIARDSPHVL

VALTRHTKAMVYYTVVFDAVTSIIVDVEKVDQSILTMFATTVPTK.
```

The 186 kDa protein encoded by CGMMV strain ONB has the following sequence.

```
                                      (SEQ ID NO: 31)
MANINEQINNQRDAAASGRNNLVSQLASKRVYDEAVRSLDHQDRRPKMNF

SRVVSTEHTRINTDAYPEFSISFTATKNSVHSLAGGLRLLELEYMMMQVP

YGSPCYDIGGNYTQHLFKGRSYVHCCNPCLDLKDVARNVMYNDMVTQHVQ

RHKGSGGCRPLPTFQIDAFRRYDNSPCAVTCSDVFQECSYDFGSGRDNHA

VSLHSIYDIPYSSIGPALHRKNVRVCYAAFHFSEALLLGSPVGNLNSIGA

QFRVDGDDVHFLFSEESTLHYTHSLENIKLIVMRTYFPADDRYVYIKEFM

VKRVDTFFFRLVRADTHMLHKSVGHYSKSKSEYFALNTPPIFQDKATFSV

WFPEAKRKVLIPKFELSRFLSGNVKISRMLVDADFVHTIINHISTYDNKA

LVWKNVQSFVESIRSRVIVNGVSVKSEWNVPVDQLTDISFSIFLLVKVRK

VQIELMSDKVVIEARGLLRRFADSLKSAVGGLGDCVYDALVQTGWFDTSS

DELKVLLPEPFMTFSDYLEGMYEADAKIERESVSELLASGDDLFKKIDEI

RNNYSGVEFDVEKFQEFCKELNVNPMLIGHVIEAIFSQKAGVTVTGLGTL

SPEMGASVALSNTSVDTCEDMDVTEDMEDIVLMADKSHSYMSPEMARWAD

VKYDNNKGGLVEYKVGTSMTLPATWAEKGKAVLPLSGICVRKPQFSKPLD

EEDDLRLSNMNFFKVSDLKLKKTITPVVYTGTIRERQMKNYIDYLSASLG

STLGNLERIVRSDWNGTEESMQTFGLYDCEKCKWLLLPAEKKHAWAVVLA

SDDTTRIIFLSYDESGSPIIDKRNWKRFAVCSETKVYSVIRSLEVLNKEA

IVDPGVHITLVDGVPGCGKTAEIIARVNWKTDLVLTPGREAAAMIRRRAC

ALHKSPVATSDNVRTFDSFVMNKKIFKFDAVYVDEGLMVHTGLLNFALKI

SGCKKAFVFGDAKQIPFINRVMNFDYPKELRTLIVDNVERRYVTHRCPRD

VTSFLNTIYKAAVATTSPVVHSVKAIKVSGAGILRPELTKIKGKIITFTQ

SDKQSLIKSGYNDVNTVHEIQGETFEETAVVRATPTPIGLIARDSPHVLV

ALTRHTKAMVYYTVVFDAVTSIIVDVEKVDQSILTMFATTVPTIOCQLMQ

NSLYVHRDIFLPVSKTGFYTDMQEFYDRCLPGNSFVLNDFDAVTMRLRDN
```

-continued

EFNLQPCRLTLSNLDPVPALVKSEAQNFLIPVLRTACERPRIPGLLENLV

AMIKRNYINTPDLAGTVDITNMSISIVDNFFSSFVRDEVLLDHLDCVRAS

SIQSFSDWFSCQPTSAVGQLANFNFIDLPAFDTYMHMIKRQPKSRLDTSI

QSEYPALQTIVYHPKVVNAVFGPVFKYLTTKFLSMVDSSKFFFYTRKKSE

DLQEFFSDLSSHSDYEILELDVSKYDKSQSDFHFSIEMAIWEKLGLDDIL

AWMWSMGHKRTILQDFQAGIKTLIYYQRKSGDVTTFIGNTFIIAACVASM

LPLDKCFKASFCGDDSLIYLPKGLEYPDIQATANLVWNFEAKLFRKKYGY

FCGKYIIHHANGCIVYPDPLKLISKLGNKSLVGYEHVEEFRISLLDVAHS

LFNGAYFHLLDDAIHELFPNAGGCSFVINCLCKYLSDKRLFRSLYID

VSK.

The coat protein encoded by CGMMV strain ONB has the following sequence.

(SEQ ID NO: 32)
MAYNPITPSKLIAFSASYVPVRTLLNFLVASQGTAFQTQAGRDSFRESLS

ALPSSVVDINSRFPNAGFYAFLNGPVLRPIFVSLLSSTDTRNRVIEVVDP

SNPTTAESLNAVKRTDDASTAARAEIDNLIESISKGFDVYDRASFEAAFS

VVWSEVTTSKA.

Mutant CGMMV Ontario Strain ONM

Directed mutation of the cDNA genome of the cloned CGMMV Ontario strain (Example 1) was carried out as described above, but using the mutagenic primers listed in Table 4, to introduce mutations (c.315G>A; c.1660C>T; and c.4144C>T) corresponding to those observed in the attenuated VIROG-43M strain (Slavokhotova, A. A., et al, *American Journal of Plant Sciences* (2016), 7: 724-732). Nucleotide residues indicated in bold indicate sites of mutation. These mutations resulted in amino acid substitutions in the encoded viral proteins (G86S and S534F in the 129 kDa protein; and G86S, S534F and P1362L in the 186 kDa protein). The resulting mutant CGMMV strain was designated Ontario strain ONM.

TABLE 4

Primers used to produce mutant CGMMV Ontario strain ONM

| Primer Sequence (5' to 3') | Sequence Identifier |
| --- | --- |
| CTCCCTTGCGGGTAGTCTGAGGCTCCT | SEQ ID NO: 33 |
| AGGAGCCTCAGACTACCCGCAAGGGAG | SEQ ID NO: 34 |
| AAAGATCGAGAGAGAGAGTGTCTTTGA GTTGCTCGC | SEQ ID NO: 35 |
| GCGAGCAACTCAAAGACACTCTCTCTC TCGATCTTT | SEQ ID NO: 36 |
| CTTGCAAACTATTGTTTATCACCTTAA AGTGGTAAATGCAGTTTTCG | SEQ ID NO: 37 |
| CGAAAACTGCATTTACCACTTTAAGGT GATAAACAATAGTTTGCAAG | SEQ ID NO: 38 |

The cDNA genome sequence of CGMMV strain ONM is shown below.

(SEQ ID NO: 39)
GTTTTAATTTTTAAAATTAAACAAACAACAACAACAACAAACAATTT

AAAACAACAATGGCAAACATTAATGAACAAATCAACAACCAACGCGACGC

CGCGGCCAGCGGGAGAAACAATCTCGTTAGCCAATTGGCGTCAAAAAGGG

TGTATGACGAGGCTGTTCGCTCGTTGGATCATCAAGACAGACGCCCAAAA

ATGAACTTTTCTCGTGTGGTCAGCACAGAGCACACCAGGCTTGTAACTGA

TGCGTATCCGGAGTTTTCGATTAGCTTTACCGCCACCAAGAACTCTGTAC

ACTCCCTTGCGGGTAGTCTGAGGCTCCTTGAACTGGAATATATGATGATG

CAAGTGCCCTACGGCTCACCTTGTTATGATATCGGCGGTAACTATACGCA

GCACTTGTTCAAAGGTAGATCATATGTGCATTGCTGCAATCCGTGCCTGG

ATCTTAAAGATGTTGCGAGGAACGTGATGTATAACGATATGGTCACACAA

CATGTACAGAGGCACAAGGGATCTGGCGGGTGCAGACCTCTTCCAACTTT

TCAGATAGATGCATTCAGGAGGTACGATAATTCTCCCTGTGCGGTCACCT

GTTCAGACGTTTTCCAAGAGTGTTCCTATGATTTTGGGAGCGGTAGGGAT

AATCATGCAGTCTCGCTGCATTCAATCTACGATATCCCTTATTCTTCGAT

CGGACCTGCTCTTCATAGGAAGAACGTGCGAGTTTGTTATGCAGCCTTTC

ACTTCTCGGAGGCATTGCTTTTAGGTTCACCTGTAGGTAATTTAAATAGT

ATTGGGGCTCAGTTTAGGGTCGATGGTGATGATGTGCATTTTCTTTTTAG

TGAAGAGTCTACTTTGCATTATACTCATAGTTTAGAAAATATCAAATTAA

TTGTGATGCGTACTTATTTTCCTGCTGATGATAGGTACGTGTATATTAAG

GAGTTTATGGTCAAGCGTGTGGATACTTTCTTCTTTAGGTTGGTCAGAGC

AGACACACATATGCTTCATAAATCTGTGGGGCACTATTCAAAATCGAAAT

CTGAGTACTTTGCGCTGAATACCCCTCCGATCTTCCAAGACAAAGCCACG

TTTTCTGTGTGGTTTCCTGAGGCGAAGCGTAAGGTGTTGATACCCAAGTT

TGAACTTTCAAGATTCCTTTCTGGGAATGTGAAAATCTCTAGGATGCTTG

TCGATGCTGATTTCGTCCATACCATTATTAATCACATTAGCACGTATGAT

AATAAGGCCTTAGTGTGGAAGAATGTTCAGTCCTTTGTGGAATCTATACG

CTCAAGAGTAATTGTAAACGGAGTTTCGGTGAAATCTGAATGGAACGTAC

CGGTTGATCAGCTCACTGATATCTCGTTCTCGATATTCCTTCTCGTGAAG

GTTAGGAAGGTACAGATCGAGTTAATGTCTGATAAAGTTGTAATCGAGGC

GAGGGGCTTGCTCCGGAGGTTCGCAGACAGTCTTAAATCCGCCGTAGAAG

GACTAGGTGATTGCGTCTATGATGCTCTAGTTCAAACCGGCTGGTTTGAT

ACCTCTAGCGACGAACTGAAAGTTTTGCTACCTGAACCGTTTATGACCTT

TTCGGATTATCTTGAAGGGATGTACGAGGCAGATGCAAAGATCGAGAGAG

AGAGTGTCTTTGAGTTGCTCGCTTCCGGTGACGATTTGTTCAAGAAAATC

GATGAGATAAGAAACAATTACAGTGGAGTCGAATTTGATGTAGAGAAATT

CCAGGAATTTTGCAAGGAACTGAATGTTAATCCTATGCTAATTGGCCATG

TTATCGAAGCTATTTTTTCGCAGAAAGCTGGGGTGACAGTAACGGGTCTG

GGTACCCTCTCTCCTGAGATGGGTGCTTCTGTTGCGTTATCCAATACCTC

TGTAGATACATGTGAAGATATGGATGTAACTGAAGATATGGAGGATATAG

TGTTGATGGCGGACAAGAGTCATTCTTACATGTCCCCAGAAATGGCGAGA

-continued

TGGGCTGATGTAAAATACGACAACAATAAAGGGGGCCTGGTCGAATACAA
AGTCGGAACCTCGATGACTTTACCTGCCACCTGGGCAGAGAAGGGTAAGG
CTGTCTTACCGTTGTCGGGGATCTGTGTGAGGAAACCCCAATTTTCGAAG
CCGCTTGATGAGGAAGACGACTTGAGGTTATCAAACATGAATTTCTTTAA
GGTGAGCGATCTGAAGTTGAAGAAAACTATCACTCCAGTTGTTTACACTG
GGACCATTCGAGAGAGGCAAATGAAGAATTATATTGATTACTTATCGGCC
TCTCTTGGTTCTACGCTGGGTAATCTGGAGAGAATTGTGCGGAGTGATTG
GAACGGTACCGAGGAGAGTATGCAAACGTTCGGGTTGTATGACTGCGAAA
AGTGCAAGTGGTTACTGTTACCAGCCGAAAAGAAGCACGCATGGGCTGTG
GTTCTGGCAAGTGATGATACCACTCGCATAATCTTCCTCTCATATGACGA
ATCTGGTTCTCCCATAATTGATAAGAGAAACTGGAAGCGATTTGCTGTTT
GCTCTGAGACCAAAGTCTATAGCGTAATTCGTAGTTTAGAGGTACTAAAT
AAGGAAGCAATAGTCGACCCCGGGGTTCATATAACATTAGTTGACGGAGT
GCCGGGTTGTGGAAAGACCGCCGAAATTATAGCGAGGGTCAATTGGAAAA
CCGATCTAGTATTGACTCCCGGGAGGGAGGCGGCTGCTATGATTAGGCGG
AGGGCCTGCGCCCTGCACAAGTCACCTGTGGCAACCAGTGACAACGTTAG
AACTTTCGATTCTTTTGTGATGAATAAGAAAATCTTCAAGTTTGACGCTG
TCTATGTTGACGAGGGTCTGATGGTCCATACGGGTTTACTTAATTTTGCG
TTGAAGATCTCAGGTTGTAAAAAGGCCTTCGTCTTTGGTGATGCTAAGCA
AATCCCGTTTATAAACAGAGTCATGAATTTTGATTATCCTAAGGAGTTAA
GAACTTTAATAGTCGATAATGTAGAGCGTAGGTATGTTACCCATAGGTGT
CCTAGAGATGTCACTAGTTTTCTTAATACTATTTACAAAGCCGCTGTCGC
TACTACTAGTCCGGTTGTACATTCTGTGAAGGCGATTAAAGTGTCAGGGG
CCGGTATTCTGAGGCCCGAGTTGACGAAGATCAAAGGAAAGATAATAACG
TTTACTCAATCTGATAAGCAGTCCTTGATCAAGAGTGGGTACAATGACGT
GAACACTGTGCATGAAATTCAGGGAGAAACCTTTGAAGAGACGGCGGTTG
TGCGTGCCACCCCGACTCCGATAGGTTTAATTGCCCGTGATTCACCACAT
GTACTAGTGGCCTTAACGAGGCACACTAAGGCAATGGTGTATTATACTGT
TGTGTTCGATGCAGTTACAAGTATAATAGCGGATGTGGAAAAGGTCGACC
AGTCGATCTTGACTATGTTTGCTACCACTGTGCCTACCAAATAGCAATTA
ATGCAGAACTCACTGTATGTCCATCGTAATATTTTCCTCCCTGTTAGTAA
AACGGGGTTTTATACAGACATGCAGGAGTTCTATGATAGATGCCTTCCTG
GGAATTCCTTCGTGCTGAATGATTTCGATGCCGTAACCATGCGGTTGAGG
GACAACGAATTTAACCTACAACCTTGTAGGCTAACCTTAAGTAATTTAGA
TCCAGTACCCGCTTTGGTTAAGAGTGAAGCGCAGAATTTTCTGATTCCCG
TTTTGCGTACGGCCTGTGAAAGGCCGCGCATTCCAGGTCTCCTTGAAAAT
CTTGTAGCTATGATAAAGAGGAATATGAATACTCCTGATCTAGCTGGGAC
TGTGGATATAACTAATATGTCGATTTCTATAGTAGATAACTTCTTTTCTT
CTTTTGTTAGAGACGAGGTTTTGCTTGATCATTTAGATTGTGTTAGGGCT
AGTTCCATTCAAAGTTTTTCTGATTGGTTTTCGTGTCAGCCAACCTCGGC
GGTTGGTCAATTAGCTAATTTCAATTTCATAGATTTGCCTGCCTTTGATA

-continued

CTTATATGCACATGATTAAGCGGCAGCCCAAGAGTCGGTTGGATACTTCG
ATTCAGTCTGAATATCCGGCCTTGCAAACTATTGTTTATCACCTTAAAGT
GGTAAATGCAGTTTTCGGTCCGGTTTTTAAGTATTTGACCACCAAGTTTC
TTAGCATGGTAGATAGTTCTAAGTTTTTCTTTTACACTAGGAAAAAACCA
GAAGATCTGCAGGAATTTTTCTCAGATCTCTCTTCCCATTCTGATTATGA
GATTCTTGAGCTGGATGTTTCTAAATATGACAAGTCACAATCCGATTTCC
ATTTCTCTATTGAGATGGCAATTTGGGAAAAATTGGGGCTGGACGATATT
TTGGCTTGGATGTGGTCTATGGGTCACAAGAGAACTATACTGCAAGATTT
CCAAGCCGGGATAAAGACGCTCATTTACTATCAACGGAAGTCTGGTGATG
TAACTACTTTCATAGGTAATACCTTTATTATCGCAGCGTGTGTAGCTAGT
ATGTTGCCGTTAGACAAGTGTTTTAAAGCTAGTTTTTGTGGTGATGATTC
GCTGATCTACCTTCCTAAGGGTTTGGAGTATCCTGATATACAGGCTACTG
CCAACTTGGTTTGGAATTTTGAGGCGAAACTTTTCCGAAAGAAGTATGGT
TACTTCTGTGGGAAGTATATAATTCACCATGCCAACGGCTGTATTGTTTA
CCCTGACCCTTTAAAATTAATTAGTAAATTAGGTAATAAGAGTCTTGTAG
GGTATGAGCATGTTGAGGAGTTTCGTATATCTCTCCTCGACGTCGCTCAT
AGTTTGTTTAATGGTGCTTATTTCCATTTACTCGACGATGCAATCCACGA
ATTATTTCCTAACGCTGGGGGTTGCAGTTTTGTAATTAATTGTTTGTGCA
AGTATTTGAGTGATAAGCGCCTTTTCCGTAGTCTTTATATAGATGTCTCT
AAGTAAGGTGTCGGTCGAGAACTCATTGAAACCCGAGAAGTTTGTTAAAA
TCTCTTGGGTCGATAAGTTGCTCCCTAACTATTTTTCCATTCTTAAGTAT
TTATCTATAACTGACTTTAGCGTAGTTAAAGCTCAGAGCTATGAATCCCT
CGTGCCTGTCAAGTTGTTGCGTGGTGTTGATCTTACAAAACACCTTTATG
TCACATTGTTGGGCGTTGTGGTTTCTGGTGTATGGAACGTACCGGAATCC
TGTAGGGGTGGTGCTACTGTTGCTCTGGTTGACACAAGGATGCATTCTGT
TGCAGAGGGAACTATATGCAAATTTTCAGCTCCCGCCACCGTCCGCGAAT
TCTCTGTTAGGTTCATACCTAACTATTCTGTCGTGGCTGCGGATGCCCTT
CGCGATCCTTGGTCTTTATTTGTGAGACTCTCTAATGTAGGGATTAAAGA
TGGTTTCCATCCTTTGACCTTAGAGGTCGCTTGTTTAGTCGCTACAACTA
ACTCTATTATCAAAAAGGGTCTTAGAGCTTCTGTAGTCGAGTCTGTCGTC
TCTTCCGATCAGTCCATTGTCCTAGATTCTTTATCCGAGAAAGTTGAACC
TTTCTTTGATAAAGTTCCTATTTCGGCGGCTGTGATGGCAAGAGACCCCA
GTTATAGGTCTAGGTCGCAGTCTGTCGGTGGTCGTGGTAAGCGGCATTCT
AAACCTCCAAATCGGAGGTTGGACTCTGCTTCTGAAGAGTCCAGTTCTGT
TTCTTTCGAAGATGGCTTACAATCCGATCACACCTAGCAAACTTATTGCG
TTTAGTGCTTCTTATGTTCCCGTCAGGACTTTACTTAATTTTCTAGTTGC
TTCACAAGGTACCGCCTTCCAGACTCAAGCGGGAAGAGATTCTTTCCGCG
AGTCCCTGTCTGCGTTACCCTCGTCTGTCGTAGATATTAATTCTAGGTTC
CCAAATGCGGGTTTTTACGCTTTCCTCAACGGTCCTGTGTTGAGGCCTAT
CTTCGTTTCGCTTCTTAGCTCTACGGATACGCGTAATAGGGTCATTGAGG

```
TTGTAGATCCTAGCAATCCTACGACTGCTGAGTCGCTTAACGCTGTAAAG

CGTACTGATGACGCATCTACGGCCGCTAGGGCTGAAATAGATAATTTAAT

AGAGTCTATTTCTAAGGGTTTTGATGTTTATGATAGGGCTTCATTTGAAG

CCGCGTTTTCGGTAGTCTGGTCAGAGGCTACCACCTCGAAAGCTTAGCTT

CGAGGGTCTTCTGATGGTGGTGCACACCAAAGTGCATAGTGCTTTCCCGT

TCACTTAAATCGAACGGTTTGCTCATTGGTTTGCGGAAACCTCTCACGTG

TGGCGTTGAAGTTTCTATGGGCAGTAATTCTGCAAGGGGTTCGAATCCCC

CCTTTCCCCGGGTAGGGCCCA.
```

The 129 kDa protein encoded by CGMMV strain ONM has the following sequence.

```
                                             (SEQ ID NO: 40)
MANINEQINNQRDAAASGRNNLVSQLASKRVYDEAVRSLDHQDRRPKMNF

SRVVSTEHTRLVTDAYPEFSISFTATKNSVHSLAGSLRLLELEYMMMQVP

YGSPCYDIGGNYTQHLFKGRSYVHCCNPCLDLKDVARNVMYNDMVTQHVQ

RHKGSGGCRPLPTFQIDAFRRYDNSPCAVTCSDVFQECSYDFGSGRDNHA

VSLHSIYDIPYSSIGPALHRKNVRVCYAAFHFSEALLLGSPVGNLNSIGA

QFRVDGDDVHFLFSEESTLHYTHSLENIKLIVMRTYFPADDRYVYIKEFM

VKRVDTFFFRLVRADTHMLHKSVGHYSKSKSEYFALNTPPIFQDKATFSV

WFPEAKRKVLIPKFELSRFLSGNVKISRMLVDADFVHTIINHISTYDNKA

LVWKNVQSFVESIRSRVIVNGVSVKSEWNVPVDQLTDISFSIFLLVKVRK

VQIELMSDKVVIEARGLLRRFADSLKSAVEGLGDCVYDALVQTGWFDTSS

DELKVLLPEPFMTFSDYLEGMYEADAKIERESVFELLASGDDLFKKIDEI

RNNYSGVEFDVEKFQEFCKELNVNPMLIGHVIEAIFSQKAGVTVTGLGTL

SPEMGASVALSNTSVDTCEDMDVTEDMEDIVLMADKSHSYMSPEMARWAD

VKYDNNKGGLVEYKVGTSMTLPATWAEKGKAVLPLSGICVRKPQFSKPLD

EEDDLRLSNMNFFKVSDLKLKKTITPVVYTGTIRERQMKNYIDYLSASLG

STLGNLERIVRSDWNGTEESMQTFGLYDCEKCKWLLLPAEKKHAWAVVLA

SDDTTRIIFLSYDESGSPIIDKRNWKRFAVCSETKVYSVIRSLEVLNKEA

IVDPGVHITLVDGVPGCGKTAEIIARVNWKTDLVLTPGREAAAMIRRRAC

ALHKSPVATSDNVRTFDSFVMNKKIFKFDAVYVDEGLMVHTGLLNFALKI

SGCKKAFVFGDAKQIPFINRVMNFDYPKELRTLIVDNVERRYVTHRCPRD

VTSFLNTIYKAAVATTSPVVHSVKAIKVSGAGILRPELTKIKGKIITFTQ

SDKQSLIKSGYNDVNTVHEIQGETFEETAVVRATPTPIGLIARDSPHVLV

ALTRHTKAMVYYTVVFDAVTSIIADVEKVDQSILTMFATTVPTK.
```

The 186 kDa protein encoded by CGMMV strain ONM has the following sequence.

```
                                             (SEQ ID NO : 41)
MANINEQINNQRDAAASGRNNLVSQLASKRVYDEAVRSLDHQDRRPKMNF

SRVVSTEHTRLVTDAYPEFSISFTATKNSVHSLAGSLRLLELEYMMMQVP

YGSPCYDIGGNYTQHLFKGRSYVHCCNPCLDLKDVARNVMYNDMVTQHVQ

RHKGSGGCRPLPTFQIDAFRRYDNSPCAVTCSDVFQECSYDFGSGRDNHA

VSLHSIYDIPYSSIGPALHRKNVRVCYAAFHFSEALLLGSPVGNLNSIGA

QFRVDGDDVHFLFSEESTLHYTHSLENIKLIVMRTYFPADDRYVYIKEFM

VKRVDTFFFRLVRADTHMLHKSVGHYSKSKSEYFALNTPPIFQDKATFSV

WFPEAKRKVLIPKFELSRFLSGNVKISRMLVDADFVHTIINHISTYDNKA

LVWKNVQSFVESIRSRVIVNGVSVKSEWNVPVDQLTDISFSIFLLVKVRK

VQIELMSDKVVIEARGLLRRFADSLKSAVEGLGDCVYDALVQTGWFDTSS

DELKVLLPEPFMTFSDYLEGMYEADAKIERESVFELLASGDDLFKKIDEI

RNNYSGVEFDVEKFQEFCKELNVNPMLIGHVIEAIFSQKAGVTVTGLGTL

SPEMGASVALSNTSVDTCEDMDVTEDMEDIVLMADKSHSYMSPEMARWAD

VKYDNNKGGLVEYKVGTSMTLPATWAEKGKAVLPLSGICVRKPQFSKPLD

EEDDLRLSNMNFFKVSDLKLKKTITPVVYTGTIRERQMKNYIDYLSASLG

STLGNLERIVRSDWNGTEESMQTFGLYDCEKCKWLLLPAEKKHAWAVVLA

SDDTTRIIFLSYDESGSPIIDKRNWKRFAVCSETKVYSVIRSLEVLNKEA

IVDPGVHITLVDGVPGCGKTAEIIARVNWKTDLVLTPGREAAAMIRRRAC

ALHKSPVATSDNVRTFDSFVMNKKIFKFDAVYVDEGLMVHTGLLNFALKI

SGCKKAFVFGDAKQIPFINRVMNFDYPKELRTLIVDNVERRYVTHRCPRD

VTSFLNTIYKAAVATTSPVVHSVKAIKVSGAGILRPELTKIKGKIITFTQ

SDKQSLIKSGYNDVNTVHEIQGETFEETAVVRATPTPIGLIARDSPHVLV

ALTRHTKAMVYYTVVFDAVTSIIADVEKVDQSILTMFATTVPTKXQLMQN

SLYVHRNIFLPVSKTGFYTDMQEFYDRCLPGNSFVLNDFDAVTMRLRDNE

FNLQPCRLTLSNLDPVPALVKSEAQNFLIPVLRTACERPRIPGLLENLVA

MIKRNMNTPDLAGTVDITNMSISIVDNFFSSFVRDEVLLDHLDCVRASSI

QSFSDWFSCQPTSAVGQLANFNFIDLPAFDTYMHMIKRQPKSRLDTSIQS

EYPALQTIVYHLKVVNAVFGPVFKYLTTKFLSMVDSSKFFFYTRKKPEDL

QEFFSDLSSHSDYEILELDVSKYDKSQSDFHFSIEMAIWEKLGLDDILAW

MWSMGHKRTILQDFQAGIKTLIYYQRKSGDVTTFIGNTFIIAACVASMLP

LDKCFKASFCGDDSLIYLPKGLEYPDIQATANLVWNFEAKLFRKKYGYFC

GKYIIHHANGCIVYPDPLKLISKLGNKSLVGYEHVEEFRISLLDVAHSLF

NGAYFHLLDDAIHELFPNAGGCSFVINCLCKYLSDKRLFRSLYIDVSK.
```

Figures 2A, 2B:
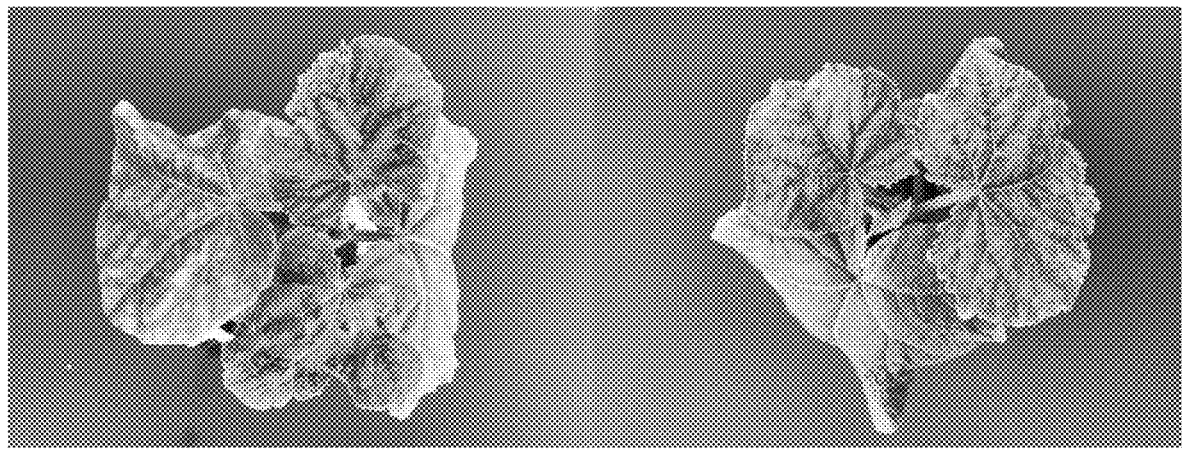
FIG. 2A is a photograph showing leaves of a cucumber plant infected with wild-type CGMMV Ontario strain and grown under laboratory conditions.
FIG. 2B is a photograph showing leaves of a cucumber plant infected with the mutant CGMMV Ontario strain ONB and grown under the laboratory conditions of FIG. 2A.
Figures 2C, 2D:
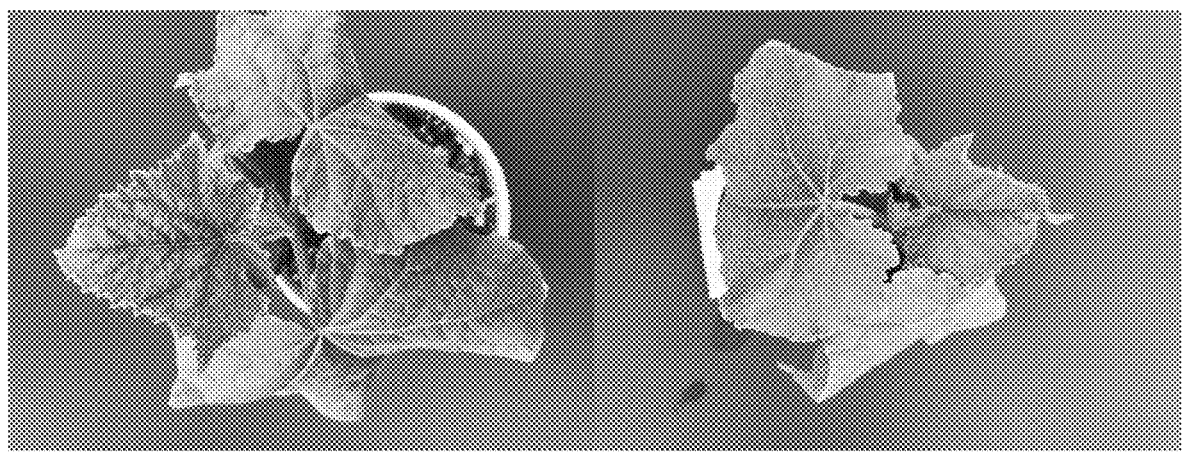
FIG. 2C is photograph showing leaves of a cucumber plant infected with the mutant CGMMV Ontario strain ONM and grown under the laboratory conditions of FIG. 2A.
FIG. 2D is a photograph showing leaves of a healthy cucumber plant without CGMMV infection grown as a control under the laboratory conditions of FIG. 2A.

The mutant clones ONB and ONM were each transformed into *Agrobacterium tumefaciens* strain EHA105 by electroporation and used to inoculate the cotyledon of 1-2 week old cucumber plants under laboratory greenhouse conditions using the method described in Example 1. As seen in FIG. 2B, two weeks after inoculation, mutant strain ONB induced visible symptoms including mottle and mosaic symptoms, Likewise, as seen in FIG. 2C, two weeks after inoculation, mutant strain ONM also induced visible symptoms, although these symptoms were milder than those induced by the mutant ONB strain. For comparison, FIG. 2A shows a plant exhibiting symptoms induced by inoculation with the wild-type Ontario strain CGMMV under the same conditions, and FIG. 2D shows an uninfected control plant grown under the same conditions.

Mutant CGMMV Ontario Strain ONBM

Directed mutation of the cDNA genome of the cloned CGMMV Ontario strain (Example 1) was carried out as described above to introduce mutations corresponding to those of mutants ONB and ONM (c.315G>A; c.1498A>G; c.1660C>T; c.3430C>T; c.3528A>G; c.4144C>T; c.4248C>T; and c.6228C>T). These mutations resulted in amino acid substitutions in the encoded viral proteins (G86S, E480G, S534F and A1124V in the 129 kDa protein; G86S, E480G, S534F, A1124V, N1157D, P1362L, and P1397S in the 186 kDa protein; and A156V in the coat protein). The resulting mutant CGMMV strain was designated Ontario strain ONBM.

The cDNA genome sequence of CGMMV strain ONBM is shown below.

(SEQ ID NO: 42)

```
GTTTTAATTTTTAAAATTAAACAAACAACAACAACAACAACAAACAATTTAAAACA
ACAATGGCAAACATTAATGAACAAATCAACAACCAACGCGACGCCGCGGCCAGCGG
GAGAAACAATCTCGTTAGCCAATTGGCGTCAAAAAGGGTGTATGACGAGGCTGTTC
GCTCGTTGGATCATCAAGACAGACGCCCAAAAATGAACTTTTCTCGTGTGGTCAGCA
CAGAGCACACCAGGCTTGTAACTGATGCGTATCCGGAGTTTTCGATTAGCTTTACCG
CCACCAAGAACTCTGTACACTCCCTTGCGGGTAGTCTGAGGCTCCTTGAACTGGAAT
ATATGATGATGCAAGTGCCCTACGGCTCACCTTGTTATGATATCGGCGGTAACTATA
CGCAGCACTTGTTCAAAGGTAGATCATATGTGCATTGCTGCAATCCGTGCCTGGATC
TTAAAGATGTTGCGAGGAACGTGATGTATAACGATATGGTCACACAACATGTACAG
AGGCACAAGGGATCTGGCGGGTGCAGACCTCTTCCAACTTTTCAGATAGATGCATTC
AGGAGGTACGATAATTCTCCCTGTGCGGTCACCTGTTCAGACGTTTTCCAAGAGTGT
TCCTATGATTTTGGGAGCGGTAGGGATAATCATGCAGTCTCGCTGCATTCAATCTAC
GATATCCCTTATTCTTCGATCGGACCTGCTCTTCATAGGAAGAACGTGCGAGTTTGTT
ATGCAGCCTTTCACTTCTCGGAGGCATTGCTTTTAGGTTCACCTGTAGGTAATTTAAA
TAGTATTGGGGCTCAGTTTAGGGTCGATGGTGATGATGTGCATTTTCTTTTTAGTGAA
GAGTCTACTTTGCATTATACTCATAGTTTAGAAAATATCAAATTAATTGTGATGCGT
ACTTATTTTCCTGCTGATGATAGGTACGTGTATATTAAGGAGTTTATGGTCAAGCGT
GTGGATACTTTCTTCTTTAGGTTGGTCAGAGCAGACACACATATGCTTCATAAATCT
GTGGGGCACTATTCAAAATCGAAATCTGAGTACTTTGCGCTGAATACCCCTCCGATC
TTCCAAGACAAAGCCACGTTTTCTGTGTGGTTTCCTGAGGCGAAGCGTAAGGTGTTG
ATACCCAAGTTTGAACTTTCAAGATTCCTTTCTGGGAATGTGAAAATCTCTAGGATG
CTTGTCGATGCTGATTTCGTCCATACCATTATTAATCACATTAGCACGTATGATAATA
AGGCCTTAGTGTGGAAGAATGTTCAGTCCTTTGTGGAATCTATACGCTCAAGAGTAA
TTGTAAACGGAGTTTCGGTGAAATCTGAATGGAACGTACCGGTTGATCAGCTCACTG
ATATCTCGTTCTCGATATTCCTTCTCGTGAAGGTTAGGAAGGTACAGATCGAGTTAA
TGTCTGATAAAGTTGTAATCGAGGCGAGGGCTTGCTCCGGAGGTTCGCAGACAGTC
TTAAATCCGCCGTAGGAGGACTAGGTGATTGCGTCTATGATGCTCTAGTTCAAACCG
GCTGGTTTGATACCTCTAGCGACGAACTGAAAGTTTTGCTACCTGAACCGTTTATGA
CCTTTTCGGATTATCTTGAAGGGATGTACGAGGCAGATGCAAAGATCGAGAGAGAG
AGTGTCTTTGAGTTGCTCGCTTCCGGTGACGATTTGTTCAAGAAAATCGATGAGATA
AGAAACAATTACAGTGGAGTCGAATTTGATGTAGAGAAATTCCAGGAATTTTGCAA
GGAACTGAATGTTAATCCTATGCTAATTGGCCATGTTATCGAAGCTATTTTTTCGCAG
AAAGCTGGGGTGACAGTAACGGGTCTGGGTACCCTCTCTCCTGAGATGGGTGCTTCT
GTTGCGTTATCCAATACCTCTGTAGATACATGTGAAGATATGGATGTAACTGAAGAT
ATGGAGGATATAGTGTTGATGGCGGACAAGAGTCATTCTTACATGTCCCCAGAAATG
GCGAGATGGGCTGATGTAAAATACGACAACAATAAAGGGGGCCTGGTCGAATACAA
```

-continued
```
AGTCGGAACCTCGATGACTTTACCTGCCACCTGGGCAGAGAAGGGTAAGGCTGTCTT
ACCGTTGTCGGGGATCTGTGTGAGGAAACCCCAATTTTCGAAGCCGCTTGATGAGGA
AGACGACTTGAGGTTATCAAACATGAATTTCTTTAAGGTGAGCGATCTGAAGTTGAA
GAAAACTATCACTCCAGTTGTTTACACTGGGACCATTCGAGAGAGGCAAATGAAGA
ATTATATTGATTACTTATCGGCCTCTCTTGGTTCTACGCTGGGTAATCTGGAGAGAAT
TGTGCGGAGTGATTGGAACGGTACCGAGGAGAGTATGCAAACGTTCGGGTTGTATG
ACTGCGAAAAGTGCAAGTGGTTACTGTTACCAGCCGAAAAGAAGCACGCATGGGCT
GTGGTTCTGGCAAGTGATGATACCACTCGCATAATCTTCCTCTCATATGACGAATCT
GGTTCTCCCATAATTGATAAGAGAAACTGGAAGCGATTTGCTGTTTGCTCTGAGACC
AAAGTCTATAGCGTAATTCGTAGTTTAGAGGTACTAAATAAGGAAGCAATAGTCGA
CCCCGGGGTTCATATAACATTAGTTGACGGAGTGCCGGGTTGTGGAAAGACCGCCG
AAATTATAGCGAGGGTCAATTGGAAAACCGATCTAGTATTGACTCCCGGGAGGGAG
GCGGCTGCTATGATTAGGCGGAGGGCCTGCGCCCTGCACAAGTCACCTGTGGCAAC
CAGTGACAACGTTAGAACTTTCGATTCTTTTGTGATGAATAAGAAAATCTTCAAGTT
TGACGCTGTCTATGTTGACGAGGGTCTGATGGTCCATACGGGTTTACTTAATTTTGCG
TTGAAGATCTCAGGTTGTAAAAAGGCCTTCGTCTTTGGTGATGCTAAGCAAATCCCG
TTTATAAACAGAGTCATGAATTTTGATTATCCTAAGGAGTTAAGAACTTTAATAGTC
GATAATGTAGAGCGTAGGTATGTTACCCATAGGTGTCCTAGAGATGTCACTAGTTTT
CTTAATACTATTTACAAAGCCGCTGTCGCTACTACTAGTCCGGTTGTACATTCTGTGA
AGGCGATTAAAGTGTCAGGGGCCGGTATTCTGAGGCCCGAGTTGACGAAGATCAAA
GGAAAGATAATAACGTTTACTCAATCTGATAAGCAGTCCTTGATCAAGAGTGGGTAC
AATGACGTGAACACTGTGCATGAAATTCAGGGAGAAACCTTTGAAGAGACGGCGGT
TGTGCGTGCCACCCCGACTCCGATAGGTTTAATTGCCCGTGATTCACCACATGTACT
AGTGGCCTTAACGAGGCACACTAAGGCAATGGTGTATTATACTGTTGTGTTCGATGC
AGTTACAAGTATAATAGTGGATGTGGAAAAGGTCGACCAGTCGATCTTGACTATGTT
TGCTACCACTGTGCCTACCAAATAGCAATTAATGCAGAACTCACTGTATGTCCATCG
TGATATTTTCCTCCCTGTTAGTAAAACGGGGTTTTATACAGACATGCAGGAGTTCTAT
GATAGATGCCTTCCTGGGAATTCCTTCGTGCTGAATGATTTCGATGCCGTAACCATG
CGGTTGAGGGACAACGAATTTAACCTACAACCTTGTAGGCTAACCTTAAGTAATTTA
GATCCAGTACCCGCTTTGGTTAAGAGTGAAGCGCAGAATTTTCTGATTCCCGTTTTG
CGTACGGCCTGTGAAAGGCCGCGCATTCCAGGTCTCCTTGAAAATCTTGTAGCTATG
ATAAAGAGGAATATGAATACTCCTGATCTAGCTGGGACTGTGGATATAACTAATATG
TCGATTTCTATAGTAGATAACTTCTTTTCTTCTTTTGTTAGAGACGAGGTTTTGCTTG
ATCATTTAGATTGTGTTAGGGCTAGTTCCATTCAAAGTTTTTCTGATTGGTTTTCGTG
TCAGCCAACCTCGGCGGTTGGTCAATTAGCTAATTTCAATTTCATAGATTTGCCTGCC
TTTGATACTTATATGCACATGATTAAGCGGCAGCCCAAGAGTCGGTTGGATACTTCG
ATTCAGTCTGAATATCCGGCCTTGCAAACTATTGTTTATCACCTTAAAGTGGTAAAT
GCAGTTTTCGGTCCGGTTTTTAAGTATTTGACCACCAAGTTTCTTAGCATGGTAGATA
GTTCTAAGTTTTTCTTTTACACTAGGAAAAAATCAGAAGATCTGCAGGAATTTTCTC
AGATCTCTCTTCCCATTCTGATTATGAGATTCTTGAGCTGGATGTTTCTAAATATGAC
AAGTCACAATCCGATTTCCATTTCTCTATTGAGATGGCAATTTGGGAAAAATTGGGG
```

-continued

```
CTGGACGATATTTTGGCTTGGATGTGGTCTATGGGTCACAAGAGAACTATACTGCAA

GATTTCCAAGCCGGGATAAAGACGCTCATTTACTATCAACGGAAGTCTGGTGATGTA

ACTACTTTCATAGGTAATACCTTTATTATCGCAGCGTGTGTAGCTAGTATGTTGCCGT

TAGACAAGTGTTTTAAAGCTAGTTTTTGTGGTGATGATTCGCTGATCTACCTTCCTAA

GGGTTTGGAGTATCCTGATATACAGGCTACTGCCAACTTGGTTTGGAATTTTGAGGC

GAAACTTTTCCGAAAGAAGTATGGTTACTTCTGTGGGAAGTATATAATTCACCATGC

CAACGGCTGTATTGTTTACCCTGACCCTTTAAAATTAATTAGTAAATTAGGTAATAA

GAGTCTTGTAGGGTATGAGCATGTTGAGGAGTTTCGTATATCTCTCCTCGACGTCGC

TCATAGTTTGTTTAATGGTGCTTATTTCCATTTACTCGACGATGCAATCCACGAATTA

TTTCCTAACGCTGGGGGTTGCAGTTTTGTAATTAATTGTTTGTGCAAGTATTTGAGTG

ATAAGCGCCTTTTCCGTAGTCTTTATATAGATGTCTCTAAGTAAGGTGTCGGTCGAG

AACTCATTGAAACCCGAGAAGTTTGTTAAAATCTCTTGGGTCGATAAGTTGCTCCCT

AACTATTTTTCCATTCTTAAGTATTTATCTATAACTGACTTTAGCGTAGTTAAAGCTC

AGAGCTATGAATCCCTCGTGCCTGTCAAGTTGTTGCGTGGTGTTGATCTTACAAAAC

ACCTTTATGTCACATTGTTGGGCGTTGTGGTTTCTGGTGTATGGAACGTACCGGAATC

CTGTAGGGGTGGTGCTACTGTTGCTCTGGTTGACACAAGGATGCATTCTGTTGCAGA

GGGAACTATATGCAAATTTTCAGCTCCCGCCACCGTCCGCGAATTCTCTGTTAGGTT

CATACCTAACTATTCTGTCGTGGCTGCGGATGCCCTTCGCGATCCTTGGTCTTTATTT

GTGAGACTCTCTAATGTAGGGATTAAAGATGGTTTCCATCCTTTGACCTTAGAGGTC

GCTTGTTTAGTCGCTACAACTAACTCTATTATCAAAAAGGGTCTTAGAGCTTCTGTA

GTCGAGTCTGTCGTCTCTTCCGATCAGTCCATTGTCCTAGATTCTTTATCCGAGAAAG

TTGAACCTTTCTTTGATAAAGTTCCTATTTCGGCGGCTGTGATGGCAAGAGACCCCA

GTTATAGGTCTAGGTCGCAGTCTGTCGGTGGTCGTGGTAAGCGGCATTCTAAACCTC

CAAATCGGAGGTTGGACTCTGCTTCTGAAGAGTCCAGTTCTGTTTCTTTCGAAGATG

GCTTACAATCCGATCACACCTAGCAAACTTATTGCGTTTAGTGCTTCTTATGTTCCCG

TCAGGACTTTACTTAATTTTCTAGTTGCTTCACAAGGTACCGCCTTCCAGACTCAAGC

GGGAAGAGATTCTTTCCGCGAGTCCCTGTCTGCGTTACCCTCGTCTGTCGTAGATATT

AATTCTAGGTTCCCAAATGCGGGTTTTTACGCTTTCCTCAACGGTCCTGTGTTGAGGC

CTATCTTCGTTTCGCTTCTTAGCTCTACGGATACGCGTAATAGGGTCATTGAGGTTGT

AGATCCTAGCAATCCTACGACTGCTGAGTCGCTTAACGCTGTAAAGCGTACTGATGA

CGCATCTACGGCCGCTAGGGCTGAAATAGATAATTTAATAGAGTCTATTTCTAAGGG

TTTTGATGTTTATGATAGGGCTTCATTTGAAGCCGCGTTTTCGGTAGTCTGGTCAGAGGTT

ACCACCTCGAAAGCTTAGCTTCGAGGGTCTTCTGATGGTGGTGCACACCAAAGTGCATAG

TGCTTTCCCGTTCACTTAAATCGAACGGTTTGCTCATTGGTTTGCGGAAACCTCTCACGTG

TGGCGTTGAAGTTTCTATGGGCAGTAATTCTGCAAGGGGTTCGAATCCCCCCTTTCCCCGG

GTAGGGCCCA.
```

The cDNA genome sequence of the attenuated CGMMV strain ONBM differs from the cDNA genome sequence of the wild type CGMMV Ontario strain (SEQ ID NO:18) at least in that:
the nucleotide at position 315 of SEQ ID NO:42 is A;
the nucleotide at position 1498 of SEQ ID NO:42 is G;
the nucleotide at position 1660 of SEQ ID NO:42 is T;
the nucleotide at position 3430 of SEQ ID NO:42 is T;
the nucleotide at position 3528 of SEQ ID NO:42 is G;
the nucleotide at position 4144 of SEQ ID NO:42 is T;
the nucleotide at position 4248 of SEQ ID NO:42 is T; and
the nucleotide at position 6228 of SEQ ID NO:42 is T.

The 129 kDa protein encoded by the attenuated CGMMV strain ONBM has the following sequence.

(SEQ ID NO: 43)
MANINEQINNQRDAAASGRNNLVSQLASKRVYDEAVRSLDHQDRRPKMNF

SRVVSTEHTRLVTDAYPEFSISFTATKNSVHSLAGSLRLLELEYMMMQVP

YGSPCYDIGGNYTQHLFKGRSYVHCCNPCLDLKDVARNVMYNDMVTQHVQ

RHKGSGGCRPLPTFQIDAFRRYDNSPCAVTCSDVFQECSYDFGSGRDNHA

VSLHSIYDIPYSSIGPALHRKNVRVCYAAFHFSEALLLGSPVGNLNSIGA

QFRVDGDDVHFLFSEESTLHYTHSLENIKLIVMRTYFPADDRYVYIKEFM

VKRVDTFFFRLVRADTHMLHKSVGHYSKSKSEYFALNTPPIFQDKATFSV

WFPEAKRKVLIPKFELSRFLSGNVKISRMLVDADFVHTIINHISTYDNKA

LVWKNVQSFVESIRSRVIVNGVSVKSEWNVPVDQLTDISFSIFLLVKVRK

VQIELMSDKVVIEARGLLRRFADSLKSAVGGLGDCVYDALVQTGWFDTSS

DELKVLLPEPFMTFSDYLEGMYEADAKIERESVFELLASGDDLFKKIDEI

RNNYSGVEFDVEKFQEFCKELNVNPMLIGHVIEAIFSQKAGVTVTGLGTL

SPEMGASVALSNTSVDTCEDMDVTEDMEDIVLMADKSHSYMSPEMARWAD

VKYDNNKGGLVEYKVGTSMTLPATWAEKGKAVLPLSGICVRKPQFSKPLD

EEDDLRLSNMNFFKVSDLKLKKTITPVVYTGTIREROMKNYIDYLSASLG

STLGNLERIVRSDWNGTEESMQTFGLYDCEKCKWLLLPAEKKHAWAVVLA

SDDTTRIIFLSYDESGSPIIDKRNWKRFAVCSETKVYSVIRSLEVLNKEA

IVDPGVHITLVDGVPGCGKTAEIIARVNWKTDLVLTPGREAAAMIRRRAC

ALHKSPVATSDNVRTFDSFVMNKKIFKFDAVYVDEGLMVHTGLLNFALKI

SGCKKAFVFGDAKQIPFINRVMNFDYPKELRTLIVDNVERRYVTHRCPRD

VTSFLNTIYKAAVATTSPVVHSVKAIKVSGAGILRPELTKIKGKIITFTQ

SDKQSLIKSGYNDVNTVHEIQGETFEETAVVRATPTPIGLIARDSPHYLV

ALTRHTKAMVYYTVVFDAVTSIIVDVEKVDQSILTMFATTVPTK.

The 129 kDa protein encoded by the attenuated CGMMV strain ONBM differs from the 129 kDa protein encoded by the wild type CGMMV Ontario strain (SEQ ID NO:63) at least in that:
 position 86 of SEQ ID NO:43 is serine (S, Ser);
 position 480 of SEQ ID NO:43 is glycine (G, Gly);
 position 534 of SEQ ID NO:43 is phenylalanine (F, Phe); and
 position 1124 of SEQ ID NO:43 is valine (V, Val).

The 186 kDa protein encoded by the attenuated CGMMV strain ONBM has the following sequence.

(SEQ ID NO: 44)
MANINEQINNQRDAAASGRNNLVSQLASKRVYDEAVRSLDHQDRRPKMNF

SRVVSTEHTRLVTDAYPEFSISFTATKNSVHSLAGSLRLLELEYMMMQVP

YGSPCYDIGGNYTQHLFKGRSYVHCCNPCLDLKDVARNVMYNDMVTQHVQ

RHKGSGGCRPLPTFQIDAFRRYDNSPCAVTCSDVFQECSYDFGSGRDNHA

VSLHSIYDIPYSSIGPALHRKNVRVCYAAFHFSEALLLGSPVGNLNSIGA

QFRVDGDDVHFLFSEESTLHYTHSLENIKLIVMRTYFPADDRYVYIKEFM

VKRVDTFFFRLVRADTHMLHKSVGHYSKSKSEYFALNTPPIFQDKATFSV

WFPEAKRKVLIPKFELSRFLSGNVKISRMLVDADFVHTIINHISTYDNKA

LVWKNVQSFVESIRSRVIVNGVSVKSEWNVPVDQLTDISFSIFLLVKVRK

VQIELMSDKVVIEARGURRFADSLKSAVGGLGDCVYDALVQTGWFDTSSD

ELKVLLPEPFMTFSDYLEGMYEADAKIERESVFELLASGDDLFKKIDEIR

NNYSGVEFDVEKFQEFCKELNVNPMLIGHVIEAIFSQKAGVTVTGLGTLS

PEMGASVALSNTSVDTCEDMDVTEDMEDIVLMADKSHSYMSPEMARWADV

KYDNNKGGLVEYKVGTSMTLPATWAEKGKAVLPLSGICVRKPQFSKPLDE

EDDLRLSNMNFFKVSDLKLKKTITPVVYTGTIREROMKNYIDYLSASLGS

TLGNLERIVRSDWNGTEESMQTFGLYDCEKCKWLLLPAEKKHAWAVVLAS

DDTTRIIFLSYDESGSPIIDKRNWKRFAVCSETKVYSVIRSLEVLNKEAI

VDPGVHITLVDGVPGCGKTAEIIARVNWKTDLVLTPGREAAAMIRRRACA

LHKSPVATSDNVRTFDSFVMNKKIFKFDAVYVDEGLMVHTGLLNFALKIS

GCKKAFVFGDAKQIPFINRVMNFDYPKELRTLIVDNVERRYVTHRCPRDV

TSFLNTIYKAAVATTSPVVHSVKAIKVSGAGILRPELTKIKGKIITFTQS

DKQSLIKSGYNDVNTVHEIQGETFEETAVVRATPTPIGLIARDSPHVLVA

LTRHTKAMVYYTVVFDAVTSIIVDVEKVDQSILTMFATTVPTKXQLMQNS

LYVHRDIFLPVSKTGFYTDMQEFYDRCLPGNSFVLNDFDAVTMRLRDNEF

NLQPCRLTLSNLDPVPALVKSEAQNFLIPVLRTACERPRIPGLLENLVAM

IKRNMNTPDLAGTVDITNMSISIVDNFFSSFVRDEVLLDHLDCVRASSIQ

SFSDWFSCQPTSAVGQLANFNFIDLPAFDTYMHMIKRQPKSRLDTSIQSE

YPALQTIVYHLKVVNAVFGPVFKYLTTKFLSMVDSSKFFFYTRKKSEDLQ

EFFSDLSSHSDYEILELDVSKYDKSQSDFHFSIEMAIWEKLGLDDILAWM

WSMGHKRTILQDFQAGIKTLIYYQRKSGDVTTFIGNTFIIAACVASMLPL

DKCFKASFCGDDSLIYLPKGLEYPDIQATANLVWNFEAKLFRKKYGYFCG

KYIIHHANGCIVYPDPLKLISKLGNKSLVGYEHVEEFRISLLDVAHSLFN

GAYFHLLDDAIHELFPNAGGCSFVINCLCKYLSDKRLFRSLYIDVSK.

The 186 kDa protein encoded by the attenuated CGMMV strain ONBM differs from the 186 kDa protein encoded by the wild type CGMMV Ontario strain (SEQ ID NO:64) at least in that:
 position 86 of SEQ ID NO:44 is serine (S, Ser);
 position 480 of SEQ ID NO:44 is glycine (G, Gly);
 position 534 of SEQ ID NO:44 is phenylalanine (F, Phe);
 position 1124 of SEQ ID NO:44 is valine (V, Val);
 position 1157 of SEQ ID NO:44 is aspartic acid (D, Asp);
 position 1362 of SEQ ID NO:44 is leucine (L, Leu); and
 position 1397 of SEQ ID NO:44 is serine (S, Ser).

The coat protein encoded by the attenuated CGMMV strain ONBM has the sequence of SEQ ID NO:32 and differs from the coat protein encoded by the wild type CGMMV Ontario strain (SEQ ID NO:65) at least in that position 156 of SEQ ID NO:32 is valine (V, Val).

Mutant CGMMV Ontario Strain ONBM-2

Directed mutation of the cDNA genome of the cloned CGMMV Ontario strain (Example 1) was carried out as described above to introduce mutations corresponding to those of mutants ONB and ONM (c.315G>A; c.1498A>G; c.1660C>T; c.3430C>T; c.3528A>G; c.4144C>T; c.4248C>T; and c.6228C>T) in addition to the mutation c.3334C>T introduced by randomly replacing C by T during PCR amplification. These mutations resulted in amino acid substitutions in the encoded viral proteins (G86S, E480G, S534F, A1092V and A1124V in the 129 kDa protein; G86S, E480G, S534F, A1092V, A1124V, N1157D, P1362L, and P1397S in the 186 kDa protein; and A156V in the coat protein). The resulting mutant CGMMV strain was designated Ontario strain ONBM-2.

The cDNA genome sequence of CGMMV strain ONBM-2 is shown below.

(SEQ ID NO: 45)
```
GTTTTAATTTTTAAAATTAAACAAACAACAACAACAACAAACAATTTAAAACA
ACAATGGCAAACATTAATGAACAAATCAACAACCAACGCGACGCCGCGGCCAGCGG
GAGAAACAATCTCGTTAGCCAATTGGCGTCAAAAAGGGTGTATGACGAGGCTGTTC
GCTCGTTGGATCATCAAGACAGACGCCCAAAAATGAACTTTTCTCGTGTGGTCAGCA
CAGAGCACACCAGGCTTGTAACTGATGCGTATCCGGAGTTTTCGATTAGCTTTACCG
CCACCAAGAACTCTGTACACTCCCTTGCGGGTAGTCTGAGGCTCCTTGAACTGGAAT
ATATGATGATGCAAGTGCCCTACGGCTCACCTTGTTATGATATCGGCGGTAACTATA
CGCAGCACTTGTTCAAAGGTAGATCATATGTGCATTGCTGCAATCCGTGCCTGGATC
TTAAAGATGTTGCGAGGAACGTGATGTATAACGATATGGTCACACAACATGTACAG
AGGCACAAGGGATCTGGCGGGTGCAGACCTCTTCCAACTTTTCAGATAGATGCATTC
AGGAGGTACGATAATTCTCCCTGTGCGGTCACCTGTTCAGACGTTTTCCAAGAGTGT
TCCTATGATTTTGGGAGCGGTAGGGATAATCATGCAGTCTCGCTGCATTCAATCTAC
GATATCCCTTATTCTTCGATCGGACCTGCTCTTCATAGGAAGAACGTGCGAGTTTGTT
ATGCAGCCTTTCACTTCTCGGAGGCATTGCTTTTAGGTTCACCTGTAGGTAATTTAAA
TAGTATTGGGGCTCAGTTTAGGGTCGATGGTGATGATGTGCATTTTCTTTTTAGTGAA
GAGTCTACTTTGCATTATACTCATAGTTTAGAAAATATCAAATTAATTGTGATGCGT
ACTTATTTTCCTGCTGATGATAGGTACGTGTATATTAAGGAGTTTATGGTCAAGCGT
GTGGATACTTTCTTCTTTAGGTTGGTCAGAGCAGACACACATATGCTTCATAAATCT
GTGGGGCACTATTCAAAATCGAAATCTGAGTACTTTGCGCTGAATACCCCTCCGATC
TTCCAAGACAAAGCCACGTTTTCTGTGTGGTTTCCTGAGGCGAAGCGTAAGGTGTTG
ATACCCAAGTTTGAACTTTCAAGATTCCTTTCTGGGAATGTGAAAATCTCTAGGATG
CTTGTCGATGCTGATTTCGTCCATACCATTATTAATCACATTAGCACGTATGATAATA
AGGCCTTAGTGTGGAAGAATGTTCAGTCCTTTGTGGAATCTATACGCTCAAGAGTAA
TTGTAAACGGAGTTTCGGTGAAATCTGAATGGAACGTACCGGTTGATCAGCTCACTG
ATATCTCGTTCTCGATATTCCTTCTCGTGAAGGTTAGGAAGGTACAGATCGAGTTAA
TGTCTGATAAAGTTGTAATCGAGGCGAGGGGCTTGCTCCGGAGGTTCGCAGACAGTC
TTAAATCCGCCGTAGGAGGACTAGGTGATTGCGTCTATGATGCTCTAGTTCAAACCG
GCTGGTTTGATACCTCTAGCGACGAACTGAAAGTTTTGCTACCTGAACCGTTTATGA
CCTTTTCGGATTATCTTGAAGGGATGTACGAGGCAGATGCAAAGATCGAGAGAGAG
AGTGTCTTTGAGTTGCTCGCTTCCGGTGACGATTTGTTCAAGAAAATCGATGAGATA
AGAAACAATTACAGTGGAGTCGAATTTGATGTAGAGAAATTCCAGGAATTTTGCAA
GGAACTGAATGTTAATCCTATGCTAATTGGCCATGTTATCGAAGCTATTTTTTCGCAG
AAAGCTGGGGTGACAGTAACGGGTCTGGGTACCCTCTCTCCTGAGATGGGTGCTTCT
GTTGCGTTATCCAATACCTCTGTAGATACATGTGAAGATATGGATGTAACTGAAGAT
ATGGAGGATATAGTGTTGATGGCGGACAAGAGTCATTCTTACATGTCCCCAGAAATG
GCGAGATGGGCTGATGTAAAATACGACAACAATAAAGGGGGCCTGGTCGAATACAA
AGTCGGAACCTCGATGACTTTACCTGCCACCTGGGCAGAGAAGGGTAAGGCTGTCTT
```

-continued

```
ACCGTTGTCGGGGATCTGTGTGAGGAAACCCCAATTTTCGAAGCCGCTTGATGAGGA
AGACGACTTGAGGTTATCAAACATGAATTTCTTTAAGGTGAGCGATCTGAAGTTGAA
GAAAACTATCACTCCAGTTGTTTACACTGGGACCATTCGAGAGAGGCAAATGAAGA
ATTATATTGATTACTTATCGGCCTCTCTTGGTTCTACGCTGGGTAATCTGGAGAGAAT
TGTGCGGAGTGATTGGAACGGTACCGAGGAGAGTATGCAAACGTTCGGGTTGTATG
ACTGCGAAAAGTGCAAGTGGTTACTGTTACCAGCCGAAAAGAAGCACGCATGGGCT
GTGGTTCTGGCAAGTGATGATACCACTCGCATAATCTTCCTCTCATATGACGAATCT
GGTTCTCCCATAATTGATAAGAGAAACTGGAAGCGATTTGCTGTTTGCTCTGAGACC
AAAGTCTATAGCGTAATTCGTAGTTTAGAGGTACTAAATAAGGAAGCAATAGTCGA
CCCCGGGGTTCATATAACATTAGTTGACGGAGTGCCGGGTTGTGGAAAGACCGCCG
AAATTATAGCGAGGGTCAATTGGAAAACCGATCTAGTATTGACTCCCGGGAGGGAG
GCGGCTGCTATGATTAGGCGGAGGGCCTGCGCCCTGCACAAGTCACCTGTGGCAAC
CAGTGACAACGTTAGAACTTTCGATTCTTTTGTGATGAATAAGAAAATCTTCAAGTT
TGACGCTGTCTATGTTGACGAGGGTCTGATGGTCCATACGGGTTTACTTAATTTTGCG
TTGAAGATCTCAGGTTGTAAAAAGGCCTTCGTCTTTGGTGATGCTAAGCAAATCCCG
TTTATAAACAGAGTCATGAATTTTGATTATCCTAAGGAGTTAAGAACTTTAATAGTC
GATAATGTAGAGCGTAGGTATGTTACCCATAGGTGTCCTAGAGATGTCACTAGTTTT
CTTAATACTATTTACAAAGCCGCTGTCGCTACTACTAGTCCGGTTGTACATTCTGTGA
AGGCGATTAAAGTGTCAGGGGCCGGTATTCTGAGGCCCGAGTTGACGAAGATCAAA
GGAAAGATAATAACGTTTACTCAATCTGATAAGCAGTCCTTGATCAAGAGTGGGTAC
AATGACGTGAACACTGTGCATGAAATTCAGGGAGAAACCTTTGAAGAGACGGCGGT
TGTGCGTGCCACCCCGACTCCGATAGGTTTAATTGTCCGTGATTCACCACATGTACT
AGTGGCCTTAACGAGGCACACTAAGGCAATGGTGTATTATACTGTTGTGTTCGATGC
AGTTACAAGTATAATAGTGGATGTGGAAAAGGTCGACCAGTCGATCTTGACTATGTT
TGCTACCACTGTGCCTACCAAATAGCAATTAATGCAGAACTCACTGTATGTCCATCG
TGATATTTTCCTCCCTGTTAGTAAAACGGGGTTTTATACAGACATGCAGGAGTTCTAT
GATAGATGCCTTCCTGGGAATTCCTTCGTGCTGAATGATTTCGATGCCGTAACCATG
CGGTTGAGGGACAACGAATTTAACCTACAACCTTGTAGGCTAACCTTAAGTAATTTA
GATCCAGTACCCGCTTTGGTTAAGAGTGAAGCGCAGAATTTTCTGATTCCCGTTTTG
CGTACGGCCTGTGAAAGGCCGCGCATTCCAGGTCTCCTTGAAAATCTTGTAGCTATG
ATAAAGAGGAATATGAATACTCCTGATCTAGCTGGGACTGTGGATATAACTAATATG
TCGATTTCTATAGTAGATAACTTCTTTTCTTCTTTTGTTAGAGACGAGGTTTTGCTTG
ATCATTTAGATTGTGTTAGGGCTAGTTCCATTCAAAGTTTTTCTGATTGGTTTTCGTG
TCAGCCAACCTCGGCGGTTGGTCAATTAGCTAATTTCAATTTCATAGATTTGCCTGCC
TTTGATACTTATATGCACATGATTAAGCGGCAGCCCAAGAGTCGGTTGGATACTTCG
ATTCAGTCTGAATATCCGGCCTTGCAAACTATTGTTTATCACCTTAAAGTGGTAAAT
GCAGTTTTCGGTCCGGTTTTTAAGTATTTGACCACCAAGTTTCTTAGCATGGTAGATA
GTTCTAAGTTTTTCTTTTACACTAGGAAAAAATCAGAAGATCTGCAGGAATTTTCTC
AGATCTCTCTTCCCATTCTGATTATGAGATTCTTGAGCTGGATGTTTCTAAATATGAC
AAGTCACAATCCGATTTCCATTTCTCTATTGAGATGGCAATTTGGGAAAAATTGGGG
```

```
-continued
CTGGACGATATTTTGGCTTGGATGTGGTCTATGGGTCACAAGAGAACTATACTGCAA

GATTTCCAAGCCGGGATAAAGACGCTCATTTACTATCAACGGAAGTCTGGTGATGTA

ACTACTTTCATAGGTAATACCTTTATTATCGCAGCGTGTGTAGCTAGTATGTTGCCGT

TAGACAAGTGTTTTAAAGCTAGTTTTTGTGGTGATGATTCGCTGATCTACCTTCCTAA

GGGTTTGGAGTATCCTGATATACAGGCTACTGCCAACTTGGTTTGGAATTTTGAGGC

GAAACTTTTCCGAAAGAAGTATGGTTACTTCTGTGGGAAGTATATAATTCACCATGC

CAACGGCTGTATTGTTTACCCTGACCCTTTAAAATTAATTAGTAAATTAGGTAATAA

GAGTCTTGTAGGGTATGAGCATGTTGAGGAGTTTCGTATATCTCCTCGACGTCGC

TCATAGTTTGTTTAATGGTGCTTATTTCCATTTACTCGACGATGCAATCCACGAATTA

TTTCCTAACGCTGGGGGTTGCAGTTTTGTAATTAATTGTTTGTGCAAGTATTTGAGTG

ATAAGCGCCTTTTCCGTAGTCTTTATATAGATGTCTCTAAGTAAGGTGTCGGTCGAG

AACTCATTGAAACCCGAGAAGTTTGTTAAAATCTCTTGGGTCGATAAGTTGCTCCCT

AACTATTTTTCCATTCTTAAGTATTTATCTATAACTGACTTTAGCGTAGTTAAAGCTC

AGAGCTATGAATCCCTCGTGCCTGTCAAGTTGTTGCGTGGTGTTGATCTTACAAAAC

ACCTTTATGTCACATTGTTGGGCGTTGTGGTTTCTGGTGTATGGAACGTACCGGAATC

CTGTAGGGGTGGTGCTACTGTTGCTCTGGTTGACACAAGGATGCATTCTGTTGCAGA

GGGAACTATATGCAAATTTTCAGCTCCCGCCACCGTCCGCGAATTCTCTGTTAGGTT

CATACCTAACTATTCTGTCGTGGCTGCGGATGCCCTTCGCGATCCTTGGTCTTTATTT

GTGAGACTCTCTAATGTAGGGATTAAAGATGGTTTCCATCCTTTGACCTTAGAGGTC

GCTTGTTTAGTCGCTACAACTAACTCTATTATCAAAAAGGGTCTTAGAGCTTCTGTA

GTCGAGTCTGTCGTCTCTTCCGATCAGTCCATTGTCCTAGATTCTTTATCCGAGAAAG

TTGAACCTTTCTTTGATAAAGTTCCTATTTCGGCGGCTGTGATGGCAAGAGACCCCA

GTTATAGGTCTAGGTCGCAGTCTGTCGGTGGTCGTGGTAAGCGGCATTCTAAACCTC

CAAATCGGAGGTTGGACTCTGCTTCTGAAGAGTCCAGTTCTGTTTCTTTCGAAGATG

GCTTACAATCCGATCACACCTAGCAAACTTATTGCGTTTAGTGCTTCTTATGTTCCCG

TCAGGACTTTACTTAATTTTCTAGTTGCTTCACAAGGTACCGCCTTCCAGACTCAAGC

GGGAAGAGATTCTTTCCGCGAGTCCCTGTCTGCGTTACCCTCGTCTGTCGTAGATATT

AATTCTAGGTTCCCAAATGCGGGTTTTTACGCTTTCCTCAACGGTCCTGTGTTGAGGC

CTATCTTCGTTTCGCTTCTTAGCTCTACGGATACGCGTAATAGGGTCATTGAGGTTGT

AGATCCTAGCAATCCTACGACTGCTGAGTCGCTTAACGCTGTAAAGCGTACTGATGA

CGCATCTACGGCCGCTAGGGCTGAAATAGATAATTTAATAGAGTCTATTTCTAAGGG

TTTTGATGTTTATGATAGGGCTTCATTTGAAGCCGCGTTTTCGGTAGTCTGGTCAGAGGTT

ACCACCTCGAAAGCTTAGCTTCGAGGGTCTTCTGATGGTGGTGCACACCAAAGTGCATAG

TGCTTTCCCGTTCACTTAAATCGAACGGTTTGCTCATTGGTTTGCGGAAACCTCTCACGTG

TGGCGTTGAAGTTTCTATGGGCAGTAATTCTGCAAGGGGTTCGAATCCCCCCTTTCCCCGG

GTAGGGGCCCA.
```

The cDNA genome sequence of the attenuated CGMMV strain ONBM-2 differs from the cDNA genome sequence of the wild type CGMMV Ontario strain (SEQ ID NO:18) at least in that:
the nucleotide at position 315 of SEQ ID NO:45 is A;
the nucleotide at position 1498 of SEQ ID NO:45 is G;
the nucleotide at position 1660 of SEQ ID NO:45 is T;
the nucleotide at position 3334 of SEQ ID NO:45 is T;
the nucleotide at position 3430 of SEQ ID NO:45 is T;
the nucleotide at position 3528 of SEQ ID NO:45 is G;
the nucleotide at position 4144 of SEQ ID NO:45 is T;
the nucleotide at position 4248 of SEQ ID NO:45 is T; and
the nucleotide at position 6228 of SEQ ID NO:45 is T.

The 129 kDa protein encoded by the attenuated CGMMV strain ONBM-2 has the following sequence.

(SEQ ID NO: 46)
MANINEQINNQRDAAASGRNNLVSQLASKRVYDEAVRSLDHQDRRPKMNF
SRVVSTEHTRLVTDAYPEFSISFTATKNSVHSLAGSLRLLELEYMMMQVP
YGSPCYDIGGNYTQHLFKGRSYVHCCNPCLDLKDVARNVMYNDMVTQHVQ
RHKGSGGCRPLPTFQIDAFRRYDNSPCAVTCSDVFQECSYDFGSGRDNHA
VSLHSIYDIPYSSIGPALHRKNVRVCYAAFHFSEALLLGSPVGNLNSIGA
QFRVDGDDVHFLFSEESTLHYTHSLENIKLIVMRTYFPADDRYVYIKEFM
VKRVDTFFFRLVRADTHMLHKSVGHYSKSKSEYFALNTPPIFQDKATFSV
WFPEAKRKVLIPKFELSRFLSGNVKISRMLVDADFVHTIINHISTYDNKA
LVWKNVQSFVESIRSRVIVNGVSVKSEWNVPVDQLTDISFSIFLLVKVRK
VQIELMSDKVVIEARGLLRRFADSLKSAVGGLGDCVYDALVQTGWFDTSS
DELKVLLPEPFMTFSDYLEGMYEADAKIERESVFELLASGDDLFKKIDEI
RNNYSGVEFDVEKFQEFCKELNVNPMLIGHVIEAIFSQKAGVTVTGLGTL
SPEMGASVALSNTSVDTCEDMDVTEDMEDIVLMADKSHSYMSPEMARWAD
VKYDNNKGGLVEYKVGTSMTLPATWAEKGKAVLPLSGICVRKPQFSKPLD
EEDDLRLSNMNFFKVSDLKLKKTITPVVYTGTIRERQMKNYIDYLSASLG
STLGNLERIVRSDWNGTEESMQTFGLYDCEKCKWLLLPAEKKHAWAVVLA
SDDTTRIIFLSYDESGSPIIDKRNWKRFAVCSETKVYSVIRSLEVLNKEA
IVDPGVHITLVDGVPGCGKTAEIIARVNWKTDLVLTPGREAAAMIRRRAC
ALHKSPVATSDNVRTFDSFVMNKKIFKFDAVYVDEGLMVHTGLLNFALKI
SGCKKAFVFGDAKQIPFINRVMNFDYPKELRTLIVDNVERRYVTHRCPRD
VTSFLNTIYKAAVATTSPVVHSVKAIKVSGAGILRPELTKIKGKIITFTQ
SDKQSLIKSGYNDVNTVHEIQGETFEETAVVRATPTPIGLIVRDSPHVLV
ALTRHTKAMVYYTVVFDAVTSIIVDVEKVDQSILTMFATTVPTK.

The 129 kDa protein encoded by the attenuated CGMMV strain ONBM-2 differs from the 129 kDa protein encoded by the wild type CGMMV Ontario strain (SEQ ID NO:63) at least in that:
 position 86 of SEQ ID NO:46 is serine (S, Ser);
 position 480 of SEQ ID NO:46 is glycine (G, Gly);
 position 534 of SEQ ID NO:46 is phenylalanine (F, Phe);
 position 1092 of SEQ ID NO:46 is valine (V, Val); and
 position 1124 of SEQ ID NO:46 is valine (V, Val).
The 186 kDa protein encoded by the attenuated CGMMV strain ONBM-2 has the following sequence.

(SEQ ID NO: 47)
MANINEQINNQRDAAASGRNNLVSQLASKRVYDEAVRSLDHQDRRPKMNF
SRVVSTEHTRLVTDAYPEFSISFTATKNSVHSLAGSLRLLELEYMMMQVP
YGSPCYDIGGNYTQHLFKGRSYVHCCNPCLDLKDVARNVMYNDMVTQHVQ
RHKGSGGCRPLPTFQIDAFRRYDNSPCAVTCSDVFQECSYDFGSGRDNHA
VSLHSIYDIPYSSIGPALHRKNVRVCYAAFHFSEALLLGSPVGNLNSIGA
QFRVDGDDVHFLFSEESTLHYTHSLENIKLIVMRTYFPADDRYVYIKEFM
VKRVDTFFFRLVRADTHMLHKSVGHYSKSKSEYFALNTPPIFQDKATFSV
WFPEAKRKVLIPKFELSRFLSGNVKISRMLVDADFVHTIINHISTYDNKA
LVWKNVQSFVESIRSRVIVNGVSVKSEWNVPVDQLTDISFSIFLLVKVRK
VQIELMSDKVVIEARGLLRRFADSLKSAVGGLGDCVYDALVQTGWFDTSS
DELKVLLPEPFMTFSDYLEGMYEADAKIERESVFELLASGDDLFKKIDEI
RNNYSGVEFDVEKFQEFCKELNVNPMLIGHVIEAIFSQKAGVTVTGLGTL
SPEMGASVALSNTSVDTCEDMDVTEDMEDIVLMADKSHSYMSPEMARWAD
VKYDNNKGGLVEYKVGTSMTLPATWAEKGKAVLPLSGICVRKPQFSKPLD
EEDDLRLSNMNFFKVSDLKLKKTITPVVYTGTIRERQMKNYIDYLSASLG
STLGNLERIVRSDWNGTEESMQTFGLYDCEKCKWLLLPAEKKHAWAVVLA
SDDTTRIIFLSYDESGSPIIDKRNWKRFAVCSETKVYSVIRSLEVLNKEA
IVDPGVHITLVDGVPGCGKTAEIIARVNWKTDLVLTPGREAAAMIRRRAC
ALHKSPVATSDNVRTFDSFVMNKKIFKFDAVYVDEGLMVHTGLLNFALKI
SGCKKAFVFGDAKQIPFINRVMNFDYPKELRTLIVDNVERRYVTHRCPRD
VTSFLNTIYKAAVATTSPVVHSVKAIKVSGAGILRPELTKIKGKIITFTQ
SDKQSLIKSGYNDVNTVHEIQGETFEETAVVRATPTPIGLIVRDSPHVLV
ALTRHTKAMVYYTVVFDAVTSIIVDVEKVDQSILTMFATTVPTKXQLMQN
SLYVHRDIFLPVSKTGFYTDMQEFYDRCLPGNSFVLNDFDAVTMRLRDNE
FNLQPCRLTLSNLDPVPALVKSEAQNFLIPVLRTACERPRIPGLLENLVA
MIKRNMNTPDLAGTVDITNMSISIVDNFFSSFVRDEVLLDHLDCVRASSI
QSFSDWFSCQPTSAVGQLANFNFIDLPAFDTYMHMIKRQPKSRLDTSIQS
EYPALQTIVYHLKVVNAVFGPVFKYLTTKFLSMVDSSKFFFYTRKKSEDL
QEFFSDLSSHSDYEILELDVSKYDKSQSDFHFSIEMAIWEKLGLDDILAW
MWSMGHKRTILQDFQAGIKTLIYYQRKSGDVTTFIGNTFIIAACVASMLP
LDKCFKASFCGDDSLIYLPKGLEYPDIQATANLVWNFEAKLFRKKYGYFC
GKYIIHHANGCIVYPDPLKLISKLGNKSLVGYEHVEEFRISLLDVAHSLF
NGAYFHLLDDAIHELFPNAGGCSFVINCLCKYLSDKRLFRSLYIDVSK.

The 186 kDa protein encoded by the attenuated CGMMV strain ONBM-2 differs from the 186 kDa protein encoded by the wild type CGMMV Ontario strain (SEQ ID NO:64) at least in that:
 position 86 of SEQ ID NO:47 is serine (S, Ser);
 position 480 of SEQ ID NO:47 is glycine (G, Gly);
 position 534 of SEQ ID NO:47 is phenylalanine (F, Phe);
 position 1092 of SEQ ID NO:47 is valine (V, Val);
 position 1124 of SEQ ID NO:47 is valine (V, Val);
 position 1157 of SEQ ID NO:47 is aspartic acid (D, Asp);
 position 1362 of SEQ ID NO:47 is leucine (L, Leu); and
 position 1397 of SEQ ID NO:47 is serine (S, Ser).
The coat protein encoded by the attenuated CGMMV ONBM-2 strain has the sequence of SEQ ID NO:32 and differs from the coat protein encoded by the wild type CGMMV Ontario strain (SEQ ID NO:65) at least in that position 156 of SEQ ID NO:32 is valine (V, Val).

Mutant CGMMV Ontario Strain ONBM-3

Directed mutation of the cloned cDNA genome of the cloned CGMMV Ontario strain (Example 1) was carried out as described above to introduce mutations corresponding to those induced in the cDNA genome of the cloned CGMMV Ontario strain mutants ONB and ONM (c.315G>A;

c.1498A>G; c.1660C>T; c.3430C>T; c.3528A>G; c.4144C>T; c.4248C>T; and c.6228C>T) in addition to the mutation c.4969G>A introduced by randomly replacing G by A during PCR amplification. These mutations resulted in amino acid substitutions in the encoded viral proteins (G86S, E480G, S534F and A1124V in the 129 kDa protein; G86S, E480G, S534F, A1124V, N1157D, P1362L, P1397S and R1637H in the 186 kDa protein; and A156V in the coat protein). The resulting mutant CGMMV strain was designated Ontario strain ONBM-3.

The cDNA genome sequence of CGMMV strain ONBM-3 is shown below.

(SEQ ID NO: 48)
```
GTTTTAATTTTTAAAATTAAACAAACAACAACAACAACAACAAACAATTTAAAACA
ACAATGGCAAACATTAATGAACAAATCAACAACCAACGCGACGCCGCGGCCAGCGG
GAGAAACAATCTCGTTAGCCAATTGGCGTCAAAAAGGGTGTATGACGAGGCTGTTC
GCTCGTTGGATCATCAAGACAGACGCCCAAAAATGAACTTTTCTCGTGTGGTCAGCA
CAGAGCACACCAGGCTTGTAACTGATGCGTATCCGGAGTTTTCGATTAGCTTTACCG
CCACCAAGAACTCTGTACACTCCCTTGCGGGTAGTCTGAGGCTCCTTGAACTGGAAT
ATATGATGATGCAAGTGCCCTACGGCTCACCTTGTTATGATATCGGCGGTAACTATA
CGCAGCACTTGTTCAAAGGTAGATCATATGTGCATTGCTGCAATCCGTGCCTGGATC
TTAAAGATGTTGCGAGGAACGTGATGTATAACGATATGGTCACACAACATGTACAG
AGGCACAAGGGATCTGGCGGGTGCAGACCTCTTCCAACTTTTCAGATAGATGCATTC
AGGAGGTACGATAATTCTCCCTGTGCGGTCACCTGTTCAGACGTTTTCCAAGAGTGT
TCCTATGATTTTGGGAGCGGTAGGGATAATCATGCAGTCTCGCTGCATTCAATCTAC
GATATCCCTTATTCTTCGATCGGACCTGCTCTTCATAGGAAGAACGTGCGAGTTTGTT
ATGCAGCCTTTCACTTCTCGGAGGCATTGCTTTTAGGTTCACCTGTAGGTAATTTAAA
TAGTATTGGGGCTCAGTTTAGGGTCGATGGTGATGATGTGCATTTTCTTTTTAGTGAA
GAGTCTACTTTGCATTATACTCATAGTTTAGAAAATATCAAATTAATTGTGATGCGT
ACTTATTTTCCTGCTGATGATAGGTACGTGTATATTAAGGAGTTTATGGTCAAGCGT
GTGGATACTTTCTTCTTTAGGTTGGTCAGAGCAGACACACATATGCTTCATAAATCT
GTGGGGCACTATTCAAAATCGAAATCTGAGTACTTTGCGCTGAATACCCCTCCGATC
TTCCAAGACAAAGCCACGTTTTCTGTGTGGTTTCCTGAGGCGAAGCGTAAGGTGTTG
ATACCCAAGTTTGAACTTTCAAGATTCCTTTCTGGGAATGTGAAAATCTCTAGGATG
CTTGTCGATGCTGATTTCGTCCATACCATTATTAATCACATTAGCACGTATGATAATA
AGGCCTTAGTGTGGAAGAATGTTCAGTCCTTTGTGGAATCTATACGCTCAAGAGTAA
TTGTAAACGGAGTTTCGGTGAAATCTGAATGGAACGTACCGGTTGATCAGCTCACTG
ATATCTCGTTCTCGATATTCCTTCTCGTGAAGGTTAGGAAGGTACAGATCGAGTTAA
TGTCTGATAAAGTTGTAATCGAGGCGAGGGCTTGCTCCGGAGGTTCGCAGACAGTC
TTAAATCCGCCGTAGGAGGACTAGGTGATTGCGTCTATGATGCTCTAGTTCAAACCG
GCTGGTTTGATACCTCTAGCGACGAACTGAAAGTTTTGCTACCTGAACCGTTTATGA
CCTTTTCGGATTATCTTGAAGGGATGTACGAGGCAGATGCAAAGATCGAGAGAGAG
AGTGTCTTTGAGTTGCTCGCTTCCGGTGACGATTTGTTCAAGAAAATCGATGAGATA
AGAAACAATTACAGTGGAGTCGAATTTGATGTAGAGAAATTCCAGGAATTTTGCAA
GGAACTGAATGTTAATCCTATGCTAATTGGCCATGTTATCGAAGCTATTTTTTCGCAG
AAAGCTGGGGTGACAGTAACGGGTCTGGGTACCCTCTCTCCTGAGATGGGTGCTTCT
GTTGCGTTATCCAATACCTCTGTAGATACATGTGAAGATATGGATGTAACTGAAGAT
ATGGAGGATATAGTGTTGATGGCGGACAAGAGTCATTCTTACATGTCCCCAGAAATG
GCGAGATGGGCTGATGTAAAATACGACAACAATAAAGGGGGCCTGGTCGAATACAA
```

-continued
```
AGTCGGAACCTCGATGACTTTACCTGCCACCTGGGCAGAGAAGGGTAAGGCTGTCTT

ACCGTTGTCGGGGATCTGTGTGAGGAAACCCCAATTTTCGAAGCCGCTTGATGAGGA

AGACGACTTGAGGTTATCAAACATGAATTTCTTTAAGGTGAGCGATCTGAAGTTGAA

GAAAACTATCACTCCAGTTGTTTACACTGGGACCATTCGAGAGAGGCAAATGAAGA

ATTATATTGATTACTTATCGGCCTCTCTTGGTTCTACGCTGGGTAATCTGGAGAGAAT

TGTGCGGAGTGATTGGAACGGTACCGAGGAGAGTATGCAAACGTTCGGGTTGTATG

ACTGCGAAAAGTGCAAGTGGTTACTGTTACCAGCCGAAAAGAAGCACGCATGGGCT

GTGGTTCTGGCAAGTGATGATACCACTCGCATAATCTTCCTCTCATATGACGAATCT

GGTTCTCCCATAATTGATAAGAGAAACTGGAAGCGATTTGCTGTTTGCTCTGAGACC

AAAGTCTATAGCGTAATTCGTAGTTTAGAGGTACTAAATAAGGAAGCAATAGTCGA

CCCCGGGGTTCATATAACATTAGTTGACGGAGTGCCGGGTTGTGGAAAGACCGCCG

AAATTATAGCGAGGGTCAATTGGAAAACCGATCTAGTATTGACTCCCGGGAGGGAG

GCGGCTGCTATGATTAGGCGGAGGGCCTGCGCCCTGCACAAGTCACCTGTGGCAAC

CAGTGACAACGTTAGAACTTTCGATTCTTTTGTGATGAATAAGAAAATCTTCAAGTT

TGACGCTGTCTATGTTGACGAGGGTCTGATGGTCCATACGGGTTTACTTAATTTTGCG

TTGAAGATCTCAGGTTGTAAAAAGGCCTTCGTCTTTGGTGATGCTAAGCAAATCCCG

TTTATAAACAGAGTCATGAATTTTGATTATCCTAAGGAGTTAAGAACTTTAATAGTC

GATAATGTAGAGCGTAGGTATGTTACCCATAGGTGTCCTAGAGATGTCACTAGTTTT

CTTAATACTATTTACAAAGCCGCTGTCGCTACTACTAGTCCGGTTGTACATTCTGTGA

AGGCGATTAAAGTGTCAGGGGCCGGTATTCTGAGGCCCGAGTTGACGAAGATCAAA

GGAAAGATAATAACGTTTACTCAATCTGATAAGCAGTCCTTGATCAAGAGTGGGTAC

AATGACGTGAACACTGTGCATGAAATTCAGGGAGAAACCTTTGAAGAGACGGCGGT

TGTGCGTGCCACCCCGACTCCGATAGGTTTAATTGCCCGTGATTCACCACATGTACT

AGTGGCCTTAACGAGGCACACTAAGGCAATGGTGTATTATACTGTTGTGTTCGATGC

AGTTACAAGTATAATAGTGGATGTGGAAAAGGTCGACCAGTCGATCTTGACTATGTT

TGCTACCACTGTGCCTACCAAATAGCAATTAATGCAGAACTCACTGTATGTCCATCG

TGATATTTTCCTCCCTGTTAGTAAAACGGGGTTTTATACAGACATGCAGGAGTTCTAT

GATAGATGCCTTCCTGGGAATTCCTTCGTGCTGAATGATTTCGATGCCGTAACCATG

CGGTTGAGGGACAACGAATTTAACCTACAACCTTGTAGGCTAACCTTAAGTAATTTA

GATCCAGTACCCGCTTTGGTTAAGAGTGAAGCGCAGAATTTTCTGATTCCCGTTTTG

CGTACGCCTGTGAAAGGCCGCGCATTCCAGGTCTCCTTGAAAATCTTGTAGCTATG

ATAAAGAGGAATATGAATACTCCTGATCTAGCTGGGACTGTGGATATAACTAATATG

TCGATTTCTATAGTAGATAACTTCTTTTCTTCTTTTGTTAGAGACGAGGTTTTGCTTG

ATCATTTAGATTGTGTTAGGGCTAGTTCCATTCAAAGTTTTTCTGATTGGTTTTCGTG

TCAGCCAACCTCGGCGGTTGGTCAATTAGCTAATTTCAATTTCATAGATTTGCCTGCC

TTTGATACTTATATGCACATGATTAAGCGGCAGCCCAAGAGTCGGTTGGATACTTCG

ATTCAGTCTGAATATCCGGCCTTGCAAACTATTGTTTATCACCTTAAAGTGGTAAAT

GCAGTTTTCGGTCCGGTTTTTAAGTATTTGACCACCAAGTTTCTTAGCATGGTAGATA

GTTCTAAGTTTTTCTTTTACACTAGGAAAAAATCAGAAGATCTGCAGGAATTTTCTC

AGATCTCTCTTCCCATTCTGATTATGAGATTCTTGAGCTGGATGTTTCTAAATATGAC

AAGTCACAATCCGATTTCCATTTCTCTATTGAGATGGCAATTTGGGAAAAATTGGGG
```

-continued

```
CTGGACGATATTTTGGCTTGGATGTGGTCTATGGGTCACAAGAGAACTATACTGCAA

GATTTCCAAGCCGGGATAAAGACGCTCATTTACTATCAACGGAAGTCTGGTGATGTA

ACTACTTTCATAGGTAATACCTTTATTATCGCAGCGTGTGTAGCTAGTATGTTGCCGT

TAGACAAGTGTTTTAAAGCTAGTTTTTGTGGTGATGATTCGCTGATCTACCTTCCTAA

GGGTTTGGAGTATCCTGATATACAGGCTACTGCCAACTTGGTTTGGAATTTTGAGGC

GAAACTTTTCCGAAAGAAGTATGGTTACTTCTGTGGGAAGTATATAATTCACCATGC

CAACGGCTGTATTGTTTACCCTGACCCTTTAAAATTAATTAGTAAATTAGGTAATAA

GAGTCTTGTAGGGTATGAGCATGTTGAGGAGTTTCGTATATCTCCTCGACGTCGC

TCATAGTTTGTTTAATGGTGCTTATTTCCATTTACTCGACGATGCAATCCACGAATTA

TTTCCTAACGCTGGGGGTTGCAGTTTTGTAATTAATTGTTTGTGCAAGTATTTGAGTG

ATAAGCACCTTTTCCGTAGTCTTTATATAGATGTCTCTAAGTAAGGTGTCGGTCGAG

AACTCATTGAAACCCGAGAAGTTTGTTAAAATCTCTTGGGTCGATAAGTTGCTCCCT

AACTATTTTTCCATTCTTAAGTATTTATCTATAACTGACTTTAGCGTAGTTAAAGCTC

AGAGCTATGAATCCCTCGTGCCTGTCAAGTTGTTGCGTGGTGTTGATCTTACAAAAC

ACCTTTATGTCACATTGTTGGGCGTTGTGGTTTCTGGTGTATGGAACGTACCGGAATC

CTGTAGGGGTGGTGCTACTGTTGCTCTGGTTGACACAAGGATGCATTCTGTTGCAGA

GGGAACTATATGCAAATTTTCAGCTCCCGCCACCGTCCGCGAATTCTCTGTTAGGTT

CATACCTAACTATTCTGTCGTGGCTGCGGATGCCCTTCGCGATCCTTGGTCTTTATTT

GTGAGACTCTCTAATGTAGGGATTAAAGATGGTTTCCATCCTTTGACCTTAGAGGTC

GCTTGTTTAGTCGCTACAACTAACTCTATTATCAAAAAGGGTCTTAGAGCTTCTGTA

GTCGAGTCTGTCGTCTCTTCCGATCAGTCCATTGTCCTAGATTCTTTATCCGAGAAAG

TTGAACCTTTCTTTGATAAAGTTCCTATTTCGGCGGCTGTGATGGCAAGAGACCCCA

GTTATAGGTCTAGGTCGCAGTCTGTCGGTGGTCGTGGTAAGCGGCATTCTAAACCTC

CAAATCGGAGGTTGGACTCTGCTTCTGAAGAGTCCAGTTCTGTTTCTTTCGAAGATG

GCTTACAATCCGATCACACCTAGCAAACTTATTGCGTTTAGTGCTTCTTATGTTCCCG

TCAGGACTTTACTTAATTTTCTAGTTGCTTCACAAGGTACCGCCTTCCAGACTCAAGC

GGGAAGAGATTCTTTCCGCGAGTCCCTGTCTGCGTTACCCTCGTCTGTCGTAGATATT

AATTCTAGGTTCCCAAATGCGGGTTTTTACGCTTTCCTCAACGGTCCTGTGTTGAGGC

CTATCTTCGTTTCGCTTCTTAGCTCTACGGATACGCGTAATAGGGTCATTGAGGTTGT

AGATCCTAGCAATCCTACGACTGCTGAGTCGCTTAACGCTGTAAAGCGTACTGATGA

CGCATCTACGGCCGCTAGGGCTGAAATAGATAATTTAATAGAGTCTATTTCTAAGGG

TTTTGATGTTTATGATAGGGCTTCATTTGAAGCCGCGTTTTCGGTAGTCTGGTCAGAGGTT

ACCACCTCGAAAGCTTAGCTTCGAGGGTCTTCTGATGGTGGTGCACACCAAAGTGCATAG

TGCTTTCCCGTTCACTTAAATCGAACGGTTTGCTCATTGGTTTGCGGAAACCTCTCACGTG

TGGCGTTGAAGTTTCTATGGGCAGTAATTCTGCAAGGGGTTCGAATCCCCCCTTTCCCCGG

GTAGGGGCCCA.
```

60

The cDNA genome sequence of the attenuated CGMMV strain ONBM-3 differs from the cDNA genome sequence of the wild type CGMMV Ontario strain (SEQ ID NO:18) at least in that:
the nucleotide at position 315 of SEQ ID NO:48 is A;
the nucleotide at position 1498 of SEQ ID NO:48 is G;
the nucleotide at position 1660 of SEQ ID NO:48 is T;
the nucleotide at position 3430 of SEQ ID NO:48 is T;
the nucleotide at position 3528 of SEQ ID NO:48 is G;
the nucleotide at position 4144 of SEQ ID NO:48 is T;
the nucleotide at position 4248 of SEQ ID NO:48 is T;
the nucleotide at position 4969 of SEQ ID NO:48 is A; and
the nucleotide at position 6228 of SEQ ID NO:48 is T.

The 129 kDa protein encoded by the attenuated CGMMV strain ONBM-3 has the following sequence.

(SEQ ID NO: 49)
MANINEQINNQRDAAASGRNNLVSQLASKRVYDEAVRSLDHQDRRPKMNFS
RVVSTEHTRLVTDAYPEFSISFTATKNSVHSLAGSLRLLELEYMMMQVPYG
SPCYDIGGNYTQHLFKGRSYVHCCNPCLDLKDVARNVMYNDMVTQHVQRHK
GSGGCRPLPTFQIDAFRRYDNSPCAVTCSDVFQECSYDFGSGRDNHAVSLH
SIYDIPYSSIGPALHRKNVRVCYAAFHFSEALLLGSPVGNLNSIGAQFRVD
GDDVHFLFSEESTLHYTHSLENIKLIVMRTYFPADDRYVYIKEFMVKRVDT
FFFRLVRADTHMLHKSVGHYSKSKSEYFALNTPPIFQDKATFSVWFPEAKR
KVLIPKFELSRFLSGNVKISRMLVDADFVHTIINHISTYDNKALVWKNVQS
FVESIRSRVIVNGVSVKSEWNVPVDQLTDISFSIFLLVKVRKVQIELMSDK
VVIEARGLLRRFADSLKSAVGGLGDCVYDALVQTGWFDTSSDELKVLLPEP
FMTFSDYLEGMYEADAKIERESVFELLASGDDLFKKIDEIRNNYSGVEFDV
EKFQEFCKELNVNPMLIGHVIEAIFSQKAGVTVTGLGTLSPEMGASVALSN
TSVDTCEDMDVTEDMEDIVLMADKSHSYMSPEMARWADVKYDNNKGGLVEY
KVGTSMTLPATWAEKGKAVLPLSGICVRKPQFSKPLDEEDDLRLSNMNFFK
VSDLKLKKTITPVVYTGTIRERQMKNYIDYLSASLGSTLGNLERIVRSDWN
GTEESMQTFGLYDCEKCKWLLLPAEKKHAWAVVLASDDTTRIIFLSYDESG
SPIIDKRNWKRFAVCSETKVYSVIRSLEVLNKEAIVDPGVHITLVDGVPGC
GKTAEIIARVNWKTDLVLTPGREAAAMIRRRACALHKSPVATSDNVRTFDS
FVMNKKIFKFDAVYVDEGLMVHTGLLNFALKISGCKKAFVFGDAKQIPFIN
RVMNFDYPKELRTLIVDNVERRYVTHRCPRDVTSFLNTIYKAAVATTSPVV
HSVKAIKVSGAGILRPELTKIKGKIITFTQSDKQSLIKSGYNDVNTVHEIQ
GETFEETAVVRATPTPIGLIARDSPHVLVALTRHTKAMVYYTVVFDAVTSI
IVDVEKVDQSILTMFATTVPTK.

The 129 kDa protein encoded by the attenuated CGMMV strain ONBM-3 differs from the 129 kDa protein encoded by the wild type CGMMV Ontario strain (SEQ ID NO:63) at least in that:
position 86 of SEQ ID NO:49 is serine (S, Ser);
position 480 of SEQ ID NO:49 is glycine (G, Gly);
position 534 of SEQ ID NO:49 is phenylalanine (F, Phe); and
position 1124 of SEQ ID NO:49 is valine (V, Val).

The 186 kDa protein encoded by the attenuated CGMMV strain ONBM-3 has the following sequence.

(SEQ ID NO: 50)
MANINEQINNQRDAAASGRNNLVSQLASKRVYDEAVRSLDHQDRRPKMNFS
RVVSTEHTRLVTDAYPEFSISFTATKNSVHSLAGSLRLLELEYMMMQVPYG
SPCYDIGGNYTQHLFKGRSYVHCCNPCLDLKDVARNVMYNDMVTQHVQRHK
GSGGCRPLPTFQIDAFRRYDNSPCAVTCSDVFQECSYDFGSGRDNHAVSLH
SIYDIPYSSIGPALHRKNVRVCYAAFHFSEALLLGSPVGNLNSIGAQFRVD
GDDVHFLFSEESTLHYTHSLENIKLIVMRTYFPADDRYVYIKEFMVKRVDT
FFFRLVRADTHMLHKSVGHYSKSKSEYFALNTPPIFQDKATFSVWFPEAKR
KVLIPKFELSRFLSGNVKISRMLVDADFVHTIINHISTYDNKALVWKNVQS
FVESIRSRVIVNGVSVKSEWNVPVDQLTDISFSIFLLVKVRKVQIELMSDK
VVIEARGLLRRFADSLKSAVGGLGDCVYDALVQTGWFDTSSDELKVLLPEP
FMTFSDYLEGMYEADAKIERESVFELLASGDDLFKKIDEIRNNYSGVEFDV
EKFQEFCKELNVNPMLIGHVIEAIFSQKAGVTVTGLGTLSPEMGASVALSN
TSVDTCEDMDVTEDMEDIVLMADKSHSYMSPEMARWADVKYDNNKGGLVEY
KVGTSMTLPATWAEKGKAVLPLSGICVRKPQFSKPLDEEDDLRLSNMNFFK
VSDLKLKKTITPVVYTGTIRERQMKNYIDYLSASLGSTLGNLERIVRSDWN
GTEESMQTFGLYDCEKCKWLLLPAEKKHAWAVVLASDDTTRIIFLSYDESG
SPIIDKRNWKRFAVCSETKVYSVIRSLEVLNKEAIVDPGVHITLVDGVPGC
GKTAEIIARVNWKTDLVLTPGREAAAMIRRRACALHKSPVATSDNVRTFDS
FVMNKKIFKFDAVYVDEGLMVHTGLLNFALKISGCKKAFVFGDAKQIPFIN
RVMNFDYPKELRTLIVDNVERRYVTHRCPRDVTSFLNTIYKAAVATTSPVV
HSVKAIKVSGAGILRPELTKIKGKIITFTQSDKQSLIKSGYNDVNTVHEIQ
GETFEETAVVRATPTPIGLIARDSPHVLVALTRHTKAMVYYTVVFDAVISI
IVDVEKVDQSILTMFATTVPTIOCQLMQNSLYVHRDIFLPVSKTGFYTDMQ
EFYDRCLPGNSFVLNDFDAVTMRLRDNEFNLQPCRLTLSNLDPVPALVKSE
AQNFLIPVLRTACERPRIPGLLENLVAMIKRNMNTPDLAGTVDITNMSISI
VDNFFSSFVRDEVLLDHLDCVRASSIQSFSDWFSCQPTSAVGQLANFNFID
LPAFDTYMHMIKRQPKSRLDTSIQSEYPALQTIVYHLKVVNAVFGPVFKYL
TTKFLSMVDSSKFFFYTRKKSEDLQEFFSDLSSHSDYEILELDVSKYDKSQ
SDFHFSIEMAIWEKLGLDDILAWMWSMGHKRTILQDFQAGIKTLIYYQRKS
GDVTTFIGNTFIIAACVASMLPLDKCFKASFCGDDSLIYLPKGLEYPDIQA
TANLVWNFEAKLFRKKYGYFCGKYIIHHANGCIVYPDPLKLISKLGNKSLV
GYEHVEEFRISLLDVAHSLINGAYFHLLDDAIHELFPNAGGCSEVINCLCK
YLSDKHLFRSLYIDVSK.

The 186 kDa protein encoded by the attenuated CGMMV strain ONBM-3 differs from the 186 kDa protein encoded by the wild type CGMMV Ontario strain (SEQ ID NO:64) at least in that:
position 86 of SEQ ID NO:50 is serine (S, Ser);
position 480 of SEQ ID NO:50 is glycine (G, Gly);
position 534 of SEQ ID NO:50 is phenylalanine (F, Phe);
position 1124 of SEQ ID NO:50 is valine (V, Val);
position 1157 of SEQ ID NO:50 is aspartic acid (D, Asp);
position 1362 of SEQ ID NO:50 is leucine (L, Leu);
position 1397 of SEQ ID NO:50 is serine (S, Ser); and
position 1637 of SEQ ID NO:50 is histidine (H, His).

The coat protein encoded by the attenuated CGMMV strain ONBM-3 has the sequence of SEQ ID NO:32 and differs from the coat protein encoded by the wild type CGMMV Ontario strain (SEQ ID NO:65) at least in that position 156 of SEQ ID NO:32 is valine (V, Val).

Mutant CGMMV Ontario Strain ONAL-1

Directed mutation of the cDNA genome of the cloned CGMMV Ontario strain (Example 1) was carried out as described above, using the mutagenic primers listed in Table 5 to introduce the mutation c.3334C>T. Nucleotide residues indicated in bold indicate sites of mutation. This mutation resulted in an A1092V amino acid substitution in the encoded viral 129 kDa and 186 kDa proteins. The resulting mutant CGMMV strain was designated Ontario strain ONAL-1.

TABLE 5

Primers used to produce mutant CGMMV Ontario strain ONAL-1

| Primer Sequence (5' to 3') | Sequence Identifier |
|---|---|
| TGTGGTGAATCACGGACAATTAAACCTATCGGAGTCG | SEQ ID NO: 51 |
| CGACTCCGATAGGTTTAATTGTCCGTGATTCACCACA | SEQ ID NO: 52 |

The cDNA genome sequence of CGMMV strain ONAL-1 is shown below.

(SEQ ID NO: 53)
GTTTTAATTTTTAAAATTAAACAAACAACAACAACAACAAACAATTTA
AAACAACAATGGCAAACATTAATGAACAAATCAACAACCAACGCGACGCCG
CGGCCAGCGGGAGAAACAATCTCGTTAGCCAATTGGCGTCAAAAAGGGTGT
ATGACGAGGCTGTTCGCTCGTTGGATCATCAAGACAGACGCCCAAAAATGA
ACTTTTCTCGTGTGGTCAGCACAGAGCACACCAGGCTTGTAACTGATGCGT
ATCCGGAGTTTTCGATTAGCTTTACCGCCACCAAGAACTCTGTACACTCCC
TTGCGGGTGGTCTGAGGCTCCTTGAACTGGAATATATGATGATGCAAGTGC
CCTACGGCTCACCTTGTTATGATATCGGCGGTAACTATACGCAGCACTTGT
TCAAAGGTAGATCATATGTGCATTGCTGCAATCCGTGCCTGGATCTTAAAG
ATGTTGCGAGGAACGTGATGTATAACGATATGGTCACACAACATGTACAGA
GGCACAAGGGATCTGGCGGGTGCAGACCTCTTCCAACTTTTCAGATAGATG
CATTCAGGAGGTACGATAATTCTCCCTGTGCGGTCACCTGTTCAGACGTTT
TCCAAGAGTGTTCCTATGATTTTGGGAGCGGTAGGGATAATCATGCAGTCT
CGCTGCATTCAATCTACGATATCCCTTATTCTTCGATCGGACCTGCTCTTC
ATAGGAAGAACGTGCGAGTTTGTTATGCAGCCTTTCACTTCTCGGAGGCAT
TGCTTTTAGGTTCACCTGTAGGTAATTTAAATAGTATTGGGGCTCAGTTTA
GGGTCGATGGTGATGATGTGCATTTTCTTTTTAGTGAAGAGTCTACTTTGC
ATTATACTCATAGTTTAGAAAATATCAAATTAATTGTGATGCGTACTTATT
TTCCTGCTGATGATAGGTACGTGTATATTAAGGAGTTTATGGTCAAGCGTG
TGGATACTTTCTTCTTTAGGTTGGTCAGAGCAGACACACATATGCTTCATA
AATCTGTGGGGCACTATTCAAAATCGAAATCTGAGTACTTTGCGCTGAATA
CCCCTCCGATCTTCCAAGACAAAGCCACGTTTTCTGTGTGGTTTCCTGAGG
CGAAGCGTAAGGTGTTGATACCCAAGTTTGAACTTTCAAGATTCCTTTCTG
GGAATGTGAAAATCTCTAGGATGCTTGTCGATGCTGATTTCGTCCATACCA
TTATTAATCACATTAGCACGTATGATAATAAGGCCTTAGTGTGGAAGAATG
TTCAGTCCTTTGTGGAATCTATACGCTCAAGAGTAATTGTAAACGGAGTTT
CGGTGAAATCTGAATGGAACGTACCGGTTGATCAGCTCACTGATATCTCGT
TCTCGATATTCCTTCTCGTGAAGGTTAGGAAGGTACAGATCGAGTTAATGT
CTGATAAAGTTGTAATCGAGGCGAGGGGCTTGCTCCGGAGGTTCGCAGACA

GTCTTAAATCCGCCGTAGAAGGACTAGGTGATTGCGTCTATGATGCTCTAG
TTCAAACCGGCTGGTTTGATACCTCTAGCGACGAACTGAAAGTTTTGCTAC
CTGAACCGTTTATGACCTTTTCGGATTATCTTGAAGGGATGTACGAGGCAG
ATGCAAAGATCGAGAGAGAGAGTGTCTCTGAGTTGCTCGCTTCCGGTGACG
ATTTGTTCAAGAAAATCGATGAGATAAGAAACAATTACAGTGGAGTCGAAT
TTGATGTAGAGAAATTCCAGGAATTTTGCAAGGAACTGAATGTTAATCCTA
TGCTAATTGGCCATGTTATCGAAGCTATTTTTTCGCAGAAAGCTGGGGTGA
CAGTAACGGGTCTGGGTACCCTCTCTCCTGAGATGGGTGCTTCTGTTGCGT
TATCCAATACCTCTGTAGATACATGTGAAGATATGGATGTAACTGAAGATA
TGGAGGATATAGTGTTGATGGCGGACAAGAGTCATTCTTACATGTCCCCAG
AAATGGCGAGATGGGCTGATGTAAAATACGACAACAATAAAGGGGCCTGG
TCGAATACAAAGTCGGAACCTCGATGACTTTACCTGCCACCTGGGCAGAGA
AGGGTAAGGCTGTCTTACCGTTGTCGGGGATCTGTGTGAGGAAACCCCAAT
TTTCGAAGCCGCTTGATGAGGAAGACGACTTGAGGTTATCAAACATGAATT
TCTTTAAGGTGAGCGATCTGAAGTTGAAGAAAACTATCACTCCAGTTGTTT
ACACTGGGACCATTCGAGAGAGGCAAATGAAGAATTATATTGATTACTTAT
CGGCCTCTCTTGGTTCTACGCTGGGTAATCTGGAGAGAATTGTGCGGAGTG
ATTGGAACGGTACCGAGGAGAGTATGCAAACGTTCGGGTTGTATGACTGCG
AAAAGTGCAAGTGGTTACTGTTACCAGCCGAAAAGAAGCACGCATGGGCTG
TGGTTCTGGCAAGTGATGATACCACTCGCATAATCTTCCTCTCATATGACG
AATCTGGTTCTCCCATAATTGATAAGAGAAACTGGAAGCGATTTGCTGTTT
GCTCTGAGACCAAAGTCTATAGCGTAATTCGTAGTTTAGAGGTACTAAATA
AGGAAGCAATAGTCGACCCCGGGGTTCATATAACATTAGTTGACGGAGTGC
CGGGTTGTGGAAAGACCGCCGAAATTATAGCGAGGGTCAATTGGAAAACCG
ATCTAGTATTGACTCCCGGGAGGGAGGCGGCTGCTATGATTAGGCGGAGGG
CCTGCGCCCTGCACAAGTCACCTGTGGCAACCAGTGACAACGTTAGAACTT
TCGATTCTTTTGTGATGAATAAGAAAATCTTCAAGTTTGACGCTGTCTATG
TTGACGAGGGTCTGATGGTCCATACGGGTTTACTTAATTTTGCGTTGAAGA
TCTCAGGTTGTAAAAAGGCCTTCGTCTTTGGTGATGCTAAGCAAATCCCGT
TTATAAACAGAGTCATGAATTTTGATTATCCTAAGGAGTTAAGAACTTTAA
TAGTCGATAATGTAGAGCGTAGGTATGTTACCCATAGGTGTCCTAGAGATG
TCACTAGTTTTCTTAATACTATTTACAAAGCCGCTGTCGCTACTACTAGTC
CGGTTGTACATTCTGTGAAGGCGATTAAAGTGTCAGGGGCCGGTATTCTGA
GGCCCGAGTTGACGAAGATCAAAGGAAAGATAATAACGTTTACTCAATCTG
ATAAGCAGTCCTTGATCAAGAGTGGGTACAATGACGTGAACACTGTGCATG
AAATTCAGGGAGAAACCTTTGAAGAGACGGCGGTTGTGCGTGCCACCCCGA
CTCCGATAGGTTTAATTGTCCGTGATTCACCACATGTACTAGTGGCCTTAA
CGAGGCACACTAAGGCAATGGTGTATTATACTGTTGTGTTCGATGCAGTTA
CAAGTATAATAGCGGATGTGGAAAAGGTCGACCAGTCGATCTTGACTATGT
TTGCTACCACTGTGCCTACCAAATAGCAATTAATGCAGAACTCACTGTATG

-continued
```
TCCATCGTAATATTTTCCTCCCTGTTAGTAAAACGGGGTTTTATACAGACA
TGCAGGAGTTCTATGATAGATGCCTTCCTGGGAATTCCTTCGTGCTGAATG
ATTTCGATGCCGTAACCATGCGGTTGAGGGACAACGAATTTAACCTACAAC
CTTGTAGGCTAACCTTAAGTAATTTAGATCCAGTACCCGCTTTGGTTAAGA
GTGAAGCGCAGAATTTTCTGATTCCCGTTTTGCGTACGGCCTGTGAAAGGC
CGCGCATTCCAGGTCTCCTTGAAAATCTTGTAGCTATGATAAAGAGGAATA
TGAATACTCCTGATCTAGCTGGGACTGTGGATATAACTAATATGTCGATTT
CTATAGTAGATAACTTCTTTTCTTCTTTTGTTAGAGACGAGGTTTTGCTTG
ATCATTTAGATTGTGTTAGGGCTAGTTCCATTCAAAGTTTTTCTGATTGGT
TTTCGTGTCAGCCAACCTCGGCGGTTGGTCAATTAGCTAATTTCAATTTCA
TAGATTTGCCTGCCTTTGATACTTATATGCACATGATTAAGCGGCAGCCCA
AGAGTCGGTTGGATACTTCGATTCAGTCTGAATATCCGGCCTTGCAAACTA
TTGTTTATCACCCTAAAGTGGTAAATGCAGTTTTCGGTCCGGTTTTTAAGT
ATTTGACCACCAAGTTTCTTAGCATGGTAGATAGTTCTAAGTTTTTCTTTT
ACACTAGGAAAAAACCAGAAGATCTGCAGGAATTTTTCTCAGATCTCTCTT
CCCATTCTGATTATGAGATTCTTGAGCTGGATGTTTCTAAATATGACAAGT
CACAATCCGATTTCCATTTCTCTATTGAGATGGCAATTTGGGAAAAATTGG
GGCTGGACGATATTTTGGCTTGGATGTGGTCTATGGGTCACAAGAGAACTA
TACTGCAAGATTTCCAAGCCGGGATAAAGACGCTCATTTACTATCAACGGA
AGTCTGGTGATGTAACTACTTTCATAGGTAATACCTTTATTATCGCAGCGT
GTGTAGCTAGTATGTTGCCGTTAGACAAGTGTTTTAAAGCTAGTTTTTGTG
GTGATGATTCGCTGATCTACCTTCCTAAGGGTTTGGAGTATCCTGATATAC
AGGCTACTGCCAACTTGGTTTGGAATTTTGAGGCGAAACTTTTCCGAAAGA
AGTATGGTTACTTCTGTGGGAAGTATATAATTCACCATGCCAACGGCTGTA
TTGTTTACCCTGACCCTTTAAAATTAATTAGTAAATTAGGTAATAAGAGTC
TTGTAGGGTATGAGCATGTTGAGGAGTTTCGTATATCTCCTCGACGTCG
CTCATAGTTTGTTTAATGGTGCTTATTTCCATTTACTCGACGATGCAATCC
ACGAATTATTTCCTAACGCTGGGGGTTGCAGTTTTGTAATTAATTGTTTGT
GCAAGTATTTGAGTGATAAGCGCCTTTTCCGTAGTCTTTATATAGATGTCT
CTAAGTAAGGTGTCGGTCGAGAACTCATTGAAACCCGAGAAGTTTGTTAAA
ATCTCTTGGGTCGATAAGTTGCTCCCTAACTATTTTTCCATTCTTAAGTAT
TTATCTATAACTGACTTTAGCGTAGTTAAAGCTCAGAGCTATGAATCCCTC
GTGCCTGTCAAGTTGTTGCGTGGTGTTGATCTTACAAAACACCTTTATGTC
ACATTGTTGGGCGTTGTGGTTTCTGGTGTATGGAACGTACCGGAATCCTGT
AGGGGTGGTGCTACTGTTGCTCTGGTTGACACAAGGATGCATTCTGTTGCA
GAGGGAACTATATGCAAATTTTCAGCTCCCGCCACCGTCCGCGAATTCTCT
GTTAGGTTCATACCTAACTATTCTGTCGTGGCTGCGGATGCCCTTCGCGAT
CCTTGGTCTTTATTTGTGAGACTCTCTAATGTAGGGATTAAAGATGGTTTC
CATCCTTTGACCTTAGAGGTCGCTTGTTTAGTCGCTACAACTAACTCTATT
ATCAAAAAGGGTCTTAGAGCTTCTGTAGTCGAGTCTGTCGTCTCTTCCGAT
CAGTCCATTGTCCTAGATTCTTTATCCGAGAAAGTTGAACCTTTCTTTGAT
AAAGTTCCTATTTCGGCGGCTGTGATGGCAAGAGACCCCAGTTATAGGTCT
AGGTCGCAGTCTGTCGGTGGTCGTGGTAAGCGGCATTCTAAACCTCCAAAT
CGGAGGTTGGACTCTGCTTCTGAAGAGTCCAGTTCTGTTTCTTTCGAAGAT
GGCTTACAATCCGATCACACCTAGCAAACTTATTGCGTTTAGTGCTTCTTA
TGTTCCCGTCAGGACTTTACTTAATTTTCTAGTTGCTTCACAAGGTACCGC
CTTCCAGACTCAAGCGGGAAGAGATTCTTTCCGCGAGTCCCTGTCTGCGTT
ACCCTCGTCTGTCGTAGATATTAATTCTAGGTTCCCAAATGCGGGTTTTTA
CGCTTTCCTCAACGGTCCTGTGTTGAGGCCTATCTTCGTTTCGCTTCTTAG
CTCTACGGATACGCGTAATAGGGTCATTGAGGTTGTAGATCCTAGCAATCC
TACGACTGCTGAGTCGCTTAACGCTGTAAAGCGTACTGATGACGCATCTAC
GGCCGCTAGGGCTGAAATAGATAATTTAATAGAGTCTATTTCTAAGGGTTT
TGATGTTTATGATAGGGCTTCATTTGAAGCCGCGTTTTCGGTAGTCTGGTC
AGAGGCTACCACCTCGAAAGCTTAGCTTCGAGGGTCTTCTGATGGTGGTGC
ACACCAAAGTGCATAGTGCTTTCCCGTTCACTTAAATCGAACGGTTTGCTC
ATTGGTTTGCGGAAACCTCTCACGTGTGGCGTTGAAGTTTCTATGGGCAGT
AATTCTGCAAGGGGTTCGAATCCCCCTTTCCCCGGGTAGGGCCCA.
```

The cDNA genome sequence of the attenuated CGMMV strain ONAL-1 differs from the cDNA genome sequence of the wild type CGMMV Ontario strain (SEQ ID NO:18) at least in that the nucleotide at position 3334 of SEQ ID NO:53 is T.

The 129 kDa protein encoded by the attenuated CGMMV strain ONAL-1 has the following sequence.

(SEQ ID NO: 54)
```
MANINEQINNQRDAAASGRNNLVSQLASKRVYDEAVRSLDHQDRRPKMNFS
RVVSTEHTRLVTDAYPEFSISFTATKNSVHSLAGGLRLLELEYMMMQVPYG
SPCYDIGGNYTQHLFKGRSYVHCCNPCLDLKDVARNVMYNDMVTQHVQRHK
GSGGCRPLPTFQIDAFRRYDNSPCAVTCSDVFQECSYDFGSGRDNHAVSLH
SIYDIPYSSIGPALHRKNVRVCYAAFHFSEALLLGSPVGNLNSIGAQFRVD
GDDVHFLFSEESTLHYTHSLENIKLIVMRTYFPADDRYVYIKEFMVKRVDT
FFFRLVRADTHMLHKSVGHYSKSKSEYFALNTPPIFQDKATFSVWFPEAKR
KVLIPKFELSRFLSGNVKISRMLVDADFVHTIINHISTYDNKALVWKNVQS
FVESIRSRVIVNGVSVKSEWNVPVDQLTDISFSIFLLVKVRKVQIELMSDK
VVIEARGLLRRFADSLKSAVEGLGDCVYDALVQTGWFDTSSDELKVLLPEP
FMTFSDYLEGMYEADAKIERESVSELLASGDDLEKKIDEIRNNYSGVEFDV
EKFQEFCKELNVNPMLIGHVIEAIFSQKAGVTVTGLGTLSPEMGASVALSN
TSVDTCEDMDVTEDMEDIVLMADKSHSYMSPEMARWADVKYDNNKGGLVEY
KVGTSMTLPATWAEKGKAVLPLSGICVRKPQFSKPLDEEDDLRLSNMNFFK
VSDLKLKKTITPVVYTGTIRERQMKNYIDYLSASLGSTLGNLERIVRSDWN
GTEESMQTFGLYDCEKCKWLLLPAEKKHAWAVVLASDDTTRIIFLSYDESG
SPIIDKRNWKRFAVCSETKVYSVIRSLEVLNKEAIVDPGVHITLVDGVPGC
GKTAEIIARVNWKTDLVLTPGREAAAMIRRRACALHKSPVATSDNVRTFDS
```

-continued

FVMNKKIFKFDAVYVDEGLMVHTGLLNFALKISGCKKAFVFGDAKQIPFIN

RVMNFDYPKELRTLIVDNVERRYVTHRCPRDVTSFLNTIYKAAVATTSPVV

HSVKAIKVSGAGILRPELTKIKGKIITFTQSDKQSLIKSGYNDVNTVHEIQ

GETFEETAVVRATPTPIGLIVRDSPHVLVALTRHTKAMVYYTVVFDAVTSI

IADVEKVDQSILTMFATTVPTK.

The 129 kDa protein encoded by the attenuated CGMMV strain ONAL-1 differs from the 129 kDa protein encoded by the wild type CGMMV Ontario strain (SEQ ID NO:63) at least in that position 1092 of SEQ ID NO:54 is valine (V, Val).

The 186 kDa protein encoded by the attenuated CGMMV strain ONAL-1 has the following sequence.

(SEQ ID NO: 55)
MANINEQINNQRDAAASGRNNLVSQLASKRVYDEAVRSLDHQDRRPKMNFS

RVVSTEHTRLVTDAYPEFSISFTATKNSVHSLAGGLRLLELEYMMMQVPYG

SPCYDIGGNYTQHLFKGRSYVHCCNPCLDLKDVARNVMYNDMVTQHVQRHK

GSGGCRPLPTFQIDAFRRYDNSPCAVTCSDVFQECSYDFGSGRDNHAVSLH

SIYDIPYSSIGPALHRKNVRVCYAAFHFSEALLLGSPVGNLNSIGAQFRVD

GDDVHFLFSEESTLHYTHSLENIKLIVMRTYFPADDRYVYIKEFMVKRVDT

FFFRLVRADTHMLHKSVGHYSKSKSEYFALNTPPIFQDKATFSVWFPEAKR

KVLIPKFELSRFLSGNVKISRMLVDADFVHTIINHISTYDNKALVWKNVQS

FVESIRSRVIVNGVSVKSEWNVPVDQLTDISFSIFLLVKVRKVQIELMSDK

VVIEARGLLRRFADSLKSAVEGLGDCVYDALVQTGWFDTSSDELKVLLPEP

FMTESDYLEGMYEADAKIERESVSELLASGDDLEKKIDEIRNNYSGVEFDV

EKFQEFCKELNVNPMLIGHVIEAIFSQKAGVTVTGLGTLSPEMGASVALSN

TSVDTCEDMDVTEDMEDIVLMADKSHSYMSPEMARWADVKYDNNKGGLVEY

KVGTSMTLPATWAEKGKAVLPLSGICVRKPQFSKPLDEEDDLRLSNMNFFK

VSDLKLKKTITPVVYTGTIREROMKNYIDYLSASLGSTLGNLERIVRSDWN

GTEESMQTFGLYDCEKCKWLLLPAEKKHAWAVVLASDDTTRIIFLSYDESG

SPIIDKRNWKRFAVCSETKVYSVIRSLEVLNKEAIVDPGVHITLVDGVPGC

GKTAEIIARVNWKTDLVLTPGREAAAMIRRRACALHKSPVATSDNVRTFDS

FVMNKKIFKFDAVYVDEGLMVHTGLLNFALKISGCKKAFVFGDAKQIPFIN

RVMNFDYPKELRTLIVDNVERRYVTHRCPRDVTSFLNTIYKAAVATTSPVV

HSVKAIKVSGAGILRPELTKIKGKIITFTQSDKQSLIKSGYNDVNTVHEIQ

GETFEETAVVRATPTP1GLIVRDSPHVLVALTRHTKAMVYYTVVFDAVTSI

IADVEKVDQSILTMFATTVPTKXQLMQNSLYVHRNIFLPVSKTGFYTDMQE

FYDRCLPGNSFVLNDFDAVTMRLRDNEFNLQPCRLTLSNLDPVPALVKSEA

QNFLIPVLRTACERPRIPGLLENLVAMIKRNMNTPDLAGTVDITNMSISIV

DNFFSSFVRDEVLLDHLDCVRASSIQSFSDWFSCQPTSAVGQLANFNFIDL

PAFDTYMHMIKRQPKSRLDTSIQSEYPALQTIVYHPKVVNAVFGPVFKYLT

TKFLSMVDSSKFFFYTRKKPEDLQEFFSDLSSHSDYEILELDVSKYDKSQS

DFHFSIEMAIWEKLGLDDILAWMWSMGHKRTILQDFQAGIKTLIYYQRKSG

DVTTFIGNIFIIAACVASMLPLDKCFKASFCGDDSLIYLPKGLEYPDIQAT

ANLVWNFEAKLFRKKYGYFCGKYIIHHANGCIVYPDPLKLISKLGNKSLVG

YEHVEEFRISLLDVAHSLFNGAYFHLLDDAIHELFPNAGGCSFVINCLCKY

LSDKRLFRSLYIDVSK.

The 186 kDa protein encoded by the attenuated CGMMV strain ONAL-1 differs from the 186 kDa protein encoded by the wild type CGMMV Ontario strain (SEQ ID NO:64) at least in that position 1092 of SEQ ID NO:55 is valine (V, Val).

Mutant CGMMV Ontario Strain ONAL-2

Directed mutation of the cDNA genome of the cloned CGMMV Ontario strain (Example 1) was carried out as described above, using the mutagenic primers listed in Table 6 to introduce the mutation c.4969G>A. Nucleotide residues indicated in bold indicate sites of mutation. This mutation resulted in an R1637H amino acid substitution in the encoded viral 186 kDa protein. The resulting mutant CGMMV strain was designated Ontario strain ONAL-2.

TABLE 6

Primers used to produce mutant CGMMV Ontario strain ONAL-2

| Primer Sequence (5' to 3') | Sequence Identifier |
|---|---|
| CTATATAAAGACTACGGAAAAGGTGCTTATCACTCAA ATACTTGCAC | SEQ ID NO: 56 |
| GTGCAAGTATTTGAGTGATAAGCACCTTTTCCGTAGT CTTTATATAG | SEQ ID NO: 57 |

The cDNA genome sequence of CGMMV strain ONAL-2 is shown below.

(SEQ ID NO: 58)
GTTTTAATTTTTAAAATTAAACAAACAACAACAACAACAAACAATTTA

AAACAACAATGGCAAACATTAATGAACAAATCAACAACCAACGCGACGCCG

CGGCCAGCGGGAGAAACAATCTCGTTAGCCAATTGGCGTCAAAAAGGGTGT

ATGACGAGGCTGTTCGCTCGTTGGATCATCAAGACAGACGCCCAAAAATGA

ACTTTTCTCGTGTGGTCAGCACAGAGCACACCAGGCTTGTAACTGATGCGT

ATCCGGAGTTTTCGATTAGCTTTACCGCCACCAAGAACTCTGTACACTCCC

TTGCGGGTGGTCTGAGGCTCCTTGAACTGGAATATATGATGATGCAAGTGC

CCTACGGCTCACCTTGTTATGATATCGGCGGTAACTATACGCAGCACTTGT

TCAAAGGTAGATCATATGTGCATTGCTGCAATCCGTGCCTGGATCTTAAAG

ATGTTGCGAGGAACGTGATGTATAACGATATGGTCACACAACATGTACAGA

GGCACAAGGGATCTGGCGGGTGCAGACCTCTTCCAACTTTTCAGATAGATG

CATTCAGGAGGTACGATAATTCTCCCTGTGCGGTCACCTGTTCAGACGTTT

TCCAAGAGTGTTCCTATGATTTTGGGAGCGGTAGGGATAATCATGCAGTCT

CGCTGCATTCAATCTACGATATCCCTTATTCTTCGATCGGACCTGCTCTTC

ATAGGAAGAACGTGCGAGTTTGTTATGCAGCCTTTCACTTCTCGGAGGCAT

TGCTTTTAGGTTCACCTGTAGGTAATTTAAATAGTATTGGGGCTCAGTTTA

GGGTCGATGGTGATGATGTGCATTTTCTTTTTAGTGAAGAGTCTACTTTGC

-continued

ATTATACTCATAGTTTAGAAAATATCAAATTAATTGTGATGCGTACTTATT
TTCCTGCTGATGATAGGTACGTGTATATTAAGGAGTTTATGGTCAAGCGTG
TGGATACTTTCTICTITAGGITGGTCAGAGCAGACACACATATGCTTCATA
AATCTGTGGGCACTATTCAAAATCGAAATCTGAGTACTTTGCGCTGAATA
CCCCTCCGATCTTCCAAGACAAAGCCACGTTTTCTGTGTGGTTTCCTGAGG
CGAAGCGTAAGGTGTTGATACCCAAGTTTGAACTTTCAAGATTCCTTTCTG
GGAATGTGAAAATCTCTAGGATGCTTGTCGATGCTGATTTCGTCCATACCA
TTATTAATCACATTAGCACGTATGATAATAAGGCCTTAGTGTGGAAGAATG
TTCAGTCCTTTGTGGAATCTATACGCTCAAGAGTAATTGTAAACGGAGTTT
CGGTGAAATCTGAATGGAACGTACCGGTTGATCAGCTCACTGATATCTCGT
TCTCGATATTCCTTCTCGTGAAGGTTAGGAAGGTACAGATCGAGTTAATGT
CTGATAAAGTTGTAATCGAGGCGAGGGGCTTGCTCCGGAGGTTCGCAGACA
GTCTTAAATCCGCCGTAGAAGGACTAGGTGATTGCGTCTATGATGCTCTAG
TTCAAACCGGCTGGTTTGATACCTCTAGCGACGAACTGAAAGTTTTGCTAC
CTGAACCGTTTATGACCTTTTCGGATTATCTTGAAGGGATGTACGAGGCAG
ATGCAAAGATCGAGAGAGAGAGTGTCTCTGAGTTGCTCGCTTCCGGTGACG
ATTTGTTCAAGAAAATCGATGAGATAAGAAACAATTACAGTGGAGTCGAAT
TTGATGTAGAGAAATTCCAGGAATTTTGCAAGGAACTGAATGTTAATCCTA
TGCTAATTGGCCATGTTATCGAAGCTATTTTTCGCAGAAAGCTGGGGTGA
CAGTAACGGGTCTGGGTACCCTCTCTCCTGAGATGGGTGCTTCTGTTGCGT
TATCCAATACCTCTGTAGATACATGTGAAGATATGGATGTAACTGAAGATA
TGGAGGATATAGTGTTGATGGCGGACAAGAGTCATTCTTACATGTCCCCAG
AAATGGCGAGATGGGCTGATGTAAAATACGACAACAATAAAGGGGGCCTGG
TCGAATACAAAGTCGGAACCTCGATGACTTTACCTGCCACCTGGGCAGAGA
AGGGTAAGGCTGTCTTACCGTTGTCGGGGATCTGTGTGAGGAAACCCCAAT
TTTCGAAGCCGCTTGATGAGGAAGACGACTTGAGGTTATCAAACATGAATT
TCTTTAAGGTGAGCGATCTGAAGTTGAAGAAAACTATCACTCCAGTTGTTT
ACACTGGGACCATTCGAGAGAGGCAAATGAAGAATTATATTGATTACTTAT
CGGCCTCTCTTGGTTCTACGCTGGGTAATCTGGAGAGAATTGTGCGGAGTG
ATTGGAACGGTACCGAGGAGAGTATGCAAACGTTCGGGTTGTATGACTGCG
AAAAGTGCAAGTGGTTACTGTTACCAGCCGAAAAGAAGCACGCATGGGCTG
TGGTTCTGGCAAGTGATGATACCACTCGCATAATCTTCCTCTCATATGACG
AATCTGGTTCTCCCATAATTGATAAGAGAAACTGGAAGCGATTTGCTGTTT
GCTCTGAGACCAAAGTCTATAGCGTAATTCGTAGTTTAGAGGTACTAAATA
AGGAAGCAATAGTCGACCCCGGGGTTCATATAACATTAGTTGACGGAGTGC
CGGGGTTGTGGAAAGACCGCCGAAATTATAGCGAGGGTCAATTGGAAACCG
ATCTAGTATTGACTCCCGGAGGGAGGCGGCTGCTATGATTAGGCGGAGGG
CCTGCGCCCTGCACAAGTCACCTGTGGCAACCAGTGACAACGTTAGAACTT
TCGATTCTTTTGTGATGAATAAGAAAATCTTCAAGTTTGACGCTGTCTATG
TTGACGAGGGTCTGATGGTCCATACGGGTTTACTTAATTTTGCGTTGAAGA
TCTCAGGTTGTAAAAAGGCCTTCGTCTTTGGTGATGCTAAGCAAATCCCGT

-continued

TTATAAACAGAGTCATGAATTTTGATTATCCTAAGGAGTTAAGAACTTTAA
TAGTCGATAATGTAGAGCGTAGGTATGTTACCCATAGGTGTCCTAGAGATG
TCACTAGTTTTCTTAATACTATTTACAAAGCCGCTGTCGCTACTACTAGTC
CGGTTGTACATTCTGTGAAGGCGATTAAAGTGTCAGGGGCCGGTATTCTGA
GGCCCGAGTTGACGAAGATCAAAGGAAAGATAATAACGTTTACTCAATCTG
ATAAGCAGTCCTTGATCAAGAGTGGGTACAATGACGTGAACACTGTGCATG
AAATTCAGGGAGAAACCTTTGAAGAGACGGCGGTTGTGCGTGCCACCCCGA
CTCCGATAGGTTTAATTGCCCGTGATTCACCACATGTACTAGTGGCCTTAA
CGAGGCACACTAAGGCAATGGTGTATTATACTGTTGTGTTCGATGCAGTTA
CAAGTATAATAGCGGATGTGGAAAAGGTCGACCAGTCGATCTTGACTATGT
TTGCTACCACTGTGCCTACCAAATAGCAATTAATGCAGAACTCACTGTATG
TCCATCGTAATATTTTCCTCCCTGTTAGTAAAACGGGGTTTTATACAGACA
TGCAGGAGTTCTATGATAGATGCCTTCCTGGGAATTCCTTCGTGCTGAATG
ATTTCGATGCCGTAACCATGCGGTTGAGGGACAACGAATTTAACCTACAAC
CTTGTAGGCTAACCTTAAGTAATTTAGATCCAGTACCCGCTTTGGTTAAGA
GTGAAGCGCAGAATTTTCTGATTCCCGTTTTGCGTACGGCCTGTGAAAGGC
CGCGCATTCCAGGTCTCCTTGAAAATCTTGTAGCTATGATAAAGAGGAATA
TGAATACTCCTGATCTAGCTGGGACTGTGGATATAACTAATATGTCGATTT
CTATAGTAGATAACTTCTTTTCTTTTGTTAGAGACGAGGTTTTGCTTG
ATCATTTAGATTGTGTTAGGGCTAGTTCCATTCAAAGTTTTTCTGATTGGT
TTTCGTGTCAGCCAACCTCGGCGGTTGGTCAATTAGCTAATTTCAATTTCA
TAGATTTGCCTGCCTTTGATACTTATATGCACATGATTAAGCGGCAGCCCA
AGAGTCGGTTGGATACTTCGATTCAGTCTGAATATCCGGCCTTGCAAACTA
TTGTTTATCACCCTAAAGTGGTAAATGCAGTTTTCGGTCCGGTTTTTAAGT
ATTTGACCACCAAGTTTCTTAGCATGGTAGATAGTTCTAAGTTTTTCTTTT
ACACTAGGAAAAAACCAGAAGATCTGCAGGAATTTTTCTCAGATCTCTCTT
CCCATTCTGATTATGAGATTCTTGAGCTGGATGTTTCTAAATATGACAAGT
CACAATCCGATTTCCATTTCTCTATTGAGATGGCAATTTGGGAAAAATTGG
GGCTGGACGATATTTTGGCTTGGATGTGGTCTATGGGTCACAAGAGAACTA
TACTGCAAGATTTCCAAGCCGGGATAAAGACGCTCATTTACTATCAACGGA
AGTCTGGTGATGTAACTACTTTCATAGGTAATACCTTTATTATCGCAGCGT
GTGTAGCTAGTATGTTGCCGTTAGACAAGTGTTTTAAAGCTAGTTTTTGTG
GTGATGATTCGCTGATCTACCTTCCTAAGGGTTTGGAGTATCCTGATATAC
AGGCTACTGCCAACTTGGTTTGGAATTTTGAGGCGAAACTTTTCCGAAAGA
AGTATGGTTACTTCTGTGGGAAGTATATAATTCACCATGCCAACGGCTGTA
TTGTTTACCCTGACCCTTTAAAATTAATTAGTAAATTAGGTAATAAGAGTC
TTGTAGGGTATGAGCATGTTGAGGAGTTTCGTATATCTCCTCGACGTCG
CTCATAGTTTGTTTAATGGTGCTTATTTCCATTTACTCGACGATGCAATCC
ACGAATTATTTCCTAACGCTGGGGGTTGCAGTTTTGTAATTAATTGTTTGT
GCAAGTATTTGAGTGATAAGCACCTTTTCCGTAGTCTTTATATAGATGTCT

-continued
```
CTAAGTAAGGTGTCGGTCGAGAACTCATTGAAACCCGAGAAGTTTGTTAAA

ATCTCTTGGGTCGATAAGTTGCTCCCTAACTATTTTTCCATTCTTAAGTAT

TTATCTATAACTGACTTTAGCGTAGTTAAAGCTCAGAGCTATGAATCCCTC

GTGCCTGTCAAGTTGTTGCGTGGTGTTGATCTTACAAAACACCTTTATGTC

ACATTGTTGGGCGTTGTGGTTTCTGGTGTATGGAACGTACCGGAATCCTGT

AGGGGTGGTGCTACTGTTGCTCTGGTTGACACAAGGATGCATTCTGTTGCA

GAGGGAACTATATGCAAATTTTCAGCTCCCGCCACCGTCCGCGAATTCTCT

GTTAGGTTCATACCTAACTATTCTGTCGTGGCTGCGGATGCCCTTCGCGAT

CCTTGGTCTTTATTTGTGAGACTCTCTAATGTAGGGATTAAAGATGGTTTC

CATCCTTTGACCTTAGAGGTCGCTTGTTTAGTCGCTACAACTAACTCTATT

ATCAAAAAGGGTCTTAGAGCTTCTGTAGTCGAGTCTGTCGTCTCTTCCGAT

CAGTCCATTGTCCTAGATTCTTTATCCGAGAAAGTTGAACCTTTCTTTGAT

AAAGTTCCTATTTCGGCGGCTGTGATGGCAAGAGACCCCAGTTATAGGTCT

AGGTCGCAGTCTGTCGGTGGTCGTGGTAAGCGGCATTCTAAACCTCCAAAT

CGGAGGTTGGACTCTGCTTCTGAAGAGTCCAGTTCTGTTTCTTTCGAAGAT

GGCTTACAATCCGATCACACCTAGCAAACTTATTGCGTTTAGTGCTTCTTA

TGTTCCCGTCAGGACTTTACTTAATTTTCTAGTTGCTTCACAAGGTACCGC

CTTCCAGACTCAAGCGGGAAGAGATTCTTTCCGCGAGTCCCTGTCTGCGTT

ACCCTCGTCTGTCGTAGATATTAATTCTAGGTTCCCAAATGCGGGTTTTTA

CGCTTTCCTCAACGGTCCTGTGTTGAGGCCTATCTTCGTTTCGCTTCTTAG

CTCTACGGATACGCGTAATAGGGTCATTGAGGTTGTAGATCCTAGCAATCC

TACGACTGCTGAGTCGCTTAACGCTGTAAAGCGTACTGATGACGCATCTAC

GGCCGCTAGGGCTGAAATAGATAATTTAATAGAGTCTATTTCTAAGGGTTT

TGATGTTTATGATAGGGCTTCATTTGAAGCCGCGTTTTCGGTAGTCTGGTC

AGAGGCTACCACCTCGAAAGCTTAGCTTCGAGGGTCTTCTGATGGTGGTGC

ACACCAAAGTGCATAGTGCTTTCCCGTTCACTTAAATCGAACGGTTTGCTC

ATTGGTTTGCGGAAACCTCTCACGTGTGGCGTTGAAGTTTCTATGGGCAGT

AATTCTGCAAGGGGTTCGAATCCCCCTTTCCCCGGGTAGGGCCCA.
```

The cDNA genome sequence of the attenuated CGMMV strain ONAL-2 differs from the cDNA genome sequence of the wild type CGMMV Ontario strain (SEQ ID NO:18) at least in that the nucleotide at position 4969 of SEQ ID NO:58 is A.

The 186 kDa protein encoded by the attenuated CGMMV strain ONAL-2 has the following sequence.

(SEQ ID NO: 59)
```
MANINEQINNQRDAAASGRNNLVSQLASKRVYDEAVRSLDHQDRRPKMNFS

RVVSTEHTRLVTDAYPEFSISFTATKNSVHSLAGGLRLLELEYMMMQVPYG

SPCYDIGGNYTQHLFKGRSYVHCCNPCLDLKDVARNVMYNDMVTQHVQRHK

GSGGCRPLPTFQIDAFRRYDNSPCAVTCSDVFQECSYDFGSGRDNHAVSLH

SIYDIPYSSIGPALHRKNVRVCYAAFHFSEALLLGSPVGNLNSIGAQFRVD

GDDVHFLFSEESTLHYTHSLENIKLIVMRTYFPADDRYVYIKEFMVKRVDT

FFFRLVRADTHMLHKSVGHYSKSKSEYFALNIPPIFQDKATFSVWFPEAKR

KVLIPKFELSRFLSGNVKISRMLVDADFVHTIINHISTYDNKALVWKNVQS

FVESIRSRVIVNGVSVKSEWNVPVDQLTDISFSIFLLVKVRKVQIELMSDK

VVIEARGLLRRFADSLKSAVEGLGDCVYDALVQTGWFDTSSDELKVLLPEP

FMTFSDYLEGMYEADAKIERESVSELLASGDDLFKKIDEIRNNYSGVEFDV

EKFQEFCKELNVNPMLIGHVIEAIFSQKAGVTVTGLGTLSPEMGASVALSN

TSVDTCEDMDVTEDMEDIVLMADKSHSYMSPEMARWADVKYDNNKGGLVEY

KVGTSMTLPATWAEKGKAVLPLSGICVRKPQFSKPLDEEDDLRLSNMNFFK

VSDLKLICKTITPVVYTGTIRERQMKNYIDYLSASLGSTLGNLERIVRSDW

NGTEESMQTFGLYDCEKCKWLLLPAEKKHAWAVVLASDDTTRIIFLSYDES

GSPIIDKRNWKRFAVCSETKVYSVIRSLEVLNKEAIVDPGVHITLVDGVPG

CGKTAEHARVNWKTDLVLTPGREAAAMIRRRACALHKSPVATSDNVRTFDS

FVMNKKIFKFDAVYVDEGLMVHTGLLNFALKISGCKKAFVFGDAKQIPFIN

RVMNFDYPKELRTLIVDNVERRYVTHRCPRDVTSFLNTIYKAAVATTSPVV

HSVKAIKVSGAGILRPELTKIKGKIITFTQSDKQSLIKSGYNDVNTVHEIQ

GETFEETAVVRATPTPIGLIARDSPHVLVALTRETKAMVYYTVVFDAVTSI

IADVEKVDQSILTMFATTVPTKXQLMQNSLYVHRNIFLPVSKTGFYTDMQE

FYDRCLPGNSFVLNDFDAVTMRLRDNEFNLQPCRLTLSNLDPVPALVKSEA

QNFLIPVLRTACERPRIPGLLENLVAMIKRNMNTPDLAGTVDITNMSISIV

DNFFSSFVRDEVLLDHLDCVRASSIQSFSDWFSCQPTSAVGQLANFNFIDL

PAFDTYMHMIKRQPKSRLDTSIQSEYPALQTIVYHPKVVNAVFGPVFKYLT

TKFLSMVDSSKFFFYTRKKPEDLQEFFSDLSSHSDYEILELDVSKYDKSQS

DFHFSIEMAIWEKLGLDDILAWMWSMGHKRTILQDFQAGIKTLIYYQRKSG

DVTTFIGNTFIIAACVASMLPLDKCFKASFCGDDSLIYLPKGLEYPDIQAT

ANLVWNFEAKLFRKKYGYFCGKYIIHHANGCIVYPDPLKLISKLGNKSLVG

YEHVEEFRISLLDVAHSLFNGAYFHLLDDAIHELFPNAGGCSFVINCLCKY

LSDKHLFRSLYIDVSK.
```

The 186 kDa protein encoded by the attenuated CGMMV strain ONAL-2 differs from the 186 kDa protein encoded by the wild type CGMMV Ontario strain (SEQ ID NO:64) at least in that position 1637 of SEQ ID NO:59 is histidine (H, His).

Mutant CGMMV Ontario Strain ONBM-32

Directed mutation of the cDNA genome of the cloned CGMMV Ontario strain (Example 1) was carried out as described above to introduce mutations corresponding to those induced in the cDNA genome of the cloned CGMMV Ontario strain mutants ONBM, ONAL-1 and ONAL-2 (c.315G>A; c.1498A>G; c.1660C>T; c.3334C>T c.3430C>T; c.3528A>G; c.4144C>T; c.4248C>T; c.4969G>A; and c.6228C>T). These mutations resulted in amino acid substitutions in the encoded viral proteins (G86S, E480G, S534F, A1092V and A1124V in the 129 kDa protein; G86S, E480G, S534F, A1092V, A1124V, N1157D, P1362L, P1397S and R1637H in the 186 kDa protein; and A156V in the coat protein). The resulting mutant CGMMV strain was designated Ontario strain ONBM-32.

The cDNA genome sequence of CGMMV strain ONBM-32 is shown below.

(SEQ ID NO: 60)
GTTTTAATTTTTAAAATTAAACAAACAACAACAACAACAACAAACAATTTA

AAACAACAATGGCAAACATTAATGAACAAATCAACAACCAACGCGACGCCG

CGGCCAGCGGGAGAAACAATCTCGTTAGCCAATTGGCGTCAAAAAGGGTGT

ATGACGAGGCTGTTCGCTCGTTGGATCATCAAGACAGACGCCCAAAAATGA

ACTTTTCTCGTGTGGTCAGCACAGAGCACACCAGGCTTGTAACTGATGCGT

ATCCGGAGTTTTCGATTAGCTTTACCGCCACCAAGAACTCTGTACACTCCC

TTGCGGGTAGTCTGAGGCTCCTTGAACTGGAATATATGATGATGCAAGTGC

CCTACGGCTCACCTTGTTATGATATCGGCGGTAACTATACGCAGCACTTGT

TCAAAGGTAGATCATATGTGCATTGCTGCAATCCGTGCCTGGATCTTAAAG

ATGTTGCGAGGAACGTGATGTATAACGATATGGTCACACAACATGTACAGA

GGCACAAGGGATCTGGCGGGTGCAGACCTCTTCCAACTTTTCAGATAGATG

CATTCAGGAGGTACGATAATTCTCCCTGTGCGGTCACCTGTTCAGACGTTT

TCCAAGAGTGTTCCTATGATTTTGGGAGCGGTAGGGATAATCATGCAGTCT

CGCTGCATTCAATCTACGATATCCCTTATTCTTCGATCGGACCTGCTCTTC

ATAGGAAGAACGTGCGAGTTTGTTATGCAGCCTTTCACTTCTCGGAGGCAT

TGCTTTTAGGTTCACCTGTAGGTAATTTAAATAGTATTGGGGCTCAGTTTA

GGGTCGATGGTGATGATGTGCATTTTCTTTTAGTGAAGAGTCTACTTTGC

ATTATACTCATAGTTTAGAAAATATCAAATTAATTGTGATGCGTACTTATT

TTCCTGCTGATGATAGGTACGTGTATATTAAGGAGTTTATGGTCAAGCGTG

TGGATACTTTCTTCTTTAGGTTGGTCAGAGCAGACACACATATGCTTCATA

AATCTGTGGGCACTATTCAAAATCGAAATCTGAGTACTTTGCGCTGAATA

CCCCTCCGATCTTCCAAGACAAAGCCACGTTTTCTGTGTGGTTTCCTGAGG

CGAAGCGTAAGGTGTTGATACCCAAGTTTGAACTTTCAAGATTCCTTTCTG

GGAATGTGAAAATCTCTAGGATGCTTGTCGATGCTGATTTCGTCCATACCA

TTATTAATCACATTAGCACGTATGATAATAAGGCCTTAGTGTGGAAGAATG

TTCAGTCCTTTGTGGAATCTATACGCTCAAGAGTAATTGTAAACGGAGTTT

CGGTGAAATCTGAATGGAACGTACCGGTTGATCAGCTCACTGATATCTCGT

TCTCGATATTCCTTCTCGTGAAGGTTAGGAAGGTACAGATCGAGTTAATGT

CTGATAAAGTTGTAATCGAGGCGAGGGCTTGCTCCGGAGGTTCGCAGACA

GTCTTAAATCCGCCGTAGGAGGACTAGGTGATTGCGTCTATGATGCTCTAG

TTCAAACCGGCTGGTTTGATACCTCTAGCGACGAACTGAAAGTTTTGCTAC

CTGAACCGTTTATGACCTTTTCGGATTATCTTGAAGGGATGTACGAGGCAG

ATGCAAAGATCGAGAGAGAGAGTGTCTTTGAGTTGCTCGCTTCCGGTGACG

ATTTGTTCAAGAAAATCGATGAGATAAGAAACAATTACAGTGGAGTCGAAT

TTGATGTAGAGAAATTCCAGGAATTTTGCAAGGAACTGAATGTTAATCCTA

TGCTAATTGGCCATGTTATCGAAGCTATTTTTTCGCAGAAAGCTGGGGTGA

CAGTAACGGGTCTGGGTACCCTCTCTCCTGAGATGGGTGCTTCTGTTGCGT

TATCCAATACCTCTGTAGATACATGTGAAGATATGGATGTAACTGAAGATA

TGGAGGATATAGTGTTGATGGCGGACAAGAGTCATTCTTACATGTCCCAG

AAATGGCGAGATGGGCTGATGTAAAATACGACAACAATAAAGGGGCCTGG

TCGAATACAAAGTCGGAACCTCGATGACTTTACCTGCCACCTGGGCAGAGA

AGGGTAAGGCTGTCTTACCGTTGTCGGGGATCTGTGTGAGGAAACCCCAAT

TTTCGAAGCCGCTTGATGAGGAAGACGACTTGAGGTTATCAAACATGAATT

TCTTTAAGGTGAGCGATCTGAAGTTGAAGAAAACTATCACTCCAGTTGTTT

ACACTGGGACCATTCGAGAGAGGCAAATGAAGAATTATATTGATTACTTAT

CGGCCTCTCTTGGTTCTACGCTGGGTAATCTGGAGAGAATTGTGCGGAGTG

ATTGGAACGGTACCGAGGAGAGTATGCAAACGTTCGGGTTGTATGACTGCG

AAAAGTGCAAGTGGTTACTGTTACCAGCCGAAAAGAAGCACGCATGGGCTG

TGGTTCTGGCAAGTGATGATACCACTCGCATAATCTTCCTCTCATATGACG

AATCTGGTTCTCCCATAATTGATAAGAGAAACTGGAAGCGATTTGCTGTTT

GCTCTGAGACCAAAGTCTATAGCGTAATTCGTAGTTTAGAGGTACTAAATA

AGGAAGCAATAGTCGACCCCGGGGTTCATATAACATTAGTTGACGGAGTGC

CGGGTTGTGGAAAGACCGCCGAAATTATAGCGAGGGTCAATTGGAAAACCG

ATCTAGTATTGACTCCCGGGAGGGAGGCGGCTGCTATGATTAGGCGGAGGG

CCTGCGCCCTGCACAAGTCACCTGTGGCAACCAGTGACAACGTTAGAACTT

TCGATTCTTTTGTGATGAATAAGAAAATCTTCAAGTTTGACGCTGTCTATG

TTGACGAGGGTCTGATGGTCCATACGGGTTTACTTAATTTTGCGTTGAAGA

TCTCAGGTTGTAAAAAGGCCTTCGTCTTTGGTGATGCTAAGCAAATCCCGT

TTATAAACAGAGTCATGAATTTTGATTATCCTAAGGAGTTAAGAACTTTAA

TAGTCGATAATGTAGAGCGTAGGTATGTTACCCATAGGTGTCCTAGAGATG

TCACTAGTTTTCTTAATACTATTTACAAAGCCGCTGTCGCTACTACTAGTC

CGGTTGTACATTCTGTGAAGGCGATTAAAGTGTCAGGGGCCGGTATTCTGA

GGCCCGAGTTGACGAAGATCAAAGGAAAGATAATAACGTTTACTCAATCTG

ATAAGCAGTCCTTGATCAAGAGTGGGTACAATGACGTGAACACTGTGCATG

AAATTCAGGGAGAAACCTTTGAAGAGACGGCGGTTGTGCGTGCCACCCCGA

CTCCGATAGGTTTAATTGTCCGTGATTCACCACATGTACTAGTGGCCTTAA

CGAGGCACACTAAGGCAATGGTGTATTATACTGTTGTGTTCGATGCAGTTA

CAAGTATAATAGTGGATGTGGAAAAGGTCGACCAGTCGATCTTGACTATGT

TTGCTACCACTGTGCCTACCAAATAGCAATTAATGCAGAACTCACTGTATG

TCCATCGTGATATTTTCCTCCCTGTTAGTAAAACGGGGTTTTATACAGACA

TGCAGGAGTTCTATGATAGATGCCTTCCTGGGAATTCCTTCGTGCTGAATG

ATTTCGATGCCGTAACCATGCGGTTGAGGGACAACGAATTTAACCTACAAC

CTTGTAGGCTAACCTTAAGTAATTTAGATCCAGTACCCGCTTTGGTTAAGA

GTGAAGCGCAGAATTTTCTGATTCCCGTTTTGCGTACGGCCTGTGAAAGGC

CGCGCATTCCAGGTCTCCTTGAAAATCTTGTAGCTATGATAAAGAGGAATA

TGAATACTCCTGATCTAGCTGGGACTGTGGATATAACTAATATGTCGATTT

CTATAGTAGATAACTTCTTTTCTTCTTTTGTTAGAGACGAGGTTTTGCTTG

ATCATTTAGATTGTGTTAGGGCTAGTTCCATTCAAAGTTTTTCTGATTGGT

TTTCGTGTCAGCCAACCTCGGCGGTTGGTCAATTAGCTAATTTCAATTTCA

-continued

TAGATTTGCCTGCCTTTGATACTTATATGCACATGATTAAGCGGCAGCCCA
AGAGTCGGTTGGATACTTCGATTCAGTCTGAATATCCGGCCTTGCAAACTA
TTGTTTATCACCTTAAAGTGGTAAATGCAGTTTTCGGTCCGGTTTTTAAGT
ATTTGACCACCAAGTTTCTTAGCATGGTAGATAGTTCTAAGTTTTTCTTTT
ACACTAGGAAAAAATCAGAAGATCTGCAGGAATTTTTCTCAGATCTCTCTT
CCCATTCTGATTATGAGATTCTTGAGCTGGATGTTTCTAAATATGACAAGT
CACAATCCGATTTCCATTTCTCTATTGAGATGGCAATTTGGGAAAAATTGG
GGCTGGACGATATTTTGGCTTGGATGTGGTCTATGGGTCACAAGAGAACTA
TACTGCAAGATTTCCAAGCCGGGATAAAGACGCTCATTTACTATCAACGGA
AGTCTGGTGATGTAACTACTTTCATAGGTAATACCTTTATTATCGCAGCGT
GTGTAGCTAGTATGTTGCCGTTAGACAAGTGTTTTAAAGCTAGTTTTTGTG
GTGATGATTCGCTGATCTACCTTCCTAAGGGTTTGGAGTATCCTGATATAC
AGGCTACTGCCAACTTGGTTTGGAATTTTGAGGCGAAACTTTTCCGAAAGA
AGTATGGTTACTTCTGTGGGAAGTATATAATTCACCATGCCAACGGCTGTA
TTGTTTACCCTGACCCTTTAAAATTAATTAGTAAATTAGGTAATAAGAGTC
TTGTAGGGTATGAGCATGTTGAGGAGTTTCGTATATCTCTCCTCGACGTCG
CTCATAGTTTGTTTAATGGTGCTTATTTCCATTTACTCGACGATGCAATCC
ACGAATTATTTCCTAACGCTGGGGGTTGCAGTTTTGTAATTAATTGTTTGT
GCAAGTATTTGAGTGATAAGCACCTTTTCCGTAGTCTTTATATAGATGTCT
CTAAGTAAGGTGTCGGTCGAGAACTCATTGAAACCCGAGAAGTTTGTTAAA
ATCTCTTGGGTCGATAAGTTGCTCCCTAACTATTTTTCCATTCTTAAGTAT
TTATCTATAACTGACTTTAGCGTAGTTAAAGCTCAGAGCTATGAATCCCTC
GTGCCTGTCAAGTTGTTGCGTGGTGTTGATCTTACAAAACACCTTTATGTC
ACATTGTTGGGCGTTGTGGTTTCTGGTGTATGGAACGTACCGGAATCCTGT
AGGGGTGGTGCTACTGTTGCTCTGGTTGACACAAGGATGCATTCTGTTGCA
GAGGGAACTATATGCAAATTTTCAGCTCCCGCCACCGTCCGCGAATTCTCT
GTTAGGTTCATACCTAACTATTCTGTCGTGGCTGCGGATGCCCTTCGCGAT
CCTTGGTCTTTATTTGTGAGACTCTCTAATGTAGGGATTAAAGATGGTTTC
CATCCTTTGACCTTAGAGGTCGCTTGTTTAGTCGCTACAACTAACTCTATT
ATCAAAAGGGTCTTAGAGCTTCTGTAGTCGAGTCTGTCGTCTCTTCCGAT
CAGTCCATTGTCCTAGATTCTTTATCCGAGAAAGTTGAACCTTTCTTTGAT
AAAGTTCCTATTTCGGCGGCTGTGATGGCAAGAGACCCCAGTTATAGGTCT
AGGTCGCAGTCTGTCGGTGGTCGTGGTAAGCGGCATTCTAAACCTCCAAAT
CGGAGGTTGGACTCTGCTTCTGAAGAGTCCAGTTCTGTTTCTTTCGAAGAT
GGCTTACAATCCGATCACACCTAGCAAACTTATTGCGTTTAGTGCTTCTTA
TGTTCCCGTCAGGACTTTACTTAATTTTCTAGTTGCTTCACAAGGTACCGC
CTTCCAGACTCAAGCGGGAAGAGATTCTTTCCGCGAGTCCCTGTCTGCGTT
ACCCTCGTCTGTCGTAGATATTAATTCTAGGTTCCCAAATGCGGGTTTTTA
CGCTTTCCTCAACGGTCCTGTGTTGAGGCCTATCTTCGTTTCGCTTCTTAG
CTCTACGGATACGCGTAATAGGGTCATTGAGGTTGTAGATCCTAGCAATCC

-continued

TACGACTGCTGAGTCGCTTAACGCTGTAAAGCGTACTGATGACGCATCTAC
GGCCGCTAGGGCTGAAATAGATAATTTAATAGAGTCTATTTCTAAGGGTTT
TGATGTTTATGATAGGGCTTCATTTGAAGCCGCGTTTTCGGTAGTCTGGTC
AGAGGTTACCACCTCGAAAGCTTAGCTTCGAGGGTCTTCTGATGGTGGTGC
ACACCAAAGTGCATAGTGCTTTCCCGTTCACTTAAATCGAACGGTTTGCTC
ATTGGTTTGCGGAAACCTCTCACGTGTGGCGTTGAAGTTTCTATGGGCAGT
AATTCTGCAAGGGGTTCGAATCCCCCCTTTCCCGGGTAGGGCCCA.

The cDNA genome sequence of the attenuated CGMMV strain ONBM-32 differs from the cDNA genome sequence of the wild type CGMMV Ontario strain (SEQ ID NO:18) at least in that:

the nucleotide at position 315 of SEQ ID NO:60 is A;
the nucleotide at position 1498 of SEQ ID NO:60 is G;
the nucleotide at position 1660 of SEQ ID NO:60 is T;
the nucleotide at position 3334 of SEQ ID NO:60 is T;
the nucleotide at position 3430 of SEQ ID NO:60 is T;
the nucleotide at position 3528 of SEQ ID NO:60 is G;
the nucleotide at position 4144 of SEQ ID NO:60 is T;
the nucleotide at position 4248 of SEQ ID NO:60 is T;
the nucleotide at position 4969 of SEQ ID NO:60 is A; and
the nucleotide at position 6228 of SEQ ID NO:60 is T.

The 129 kDa protein encoded by the attenuated CGMMV strain ONBM-32 has the following sequence.

(SEQ ID NO: 61)
MANINEQINNQRDAAASGRNNLVSQLASKRVYDEAVRSLDHQDRRPKMNFS
RVVSTEHTRLVTDAYPEFSISFTATKNSVHSLAGSLRLLELEYMMMQVPYG
SPCYDIGGNYTQHLFKGRSYVHCCNPCLDLKDVARNVMYNDMVTQHVQRHK
GSGGCRPLPTFQIDAFRRYDNSPCAVTCSDVFQECSYDFGSGRDNHAVSLH
SIYDIPYSSIGPALHRKNVRVCYAAFHFSEALLLGSPVGNLNSIGAQFRVD
GDDVHFLFSEESTLHYTHSLENIKLIVMRTYFPADDRYVYIKEFMVKRVDT
FFFRLVRADTHMLHKSVGHYSKSKSEYFALNTPPIFQDKATFSVWFPEAKR
KVLIPKFELSRFLSGNVKISRMLVDADFVHTIINHISTYDNKALVWKNVQS
FVESIRSRVIVNGVSVKSEWNVPVDQLTDISFSIPLLVKVRKVQIELMSDK
VVIEARGLLRRFADSLKSAVGGLGDCVYDALVQTGWFDTSSDELKVLLPEP
FMTFSDYLEGMYEADAKIERESVFELLASGDDLFKKIDEIRNNYSGVEFDV
EKFQEFCKELNVNPMLIGHVIEAIFSQKAGVTVTGLGTLSPEMGASVALSN
TSVDTCEDMDVTEDMEDIVLMADKSHSYMSPEMARWADVKYDNNKGGLVEY
KVGTSMTLPATWAEKGKAVLPLSGICVRKPQFSKPLDEEDDLRLSNMNFFK
VSDLKLKKTITPVVYTGTIRERQMKNYIDYLSASLGSTLGNLERIVRSDWN
GTEESMQTFGLYDCEKCKWLLLPAEKKHAWAVVLASDDTTRIIFLSYDESG
SPIIDKRNWKRFAVCSETKVYSVIRSLEVLNKEAIVDPGVHITLVDGVPGC
GKTAEHARVNWKTDLVLTPGREAAAMIRRRACALHKSPVATSDNVRTFDSF
VMNKKIFKFDAVYVDEGLMVHTGLLNFALKISGCKKAFVFGDAKQIPFINR
VMNFDYPKELRTLIVDNVERRYVTHRCPRDVTSFLNTIYKAAVATTSPVVH
SVKAIKVSGAGILRPELTKIKGKIITFTQSDKQSLIKSGYNDVNTVHEIQG

-continued

ETFEETAVVRATPTPIGLIVRDSPHVLVALTRHTKAMVYYTVVFDAVTSII

VDVEKVDQSILTMFATTVPTK

The 129 kDa protein encoded by the attenuated CGMMV strain ONBM-32 differs from the 129 kDa protein encoded by the wild type CGMMV Ontario strain (SEQ ID NO:63) at least in that:
position 86 of SEQ ID NO:61 is serine (S, Ser);
position 480 of SEQ ID NO:61 is glycine (G, Gly);
position 534 of SEQ ID NO:61 is phenylalanine (F, Phe);
position 1092 of SEQ ID NO:61 is valine (V, Val); and
position 1124 of SEQ ID NO:61 is valine (V, Val).

The 186 kDa protein encoded by the attenuated CGMMV strain ONBM-32 has the following sequence.

(SEQ ID NO: 62)
MANINEQINNQRDAAASGRNNLVSQLASKRVYDEAVRSLDHQDRRPKMNFS

RVVSTEHTRLVTDAYPEFSISFTATKNSVHSLAGSLRLLELEYMMMQVPYG

SPCYDIGGNYTQHLFKGRSYVHCCNPCLDLKDVARNVMYNDMVTQHVQRHK

GSGGCRPLPTFQIDAFRRYDNSPCAVTCSDVFQECSYDFGSGRDNHAVSLH

SIYDIPYSSIGPALHRKNVRVCYAAFHFSEALLLGSPVGNLNSIGAQFRVD

GDDVHFLFSEESTLHYTHSLENIKLIVMRTYFPADDRYVYIKEFMVKRVDT

FFFRLVRADTHMLHKSVGHYSKSKSEYFALNTPPIFQDKATFSVWFPEAKR

KVLIPKFELSRFLSGNVKISRMLVDADFVHTIINHISTYDNKALVWKNVQS

FVESIRSRVIVNGVSVKSEWNVPVDQLTDISFSIFLLVKVRKVQIELMSDK

VVIEARGLLRRFADSLKSAVGGLGDCVYDALVQTGWFDTSSDELKVLLPEP

FMTFSDYLEGMYEADAKIEREVFELLASGDDLFKKIDEIRNNYSGVEFDVE

KFQEFCKELNVNPMLIGHVIEAIFSQKAGVTVTGLGTLSPEMGASVALSNT

SVDTCEDMDVTEDMEDIVLMADKSHSYMSPEMARWADVKYDNNKGGLVEYK

VGTSMTLPATWAEKGKAVLPLSGICVRKPQFSKPLDEEDDLRLSNMNFFKV

SDLKLKKTITPVVYTGTIREREMQMKNYIDYLSASLGSTLGNLERIVRSDWNG

TEESMQTFGLYDCEKCKWLLLPAEKKHAWAVVLASDDTTRIIFLSYDESGS

PIIDKRNWKRFAVCSETKVYSVIRSLEVLNKEAIVDPGVHITLVDGVPGCG

KTAEIIARVNWKTDLVLTPGREAAAMIRRRACALHKSPVATSDNVRTFDSF

VMNKKIFKFDAVYVDEGLMVHTGLLNFALKISGCKKAFVFGDAKQIPFINR

VMNFDYPKELRTLIVDNVERRYVTHRCPRDVTSFLNTIYKAAVATTSPVVH

SVKAIKVSGAGILRPELTKIKGKIITFTQSDKQSLIKSGYNDVNTVHEIQG

ETFEETAVVRATPTPIGLIVRDSPHVLVALTRHTKAMVYYTVVFDAVTSII

VDVEKVDQSILTMFATTVPTKXQLMQNSLYVHRDIFLPVSKTGFYTDMQEF

YDRCLPGNSFVLNDFDAVTMRLRDNEFNLQPCRLTLSNLDPVPALVKSEAQ

NFLIPVLRTACERPRIPGLLENLVAMIKRNMNTPDLAGTVDITNMSISIVD

NFFSSFVRDEVLLDHLDCVRASSIQSFSDWFSCQPTSAVGQLANFNFIDLP

AFDTYMHMIKRQPKSRLDTSIQSEYPALQTIVYHLKVVNAVFGPVFKYLTT

KFLSMVDSSKFFFYTRKKSEDLQEFFSDLSSHSDYEILELDVSKYDKSQSD

FHFSIEMAIWEKLGLDDILAWMWSMGHKRTILQDFQAGIKTLIYYQRKSGD

VTTFIGNTFIIAACVASMLPLDKCFKASFCGDDSLIYLPKGLEYPDIQATA

-continued

NLVWNFEAKLFRKKYGYFCGKYIIHHANGCIVYPDPLKLISKLGNKSLVGY

EHVEEFRISLLDVAHSLFNGAYFHLLDDAIHELFPNAGGCSFVINCLCKYL

SDKHLFRSLYIDVSK.

The 186 kDa protein encoded by the attenuated CGMMV strain ONBM-32 differs from the 186 kDa protein encoded by the wild type CGMMV Ontario strain (SEQ ID NO:64) at least in that:
position 86 of SEQ ID NO:62 is serine (S, Ser);
position 480 of SEQ ID NO:62 is glycine (G, Gly);
position 534 of SEQ ID NO:62 is phenylalanine (F, Phe);
position 1092 of SEQ ID NO:62 is valine (V, Val);
position 1124 of SEQ ID NO:62 is valine (V, Val);
position 1157 of SEQ ID NO:62 is aspartic acid (D, Asp);
position 1362 of SEQ ID NO:62 is leucine (L, Leu);
position 1397 of SEQ ID NO:62 is serine (S, Ser); and
position 1637 of SEQ ID NO:62 is histidine (H, His).

The coat protein encoded by the attenuated CGMMV strain ONBM-32 has the sequence of SEQ ID NO:32 and differs from the coat protein encoded by the wild type CGMMV Ontario strain (SEQ ID NO:65) at least in that position 156 of SEQ ID NO:32 is valine (V, Val).

Figure 3A:
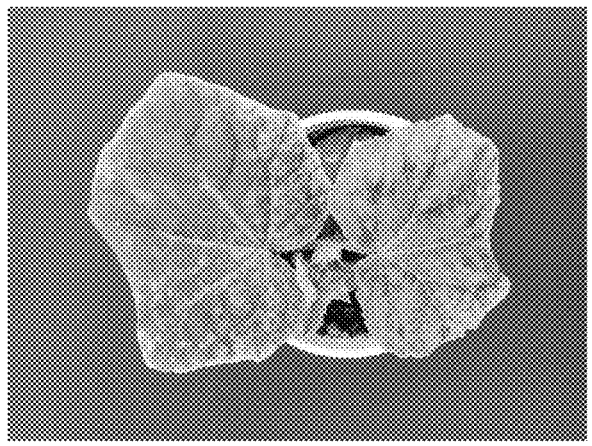
FIG. 3A is a photograph showing leaves of a cucumber plant infected with wild-type CGMMV Ontario strain and grown under laboratory conditions.
Figure 3B:
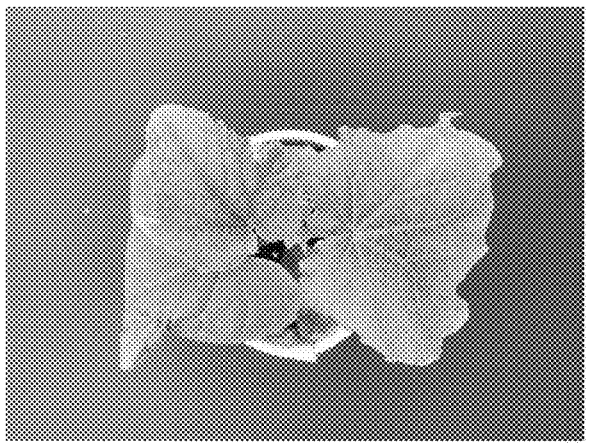
FIG. 3B is a photograph showing leaves of a healthy cucumber plant without CGMMV infection grown as a control under the laboratory conditions of FIG. 3A.
Figure 3C:
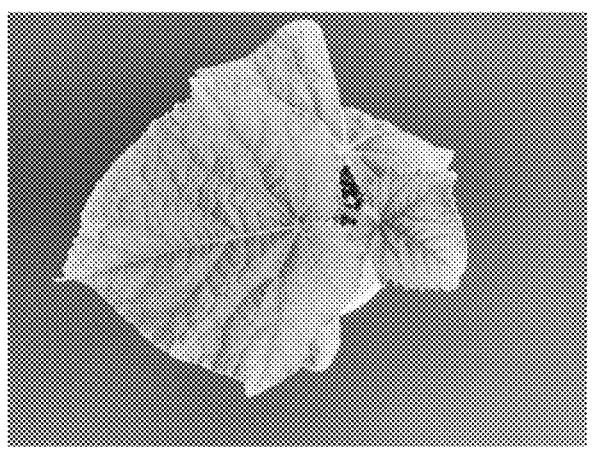
FIG. 3C is a photograph showing leaves of a cucumber plant exposed to an attenuated CGMMV strain according to the present invention (ONBM) and grown under the laboratory conditions of FIG. 3A.
Figure 3D:
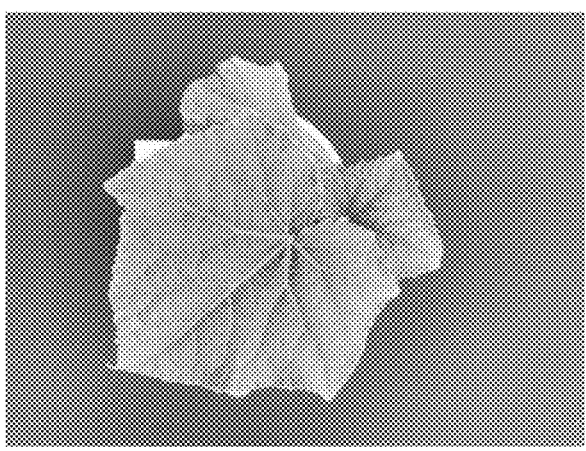
FIG. 3D is a photograph showing leaves of a cucumber plant exposed to another attenuated CGMMV strain according to the present invention (ONBM-2) and grown under the laboratory conditions of FIG. 3A.
Figure 3E:
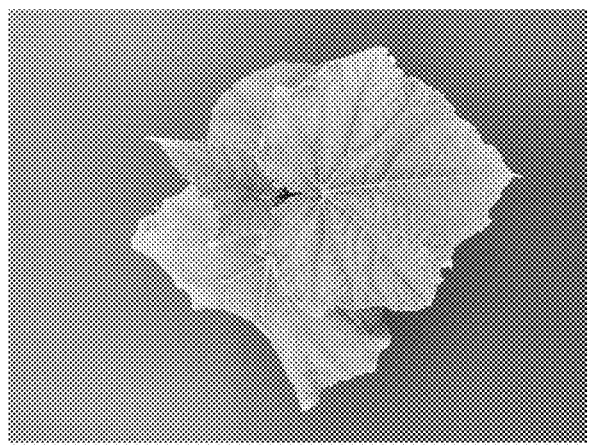
FIG. 3E is a photograph showing leaves of a cucumber plant exposed to yet another attenuated CGMMV strain according to the present invention (ONBM-3) and grown under the laboratory conditions of FIG. 3A.

Example 3: Inoculation of Cucumber Plants with the Attenuated CGMMV ONBM, ONBM-2 and ONBM-3 Strains The attenuated CGMMV Ontario strains ONBM, ONBM-2 and ONBM-3 were transformed into *Agrobacterium tumefaciens* strain EHA105 by electroporation and used to inoculate the cotyledon of 1-2 week old cucumber plants as described in Example 1. Two weeks after inoculation, plants were inspected for visible symptoms of CGMMV infection and leaf tissue was collected for detection of virus infection. The attenuated CGMMV Ontario strains ONBM, ONBM-2 and ONBM-3 were detected in leaf tissue by real-time TaqMan reverse-transcription PCR (Chen et al., Journal of Virological Methods (2008), 149: 326-329). As seen from the results shown in FIGS. 3A to 3E, no symptoms were induced by inoculation with ONBM (FIG. 3C), ONBM-2 (FIG. 3D) or ONBM-3 (FIG. 3E) while the typical green mottle and mosaic symptoms were induced by inoculation with wild-type CGMMV under laboratory greenhouse conditions (FIG. 3A). FIG. 3B shows leaves of a healthy cucumber plant grown as a control.

The attenuated CGMMV Ontario strains ONBM, ONBM-2 and ONBM-3 were tested for the protection of cucumber plants from infection by wild-type CGMMV. Seven day old cucumber seedlings were inoculated with CGMMV Ontario strains ONBM, ONBM-2 or ONBM-3 or were not inoculated, under laboratory greenhouse conditions as described in Example 1. Two weeks after inoculation, the plants were challenged with wild-type CGMMV Ontario strain. As seen from the results shown in FIG. 4A to 4E, no symptoms were observed 4 weeks after challenge with the wild-type CGMMV on plants inoculated with ONBM-2 (FIG. 4B) or ONBM-3 (FIG. 4C), and very mild or undetectable symptoms were observed 4 weeks after challenge with the wild-type CGMMV on plants inoculated with ONBM (FIG. 4A). In contrast, the typical green mottle and mosaic symptoms were observed in uninoculated plants challenged with wild-type CGMMV (FIG. 4D). FIG. 4E shows leaves of an uninoculated and unchallenged healthy cucumber plant (control).

Figure 5A:
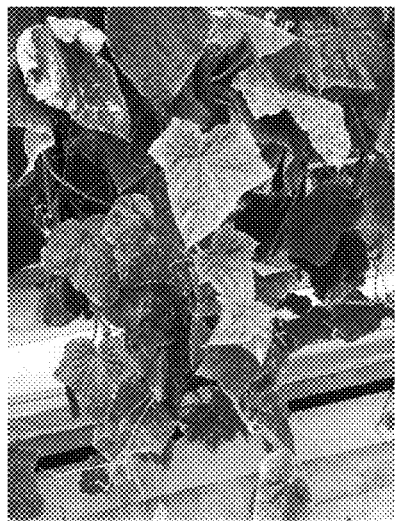
FIG. 5A is a photograph showing leaves of a cucumber plant grown in a commercial greenhouse and infected with a wild-type CGMMV Ontario strain.
Figure 5B:
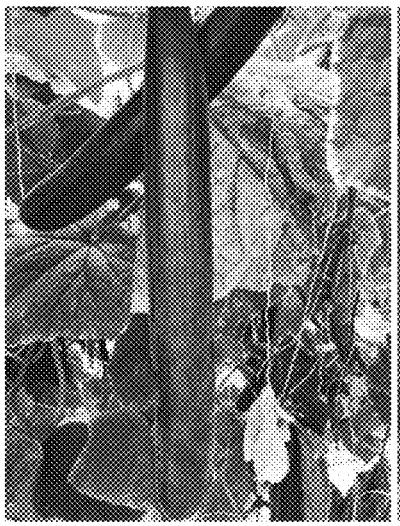
FIG. 5B is a photograph showing a mosaic pattern on fruit of a cucumber plant grown in the commercial greenhouse of FIG. 5A and infected with a wild-type CGMMV Ontario strain.
Figure 5C:
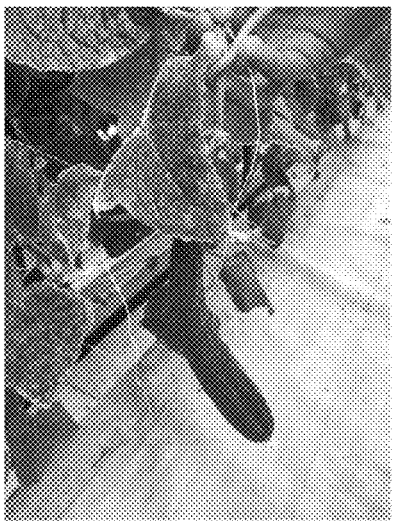
FIG. 5C is a photograph showing curling of fruit of a cucumber plant grown in the commercial greenhouse of FIG. 5A and infected with a wild-type CGMMV Ontario strain.
Figure 5D:
FIG. 5D is a photograph showing leaves and fruit of a cucumber plant exposed to an attenuated CGMMV strain according to the present invention (ONBM-2) and grown in the commercial greenhouse of FIG. 5A.
Figure 5E:
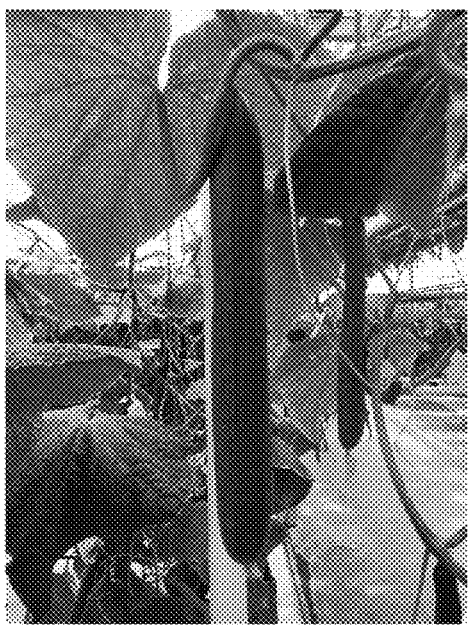
FIG. 5E is a photograph showing leaves and fruit of a cucumber plant exposed to another attenuated CGMMV strain according to the present invention (ONBM-3) and grown in the commercial greenhouse of FIG. 5A.
Figure 6A:
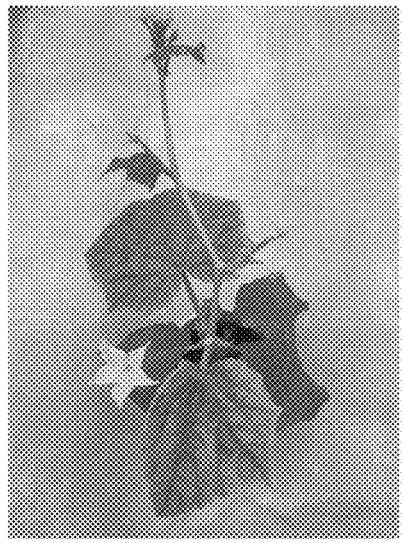
FIG. 6A is a photograph showing leaves of a cucumber plant exposed to another attenuated CGMMV strain according to the present invention (ONAL-1) and grown under laboratory conditions.
Figure 6B:
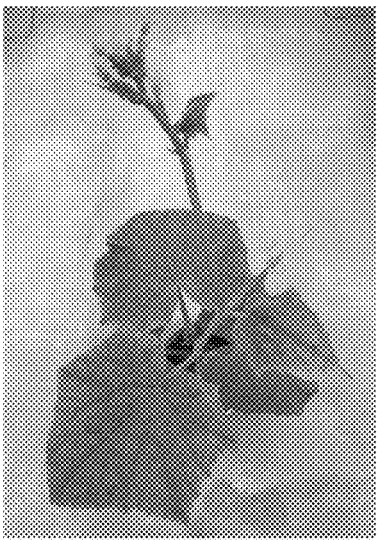
FIG. 6B is a photograph showing leaves of a cucumber plant exposed to another attenuated CGMMV strain according to the present invention (ONAL-2) and grown under the laboratory conditions of FIG. 6A.
Figure 6C:
FIG. 6C is a photograph showing leaves of a cucumber plant exposed to another attenuated CGMMV strain according to the present invention (ONBM-32) and grown under the laboratory conditions of FIG. 6A.
Figure 6D:
FIG. 6D is a photograph showing leaves of a cucumber plant exposed to the mutant CGMMV Ontario strain ONB and grown under the laboratory conditions of FIG. 6A.
Figure 6E:
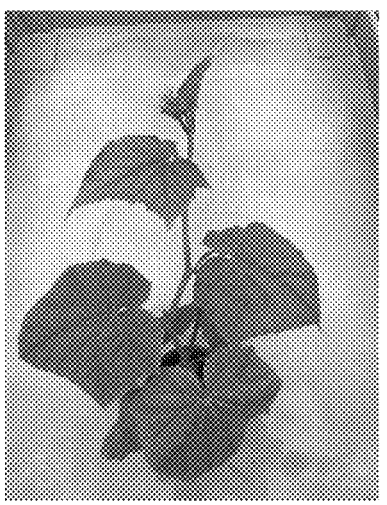
FIG. 6E is a photograph showing leaves of a healthy cucumber plant without CGMMV infection grown as a control under the laboratory conditions of FIG. 6A.
Figure 6F:
FIG. 6F is a photograph showing leaves of a cucumber plant infected with wild-type CGMMV Ontario strain and grown under the laboratory conditions of FIG. 6A.

The attenuated CGMMV Ontario strains ONBM-2 and ONBM-3 were tested for the protection of cucumber plants from natural infection by wild-type CGMMV under commercial greenhouse conditions. Cotyledons of 1-2 week old cucumber plants were inoculated with the strains ONBM-2 and ONBM-3 as described in Example 1. Uninoculated cucumber plants were used as a control. As seen from the results presented in FIGS. 5A to 5E, no visible symptoms were observed on the cucumber plants after inoculation with ONBM-2 or ONBM-3 for a period of 100 days (until the end of production) in a commercial greenhouse. In contrast, uninoculated plants showed symptoms of CGMMV infection of leaves, showing green mottle and mosaic symptoms (FIG. 5A), and CGMMV infection of fruits (FIG. 5B and FIG. 5C). The cucumber fruits produced from the cucumber plants inoculated with the attenuated strains ONBM-2 (FIG. 5D) or ONBM-3 (FIG. 5E) were healthy, while the uninoculated cucumber plants produced diseased and unmarketable cucumber fruits showing mosaic and soft (FIG. 5B) or curling (FIG. 5C) symptoms. In addition, over a harvest period of two months, the cucumber fruit yield was increased by 12.7% during the second month of harvest for plants treated with the attenuated CGMMV ONBM-3 strain compared with untreated cucumber plants exposed to natural CGMMV infection in commercial greenhouse conditions.

Example 4: Inoculation of Cucumber Plants with the Attenuated CGMMV ONAL-1, ONAL-2 and ONBM-32 Strains The attenuated CGMMV Ontario strains ONAL-1, ONAL-2, and ONBM-32 were transformed into *Agrobacterium tumefaciens* strain EHA105 by electroporation. *Agrobacterium tumefaciens* containing mutant CGMMV strains ONAL-1, ONAL-2, ONBM-32 and ONB (Example 2) were used to inoculate the cotyledon of 1-2 week old cucumber plants using the method described in Example 1. Two weeks after inoculation, plants were inspected for visible symptoms of CGMMV infection and leaf tissue was collected for detection of virus infection. The attenuated CGMMV Ontario strains ONAL-1, ONAL-2, ONBM-32 and ONB were detected in leaf tissue by real-time TaqMan reverse-transcription PCR (Chen et al., Journal of Virological Methods (2008), 149: 326-329).

As seen from the results shown in FIGS. 6A to 6F, plants inoculated with either mutant strains ONAL-1 (FIG. 6A) or ONAL-2 (FIG. 6B) under laboratory greenhouse conditions showed mild symptoms compared with plants inoculated with the wild-type CGMMV Ontario strain, which showed typical green mottle and mosaic symptoms (FIG. 6F). No symptoms were observed after inoculation with the mutant strain ONBM-32 (FIG. 6C). The symptoms observed after inoculation with mutant strain ONAL-2 (FIG. 6B) were milder than those observed after inoculation with mutant strain ONAL-1 (FIG. 6A), and milder than those observed after inoculation with mutant strain ONB (FIG. 6D). FIG. 1E shows leaves of a healthy cucumber plant grown as a control.

The embodiments described herein are intended to be illustrative of the present compositions and methods and are not intended to limit the scope of the present invention. Various modifications and changes consistent with the description as a whole and which are readily apparent to the person of skill in the art are intended to be included. The appended claims should not be limited by the specific embodiments set forth in the examples, but should be given the broadest interpretation consistent with the description as a whole.

What is claimed is:

1. A polydeoxyribonucleotide having a sequence functionally equivalent to a sequence of a genome of an attenuated strain of cucumber green mottle mosaic virus (CGMMV), wherein the sequence of the polydeoxyribonucleotide is a variant of SEQ ID NO:18 comprising at least one of the following options a), b) and c):
   a) A at the position corresponding to position 4969 of SEQ ID NO:18;
   b) T at the position corresponding to position 3334 of SEQ ID NO:18; and
   c) at least six nucleic acid bases selected from:
      A at the position corresponding to position 315 of SEQ ID NO:18;
      G at the position corresponding to position 1498 of SEQ ID NO:18;
      T at the position corresponding to position 1660 of SEQ ID NO:18;
      T at the position corresponding to position 3430 of SEQ ID NO:18;
      G at the position corresponding to position 3528 of SEQ ID NO:18;
      T at the position corresponding to position 4144 of SEQ ID NO:18;
      T at the position corresponding to position 4248 of SEQ ID NO:18; and
      T at the position corresponding to position 6228 of SEQ ID NO:18.

2. The polydeoxyribonucleotide according to claim 1, wherein the sequence of the polydeoxyribonucleotide comprises one or more of A at the position corresponding to position 4969 of SEQ ID NO:18 and T at the position corresponding to position 3334 of SEQ ID NO:18.

3. The polydeoxyribonucleotide according to claim 1, wherein the sequence of the polydeoxyribonucleotide comprises:
   A at the position corresponding to position 315 of SEQ ID NO:18;
   G at the position corresponding to position 1498 of SEQ ID NO:18;
   T at the position corresponding to position 1660 of SEQ ID NO:18;
   T at the position corresponding to position 3430 of SEQ ID NO:18;
   G at the position corresponding to position 3528 of SEQ ID NO:18;
   T at the position corresponding to position 4144 of SEQ ID NO:18;
   T at the position corresponding to position 4248 of SEQ ID NO:18; and
   T at the position corresponding to position 6228 of SEQ ID NO:18.

4. The polydeoxyribonucleotide according to claim 3, wherein the sequence of the polydeoxyribonucleotide comprises one or more of A at the position corresponding to position 4969 of SEQ ID NO:18 and T at the position corresponding to position 3334 of SEQ ID NO:18.

5. The polydeoxyribonucleotide according to claim 1, wherein the sequence of the polydeoxyribonucleotide is selected from SEQ ID NO:42, SEQ ID NO:45, SEQ ID NO:48, SEQ ID NO:53, SEQ ID NO:58, SEQ ID NO:60, and variants thereof.

6. The polydeoxyribonucleotide according to claim 1, wherein the sequence of the polydeoxyribonucleotide is selected from SEQ ID NO:42, SEQ ID NO:45, SEQ ID NO:48, SEQ ID NO:60, and variants thereof.

7. The polydeoxyribonucleotide according to claim 1, wherein the polydeoxyribonucleotide encodes one or more proteins selected from:
   a 129 kDa protein having an amino acid sequence selected from SEQ ID NO:43, SEQ ID NO:46, SEQ ID NO:49, SEQ ID NO:54, SEQ ID NO:61 and variants thereof;
   a 186 kDa protein having an amino acid sequence selected from SEQ ID NO:44, SEQ ID NO:47, SEQ ID NO:50, SEQ ID NO:55, SEQ ID NO:59, SEQ ID NO:62 and variants thereof; and
   a coat protein having an amino acid sequence selected from SEQ ID NO:32 and variants thereof.

8. A vector comprising the polydeoxyribonucleotide according to claim 1.

9. A genetically modified cell, wherein the cell expresses the polydeoxyribonucleotide according to claim 1.

10. The genetically modified cell according to claim 9, wherein the cell is a microorganism.

11. The genetically modified cell according to claim 9, wherein the cell is a plant cell.

12. A composition for preventing symptoms associated with infection by wild-type CGMMV in a plant or for increasing resistance of a plant to infection by wild-type CGMMV, wherein the composition comprises a genetically modified cell according to claim 9 and an agriculturally acceptable carrier.

13. A method for preventing symptoms associated with infection by wild-type CGMMV in a plant or for increasing resistance of a plant to infection by wild-type CGMMV, wherein the method comprises inoculating the plant with a genetically modified cell according to claim 9.

14. A method for preventing symptoms associated with infection by wild-type CGMMV in a plant or for increasing resistance of a plant to infection by wild-type CGMMV, wherein the method comprises inoculating the plant with a composition according to claim 12.

* * * * *

SEQUENCE LISTING

```
<160> NUMBER OF SEQ ID NOS: 65

<210> SEQ ID NO 1
<211> LENGTH: 87
<212> TYPE: DNA
<213> ORGANISM: Artificial Sequence
<220> FEATURE:
<223> OTHER INFORMATION: Primer

<400> SEQUENCE: 1
cggctcgagc ccgtttcgtc ctttagggac tcgtcagtgt actgatataa gtacagactg      60
ggcccctacc cggggaaagg ggggatt                                           87

<210> SEQ ID NO 2
<211> LENGTH: 45
<212> TYPE: DNA
<213> ORGANISM: Artificial Sequence
<220> FEATURE:
<223> OTHER INFORMATION: Primer

<400> SEQUENCE: 2
gttttaattt ttaaaattaa acaaacaaca acaacaacaa caaac                       45

<210> SEQ ID NO 3
<211> LENGTH: 37
<212> TYPE: DNA
<213> ORGANISM: Artificial Sequence
<220> FEATURE:
<223> OTHER INFORMATION: Primer
```

```
<400> SEQUENCE: 3
ccccggctcg agcccgtttc gtcctttagg gactcgt                              37

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
cgtacctcct gaatgcatct atc                                             23

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
cggtaactat acgcagcact t                                               21

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
cagtttaggg tcgatggtga tg                                              22

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
caaggcctta gtgtggaaga a                                               21

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ctcgcttccg gtgatgattt                                                 20

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
gtcggaacct cgatgacttt ac                                              22

<210> SEQ ID NO 10
<211> LENGTH: 22
```

```
<212> TYPE: DNA
<213> ORGANISM: Artificial Sequence
<220> FEATURE:
<223> OTHER INFORMATION: Primer

<400> SEQUENCE: 10
gtgacgatac cactcgcata at                                              22

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
ctgatggtcc atacgggatt ac                                              22

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
ggccttaact aggcacacta ag                                              22

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
ccgggtcttc ttgagaatct tg                                              22

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tggcttggat gtggtctatg                                                 20

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
ggtcgataag ttgctcccta ac                                              22

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
```
tagtcgagtc tgtcgtctct tc                                              22

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
cctgtgttga ggcctatctt c                                               21

<210> SEQ ID NO 18
<211> LENGTH: 6422
<212> TYPE: DNA
<213> ORGANISM: Cucumber green mottle mosaic virus

<400> SEQUENCE: 18
gttttaattt ttaaaattaa acaaacaaca acaacaacaa caaacaattt aaaacaacaa 60
tggcaaacat taatgaacaa atcaacaacc aacgcgacgc cgcggccagc gggagaaaca 120
atctcgttag ccaattggcg tcaaaaaggg tgtatgacga ggctgttcgc tcgttggatc 180
atcaagacag acgcccaaaa atgaactttt ctcgtgtggt cagcacagag cacaccaggc 240
ttgtaactga tgcgtatccg gagttttcga ttagctttac cgccaccaag aactctgtac 300
actcccttgc gggtggtctg aggctccttg aactggaata tatgatgatg caagtgccct 360
acggctcacc ttgttatgat atcggcggta actatacgca gcacttgttc aaaggtagat 420
catatgtgca ttgctgcaat ccgtgcctgg atcttaaaga tgttgcgagg aacgtgatgt 480
ataacgatat ggtcacacaa catgtacaga ggcacaaggg atctggcggg tgcagacctc 540
ttccaacttt tcagatagat gcattcagga ggtacgataa ttctccctgt gcggtcacct 600
gttcagacgt tttccaagag tgttcctatg attttgggag cggtagggat aatcatgcag 660
tctcgctgca ttcaatctac gatatccctt attcttcgat cggacctgct cttcatagga 720
agaacgtgcg agtttgttat gcagcctttc acttctcgga ggcattgctt ttaggttcac 780
ctgtaggtaa tttaaatagt attggggctc agtttagggt cgatggtgat gatgtgcatt 840
ttctttttag tgaagagtct actttgcatt atactcatag tttagaaaat atcaaattaa 900
ttgtgatgcg tacttatttt cctgctgatg ataggtacgt gtatattaag gagtttatgg 960
tcaagcgtgt ggatactttc ttctttaggt tggtcagagc agacacacat atgcttcata 1020
aatctgtggg gcactattca aaatcgaaat ctgagtactt tgcgctgaat acccctccga 1080
tcttccaaga caaagccacg ttttctgtgt ggtttcctga ggcgaagcgt aaggtgttga 1140
tacccaagtt tgaactttca agattccttt ctgggaatgt gaaaatctct aggatgcttg 1200
tcgatgctga tttcgtccat accattatta atcacattag cacgtatgat aataaggcct 1260
tagtgtggaa gaatgttcag tcctttgtgg aatctatacg ctcaagagta attgtaaacg 1320
gagtttcggt gaaatctgaa tggaacgtac cggttgatca gctcactgat atctcgttct 1380
cgatattcct tctcgtgaag gttaggaagg tacagatcga gttaatgtct gataaagttg 1440
taatcgaggc gaggggcttg ctccggaggt tcgcagacag tcttaaatcc gccgtagaag 1500
gactaggtga ttgcgtctat gatgctctag ttcaaaccgg ctggtttgat acctctagcg 1560
acgaactgaa agttttgcta cctgaaccgt ttatgacctt ttcggattat cttgaaggga 1620
tgtacgaggc agatgcaaag atcgagagag agagtgtctc tgagttgctc gcttccggtg 1680
acgatttgtt caagaaaatc gatgagataa gaaacaatta cagtggagtc gaatttgatg 1740

```
tagagaaatt ccaggaattt tgcaaggaac tgaatgttaa tcctatgcta attggccatg    1800
ttatcgaagc tatttttcg cagaaagctg gggtgacagt aacgggtctg ggtaccctct    1860
ctcctgagat gggtgcttct gttgcgttat ccaataccctc tgtagataca tgtgaagata   1920
tggatgtaac tgaagatatg gaggatatag tgttgatggc ggacaagagt cattcttaca   1980
tgtccccaga aatggcgaga tgggctgatg taaaatacga caacaataaa ggggcctgg    2040 tcgaatacaa agtcggaacc tcgatgactt tacctgccac ctgggcagag aagggtaagg   2100
ctgtcttacc gttgtcgggg atctgtgtga ggaaacccca attttcgaag ccgcttgatg   2160
aggaagacga cttgaggtta tcaaacatga atttctttaa ggtgagcgat ctgaagttga   2220
agaaaactat cactccagtt gtttacactg gaccattcg agagaggcaa atgaagaatt    2280
atattgatta cttatcggcc tctcttggtt ctacgctggg taatctggag agaattgtgc   2340
ggagtgattg gaacggtacc gaggagagta tgcaaacgtt cgggttgtat gactgcgaaa   2400
agtgcaagtg gttactgtta ccagccgaaa agaagcacgc atgggctgtg gttctggcaa   2460
gtgatgatac cactcgcata atcttcctct catatgacga atctggttct cccataattg   2520
ataagagaaa ctggaagcga tttgctgttt gctctgagac caaagtctat agcgtaattc   2580
gtagtttaga ggtactaaat aaggaagcaa tagtcgaccc cggggttcat ataacattag   2640
ttgacggagt gccgggttgt ggaaagaccg ccgaaattat agcgagggtc aattggaaaa   2700
ccgatctagt attgactccc ggggagggagg cggctgctat gattaggcgg agggcctgcg   2760
ccctgcacaa gtcacctgtg gcaaccagtg acaacgttag aactttcgat tcttttgtga   2820
tgaataagaa aatcttcaag tttgacgctg tctatgttga cgagggtctg atggtccata   2880 cggggtttact taatttttgcg ttgaagatct caggttgtaa aaaggccttc gtctttggtg   2940
atgctaagca aatcccgttt ataaacagag tcatgaattt tgattatcct aaggagttaa   3000
gaactttaat agtcgataat gtagagcgta ggtatgttac ccataggtgt cctagagatg   3060
tcactagttt tcttaatact atttacaaag ccgctgtcgc tactactagt ccggttgtac   3120
attctgtgaa ggcgattaaa gtgtcagggg ccggtattct gaggcccgag ttgacgaaga   3180
tcaaaggaaa gataataacg tttactcaat ctgataagca gtccttgatc aagagtgggt   3240
acaatgacgt gaacactgtg catgaaattc agggagaaac ctttgaagag acggcggttg   3300
tgcgtgccac cccgactccg ataggtttaa ttgcccgtga ttcaccacat gtactagtgg   3360
ccttaacgag gcacactaag gcaatggtgt attatactgt tgtgttcgat gcagttacaa   3420
gtataatagc ggatgtggaa aaggtcgacc agtcgatctt gactatgttt gctaccactg   3480
tgcctaccaa atagcaatta atgcagaact cactgtatgt ccatcgtaat attttcctcc   3540
ctgttagtaa aacggggttt tatacagaca tgcaggagtt ctatgataga tgccttcctg   3600
ggaattcctt cgtgctgaat gatttcgatg ccgtaaccat gcggttgagg gacaacgaat   3660
ttaacctaca accttgtagg ctaaccttaa gtaatttaga tccagtaccc gctttggtta   3720
agagtgaagc gcagaatttt ctgattcccg ttttgcgtac ggcctgtgaa aggccgcgca   3780
ttccaggtct ccttgaaaat cttgtagcta tgataaagag gaatatgaat actcctgatc   3840
tagctgggac tgtggatata actaatatgt cgatttctat agtagataac ttcttttctt   3900
cttttgttag agacgaggtt ttgcttgatc atttagattg tgttagggct agttccattc   3960 aaagttttc tgattggttt tcgtgtcagc caacctcggc ggttggtcaa ttagctaatt   4020
tcaatttcat agatttgcct gcctttgata cttatatgca catgattaag cggcagccca   4080
```

```
agagtcggtt ggatacttcg attcagtctg aatatccggc cttgcaaact attgtttatc    4140
accctaaagt ggtaaatgca gttttcggtc cggtttttaa gtatttgacc accaagtttc    4200
ttagcatggt agatagttct aagttttttct tttacactag gaaaaaacca gaagatctgc   4260
aggaattttt ctcagatctc tcttcccatt ctgattatga gattcttgag ctggatgttt    4320
ctaaatatga caagtcacaa tccgatttcc atttctctat tgagatggca atttgggaaa    4380
aattggggct ggacgatatt ttggcttgga tgtggtctat gggtcacaag agaactatac    4440
tgcaagattt ccaagccggg ataaagacgc tcatttacta tcaacggaag tctggtgatg    4500
taactacttt cataggtaat acctttatta tcgcagcgtg tgtagctagt atgttgccgt    4560
tagacaagtg tttttaaagct agttttttgtg gtgatgattc gctgatctac cttcctaagg   4620
gtttggagta tcctgatata caggctactg ccaacttggt ttggaatttt gaggcgaaac    4680
ttttccgaaa gaagtatggt tacttctgtg ggaagtatat aattcaccat gccaacggct    4740
gtattgttta ccctgaccct ttaaaattaa ttagtaaatt aggtaataag agtcttgtag    4800
ggtatgagca tgttgaggag tttcgtatat ctctcctcga cgtcgctcat agtttgttta    4860
atggtgctta tttccattta ctcgacgatg caatccacga attatttcct aacgctgggg    4920
gttgcagttt tgtaattaat tgtttgtgca agtatttgag tgataagcgc cttttccgta    4980
gtctttatat agatgtctct aagtaaggtg tcggtcgaga actcattgaa acccgagaag    5040
tttgttaaaa tctcttgggt cgataagttg ctccctaact atttttccat tcttaagtat    5100
ttatctataa ctgactttag cgtagttaaa gctcagagct atgaatccct cgtgcctgtc    5160
aagttgttgc gtggtgttga tcttacaaaa cacctttatg tcacattgtt gggcgttgtg    5220
gtttctggtg tatggaacgt accggaatcc tgtaggggtg gtgctactgt tgctctggtt    5280
gacacaagga tgcattctgt tgcagaggga actatatgca aattttcagc tcccgccacc    5340
gtccgcgaat tctctgttag gttcatacct aactattctg tcgtggctgc ggatgccctt    5400
cgcgatcctt ggtctttatt tgtgagactc tctaatgtag ggattaaaga tggtttccat    5460
cctttgacct tagaggtcgc ttgtttagtc gctacaacta actctattat caaaaagggt    5520
cttagagctt ctgtagtcga gtctgtcgtc tcttccgatc agtccattgt cctagattct    5580
ttatccgaga aagttgaacc tttctttgat aaagttccta tttcggcggc tgtgatggca    5640
agagacccca gttataggtc taggtcgcag tctgtcggtg gtcgtggtaa gcggcattct    5700
aaacctccaa atcggaggtt ggactctgct tctgaagagt ccagttctgt ttcttttcgaa   5760
gatggcttac aatccgatca cacctagcaa acttattgcg tttagtgctt cttatgttcc    5820
cgtcaggact ttacttaatt ttctagttgc ttcacaaggt accgccttcc agactcaagc    5880
gggaagagat tctttccgcg agtccctgtc tgcgttaccc tcgtctgtcg tagatattaa    5940
ttctaggttc ccaaatgcgg gttttttacgc tttcctcaac ggtcctgtgt tgaggcctat   6000
cttcgtttcg cttcttagct ctacggatac gcgtaatagg gtcattgagg ttgtagatcc    6060
tagcaatcct acgactgctg agtcgcttaa cgctgtaaag cgtactgatg acgcatctac    6120
ggccgctagg gctgaaatag ataatttaat agagtctatt tctaagggtt ttgatgttta    6180
tgatagggct tcatttgaag ccgcgttttc ggtagtctgg tcagaggcta ccacctcgaa    6240
agcttagctt cgagggtctt ctgatggtgg tgcacaccaa agtgcatagt gctttcccgt    6300
tcacttaaat cgaacggttt gctcattggt ttgcggaaac ctctcacgtg tggcgttgaa    6360
gtttctatgg gcagtaattc tgcaaggggt tcgaatcccc cctttccccg ggtagggcc    6420
ca                                                                   6422
```

<210> SEQ ID NO 19
<211> LENGTH: 35
<212> TYPE: DNA
<213> ORGANISM: Artificial Sequence
<220> FEATURE:
<223> OTHER INFORMATION: Primer

<400> SEQUENCE: 19
tcttaaatcc gccgtaggag gactaggtga ttgcg        35

<210> SEQ ID NO 20
<211> LENGTH: 35
<212> TYPE: DNA
<213> ORGANISM: Artificial Sequence
<220> FEATURE:
<223> OTHER INFORMATION: Primer

<400> SEQUENCE: 20
cgcaatcacc tagtcctcct acggcggatt taaga        35

<210> SEQ ID NO 21
<211> LENGTH: 42
<212> TYPE: DNA
<213> ORGANISM: Artificial Sequence
<220> FEATURE:
<223> OTHER INFORMATION: Primer

<400> SEQUENCE: 21
tcgatgcagt tacaagtata atagtggatg tggaaaaggt cg        42

<210> SEQ ID NO 22
<211> LENGTH: 42
<212> TYPE: DNA
<213> ORGANISM: Artificial Sequence
<220> FEATURE:
<223> OTHER INFORMATION: Primer

<400> SEQUENCE: 22 cgacctttc cacatccact attatacttg taactgcatc ga        42

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
ctcactgtat gtccatcgtg atatttcct ccctgttag        39

<210> SEQ ID NO 24
<211> LENGTH: 39
<212> TYPE: DNA
<213> ORGANISM: Artificial Sequence
<220> FEATURE:
<223> OTHER INFORMATION: Primer

<400> SEQUENCE: 24
ctaacaggga ggaaaatatc acgatggaca tacagtgag        39

<210> SEQ ID NO 25
<211> LENGTH: 47
<212> TYPE: DNA
<213> ORGANISM: Artificial Sequence
<220> FEATURE:

<223> OTHER INFORMATION: Primer

<400> SEQUENCE: 25 tctaagttttt tcttttacac taggaaaaaa tcagaagatc tgcagga          47

<210> SEQ ID NO 26
<211> LENGTH: 47
<212> TYPE: DNA
<213> ORGANISM: Artificial Sequence
<220> FEATURE:
<223> OTHER INFORMATION: Primer

<400> SEQUENCE: 26
tcctgcagat cttctgattt tttcctagtg taaaagaaaa acttaga          47

<210> SEQ ID NO 27
<211> LENGTH: 33
<212> TYPE: DNA
<213> ORGANISM: Artificial Sequence
<220> FEATURE:
<223> OTHER INFORMATION: Primer

<400> SEQUENCE: 27
gtagtctggt cagaggttac cacctcgaaa gct          33

<210> SEQ ID NO 28
<211> LENGTH: 33
<212> TYPE: DNA
<213> ORGANISM: Artificial Sequence
<220> FEATURE:
<223> OTHER INFORMATION: Primer

<400> SEQUENCE: 28
agctttcgag gtggtaacct ctgaccagac tac          33

<210> SEQ ID NO 29
<211> LENGTH: 6422
<212> TYPE: DNA
<213> ORGANISM: Cucumber green mottle mosaic virus

<400> SEQUENCE: 29 gttttaatttt ttaaaattaa acaaacaaca acaacaacaa caaacaatttt aaaacaacaa          60 tggcaaacat taatgaacaa atcaacaacc aacgcgacgc cgcggccagc gggagaaaca         120
atctcgttag ccaattggcg tcaaaaaggg tgtatgacga ggctgttcgc tcgttggatc         180
atcaagacag acgcccaaaa atgaactttt ctcgtgtggt cagcacagag cacaccaggc         240
ttgtaactga tgcgtatccg gagttttcga ttagctttac cgccaccaag aactctgtac         300
actcccttgc gggtggtctg aggctccttg aactggaata tatgatgatg caagtgccct         360
acggctcacc ttgttatgat atcggcggta actatacgca gcacttgttc aaaggtagat         420
catatgtgca ttgctgcaat ccgtgcctgg atcttaaaga tgttgcgagg aacgtgatgt         480
ataacgatat ggtcacacaa catgtacaga ggcacaaggg atctggcggg tgcagacctc         540
ttccaacttt tcagatagat gcattcagga ggtacgataa ttctccctgt gcggtcacct         600
gttcagacgt tttccaagag tgttcctatg atttttgggag cggtagggat aatcatgcag         660
tctcgctgca ttcaatctac gatatccctt attcttcgat cggacctgct cttcatagga         720
agaacgtgcg agtttgttat gcagccttttc acttctcgga ggcattgctt ttaggttcac         780
ctgtaggtaa tttaaatagt attggggctc agtttagggt cgatggtgat gatgtgcatt         840
ttctttttag tgaagagtct actttgcatt atactcatag tttagaaaat atcaaattaa         900

```
ttgtgatgcg tacttatttt cctgctgatg ataggtacgt gtatattaag gagtttatgg    960
tcaagcgtgt ggatactttc ttctttaggt tggtcagagc agacacacat atgcttcata   1020
aatctgtggg gcactattca aaatcgaaat ctgagtactt tgcgctgaat accectccga   1080 tcttccaaga caaagccacg ttttctgtgt ggtttcctga ggcgaagcgt aaggtgttga   1140
tacccaagtt tgaactttca agattccttt ctgggaatgt gaaaatctct aggatgcttg   1200
tcgatgctga tttcgtccat accattatta atcacattag cacgtatgat aataaggcct   1260
tagtgtggaa gaatgttcag tcctttgtgg aatctatacg ctcaagagta attgtaaacg   1320 gagtttcgt gaaatctgaa tggaacgtac cggttgatca gctcactgat atctcgttct   1380
cgatattcct tctcgtgaag gttaggaagg tacagatcga gttaatgtct gataaagttg   1440
taatcgaggc gaggggcttg ctccggaggt tcgcagacag tcttaaatcc gccgtaggag   1500
gactaggtga ttgcgtctat gatgctctag ttcaaaccgg ctggtttgat acctctagcg   1560
acgaactgaa agttttgcta cctgaaccgt ttatgacctt tcggattat cttgaaggga   1620 tgtacgaggc agatgcaaag atcgagagag agagtgtctc tgagttgctc gcttccggtg   1680
acgatttgtt caagaaaatc gatgagataa gaaacaatta cagtggagtc gaatttgatg   1740
tagagaaatt ccaggaattt tgcaaggaac tgaatgttaa tcctatgcta attggccatg   1800
ttatcgaagc tattttttcg cagaaagctg gggtgacagt aacgggtctg ggtaccctct   1860
ctcctgagat gggtgcttct gttgcgttat ccaatacctc tgtagataca tgtgaagata   1920
tggatgtaac tgaagatatg gaggatatag tgttgatggc ggacaagagt cattcttaca   1980
tgtccccaga aatggcgaga tgggctgatg taaaatacga caacaataaa ggggcctgg   2040 tcgaatacaa agtcggaacc tcgatgactt tacctgccac ctgggcagag aagggtaagg   2100
ctgtcttacc gttgtcgggg atctgtgtga ggaaacccca attttcgaag ccgcttgatg   2160
aggaagacga cttgaggtta tcaaacatga atttctttaa ggtgagcgat ctgaagttga   2220
agaaaactat cactccagtt gtttacactg ggaccattcg agagaggcaa atgaagaatt   2280
atattgatta cttatcggcc tctcttggtt ctacgctggg taatctggag agaattgtgc   2340
ggagtgattg gaacggtacc gaggagagta tgcaaacgtt cgggttgtat gactgcgaaa   2400
agtgcaagtg gttactgtta ccagccgaaa agaagcacgc atgggctgtg gttctggcaa   2460
gtgatgatac cactcgcata atcttcctct catatgacga atctggttct cccataattg   2520
ataagagaaa ctggaagcga tttgctgttt gctctgagac caaagtctat agcgtaattc   2580
gtagtttaga ggtactaaat aaggaagcaa tagtcgaccc cggggttcat ataacattag   2640
ttgacggagt gccgggttgt ggaaagaccg ccgaaattat agcgagggtc aattggaaaa   2700
ccgatctagt attgactccc gggagggagg cggctgctat gattaggcgg agggcctgcg   2760
ccctgcacaa gtcacctgtg gcaaccagtg acaacgttag aactttcgat tcttttgtga   2820
tgaataagaa aatcttcaag tttgacgctg tctatgttga cgagggtctg atggtccata   2880
cgggtttact taattttgcg ttgaagatct caggttgtaa aaaggccttc gtctttggtg   2940
atgctaagca aatcccgttt ataaacagag tcatgaattt tgattatcct aaggagttaa   3000
gaactttaat agtcgataat gtagagcgta ggtatgttac ccataggtgt cctagagatg   3060
tcactagttt tcttaatact atttacaaag ccgctgtcgc tactactagt ccggttgtac   3120
attctgtgaa ggcgattaaa gtgtcagggg ccggtattct gaggcccgag ttgacgaaga   3180
tcaaaggaaa gataataacg tttactcaat ctgataagca gtccttgatc aagagtgggt   3240
```

```
acaatgacgt gaacactgtg catgaaattc agggagaaac ctttgaagag acggcggttg    3300
tgcgtgccac cccgactccg ataggtttaa ttgcccgtga ttcaccacat gtactagtgg    3360
ccttaacgag gcacactaag gcaatggtgt attatactgt tgtgttcgat gcagttacaa    3420
gtataatagt ggatgtggaa aaggtcgacc agtcgatctt gactatgttt gctaccactg    3480
tgcctaccaa atagcaatta atgcagaact cactgtatgt ccatcgtgat attttcctcc    3540
ctgttagtaa aacggggttt tatacagaca tgcaggagtt ctatgataga tgccttcctg    3600
ggaattcctt cgtgctgaat gatttcgatg ccgtaaccat gcggttgagg gacaacgaat    3660
ttaacctaca accttgtagg ctaaccttaa gtaatttaga tccagtaccc gctttggtta    3720
agagtgaagc gcagaatttt ctgattcccg ttttgcgtac ggcctgtgaa aggccgcgca    3780
ttccaggtct ccttgaaaat cttgtagcta tgataaagag gaatatgaat actcctgatc    3840
tagctgggac tgtggatata actaatatgt cgatttctat agtagataac ttcttttctt    3900
cttttgttag agacgaggtt ttgcttgatc atttagattg tgttagggct agttccattc    3960
aaagtttttc tgattggttt tcgtgtcagc caacctcggc ggttggtcaa ttagctaatt    4020
tcaatttcat agatttgcct gcctttgata cttatatgca catgattaag cggcagccca    4080
agagtcggtt ggatacttcg attcagtctg aatatccggc cttgcaaact attgtttatc    4140
accctaaagt ggtaaatgca gttttcggtc cggttttaa gtatttgacc accaagtttc    4200
ttagcatggt agatagttct aagttttct tttacactag gaaaaaatca gaagatctgc    4260
aggaattttt ctcagatctc tcttcccatt ctgattatga gattcttgag ctggatgttt    4320
ctaaatatga caagtcacaa tccgatttcc atttctctat tgagatggca atttgggaaa    4380
aattggggct ggacgatatt ttggcttgga tgtggtctat gggtcacaag agaactatac    4440
tgcaagattt ccagccgggg ataaagacgc tcatttacta tcaacggaag tctggtgatg    4500
taactacttt cataggtaat accttttatta tcgcagcgtg tgtagctagt atgttgccgt    4560
tagacaagtg ttttaaagct agttttttgtg gtgatgattc gctgatctac cttcctaagg    4620
gtttggagta tcctgatata caggctactg ccaacttggt ttggaatttt gaggcgaaac    4680
ttttccgaaa gaagtatggt tacttctgtg ggaagtatat aattcaccat gccaacggct    4740
gtattgttta ccctgacct ttaaaattaa ttagtaaatt aggtaataag agtcttgtag    4800
ggtatgagca tgttgaggag tttcgtatat ctctcctcga cgtcgctcat agtttgttta    4860
atggtgctta tttccatta ctcgacgatg caatccacga attatttcct aacgctgggg    4920
gttgcagttt tgtaattaat tgtttgtgca agtatttgag tgataagcgc ttttccgta    4980
gtctttatat agatgtctct aagtaaggtg tcggtcgaga actcattgaa acccgagaag    5040
tttgttaaaa tctcttgggt cgataagttg ctccctaact attttccat tcttaagtat    5100
ttatctataa ctgactttag cgtagttaaa gctcagagct atgaatccct cgtgcctgtc    5160
aagttgttgc gtggtgttga tcttacaaaa caccttatg tcacattgtt gggcgttgtg    5220
gtttctggtg tatggaacgt accggaatcc tgtaggggtg gtgctactgt tgctctggtt    5280
gacacaagga tgcattctgt tgcagaggga actatatgca aattttcagc tcccgccacc    5340
gtccgcgaat tctctgttag gttcataccct aactattctg tcgtggctgc ggatgcccctt    5400
cgcgatcctt ggtctttatt tgtgagactc tctaatgtag ggattaaaga tggtttccat    5460
cctttgacct tagaggtcgc ttgtttagtc gctacaacta actctattat caaaaagggt    5520
cttagagctt ctgtagtcga gtctgtcgtc tcttccgatc agtccattgt cctagattct    5580
ttatccgaga aagttgaacc tttctttgat aaagttccta tttcggcggc tgtgatggca    5640
```

```
agagacccca gttataggtc taggtcgcag tctgtcggtg gtcgtggtaa gcggcattct   5700
aaacctccaa atcggaggtt ggactctgct tctgaagagt ccagttctgt ttctttcgaa   5760
gatggcttac aatccgatca cacctagcaa acttattgcg tttagtgctt cttatgttcc   5820
cgtcaggact ttacttaatt ttctagttgc ttcacaaggt accgccttcc agactcaagc   5880
gggaagagat tctttccgcg agtccctgtc tgcgttaccc tcgtctgtcg tagatattaa   5940
ttctaggttc ccaaatgcgg ttttttacgc tttcctcaac ggtcctgtgt tgaggcctat   6000
cttcgtttcg cttcttagct ctacggatac gcgtaatagg gtcattgagg ttgtagatcc   6060
tagcaatcct acgactgctg agtcgcttaa cgctgtaaag cgtactgatg acgcatctac   6120
ggccgctagg gctgaaatag ataatttaat agagtctatt tctaagggtt ttgatgttta   6180
tgatagggct tcatttgaag ccgcgttttc ggtagtctgg tcagaggtta ccacctcgaa   6240
agcttagctt cgagggtctt ctgatggtgg tgcacaccaa agtgcatagt gctttcccgt   6300
tcacttaaat cgaacggttt gctcattggt ttgcggaaac ctctcacgtg tggcgttgaa   6360
gtttctatgg gcagtaattc tgcaaggggt tcgaatcccc cctttccccg ggtaggggcc   6420
ca                                                                 6422
```

<210> SEQ ID NO 30
<211> LENGTH: 1144
<212> TYPE: PRT
<213> ORGANISM: Cucumber green mottle mosaic virus

<400> SEQUENCE: 30

```
Met Ala Asn Ile Asn Glu Gln Ile Asn Asn Gln Arg Asp Ala Ala Ala
1               5                   10                  15

Ser Gly Arg Asn Asn Leu Val Ser Gln Leu Ala Ser Lys Arg Val Tyr
            20                  25                  30

Asp Glu Ala Val Arg Ser Leu Asp His Gln Asp Arg Arg Pro Lys Met
        35                  40                  45

Asn Phe Ser Arg Val Val Ser Thr Glu His Thr Arg Leu Val Thr Asp
    50                  55                  60

Ala Tyr Pro Glu Phe Ser Ile Ser Phe Thr Ala Thr Lys Asn Ser Val
65                  70                  75                  80

His Ser Leu Ala Gly Gly Leu Arg Leu Leu Glu Leu Glu Tyr Met Met
                85                  90                  95

Met Gln Val Pro Tyr Gly Ser Pro Cys Tyr Asp Ile Gly Gly Asn Tyr
            100                 105                 110

Thr Gln His Leu Phe Lys Gly Arg Ser Tyr Val His Cys Cys Asn Pro
        115                 120                 125

Cys Leu Asp Leu Lys Asp Val Ala Arg Asn Val Met Tyr Asn Asp Met
    130                 135                 140

Val Thr Gln His Val Gln Arg His Lys Gly Ser Gly Gly Cys Arg Pro
145                 150                 155                 160

Leu Pro Thr Phe Gln Ile Asp Ala Phe Arg Arg Tyr Asp Asn Ser Pro
                165                 170                 175

Cys Ala Val Thr Cys Ser Asp Val Phe Gln Glu Cys Ser Tyr Asp Phe
            180                 185                 190

Gly Ser Gly Arg Asp Asn His Ala Val Ser Leu His Ser Ile Tyr Asp
        195                 200                 205

Ile Pro Tyr Ser Ser Ile Gly Pro Ala Leu His Arg Lys Asn Val Arg
    210                 215                 220
```

```
Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
            245                 250                 255

Asp Asp Val His Phe Leu Phe Ser Glu Glu Ser Thr Leu His Tyr Thr
            260                 265                 270

His Ser Leu Glu Asn Ile Lys Leu Ile Val Met Arg Thr Tyr Phe Pro
        275                 280                 285

Ala Asp Asp Arg Tyr Val Tyr Ile Lys Glu Phe Met Val Lys Arg Val
    290                 295                 300

Asp Thr Phe Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
                325                 330                 335

Asn Thr Pro Pro Ile Phe Gln Asp Lys Ala Thr Phe Ser Val Trp Phe
            340                 345                 350

Pro Glu Ala Lys Arg Lys Val Leu Ile Pro Lys Phe Glu Leu Ser Arg
        355                 360                 365

Phe Leu Ser Gly Asn Val Lys Ile Ser Arg Met Leu Val Asp Ala Asp
370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
                405                 410                 415

Val Ile Val Asn Gly Val Ser Val Lys Ser Glu Trp Asn Val Pro Val
                420                 425                 430

Asp Gln Leu Thr Asp Ile Ser Phe Ser Ile Phe Leu Leu Val Lys Val
            435                 440                 445

Arg Lys Val Gln Ile Glu Leu Met Ser Asp Lys Val Val Ile Glu Ala
        450                 455                 460

Arg Gly Leu Leu Arg Arg Phe Ala Asp Ser Leu Lys Ser Ala Val Gly
465                 470                 475                 480

Gly Leu Gly Asp Cys Val Tyr Asp Ala Leu Val Gln Thr Gly Trp Phe
                485                 490                 495

Asp Thr Ser Ser Asp Glu Leu Lys Val Leu Leu Pro Glu Pro Phe Met
            500                 505                 510

Thr Phe Ser Asp Tyr Leu Glu Gly Met Tyr Glu Ala Asp Ala Lys Ile
        515                 520                 525

Glu Arg Glu Ser Val Ser Glu Leu Leu Ala Ser Gly Asp Asp Leu Phe
530                 535                 540

Lys Lys Ile Asp Glu Ile Arg Asn Asn Tyr Ser Gly Val Glu Phe Asp
545                 550                 555                 560

Val Glu Lys Phe Gln Glu Phe Cys Lys Glu Leu Asn Val Asn Pro Met
                565                 570                 575

Leu Ile Gly His Val Ile Glu Ala Ile Phe Ser Gln Lys Ala Gly Val
                580                 585                 590

Thr Val Thr Gly Leu Gly Thr Leu Ser Pro Glu Met Gly Ala Ser Val
            595                 600                 605

Ala Leu Ser Asn Thr Ser Val Asp Thr Cys Glu Asp Met Asp Val Thr
        610                 615                 620

Glu Asp Met Glu Asp Ile Val Leu Met Ala Asp Lys Ser His Ser Tyr
625                 630                 635                 640

Met Ser Pro Glu Met Ala Arg Trp Ala Asp Val Lys Tyr Asp Asn Asn
```

```
                645                 650                 655
Lys Gly Gly Leu Val Glu Tyr Lys Val Gly Thr Ser Met Thr Leu Pro
                660                 665                 670

Ala Thr Trp Ala Glu Lys Gly Lys Ala Val Leu Pro Leu Ser Gly Ile
            675                 680                 685

Cys Val Arg Lys Pro Gln Phe Ser Lys Pro Leu Asp Glu Glu Asp Asp
        690                 695                 700

Leu Arg Leu Ser Asn Met Asn Phe Phe Lys Val Ser Asp Leu Lys Leu
705                 710                 715                 720

Lys Lys Thr Ile Thr Pro Val Val Tyr Thr Gly Thr Ile Arg Glu Arg
                725                 730                 735

Gln Met Lys Asn Tyr Ile Asp Tyr Leu Ser Ala Ser Leu Gly Ser Thr
                740                 745                 750

Leu Gly Asn Leu Glu Arg Ile Val Arg Ser Asp Trp Asn Gly Thr Glu
            755                 760                 765

Glu Ser Met Gln Thr Phe Gly Leu Tyr Asp Cys Glu Lys Cys Lys Trp
        770                 775                 780

Leu Leu Leu Pro Ala Glu Lys Lys His Ala Trp Ala Val Val Leu Ala
785                 790                 795                 800

Ser Asp Asp Thr Thr Arg Ile Ile Phe Leu Ser Tyr Asp Glu Ser Gly
                805                 810                 815

Ser Pro Ile Ile Asp Lys Arg Asn Trp Lys Arg Phe Ala Val Cys Ser
            820                 825                 830

Glu Thr Lys Val Tyr Ser Val Ile Arg Ser Leu Glu Val Leu Asn Lys
        835                 840                 845

Glu Ala Ile Val Asp Pro Gly Val His Ile Thr Leu Val Asp Gly Val
850                 855                 860

Pro Gly Cys Gly Lys Thr Ala Glu Ile Ile Ala Arg Val Asn Trp Lys
865                 870                 875                 880

Thr Asp Leu Val Leu Thr Pro Gly Arg Glu Ala Ala Ala Met Ile Arg
                885                 890                 895

Arg Arg Ala Cys Ala Leu His Lys Ser Pro Val Ala Thr Ser Asp Asn
            900                 905                 910

Val Arg Thr Phe Asp Ser Phe Val Met Asn Lys Lys Ile Phe Lys Phe
        915                 920                 925

Asp Ala Val Tyr Val Asp Glu Gly Leu Met Val His Thr Gly Leu Leu
    930                 935                 940

Asn Phe Ala Leu Lys Ile Ser Gly Cys Lys Lys Ala Phe Val Phe Gly
945                 950                 955                 960

Asp Ala Lys Gln Ile Pro Phe Ile Asn Arg Val Met Asn Phe Asp Tyr
                965                 970                 975

Pro Lys Glu Leu Arg Thr Leu Ile Val Asp Asn Val Glu Arg Arg Tyr
            980                 985                 990

Val Thr His Arg Cys Pro Arg Asp Val Thr Ser Phe Leu Asn Thr Ile
        995                 1000                1005

Tyr Lys Ala Ala Val Ala Thr Thr Ser Pro Val Val His Ser Val
        1010                1015                1020

Lys Ala Ile Lys Val Ser Gly Ala Gly Ile Leu Arg Pro Glu Leu
    1025                1030                1035

Thr Lys Ile Lys Gly Lys Ile Ile Thr Phe Thr Gln Ser Asp Lys
    1040                1045                1050

Gln Ser Leu Ile Lys Ser Gly Tyr Asn Asp Val Asn Thr Val His
    1055                1060                1065
```

-continued

```
Glu Ile Gln Gly Glu Thr Phe Glu Glu Thr Ala Val Val Arg Ala
    1070                1075                1080

Thr Pro Thr Pro Ile Gly Leu Ile Ala Arg Asp Ser Pro His Val
    1085                1090                1095

Leu Val Ala Leu Thr Arg His Thr Lys Ala Met Val Tyr Tyr Thr
    1100                1105                1110

Val Val Phe Asp Ala Val Thr Ser Ile Ile Val Asp Val Glu Lys
    1115                1120                1125

Val Asp Gln Ser Ile Leu Thr Met Phe Ala Thr Thr Val Pro Thr
    1130                1135                1140

Lys

<210> SEQ ID NO 31
<211> LENGTH: 1648
<212> TYPE: PRT
<213> ORGANISM: Cucumber green mottle mosaic virus
<220

```
            260                 265                 270
His Ser Leu Glu Asn Ile Lys Leu Ile Val Met Arg Thr Tyr Phe Pro
        275                 280                 285

Ala Asp Asp Arg Tyr Val Tyr Ile Lys Glu Phe Met Val Lys Arg Val
        290                 295                 300

Asp Thr Phe Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
                325                 330                 335

Asn Thr Pro Pro Ile Phe Gln Asp Lys Ala Thr Phe Ser Val Trp Phe
            340                 345                 350

Pro Glu Ala Lys Arg Lys Val Leu Ile Pro Lys Phe Glu Leu Ser Arg
        355                 360                 365

Phe Leu Ser Gly Asn Val Lys Ile Ser Arg Met Leu Val Asp Ala Asp
    370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
                405                 410                 415

Val Ile Val Asn Gly Val Ser Val Lys Ser Glu Trp Asn Val Pro Val
                420                 425                 430

Asp Gln Leu Thr Asp Ile Ser Phe Ser Ile Phe Leu Leu Val Lys Val
            435                 440                 445

Arg Lys Val Gln Ile Glu Leu Met Ser Asp Lys Val Val Ile Glu Ala
        450                 455                 460

Arg Gly Leu Leu Arg Arg Phe Ala Asp Ser Leu Lys Ser Ala Val Gly
465                 470                 475                 480

Gly Leu Gly Asp Cys Val Tyr Asp Ala Leu Val Gln Thr Gly Trp Phe
                485                 490                 495

Asp Thr Ser Ser Asp Glu Leu Lys Val Leu Leu Pro Glu Pro Phe Met
            500                 505                 510

Thr Phe Ser Asp Tyr Leu Glu Gly Met Tyr Glu Ala Asp Ala Lys Ile
        515                 520                 525

Glu Arg Glu Ser Val Ser Glu Leu Leu Ala Ser Gly Asp Asp Leu Phe
    530                 535                 540

Lys Lys Ile Asp Glu Ile Arg Asn Asn Tyr Ser Gly Val Glu Phe Asp
545                 550                 555                 560

Val Glu Lys Phe Gln Glu Phe Cys Lys Glu Leu Asn Val Asn Pro Met
                565                 570                 575

Leu Ile Gly His Val Ile Glu Ala Ile Phe Ser Gln Lys Ala Gly Val
            580                 585                 590

Thr Val Thr Gly Leu Gly Thr Leu Ser Pro Glu Met Gly Ala Ser Val
        595                 600                 605

Ala Leu Ser Asn Thr Ser Val Asp Thr Cys Gly Asp Met Asp Val Thr
    610                 615                 620

Glu Asp Met Glu Asp Ile Val Leu Met Ala Asp Lys Ser His Ser Tyr
625                 630                 635                 640

Met Ser Pro Glu Met Ala Arg Trp Ala Asp Val Lys Tyr Asp Asn Asn
                645                 650                 655

Lys Gly Gly Leu Val Glu Tyr Lys Val Gly Thr Ser Met Thr Leu Pro
            660                 665                 670

Ala Thr Trp Ala Glu Lys Gly Lys Ala Val Leu Pro Leu Ser Gly Ile
        675                 680                 685
```

```
Cys Val Arg Lys Pro Gln Phe Ser Lys Pro Leu Asp Glu Glu Asp
690                 695                 700

Leu Arg Leu Ser Asn Met Asn Phe Phe Lys Val Ser Asp Leu Lys Leu
705                 710                 715                 720

Lys Lys Thr Ile Thr Pro Val Val Tyr Thr Gly Thr Ile Arg Glu Arg
                725                 730                 735

Gln Met Lys Asn Tyr Ile Asp Tyr Leu Ser Ala Ser Leu Gly Ser Thr
                740                 745                 750

Leu Gly Asn Leu Glu Arg Ile Val Arg Ser Asp Trp Asn Gly Thr Glu
            755                 760                 765

Glu Ser Met Gln Thr Phe Gly Leu Tyr Asp Cys Glu Lys Cys Lys Trp
770                 775                 780

Leu Leu Leu Pro Ala Glu Lys Lys His Ala Trp Ala Val Val Leu Ala
785                 790                 795                 800

Ser Asp Asp Thr Thr Arg Ile Ile Phe Leu Ser Tyr Asp Glu Ser Gly
                805                 810                 815

Ser Pro Ile Ile Asp Lys Arg Asn Trp Lys Arg Phe Ala Val Cys Ser
                820                 825                 830

Glu Thr Lys Val Tyr Ser Val Ile Arg Ser Leu Glu Val Leu Asn Lys
                835                 840                 845

Glu Ala Ile Val Asp Pro Gly Val His Ile Thr Leu Val Asp Gly Val
850                 855                 860

Pro Gly Cys Gly Lys Thr Ala Glu Ile Ile Ala Arg Val Asn Trp Lys
865                 870                 875                 880

Thr Asp Leu Val Leu Thr Pro Gly Arg Glu Ala Ala Ala Met Ile Arg
                885                 890                 895

Arg Arg Ala Cys Ala Leu His Lys Ser Pro Val Ala Thr Ser Asp Asn
                900                 905                 910

Val Arg Thr Phe Asp Ser Phe Val Met Asn Lys Lys Ile Phe Lys Phe
            915                 920                 925

Asp Ala Val Tyr Val Asp Glu Gly Leu Met Val His Thr Gly Leu Leu
            930                 935                 940

Asn Phe Ala Leu Lys Ile Ser Gly Cys Lys Lys Ala Phe Val Phe Gly
945                 950                 955                 960

Asp Ala Lys Gln Ile Pro Phe Ile Asn Arg Val Met Asn Phe Asp Tyr
                965                 970                 975

Pro Lys Glu Leu Arg Thr Leu Ile Val Asp Asn Val Glu Arg Arg Tyr
                980                 985                 990

Val Thr His Arg Cys Pro Arg Asp Val Thr Ser Phe Leu Asn Thr Ile
            995                 1000                1005

Tyr Lys Ala Ala Val Ala Thr Thr Ser Pro Val Val His Ser Val
    1010                1015                1020

Lys Ala Ile Lys Val Ser Gly Ala Gly Ile Leu Arg Pro Glu Leu
    1025                1030                1035

Thr Lys Ile Lys Gly Lys Ile Ile Thr Phe Thr Gln Ser Asp Lys
    1040                1045                1050

Gln Ser Leu Ile Lys Ser Gly Tyr Asn Asp Val Asn Thr Val His
    1055                1060                1065

Glu Ile Gln Gly Glu Thr Phe Glu Glu Thr Ala Val Val Arg Ala
    1070                1075                1080

Thr Pro Thr Pro Ile Gly Leu Ile Ala Arg Asp Ser Pro His Val
    1085                1090                1095
```

```
Leu Val Ala Leu Thr Arg His Thr Lys Ala Met Val Tyr Tyr Thr
    1100            1105            1110

Val Val Phe Asp Ala Val Thr Ser Ile Ile Val Asp Val Glu Lys
    1115            1120            1125

Val Asp Gln Ser Ile Leu Thr Met Phe Ala Thr Thr Val Pro Thr
    1130            1135            1140

Lys Xaa Gln Leu Met Gln Asn Ser Leu Tyr Val His Arg Asp Ile
    1145            1150            1155

Phe Leu Pro Val Ser Lys Thr Gly Phe Tyr Thr Asp Met Gln Glu
    1160            1165            1170

Phe Tyr Asp Arg Cys Leu Pro Gly Asn Ser Phe Val Leu Asn Asp
    1175            1180            1185

Phe Asp Ala Val Thr Met Arg Leu Arg Asp Asn Glu Phe Asn Leu
    1190            1195            1200

Gln Pro Cys Arg Leu Thr Leu Ser Asn Leu Asp Pro Val Pro Ala
    1205            1210            1215

Leu Val Lys Ser Glu Ala Gln Asn Phe Leu Ile Pro Val Leu Arg
    1220            1225            1230

Thr Ala Cys Glu Arg Pro Arg Ile Pro Gly Leu Leu Glu Asn Leu
    1235            1240            1245

Val Ala Met Ile Lys Arg Asn Met Asn Thr Pro Asp Leu Ala Gly
    1250            1255            1260

Thr Val Asp Ile Thr Asn Met Ser Ile Ser Ile Val Asp Asn Phe
    1265            1270            1275

Phe Ser Ser Phe Val Arg Asp Glu Val Leu Leu Asp His Leu Asp
    1280            1285            1290

Cys Val Arg Ala Ser Ser Ile Gln Ser Phe Ser Asp Trp Phe Ser
    1295            1300            1305

Cys Gln Pro Thr Ser Ala Val Gly Gln Leu Ala Asn Phe Asn Phe
    1310            1315            1320

Ile Asp Leu Pro Ala Phe Asp Thr Tyr Met His Met Ile Lys Arg
    1325            1330            1335

Gln Pro Lys Ser Arg Leu Asp Thr Ser Ile Gln Ser Glu Tyr Pro
    1340            1345            1350

Ala Leu Gln Thr Ile Val Tyr His Pro Lys Val Val Asn Ala Val
    1355            1360            1365

Phe Gly Pro Val Phe Lys Tyr Leu Thr Thr Lys Phe Leu Ser Met
    1370            1375            1380

Val Asp Ser Ser Lys Phe Phe Phe Tyr Thr Arg Lys Lys Ser Glu
    1385            1390            1395

Asp Leu Gln Glu Phe Phe Ser Asp Leu Ser Ser His Ser Asp Tyr
    1400            1405            1410

Glu Ile Leu Glu Leu Asp Val Ser Lys Tyr Asp Lys Ser Gln Ser
    1415            1420            1425

Asp Phe His Phe Ser Ile Glu Met Ala Ile Trp Glu Lys Leu Gly
    1430            1435            1440

Leu Asp Asp Ile Leu Ala Trp Met Trp Ser Met Gly His Lys Arg
    1445            1450            1455

Thr Ile Leu Gln Asp Phe Gln Ala Gly Ile Lys Thr Leu Ile Tyr
    1460            1465            1470

Tyr Gln Arg Lys Ser Gly Asp Val Thr Thr Phe Ile Gly Asn Thr
    1475            1480            1485

Phe Ile Ile Ala Ala Cys Val Ala Ser Met Leu Pro Leu Asp Lys
```

```
    1490                1495                1500

Cys Phe  Lys Ala Ser Phe Cys  Gly Asp Asp Ser Leu  Ile Tyr Leu
    1505                1510                1515

Pro Lys  Gly Leu Glu Tyr Pro  Asp Ile Gln Ala Thr  Ala Asn Leu
    1520                1525                1530

Val Trp  Asn Phe Glu Ala Lys  Leu Phe Arg Lys Lys  Tyr Gly Tyr
    1535                1540                1545

Phe Cys  Gly Lys Tyr Ile Ile  His His Ala Asn Gly  Cys Ile Val
    1550                1555                1560

Tyr Pro  Asp Pro Leu Lys Leu  Ile Ser Lys Leu Gly  Asn Lys Ser
    1565                1570                1575

Leu Val  Gly Tyr Glu His Val  Glu Glu Phe Arg Ile  Ser Leu Leu
    1580                1585                1590

Asp Val  Ala His Ser Leu Phe  Asn Gly Ala Tyr Phe  His Leu Leu
    1595                1600                1605

Asp Asp  Ala Ile His Glu Leu  Phe Pro Asn Ala Gly  Gly Cys Ser
    1610                1615                1620

Phe Val  Ile Asn Cys Leu Cys  Lys Tyr Leu Ser Asp  Lys Arg Leu
    1625                1630                1635

Phe Arg  Ser Leu Tyr Ile Asp  Val Ser Lys
    1640                1645

<210> SEQ ID NO 32
<211> LENGTH: 161
<212> TYPE: PRT
<213> ORGANISM: Cucumber green mottle mosaic virus

<400> SEQUENCE: 32

Met Ala Tyr Asn Pro Ile Thr Pro Ser Lys Leu Ile Ala Phe Ser Ala
1               5                   10                  15

Ser Tyr Val Pro Val Arg Thr Leu Leu Asn Phe Leu Val Ala Ser Gln
            20                  25                  30

Gly Thr Ala Phe Gln Thr Gln Ala Gly Arg Asp Ser Phe Arg Glu Ser
        35                  40                  45

Leu Ser Ala Leu Pro Ser Ser Val Val Asp Ile Asn Ser Arg Phe Pro
    50                  55                  60

Asn Ala Gly Phe Tyr Ala Phe Leu Asn Gly Pro Val Leu Arg Pro Ile
65                  70                  75                  80

Phe Val Ser Leu Leu Ser Ser Thr Asp Thr Arg Asn Arg Val Ile Glu
                85                  90                  95

Val Val Asp Pro Ser Asn Pro Thr Thr Ala Glu Ser Leu Asn Ala Val
            100                 105                 110

Lys Arg Thr Asp Asp Ala Ser Thr Ala Ala Arg Ala Glu Ile Asp Asn
        115                 120                 125

Leu Ile Glu Ser Ile Ser Lys Gly Phe Asp Val Tyr Asp Arg Ala Ser
    130                 135                 140

Phe Glu Ala Ala Phe Ser Val Val Trp Ser Glu Val Thr Thr Ser Lys
145                 150                 155                 160

Ala

<210> SEQ ID NO 33
<211> LENGTH: 27
<212> TYPE: DNA
<213> ORGANISM: Artificial Sequence
<220> FEATURE:
<223> OTHER INFORMATION: Primer
```

<400> SEQUENCE: 33
ctcccttgcg ggtagtctga ggctcct 27

<210> SEQ ID NO 34
<211> LENGTH: 27
<212> TYPE: DNA
<213> ORGANISM: Artificial Sequence
<220> FEATURE:
<223> OTHER INFORMATION: Primer

<400> SEQUENCE: 34
aggagcctca gactacccgc aagggag 27

<210> SEQ ID NO 35
<211> LENGTH: 36
<212> TYPE: DNA
<213> ORGANISM: Artificial Sequence
<220> FEATURE:
<223> OTHER INFORMATION: Primer

<400> SEQUENCE: 35
aaagatcgag agagagagtg tctttgagtt gctcgc 36

<210> SEQ ID NO 36
<211> LENGTH: 36
<212> TYPE: DNA
<213> ORGANISM: Artificial Sequence
<220> FEATURE:
<223> OTHER INFORMATION: Primer

<400> SEQUENCE: 36
gcgagcaact caaagacact ctctctctcg atcttt 36

<210> SEQ ID NO 37
<211> LENGTH: 47
<212> TYPE: DNA
<213> ORGANISM: Artificial Sequence
<220> FEATURE:
<223> OTHER INFORMATION: Primer

<400> SEQUENCE: 37
cttgcaaact attgtttatc accttaaagt ggtaaatgca gttttcg 47

<210> SEQ ID NO 38
<211> LENGTH: 47
<212> TYPE: DNA
<213> ORGANISM: Artificial Sequence
<220> FEATURE:
<223> OTHER INFORMATION: Primer

<400> SEQUENCE: 38
cgaaaactgc atttaccact ttaaggtgat aaacaatagt ttgcaag 47

<210> SEQ ID NO 39
<211> LENGTH: 6422
<212> TYPE: DNA
<213> ORGANISM: Cucumber green mottle mosaic virus

<400> SEQUENCE: 39
gttttaattt ttaaaattaa acaaacaaca acaacaacaa caaacaattt aaaacaacaa 60
tggcaaacat taatgaacaa atcaacaacc aacgcgacgc cgcggccagc gggagaaaca 120
atctcgttag ccaattggcg tcaaaaaggg tgtatgacga ggctgttcgc tcgttggatc 180

```
atcaagacag acgcccaaaa atgaactttt ctcgtgtggt cagcacagag cacaccaggc    240
ttgtaactga tgcgtatccg gagttttcga ttagctttac cgccaccaag aactctgtac    300
actcccttgc gggtagtctg aggctccttg aactggaata tatgatgatg caagtgccct    360
acggctcacc ttgttatgat atcggcggta actatacgca gcacttgttc aaaggtagat    420
catatgtgca ttgctgcaat ccgtgcctgg atcttaaaga tgttgcgagg aacgtgatgt    480
ataacgatat ggtcacacaa catgtacaga ggcacaaggg atctggcggg tgcagacctc    540
ttccaacttt tcagatagat gcattcagga ggtacgataa ttctccctgt gcggtcacct    600
gttcagacgt tttccaagag tgttcctatg attttgggag cggtagggat aatcatgcag    660
tctcgctgca ttcaatctac gatatccctt attcttcgat cggacctgct cttcatagga    720
agaacgtgcg agtttgttat gcagcctttc acttctcgga ggcattgctt ttaggttcac    780
ctgtaggtaa tttaaatagt attggggctc agtttagggt cgatggtgat gatgtgcatt    840
ttctttttag tgaagagtct actttgcatt atactcatag tttagaaaat atcaaattaa    900
ttgtgatgcg tacttatttt cctgctgatg ataggtacgt gtatattaag gagtttatgg    960
tcaagcgtgt ggatactttc ttctttaggt tggtcagagc agacacacat atgcttcata   1020
aatctgtggg gcactattca aaatcgaaat ctgagtactt tgcgctgaat accccctccga   1080 tcttccaaga caaagccacg ttttctgtgt ggtttcctga ggcgaagcgt aaggtgttga   1140
tacccaagtt tgaactttca agattccttt ctgggaatgt gaaaatctct aggatgcttg   1200
tcgatgctga tttcgtccat accattatta atcacattag cacgtatgat aataaggcct   1260
tagtgtggaa gaatgttcag tcctttgtgg aatctatacg ctcaagagta attgtaaacg   1320
gagtttcggt gaaatctgaa tggaacgtac cggttgatca gctcactgat atctcgttct   1380
cgatattcct tctcgtgaag gttaggaagg tacagatcga gttaatgtct gataaagttg   1440
taatcgaggc gaggggcttg ctccggaggt tcgcagacag tcttaaatcc gccgtagaag   1500
gactaggtga ttgcgtctat gatgctctag ttcaaaccgg ctggtttgat acctctagcg   1560
acgaactgaa agtttttgcta cctgaaccgt ttatgacctt ttcggattat cttgaaggga   1620
tgtacgaggc agatgcaaag atcgagagag agagtgtctt tgagttgctc gcttccggtg   1680
acgatttgtt caagaaaatc gatgagataa gaaacaatta cagtggagtc gaatttgatg   1740
tagagaaatt ccaggaattt tgcaaggaac tgaatgttaa tcctatgcta attggccatg   1800
ttatcgaagc tattttttcg cagaaagctg gggtgacagt aacgggtctg ggtaccctct   1860
ctcctgagat gggtgcttct gttgcgttat ccaatacctc tgtagataca tgtgaagata   1920
tggatgtaac tgaagatatg gaggatatag tgttgatggc ggacaagagt cattcttaca   1980
tgtccccaga aatggcgaga tgggctgatg taaaatacga caacaataaa ggggcctgg    2040 tcgaatacaa agtcggaacc tcgatgactt tacctgccac ctgggcagag aagggtaagg   2100
ctgtcttacc gttgtcgggg atctgtgtga ggaaacccca atttttcgaag ccgcttgatg   2160 aggaagacga cttgaggtta tcaaacatga atttctttaa ggtgagcgat ctgaagttga   2220
agaaaactat cactccagtt gtttacactg ggaccattcg agagaggcaa atgaagaatt   2280
atattgatta cttatcggcc tctcttggtt ctacgctggg taatctggag agaattgtgc   2340
ggagtgattg gaacggtacc gaggagagta tgcaaacgtt cgggttgtat gactgcgaaa   2400
agtgcaagtg gttactgtta ccagccgaaa agaagcacgc atgggctgtg gttctggcaa   2460
gtgatgatac cactcgcata atcttcctct catatgacga atctggttct cccataattg   2520
ataagagaaa ctggaagcga tttgctgttt gctctgagac caaagtctat agcgtaattc   2580
```

```
gtagtttaga ggtactaaat aaggaagcaa tagtcgaccc cggggttcat ataacattag   2640
ttgacggagt gccgggttgt ggaaagaccg ccgaaattat agcgagggtc aattggaaaa   2700
ccgatctagt attgactccc gggagggagg cggctgctat gattaggcgg agggcctgcg   2760
ccctgcacaa gtcacctgtg caaccagtg acaacgttag aactttcgat tcttttgtga    2820
tgaataagaa aatcttcaag tttgacgctg tctatgttga cgagggtctg atggtccata   2880
cgggtttact taattttgcg ttgaagatct caggttgtaa aaaggccttc gtctttggtg   2940
atgctaagca aatcccgttt ataaacagag tcatgaattt tgattatcct aaggagttaa   3000
gaactttaat agtcgataat gtagagcgta ggtatgttac ccataggtgt cctagagatg   3060
tcactagttt tcttaatact atttacaaag ccgctgtcgc tactactagt ccggttgtac   3120
attctgtgaa ggcgattaaa gtgtcagggg ccggtattct gaggcccgag ttgacgaaga   3180
tcaaaggaaa gataataacg tttactcaat ctgataagca gtccttgatc aagagtgggt   3240
acaatgacgt gaacactgtg catgaaattc agggagaaac cttttgaagag acggcggttg   3300 tgcgtgccac cccgactccg ataggtttaa ttgcccgtga ttcaccacat gtactagtgg   3360
ccttaacgag gcacactaag gcaatggtgt attatactgt tgtgttcgat gcagttacaa   3420
gtataatagc ggatgtggaa aaggtcgacc agtcgatctt gactatgttt gctaccactg   3480
tgcctaccaa atagcaatta atgcagaact cactgtatgt ccatcgtaat attttcctcc   3540
ctgttagtaa aacggggttt tatacagaca tgcaggagtt ctatgataga tgccttcctg   3600
ggaattcctt cgtgctgaat gatttcgatg ccgtaaccat gcggttgagg gacaacgaat   3660
ttaacctaca accttgtagg ctaaccttaa gtaatttaga tccagtaccc gctttggtta   3720
agagtgaagc gcagaatttt ctgattcccg ttttgcgtac ggcctgtgaa aggccgcgca   3780
ttccaggtct ccttgaaaat cttgtagcta tgataaagag gaatatgaat actcctgatc   3840
tagctgggac tgtggatata actaatatgt cgatttctat agtagataac ttcttttctt   3900
cttttgttag agacgaggtt ttgcttgatc atttagattg tgttagggct agttccattc   3960
aaagtttttc tgattggttt tcgtgtcagc caacctcggc ggttggtcaa ttagctaatt   4020
tcaatttcat agatttgcct gcctttgata cttatatgca catgattaag cggcagccca   4080
agagtcggtt ggatacttcg attcagtctg aatatccggc cttgcaaact attgtttatc   4140
accttaaagt ggtaaatgca gttttcggtc cggttttta gtatttgacc accaagtttc   4200
ttagcatggt agatagttct aagttttttct tttacactag gaaaaaacca gaagatctgc   4260
aggaattttt ctcagatctc tcttcccatt ctgattatga gattcttgag ctggatgttt   4320
ctaaatatga caagtcacaa tccgatttcc atttctctat tgagatggca atttgggaaa   4380
aattggggct ggacgatatt ttggcttgga tgtggtctat gggtcacaag agaactatac   4440
tgcaagattt ccaagccggg ataaagacgc tcatttacta tcaacggaag tctggtgatg   4500
taactacttt cataggtaat acctttatta tcgcagcgtg tgtagctagt atgttgccgt   4560
tagacaagtg ttttaaagct agtttttgtg gtgatgattc gctgatctac cttcctaagg   4620
gtttggagta tcctgatata caggctactg ccaacttggt ttggaatttt gaggcgaaac   4680
ttttccgaaa gaagtatggt tacttctgtg ggaagtatat aattcaccat gccaacggct   4740
gtattgttta ccctgaccct ttaaaattaa ttagtaaatt aggtaataag agtcttgtag   4800
ggtatgagca tgttgaggag tttcgtatat ctctcctcga cgtcgctcat agtttgttta   4860
atggtgctta tttccatttta ctcgacgatg caatccacga attatttcct aacgctgggg   4920
```

```
gttgcagttt tgtaattaat tgtttgtgca agtatttgag tgataagcgc cttttccgta    4980
gtctttatat agatgtctct aagtaaggtg tcggtcgaga actcattgaa acccgagaag    5040
tttgttaaaa tctcttgggt cgataagttg ctccctaact attttccat  tcttaagtat    5100
ttatctataa ctgactttag cgtagttaaa gctcagagct atgaatccct cgtgcctgtc    5160
aagttgttgc gtggtgttga tcttacaaaa cacctttatg tcacattgtt gggcgttgtg    5220
gtttctggtg tatggaacgt accggaatcc tgtaggggtg gtgctactgt tgctctggtt    5280
gacacaagga tgcattctgt tgcagaggga actatatgca aattttcagc tcccgccacc    5340
gtccgcgaat tctctgttag gttcatacct aactattctg tcgtggctgc ggatgccctt    5400
cgcgatcctt ggtctttatt tgtgagactc tctaatgtag ggattaaaga tggtttccat    5460
cctttgacct tagaggtcgc ttgtttagtc gctacaacta actctattat caaaaagggt    5520
cttagagctt ctgtagtcga tctgtcgtc  tcttccgatc agtccattgt cctagattct    5580
ttatccgaga aagttgaacc tttctttgat aaagttccta tttcggcggc tgtgatggca    5640
agagacccca gttataggtc taggtcgcag tctgtcggtg gtcgtggtaa gcggcattct    5700
aaacctccaa atcggaggtt ggactctgct tctgaagagt ccagttctgt ttctttcgaa    5760
gatggcttac aatccgatca cacctagcaa acttattgcg tttagtgctt cttatgttcc    5820
cgtcaggact ttacttaatt ttctagttgc ttcacaaggt accgccttcc agactcaagc    5880
gggaagagat tctttccgcg agtccctgtc tgcgttaccc tcgtctgtcg tagatattaa    5940
ttctaggttc ccaaatgcgg ttttttacgc tttcctcaac ggtcctgtgt tgaggcctat    6000
cttcgtttcg cttcttagct ctacggatac gcgtaatagg gtcattgagg ttgtagatcc    6060
tagcaatcct acgactgctg agtcgcttaa cgctgtaaag cgtactgatg acgcatctac    6120
ggccgctagg gctgaaatag ataatttaat agagtctatt tctaagggtt ttgatgttta    6180
tgatagggct tcatttgaag ccgcgttttc ggtagtctgg tcagaggcta ccacctcgaa    6240
agcttagctt cgagggtctt ctgatggtgg tgcacaccaa agtgcatagt gctttcccgt    6300
tcacttaaat cgaacggttt gctcattggt ttgcggaaac ctctcacgtg tggcgttgaa    6360
gtttctatgg gcagtaattc tgcaaggggt tcgaatcccc cctttccccg ggtaggggcc    6420
ca                                                                  6422

<210> SEQ ID NO 40
<211> LENGTH: 1144
<212> TYPE: PRT
<213> ORGANISM: Cucumber green mottle mosaic virus

<400> SEQUENCE: 40

Met Ala Asn Ile Asn Glu Gln Ile Asn Gln Arg Asp Ala Ala
1               5                   10                  15

Ser Gly Arg Asn Asn Leu Val Ser Gln Leu Ala Ser Lys Arg Val Tyr
                20                  25                  30

Asp Glu Ala Val Arg Ser Leu Asp His Gln Asp Arg Arg Pro Lys Met
            35                  40                  45

Asn Phe Ser Arg Val Val Ser Thr Glu His Thr Arg Leu Val Thr Asp
        50                  55                  60

Ala Tyr Pro Glu Phe Ser Ile Ser Phe Thr Ala Thr Lys Asn Ser Val
65                  70                  75                  80

His Ser Leu Ala Gly Ser Leu Arg Leu Leu Glu Leu Glu Tyr Met Met
                85                  90                  95

Met Gln Val Pro Tyr Gly Ser Pro Cys Tyr Asp Ile Gly Gly Asn Tyr
```

```
                100             105             110
Thr Gln His Leu Phe Lys Gly Arg Ser Tyr Val His Cys Cys Asn Pro
            115             120             125
Cys Leu Asp Leu Lys Asp Val Ala Arg Asn Val Met Tyr Asn Asp Met
            130             135             140
Val Thr Gln His Val Gln Arg His Lys Gly Ser Gly Gly Cys Arg Pro
145             150             155             160
Leu Pro Thr Phe Gln Ile Asp Ala Phe Arg Arg Tyr Asp Asn Ser Pro
            165             170             175
Cys Ala Val Thr Cys Ser Asp Val Phe Gln Glu Cys Ser Tyr Asp Phe
            180             185             190
Gly Ser Gly Arg Asp Asn His Ala Val Ser Leu His Ser Ile Tyr Asp
        195             200             205
Ile Pro Tyr Ser Ser Ile Gly Pro Ala Leu His Arg Lys Asn Val Arg
        210             215             220
Val Cys Tyr Ala Ala Phe His Phe Ser Glu Ala Leu Leu Leu Gly Ser
225             230             235             240
Pro Val Gly Asn Leu Asn Ser Ile Gly Ala Gln Phe Arg Val Asp Gly
            245             250             255
Asp Asp Val His Phe Leu Phe Ser Glu Ser Thr Leu His Tyr Thr
            260             265             270
His Ser Leu Glu Asn Ile Lys Leu Ile Val Met Arg Thr Tyr Phe Pro
        275             280             285
Ala Asp Asp Arg Tyr Val Tyr Ile Lys Glu Phe Met Val Lys Arg Val
        290             295             300
Asp Thr Phe Phe Arg Leu Val Arg Ala Asp Thr His Met Leu His
305             310             315             320
Lys Ser Val Gly His Tyr Ser Lys Ser Lys Ser Glu Tyr Phe Ala Leu
            325             330             335
Asn Thr Pro Pro Ile Phe Gln Asp Lys Ala Thr Phe Ser Val Trp Phe
            340             345             350
Pro Glu Ala Lys Arg Lys Val Leu Ile Pro Lys Phe Glu Leu Ser Arg
            355             360             365
Phe Leu Ser Gly Asn Val Lys Ile Ser Arg Met Leu Val Asp Ala Asp
        370             375             380
Phe Val His Thr Ile Ile Asn His Ile Ser Thr Tyr Asp Asn Lys Ala
385             390             395             400
Leu Val Trp Lys Asn Val Gln Ser Phe Val Glu Ser Ile Arg Ser Arg
            405             410             415
Val Ile Val Asn Gly Val Ser Val Lys Ser Glu Trp Asn Val Pro Val
            420             425             430
Asp Gln Leu Thr Asp Ile Ser Phe Ser Ile Phe Leu Leu Val Lys Val
            435             440             445
Arg Lys Val Gln Ile Glu Leu Met Ser Asp Lys Val Val Ile Glu Ala
        450             455             460
Arg Gly Leu Leu Arg Arg Phe Ala Asp Ser Leu Lys Ser Ala Val Glu
465             470             475             480
Gly Leu Gly Asp Cys Val Tyr Asp Ala Leu Val Gln Thr Gly Trp Phe
            485             490             495
Asp Thr Ser Ser Asp Glu Leu Lys Val Leu Leu Pro Glu Pro Phe Met
            500             505             510
Thr Phe Ser Asp Tyr Leu Glu Gly Met Tyr Glu Ala Asp Ala Lys Ile
            515             520             525
```

```
Glu Arg Glu Ser Val Phe Glu Leu Leu Ala Ser Gly Asp Leu Phe
    530                 535                 540
Lys Lys Ile Asp Glu Ile Arg Asn Asn Tyr Ser Gly Val Glu Phe Asp
545                 550                 555                 560
Val Glu Lys Phe Gln Glu Phe Cys Lys Glu Leu Asn Val Asn Pro Met
                565                 570                 575
Leu Ile Gly His Val Ile Glu Ala Ile Phe Ser Gln Lys Ala Gly Val
            580                 585                 590
Thr Val Thr Gly Leu Gly Thr Leu Ser Pro Glu Met Gly Ala Ser Val
        595                 600                 605
Ala Leu Ser Asn Thr Ser Val Asp Thr Cys Glu Asp Met Asp Val Thr
    610                 615                 620
Glu Asp Met Glu Asp Ile Val Leu Met Ala Asp Lys Ser His Ser Tyr
625                 630                 635                 640
Met Ser Pro Glu Met Ala Arg Trp Ala Asp Val Lys Tyr Asp Asn Asn
                645                 650                 655
Lys Gly Gly Leu Val Glu Tyr Lys Val Gly Thr Ser Met Thr Leu Pro
            660                 665                 670
Ala Thr Trp Ala Glu Lys Gly Lys Ala Val Leu Pro Leu Ser Gly Ile
        675                 680                 685
Cys Val Arg Lys Pro Gln Phe Ser Lys Pro Leu Asp Glu Glu Asp Asp
    690                 695                 700
Leu Arg Leu Ser Asn Met Asn Phe Phe Lys Val Ser Asp Leu Lys Leu
705                 710                 715                 720
Lys Lys Thr Ile Thr Pro Val Val Tyr Thr Gly Thr Ile Arg Glu Arg
                725                 730                 735
Gln Met Lys Asn Tyr Ile Asp Tyr Leu Ser Ala Ser Leu Gly Ser Thr
            740                 745                 750
Leu Gly Asn Leu Glu Arg Ile Val Arg Ser Asp Trp Asn Gly Thr Glu
        755                 760                 765
Glu Ser Met Gln Thr Phe Gly Leu Tyr Asp Cys Glu Lys Cys Lys Trp
    770                 775                 780
Leu Leu Leu Pro Ala Glu Lys Lys His Ala Trp Ala Val Val Leu Ala
785                 790                 795                 800
Ser Asp Asp Thr Thr Arg Ile Ile Phe Leu Ser Tyr Asp Glu Ser Gly
                805                 810                 815
Ser Pro Ile Ile Asp Lys Arg Asn Trp Lys Arg Phe Ala Val Cys Ser
            820                 825                 830
Glu Thr Lys Val Tyr Ser Val Ile Arg Ser Leu Glu Val Leu Asn Lys
        835                 840                 845
Glu Ala Ile Val Asp Pro Gly Val His Ile Thr Leu Val Asp Gly Val
    850                 855                 860
Pro Gly Cys Gly Lys Thr Ala Glu Ile Ile Ala Arg Val Asn Trp Lys
865                 870                 875                 880
Thr Asp Leu Val Leu Thr Pro Gly Arg Glu Ala Ala Met Ile Arg
                885                 890                 895
Arg Arg Ala Cys Ala Leu His Lys Ser Pro Val Ala Thr Ser Asp Asn
            900                 905                 910
Val Arg Thr Phe Asp Ser Phe Val Met Asn Lys Lys Ile Phe Lys Phe
        915                 920                 925
Asp Ala Val Tyr Val Asp Glu Gly Leu Met Val His Thr Gly Leu Leu
    930                 935                 940
```

```
Asn Phe Ala Leu Lys Ile Ser Gly Cys Lys Lys Ala Phe Val Phe Gly
945                 950                 955                 960

Asp Ala Lys Gln Ile Pro Phe Ile Asn Arg Val Met Asn Phe Asp Tyr
                965                 970                 975

Pro Lys Glu Leu Arg Thr Leu Ile Val Asp Asn Val Glu Arg Arg Tyr
            980                 985                 990

Val Thr His Arg Cys Pro Arg Asp Val Thr Ser Phe Leu Asn Thr Ile
        995                 1000                1005

Tyr Lys Ala Ala Val Ala Thr Thr Ser Pro Val Val His Ser Val
    1010                1015                1020

Lys Ala Ile Lys Val Ser Gly Ala Gly Ile Leu Arg Pro Glu Leu
    1025                1030                1035

Thr Lys Ile Lys Gly Lys Ile Ile Thr Phe Thr Gln Ser Asp Lys
    1040                1045                1050

Gln Ser Leu Ile Lys Ser Gly Tyr Asn Asp Val Asn Thr Val His
    1055                1060                1065

Glu Ile Gln Gly Glu Thr Phe Glu Glu Thr Ala Val Val Arg Ala
    1070                1075                1080

Thr Pro Thr Pro Ile Gly Leu Ile Ala Arg Asp Ser Pro His Val
    1085                1090                1095

Leu Val Ala Leu Thr Arg His Thr Lys Ala Met Val Tyr Tyr Thr
    1100                1105                1110

Val Val Phe Asp Ala Val Thr Ser Ile Ile Ala Asp Val Glu Lys
    1115                1120                1125

Val Asp Gln Ser Ile Leu Thr Met Phe Ala Thr Thr Val Pro Thr
    1130                1135                1140

Lys

<210> SEQ ID NO 41
<211> LENGTH: 1648
<212> TYPE: PRT
<213> ORGANISM: Cucumber green mottle mosaic virus
<220> FEATURE:
<221> NAME/KEY: misc_feature
<222> LOCATION: (1145)..(1145)
<223> OTHER INFORMATION: Xaa can be any naturally occurring amino acid

<400> SEQUENCE: 41

Met Ala Asn Ile Asn Glu Gln Ile Asn Asn Gln Arg Asp Ala Ala Ala
1               5                   10                  15

Ser Gly Arg Asn Asn Leu Val Ser Gln Leu Ala Ser Lys Arg Val Tyr
            20                  25                  30

Asp Glu Ala Val Arg Ser Leu Asp His Gln Asp Arg Arg Pro Lys Met
        35                  40                  45

Asn Phe Ser Arg Val Val Ser Thr Glu His Thr Arg Leu Val Thr Asp
    50                  55                  60

Ala Tyr Pro Glu Phe Ser Ile Ser Phe Thr Ala Thr Lys Asn Ser Val
65                  70                  75                  80

His Ser Leu Ala Gly Ser Leu Arg Leu Leu Glu Leu Glu Tyr Met Met
                85                  90                  95

Met Gln Val Pro Tyr Gly Ser Pro Cys Tyr Asp Ile Gly Gly Asn Tyr
            100                 105                 110

Thr Gln His Leu Phe Lys Gly Arg Ser Tyr Val His Cys Cys Asn Pro
        115                 120                 125

Cys Leu Asp Leu Lys Asp Val Ala Arg Asn Val Met Tyr Asn Asp Met
    130                 135                 140
```

```
Val Thr Gln His Val Gln Arg His Lys Gly Ser Gly Gly Cys Arg Pro
145                 150                 155                 160

Leu Pro Thr Phe Gln Ile Asp Ala Phe Arg Arg Tyr Asp Asn Ser Pro
            165                 170                 175

Cys Ala Val Thr Cys Ser Asp Val Phe Gln Glu Cys Ser Tyr Asp Phe
        180                 185                 190

Gly Ser Gly Arg Asp Asn His Ala Val Ser Leu His Ser Ile Tyr Asp
    195                 200                 205

Ile Pro Tyr Ser Ser Ile Gly Pro Ala Leu His Arg Lys Asn Val Arg
210                 215                 220

Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
            245                 250                 255

Asp Asp Val His Phe Leu Phe Ser Glu Glu Ser Thr Leu His Tyr Thr
        260                 265                 270

His Ser Leu Glu Asn Ile Lys Leu Ile Val Met Arg Thr Tyr Phe Pro
    275                 280                 285

Ala Asp Asp Arg Tyr Val Tyr Ile Lys Glu Phe Met Val Lys Arg Val
290                 295                 300

Asp Thr Phe Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
            325                 330                 335

Asn Thr Pro Pro Ile Phe Gln Asp Lys Ala Thr Phe Ser Val Trp Phe
        340                 345                 350

Pro Glu Ala Lys Arg Lys Val Leu Ile Pro Lys Phe Glu Leu Ser Arg
    355                 360                 365

Phe Leu Ser Gly Asn Val Lys Ile Ser Arg Met Leu Val Asp Ala Asp
370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
            405                 410                 415

Val Ile Val Asn Gly Val Ser Val Lys Ser Glu Trp Asn Val Pro Val
        420                 425                 430

Asp Gln Leu Thr Asp Ile Ser Phe Ser Ile Phe Leu Leu Val Lys Val
    435                 440                 445

Arg Lys Val Gln Ile Glu Leu Met Ser Asp Lys Val Val Ile Glu Ala
450                 455                 460

Arg Gly Leu Leu Arg Arg Phe Ala Asp Ser Leu Lys Ser Ala Val Glu
465                 470                 475                 480

Gly Leu Gly Asp Cys Val Tyr Asp Ala Leu Val Gln Thr Gly Trp Phe
            485                 490                 495

Asp Thr Ser Ser Asp Glu Leu Lys Val Leu Leu Pro Glu Pro Phe Met
        500                 505                 510

Thr Phe Ser Asp Tyr Leu Glu Gly Met Tyr Glu Ala Asp Ala Lys Ile
    515                 520                 525

Glu Arg Glu Ser Val Phe Glu Leu Leu Ala Ser Gly Asp Asp Leu Phe
530                 535                 540

Lys Lys Ile Asp Glu Ile Arg Asn Asn Tyr Ser Gly Val Glu Phe Asp
545                 550                 555                 560
```

```
Val Glu Lys Phe Gln Glu Phe Cys Lys Glu Leu Asn Val Asn Pro Met
            565                 570                 575
Leu Ile Gly His Val Ile Glu Ala Ile Phe Ser Gln Lys Ala Gly Val
            580                 585                 590
Thr Val Thr Gly Leu Gly Thr Leu Ser Pro Glu Met Gly Ala Ser Val
            595                 600                 605
Ala Leu Ser Asn Thr Ser Val Asp Thr Cys Glu Asp Met Asp Val Thr
            610                 615                 620
Glu Asp Met Glu Asp Ile Val Leu Met Ala Asp Lys Ser His Ser Tyr
625                 630                 635                 640
Met Ser Pro Glu Met Ala Arg Trp Ala Asp Val Lys Tyr Asp Asn Asn
                645                 650                 655
Lys Gly Gly Leu Val Glu Tyr Lys Val Gly Thr Ser Met Thr Leu Pro
            660                 665                 670
Ala Thr Trp Ala Glu Lys Gly Lys Ala Val Leu Pro Leu Ser Gly Ile
            675                 680                 685
Cys Val Arg Lys Pro Gln Phe Ser Lys Pro Leu Asp Glu Glu Asp Asp
            690                 695                 700
Leu Arg Leu Ser Asn Met Asn Phe Phe Lys Val Ser Asp Leu Lys Leu
705                 710                 715                 720
Lys Lys Thr Ile Thr Pro Val Val Tyr Thr Gly Thr Ile Arg Glu Arg
                725                 730                 735
Gln Met Lys Asn Tyr Ile Asp Tyr Leu Ser Ala Ser Leu Gly Ser Thr
                740                 745                 750
Leu Gly Asn Leu Glu Arg Ile Val Arg Ser Asp Trp Asn Gly Thr Glu
            755                 760                 765
Glu Ser Met Gln Thr Phe Gly Leu Tyr Asp Cys Glu Lys Cys Lys Trp
770                 775                 780
Leu Leu Leu Pro Ala Glu Lys Lys His Ala Trp Ala Val Val Leu Ala
785                 790                 795                 800
Ser Asp Asp Thr Thr Arg Ile Ile Phe Leu Ser Tyr Asp Glu Ser Gly
                805                 810                 815
Ser Pro Ile Ile Asp Lys Arg Asn Trp Lys Arg Phe Ala Val Cys Ser
                820                 825                 830
Glu Thr Lys Val Tyr Ser Val Ile Arg Ser Leu Glu Val Leu Asn Lys
            835                 840                 845
Glu Ala Ile Val Asp Pro Gly Val His Ile Thr Leu Val Asp Gly Val
850                 855                 860
Pro Gly Cys Gly Lys Thr Ala Glu Ile Ile Ala Arg Val Asn Trp Lys
865                 870                 875                 880
Thr Asp Leu Val Leu Thr Pro Gly Arg Glu Ala Ala Met Ile Arg
            885                 890                 895
Arg Arg Ala Cys Ala Leu His Lys Ser Pro Val Ala Thr Ser Asp Asn
                900                 905                 910
Val Arg Thr Phe Asp Ser Phe Val Met Asn Lys Lys Ile Phe Lys Phe
            915                 920                 925
Asp Ala Val Tyr Val Asp Glu Gly Leu Met Val His Thr Gly Leu Leu
            930                 935                 940
Asn Phe Ala Leu Lys Ile Ser Gly Cys Lys Lys Ala Phe Val Phe Gly
945                 950                 955                 960
Asp Ala Lys Gln Ile Pro Phe Ile Asn Arg Val Met Asn Phe Asp Tyr
                965                 970                 975
Pro Lys Glu Leu Arg Thr Leu Ile Val Asp Asn Val Glu Arg Arg Tyr
```

```
                      980              985              990
         Val Thr His Arg Cys Pro Arg Asp Val Thr Ser Phe Leu Asn Thr Ile
                  995              1000             1005

Tyr Lys Ala Ala Val Ala Thr Thr Ser Pro Val His Ser Val
             1010             1015             1020

Lys Ala Ile Lys Val Ser Gly Ala Gly Ile Leu Arg Pro Glu Leu
             1025             1030             1035

Thr Lys Ile Lys Gly Lys Ile Ile Thr Phe Thr Gln Ser Asp Lys
             1040             1045             1050

Gln Ser Leu Ile Lys Ser Gly Tyr Asn Asp Val Asn Thr Val His
             1055             1060             1065

Glu Ile Gln Gly Glu Thr Phe Glu Glu Thr Ala Val Val Arg Ala
             1070             1075             1080

Thr Pro Thr Pro Ile Gly Leu Ile Ala Arg Asp Ser Pro His Val
             1085             1090             1095

Leu Val Ala Leu Thr Arg His Thr Lys Ala Met Val Tyr Tyr Thr
             1100             1105             1110

Val Val Phe Asp Ala Val Thr Ser Ile Ile Ala Asp Val Glu Lys
             1115             1120             1125

Val Asp Gln Ser Ile Leu Thr Met Phe Ala Thr Thr Val Pro Thr
             1130             1135             1140

Lys Xaa Gln Leu Met Gln Asn Ser Leu Tyr Val His Arg Asn Ile
             1145             1150             1155

Phe Leu Pro Val Ser Lys Thr Gly Phe Tyr Thr Asp Met Gln Glu
             1160             1165             1170

Phe Tyr Asp Arg Cys Leu Pro Gly Asn Ser Phe Val Leu Asn Asp
             1175             1180             1185

Phe Asp Ala Val Thr Met Arg Leu Arg Asp Asn Glu Phe Asn Leu
             1190             1195             1200

Gln Pro Cys Arg Leu Thr Leu Ser Asn Leu Asp Pro Val Pro Ala
             1205             1210             1215

Leu Val Lys Ser Glu Ala Gln Asn Phe Leu Ile Pro Val Leu Arg
             1220             1225             1230

Thr Ala Cys Glu Arg Pro Arg Ile Pro Gly Leu Leu Glu Asn Leu
             1235             1240             1245

Val Ala Met Ile Lys Arg Asn Met Asn Thr Pro Asp Leu Ala Gly
             1250             1255             1260

Thr Val Asp Ile Thr Asn Met Ser Ile Ser Ile Val Asp Asn Phe
             1265             1270             1275

Phe Ser Ser Phe Val Arg Asp Glu Val Leu Leu Asp His Leu Asp
             1280             1285             1290

Cys Val Arg Ala Ser Ser Ile Gln Ser Phe Ser Asp Trp Phe Ser
             1295             1300             1305

Cys Gln Pro Thr Ser Ala Val Gly Gln Leu Ala Asn Phe Asn Phe
             1310             1315             1320

Ile Asp Leu Pro Ala Phe Asp Thr Tyr Met His Met Ile Lys Arg
             1325             1330             1335

Gln Pro Lys Ser Arg Leu Asp Thr Ser Ile Gln Ser Glu Tyr Pro
             1340             1345             1350

Ala Leu Gln Thr Ile Val Tyr His Leu Lys Val Val Asn Ala Val
             1355             1360             1365

Phe Gly Pro Val Phe Lys Tyr Leu Thr Thr Lys Phe Leu Ser Met
             1370             1375             1380
```

| | | | | | | | | | | |
|---|---|---|---|---|---|---|---|---|---|---|
| Val | Asp | Ser | Ser | Lys | Phe | Phe | Phe | Tyr | Thr | Arg | Lys | Lys | Pro | Glu |
| | 1385 | | | | 1390 | | | | 1395 | |
| Asp | Leu | Gln | Glu | Phe | Phe | Ser | Asp | Leu | Ser | Ser | His | Ser | Asp | Tyr |
| 1400 | | | | | 1405 | | | | | 1410 | |
| Glu | Ile | Leu | Glu | Leu | Asp | Val | Ser | Lys | Tyr | Asp | Lys | Ser | Gln | Ser |
| 1415 | | | | | 1420 | | | | | 1425 | |
| Asp | Phe | His | Phe | Ser | Ile | Glu | Met | Ala | Ile | Trp | Glu | Lys | Leu | Gly |
| 1430 | | | | | 1435 | | | | | 1440 | |
| Leu | Asp | Asp | Ile | Leu | Ala | Trp | Met | Trp | Ser | Met | Gly | His | Lys | Arg |
| | 1445 | | | | 1450 | | | | 1455 | |
| Thr | Ile | Leu | Gln | Asp | Phe | Gln | Ala | Gly | Ile | Lys | Thr | Leu | Ile | Tyr |
| | 1460 | | | | 1465 | | | | 1470 | |
| Tyr | Gln | Arg | Lys | Ser | Gly | Asp | Val | Thr | Thr | Phe | Ile | Gly | Asn | Thr |
| | 1475 | | | | 1480 | | | | 1485 | |
| Phe | Ile | Ile | Ala | Ala | Cys | Val | Ala | Ser | Met | Leu | Pro | Leu | Asp | Lys |
| | 1490 | | | | 1495 | | | | 1500 | |
| Cys | Phe | Lys | Ala | Ser | Phe | Cys | Gly | Asp | Asp | Ser | Leu | Ile | Tyr | Leu |
| | 1505 | | | | 1510 | | | | 1515 | |
| Pro | Lys | Gly | Leu | Glu | Tyr | Pro | Asp | Ile | Gln | Ala | Thr | Ala | Asn | Leu |
| | 1520 | | | | 1525 | | | | 1530 | |
| Val | Trp | Asn | Phe | Glu | Ala | Lys | Leu | Phe | Arg | Lys | Lys | Tyr | Gly | Tyr |
| | 1535 | | | | 1540 | | | | 1545 | |
| Phe | Cys | Gly | Lys | Tyr | Ile | Ile | His | His | Ala | Asn | Gly | Cys | Ile | Val |
| | 1550 | | | | 1555 | | | | 1560 | |
| Tyr | Pro | Asp | Pro | Leu | Lys | Leu | Ile | Ser | Lys | Leu | Gly | Asn | Lys | Ser |
| | 1565 | | | | 1570 | | | | 1575 | |
| Leu | Val | Gly | Tyr | Glu | His | Val | Glu | Glu | Phe | Arg | Ile | Ser | Leu | Leu |
| | 1580 | | | | 1585 | | | | 1590 | |
| Asp | Val | Ala | His | Ser | Leu | Phe | Asn | Gly | Ala | Tyr | Phe | His | Leu | Leu |
| | 1595 | | | | 1600 | | | | 1605 | |
| Asp | Asp | Ala | Ile | His | Glu | Leu | Phe | Pro | Asn | Ala | Gly | Gly | Cys | Ser |
| | 1610 | | | | 1615 | | | | 1620 | |
| Phe | Val | Ile | Asn | Cys | Leu | Cys | Lys | Tyr | Leu | Ser | Asp | Lys | Arg | Leu |
| | 1625 | | | | 1630 | | | | 1635 | |
| Phe | Arg | Ser | Leu | Tyr | Ile | Asp | Val | Ser | Lys |
| | 1640 | | | | 1645 |

<210> SEQ ID NO 42
<211> LENGTH: 6422
<212> TYPE: DNA
<213> ORGANISM: Cucumber green mottle mosaic virus

<400> SEQUENCE: 42

```
gttttaattt ttaaaattaa acaaacaaca acaacaacaa caaacaattt aaaacaacaa    60
tggcaaacat taatgaacaa atcaacaacc aacgcgacgc cgcggccagc gggagaaaca   120
atctcgttag ccaattggcg tcaaaaaggg tgtatgacga ggctgttcgc tcgttggatc   180
atcaagacag acgcccaaaa atgaactttt ctcgtgtggt cagcacagag cacaccaggc   240
ttgtaactga tgcgtatccg gagttttcga ttagctttac cgccaccaag aactctgtac   300
actcccttgc gggtagtctg aggctccttg aactggaata tatgatgatg caagtgccct   360
acggctcacc ttgttatgat atcggcggta actatacgca gcacttgttc aaaggtagat   420
catatgtgca ttgctgcaat ccgtgcctgg atcttaaaga tgttgcgagg aacgtgatgt   480
```

-continued

| | |
|---|---|
| ataacgatat ggtcacacaa catgtacaga ggcacaaggg atctggcggg tgcagacctc | 540 |
| ttccaacttt tcagatagat gcattcagga ggtacgataa ttctccctgt gcggtcacct | 600 |
| gttcagacgt tttccaagag tgttcctatg attttgggag cggtagggat aatcatgcag | 660 |
| tctcgctgca ttcaatctac gatatcccctt attcttcgat cggacctgct cttcatagga | 720 |
| agaacgtgcg agtttgttat gcagcctttc acttctcgga ggcattgctt ttaggttcac | 780 |
| ctgtaggtaa tttaaatagt attggggctc agtttagggt cgatggtgat gatgtgcatt | 840 |
| ttctttttag tgaagagtct actttgcatt atactcatag tttagaaaat atcaaattaa | 900 |
| ttgtgatgcg tacttatttt cctgctgatg ataggtacgt gtatattaag gagtttatgg | 960 |
| tcaagcgtgt ggatactttc ttctttaggt tggtcagagc agacacacat atgcttcata | 1020 |
| aatctgtggg gcactattca aaatcgaaat ctgagtactt tgcgctgaat accccctccga | 1080 |
| tcttccaaga caaagccacg ttttctgtgt ggtttcctga ggcgaagcgt aaggtgttga | 1140 |
| tacccaagtt tgaactttca agattccttt ctgggaatgt gaaaatctct aggatgcttg | 1200 |
| tcgatgctga tttcgtccat accattatta atcacattag cacgtatgat aataaggcct | 1260 |
| tagtgtggaa gaatgttcag tcctttgtgg aatctatacg ctcaagagta attgtaaacg | 1320 |
| gagtttcggt gaaatctgaa tggaacgtac cggttgatca gctcactgat atctcgttct | 1380 |
| cgatattcct tctcgtgaag gttaggaagg tacagatcga gttaatgtct gataaagttg | 1440 |
| taatcgaggc gaggggcttg ctccggaggt tcgcagacag tcttaaatcc gccgtaggag | 1500 |
| gactaggtga ttgcgtctat gatgctctag ttcaaaccgg ctggtttgat acctctagcg | 1560 |
| acgaactgaa agttttgcta cctgaaccgt ttatgacctt tcggattat cttgaaggga | 1620 |
| tgtacgaggc agatgcaaag atcgagagag agagtgtctt tgagttgctc gcttccggtg | 1680 |
| acgatttgtt caagaaaatc gatgagataa gaaacaatta cagtggagtc gaatttgatg | 1740 |
| tagagaaatt ccaggaattt tgcaaggaac tgaatgttaa tcctatgcta attggccatg | 1800 |
| ttatcgaagc tatttttttcg cagaaagctg gggtgacagt aacgggtctg ggtaccctct | 1860 |
| ctcctgagat gggtgcttct gttgcgttat ccaatacctc tgtagataca tgtgaagata | 1920 |
| tggatgtaac tgaagatatg gaggatatag tgttgatggc ggacaagagt cattcttaca | 1980 |
| tgtcccccaga aatggcgaga tgggctgatg taaaatacga caacaataaa gggggcctgg | 2040 |
| tcgaatacaa agtcggaacc tcgatgactt tacctgccac ctgggcagag aagggtaagg | 2100 |
| ctgtcttacc gttgtcgggg atctgtgtga ggaaacccca attttcgaag ccgcttgatg | 2160 |
| aggaagacga cttgaggtta tcaaacatga atttctttaa ggtgagcgat ctgaagttga | 2220 |
| agaaaactat cactccagtt gtttacactg ggaccattcg agagaggcaa atgaagaatt | 2280 |
| atattgatta cttatcggcc tctcttggtt ctacgctggg taatctggag agaattgtgc | 2340 |
| ggagtgattg gaacggtacc gaggagagta tgcaaacgtt cgggttgtat gactgcgaaa | 2400 |
| agtgcaagtg gttactgtta ccagccgaaa agaagcacgc atgggctgtg gttctggcaa | 2460 |
| gtgatgatac cactcgcata atcttcctct catatgacga atctggttct cccataattg | 2520 |
| ataagagaaa ctggaagcga tttgctgttt gctctgagac caaagtctat agcgtaattc | 2580 |
| gtagtttaga ggtactaaat aaggaagcaa tagtcgaccc cggggttcat ataacattag | 2640 |
| ttgacggagt gccgggttgt ggaaagaccg ccgaaattat agcgagggtc aattggaaaa | 2700 |
| ccgatctagt attgactccc gggagggagg cggctgctat gattaggcgg agggcctgcg | 2760 |
| ccctgcacaga gtcacctgtg gcaaccagtg acaacgttag aactttcgat tcttttgtga | 2820 |
| tgaataagaa aatcttcaag tttgacgctg tctatgttga cgagggtctg atggtccata | 2880 |

```
cgggtttact taattttgcg ttgaagatct caggttgtaa aaaggccttc gtctttggtg    2940
atgctaagca aatcccgttt ataaacagag tcatgaattt tgattatcct aaggagttaa    3000
gaactttaat agtcgataat gtagagcgta ggtatgttac ccataggtgt cctagagatg    3060
tcactagttt tcttaatact atttacaaag ccgctgtcgc tactactagt ccggttgtac    3120
attctgtgaa ggcgattaaa gtgtcagggg ccggtattct gaggcccgag ttgacgaaga    3180
tcaaaggaaa gataataacg tttactcaat ctgataagca gtccttgatc aagagtgggt    3240
acaatgacgt gaacactgtg catgaaattc agggagaaac ctttgaagag acggcggttg    3300
tgcgtgccac cccgactccg ataggtttaa ttgcccgtga ttcaccacat gtactagtgg    3360
ccttaacgag gcacactaag gcaatggtgt attatactgt tgtgttcgat gcagttacaa    3420
gtataatagt ggatgtggaa aaggtcgacc agtcgatctt gactatgttt gctaccactg    3480
tgcctaccaa atagcaatta atgcagaact cactgtatgt ccatcgtgat atttttcctcc    3540 ctgttagtaa aacggggttt tatacagaca tgcaggagtt ctatgataga tgccttcctg    3600
ggaattcctt cgtgctgaat gatttcgatg ccgtaaccat gcggttgagg gacaacgaat    3660
ttaacctaca accttgtagg ctaaccttaa gtaatttaga tccagtaccc gctttggtta    3720
agagtgaagc gcagaatttt ctgattcccg ttttgcgtac ggcctgtgaa aggccgcgca    3780
ttccaggtct ccttgaaaat cttgtagcta tgataaagag gaatatgaat actcctgatc    3840
tagctgggac tgtggatata actaatatgt cgatttctat agtagataac ttcttttctt    3900
cttttgttag agacgaggtt ttgcttgatc atttagattg tgttagggct agttccattc    3960 aaagttttc tgattggttt tcgtgtcagc caacctcggc ggttggtcaa ttagctaatt    4020
tcaatttcat agatttgcct gcctttgata cttatatgca catgattaag cggcagccca    4080
agagtcggtt ggatacttcg attcagtctg aatatccggc cttgcaaact attgtttatc    4140
accttaaagt ggtaaatgca gttttcggtc cggttttttaa gtatttgacc accaagtttc    4200
ttagcatggt agatagttct aagttttttct tttacactag gaaaaaatca gaagatctgc    4260
aggaattttt ctcagatctc tcttcccatt ctgattatga gattcttgag ctggatgttt    4320
ctaaatatga caagtcacaa tccgatttcc atttctctat tgagatggca atttgggaaa    4380
aattggggct ggacgatatt ttggcttgga tgtggtctat gggtcacaag agaactatac    4440
tgcaagattt ccaagccggg ataaagacgc tcatttacta tcaacggaag tctggtgatg    4500
taactacttt cataggtaat acctttatta tcgcagcgtg tgtagctagt atgttgccgt    4560
tagacaagtg ttttaaagct agttttttgtg gtgatgattc gctgatctac cttcctaagg    4620
gtttggagta tcctgatata caggctactg ccaacttggt ttggaatttt gaggcgaaac    4680
ttttccgaaa gaagtatggt tacttctgtg ggaagtatat aattcaccat gccaacggct    4740
gtattgttta ccctgacccct ttaaaattaa ttagtaaatt aggtaataag agtcttgtag    4800
ggtatgagca tgttgaggag tttcgtatat ctctcctcga cgtcgctcat agtttgttta    4860
atggtgctta tttccatttta ctcgacgatg caatccacga attatttcct aacgctgggg    4920
gttgcagttt tgtaattaat tgtttgtgca agtatttgag tgataagcgc cttttccgta    4980
gtctttatat agatgtctct aagtaaggtg tcggtcgaga actcattgaa acccgagaag    5040
tttgttaaaa tctcttgggt cgataagttg ctccctaact attttttccat tcttaagtat    5100 ttatctataa ctgactttag cgtagttaaa gctcagagct atgaatccct cgtgcctgtc    5160
aagttgttgc gtggtgttga tcttacaaaa caccttatg tcacattgtt gggcgttgtg    5220
```

```
gtttctggtg tatggaacgt accggaatcc tgtaggggtg gtgctactgt tgctctggtt    5280
gacacaagga tgcattctgt tgcagaggga actatatgca aattttcagc tcccgccacc    5340
gtccgcgaat tctctgttag gttcatacct aactattctg tcgtggctgc ggatgccctt    5400
cgcgatcctt ggtctttatt tgtgagactc tctaatgtag ggattaaaga tggtttccat    5460
cctttgacct tagaggtcgc ttgtttagtc gctacaacta actctattat caaaaagggt    5520
cttagagctt ctgtagtcga gtctgtcgtc tcttccgatc agtccattgt cctagattct    5580
ttatccgaga aagttgaacc tttctttgat aaagttccta tttcggcggc tgtgatggca    5640
agagacccca gttataggtc taggtcgcag tctgtcggtg gtcgtggtaa gcggcattct    5700
aaacctccaa atcggaggtt ggactctgct tctgaagagt ccagttctgt ttctttcgaa    5760
gatggcttac aatccgatca cacctagcaa acttattgcg tttagtgctt cttatgttcc    5820
cgtcaggact ttacttaatt ttctagttgc ttcacaaggt accgcttcc agactcaagc     5880
gggaagagat tctttccgcg agtccctgtc tgcgttaccc tcgtctgtcg tagatattaa    5940
ttctaggttc ccaaatgcgg ttttttacgc tttcctcaac ggtcctgtgt tgaggcctat    6000
cttcgtttcg cttcttagct ctacggatac gcgtaatagg gtcattgagg ttgtagatcc    6060
tagcaatcct acgactgctg agtcgcttaa cgctgtaaag cgtactgatg acgcatctac    6120
ggccgctagg gctgaaatag ataatttaat agagtctatt tctaagggtt ttgatgttta    6180
tgataggget tcatttgaag ccgcgttttc ggtagtctgg tcagaggtta ccacctcgaa    6240
agcttagctt cgagggtctt ctgatggtgg tgcacaccaa agtgcatagt gctttcccgt    6300
tcacttaaat cgaacggttt gctcattggt ttgcggaaac ctctcacgtg tggcgttgaa    6360
gtttctatgg gcagtaattc tgcaaggggt tcgaatcccc cctttcccg ggtaggggcc     6420
ca                                                                   6422

<210> SEQ ID NO 43
<211> LENGTH: 1144
<212> TYPE: PRT
<213> ORGANISM: Cucumber green mottle mosaic virus

<400> SEQUENCE: 43

Met Ala Asn Ile Asn Glu Gln Ile Asn Asn Gln Arg Asp Ala Ala Ala
1               5                   10                  15

Ser Gly Arg Asn Asn Leu Val Ser Gln Leu Ala Ser Lys Arg Val Tyr
            20                  25                  30

Asp Glu Ala Val Arg Ser Leu Asp His Gln Asp Arg Arg Pro Lys Met
        35                  40                  45

Asn Phe Ser Arg Val Val Ser Thr Glu His Thr Arg Leu Val Thr Asp
    50                  55                  60

Ala Tyr Pro Glu Phe Ser Ile Ser Phe Thr Ala Thr Lys Asn Ser Val
65                  70                  75                  80

His Ser Leu Ala Gly Ser Leu Arg Leu Leu Glu Leu Glu Tyr Met Met
                85                  90                  95

Met Gln Val Pro Tyr Gly Ser Pro Cys Tyr Asp Ile Gly Gly Asn Tyr
            100                 105                 110

Thr Gln His Leu Phe Lys Gly Arg Ser Tyr Val His Cys Cys Asn Pro
        115                 120                 125

Cys Leu Asp Leu Lys Asp Val Ala Arg Asn Val Met Tyr Asn Asp Met
    130                 135                 140

Val Thr Gln His Val Gln Arg His Lys Gly Ser Gly Gly Cys Arg Pro
145                 150                 155                 160
```

```
Leu Pro Thr Phe Gln Ile Asp Ala Phe Arg Arg Tyr Asp Asn Ser Pro
                165                 170                 175

Cys Ala Val Thr Cys Ser Asp Val Phe Gln Glu Cys Ser Tyr Asp Phe
                180                 185                 190

Gly Ser Gly Arg Asp Asn His Ala Val Ser Leu His Ser Ile Tyr Asp
                195                 200                 205

Ile Pro Tyr Ser Ser Ile Gly Pro Ala Leu His Arg Lys Asn Val Arg
                210                 215                 220

Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
                245                 250                 255

Asp Asp Val His Phe Leu Phe Ser Glu Glu Ser Thr Leu His Tyr Thr
                260                 265                 270

His Ser Leu Glu Asn Ile Lys Leu Ile Val Met Arg Thr Tyr Phe Pro
                275                 280                 285

Ala Asp Asp Arg Tyr Val Tyr Ile Lys Glu Phe Met Val Lys Arg Val
                290                 295                 300

Asp Thr Phe Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
                325                 330                 335

Asn Thr Pro Pro Ile Phe Gln Asp Lys Ala Thr Phe Ser Val Trp Phe
                340                 345                 350

Pro Glu Ala Lys Arg Lys Val Leu Ile Pro Lys Phe Glu Leu Ser Arg
                355                 360                 365

Phe Leu Ser Gly Asn Val Lys Ile Ser Arg Met Leu Val Asp Ala Asp
                370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
                405                 410                 415

Val Ile Val Asn Gly Val Ser Val Lys Ser Glu Trp Asn Val Pro Val
                420                 425                 430

Asp Gln Leu Thr Asp Ile Ser Phe Ser Ile Phe Leu Leu Val Lys Val
                435                 440                 445

Arg Lys Val Gln Ile Glu Leu Met Ser Asp Lys Val Val Ile Glu Ala
                450                 455                 460

Arg Gly Leu Leu Arg Arg Phe Ala Asp Ser Leu Lys Ser Ala Val Gly
465                 470                 475                 480

Gly Leu Gly Asp Cys Val Tyr Asp Ala Leu Val Gln Thr Gly Trp Phe
                485                 490                 495

Asp Thr Ser Ser Asp Glu Leu Lys Val Leu Leu Pro Glu Pro Phe Met
                500                 505                 510

Thr Phe Ser Asp Tyr Leu Glu Gly Met Tyr Glu Ala Asp Ala Lys Ile
                515                 520                 525

Glu Arg Glu Ser Val Phe Glu Leu Leu Ala Ser Gly Asp Asp Leu Phe
                530                 535                 540

Lys Lys Ile Asp Glu Ile Arg Asn Asn Tyr Ser Gly Val Glu Phe Asp
545                 550                 555                 560

Val Glu Lys Phe Gln Glu Phe Cys Lys Glu Leu Asn Val Asn Pro Met
                565                 570                 575
```

-continued

```
Leu Ile Gly His Val Ile Glu Ala Ile Phe Ser Gln Lys Ala Gly Val
            580                 585                 590
Thr Val Thr Gly Leu Gly Thr Leu Ser Pro Glu Met Gly Ala Ser Val
        595                 600                 605
Ala Leu Ser Asn Thr Ser Val Asp Thr Cys Glu Asp Met Asp Val Thr
    610                 615                 620
Glu Asp Met Glu Asp Ile Val Leu Met Ala Asp Lys Ser His Ser Tyr
625                 630                 635                 640
Met Ser Pro Glu Met Ala Arg Trp Ala Asp Val Lys Tyr Asp Asn Asn
                645                 650                 655
Lys Gly Gly Leu Val Glu Tyr Lys Val Gly Thr Ser Met Thr Leu Pro
            660                 665                 670
Ala Thr Trp Ala Glu Lys Gly Lys Ala Val Leu Pro Leu Ser Gly Ile
        675                 680                 685
Cys Val Arg Lys Pro Gln Phe Ser Lys Pro Leu Asp Glu Glu Asp Asp
    690                 695                 700
Leu Arg Leu Ser Asn Met Asn Phe Phe Lys Val Ser Asp Leu Lys Leu
705                 710                 715                 720
Lys Lys Thr Ile Thr Pro Val Val Tyr Thr Gly Thr Ile Arg Glu Arg
                725                 730                 735
Gln Met Lys Asn Tyr Ile Asp Tyr Leu Ser Ala Ser Leu Gly Ser Thr
            740                 745                 750
Leu Gly Asn Leu Glu Arg Ile Val Arg Ser Asp Trp Asn Gly Thr Glu
        755                 760                 765
Glu Ser Met Gln Thr Phe Gly Leu Tyr Asp Cys Glu Lys Cys Lys Trp
    770                 775                 780
Leu Leu Leu Pro Ala Glu Lys Lys His Ala Trp Ala Val Val Leu Ala
785                 790                 795                 800
Ser Asp Asp Thr Thr Arg Ile Ile Phe Leu Ser Tyr Asp Glu Ser Gly
                805                 810                 815
Ser Pro Ile Ile Asp Lys Arg Asn Trp Lys Arg Phe Ala Val Cys Ser
            820                 825                 830
Glu Thr Lys Val Tyr Ser Val Ile Arg Ser Leu Glu Val Leu Asn Lys
        835                 840                 845
Glu Ala Ile Val Asp Pro Gly Val His Ile Thr Leu Val Asp Gly Val
    850                 855                 860
Pro Gly Cys Gly Lys Thr Ala Glu Ile Ile Ala Arg Val Asn Trp Lys
865                 870                 875                 880
Thr Asp Leu Val Leu Thr Pro Gly Arg Glu Ala Ala Met Ile Arg
                885                 890                 895
Arg Arg Ala Cys Ala Leu His Lys Ser Pro Val Ala Thr Ser Asp Asn
            900                 905                 910
Val Arg Thr Phe Asp Ser Phe Val Met Asn Lys Lys Ile Phe Lys Phe
        915                 920                 925
Asp Ala Val Tyr Val Asp Glu Gly Leu Met Val His Thr Gly Leu Leu
    930                 935                 940
Asn Phe Ala Leu Lys Ile Ser Gly Cys Lys Lys Ala Phe Val Phe Gly
945                 950                 955                 960
Asp Ala Lys Gln Ile Pro Phe Ile Asn Arg Val Met Asn Phe Asp Tyr
                965                 970                 975
Pro Lys Glu Leu Arg Thr Leu Ile Val Asp Asn Val Glu Arg Arg Tyr
            980                 985                 990
Val Thr His Arg Cys Pro Arg Asp  Val Thr Ser Phe Leu  Asn Thr Ile
```

995 1000 1005

Tyr Lys Ala Ala Val Ala Thr Thr Ser Pro Val Val His Ser Val
1010 1015 1020

Lys Ala Ile Lys Val Ser Gly Ala Gly Ile Leu Arg Pro Glu Leu
1025 1030 1035

Thr Lys Ile Lys Gly Lys Ile Ile Thr Phe Thr Gln Ser Asp Lys
1040 1045 1050

Gln Ser Leu Ile Lys Ser Gly Tyr Asn Asp Val Asn Thr Val His
1055 1060 1065

Glu Ile Gln Gly Glu Thr Phe Glu Glu Thr Ala Val Val Arg Ala
1070 1075 1080

Thr Pro Thr Pro Ile Gly Leu Ile Ala Arg Asp Ser Pro His Val
1085 1090 1095

Leu Val Ala Leu Thr Arg His Thr Lys Ala Met Val Tyr Tyr Thr
1100 1105 1110

Val Val Phe Asp Ala Val Thr Ser Ile Ile Val Asp Val Glu Lys
1115 1120 1125

Val Asp Gln Ser Ile Leu Thr Met Phe Ala Thr Thr Val Pro Thr
1130 1135 1140

Lys

<210> SEQ ID NO 44
<211> LENGTH: 1648
<212> TYPE: PRT
<213> ORGANISM: Cucumber green mottle mosaic virus
<220> FEATURE:
<221> NAME/KEY: misc_feature
<222> LOCATION: (1145)..(1145)
<223> OTHER INFORMATION: Xaa can be any naturally occurring amino acid

<400> SEQUENCE: 44

Met Ala Asn Ile Asn Glu Gln Ile Asn Asn Gln Arg Asp Ala Ala Ala
1 5 10 15

Ser Gly Arg Asn Asn Leu Val Ser Gln Leu Ala Ser Lys Arg Val Tyr
20 25 30

Asp Glu Ala Val Arg Ser Leu Asp His Gln Asp Arg Arg Pro Lys Met
35 40 45

Asn Phe Ser Arg Val Val Ser Thr Glu His Thr Arg Leu Val Thr Asp
50 55 60

Ala Tyr Pro Glu Phe Ser Ile Ser Phe Thr Ala Thr Lys Asn Ser Val
65 70 75 80

His Ser Leu Ala Gly Ser Leu Arg Leu Leu Glu Leu Glu Tyr Met Met
85 90 95

Met Gln Val Pro Tyr Gly Ser Pro Cys Tyr Asp Ile Gly Gly Asn Tyr
100 105 110

Thr Gln His Leu Phe Lys Gly Arg Ser Tyr Val His Cys Cys Asn Pro
115 120 125

Cys Leu Asp Leu Lys Asp Val Ala Arg Asn Val Met Tyr Asn Asp Met
130 135 140

Val Thr Gln His Val Gln Arg His Lys Gly Ser Gly Gly Cys Arg Pro
145 150 155 160

Leu Pro Thr Phe Gln Ile Asp Ala Phe Arg Arg Tyr Asp Asn Ser Pro
165 170 175

Cys Ala Val Thr Cys Ser Asp Val Phe Gln Glu Cys Ser Tyr Asp Phe
180 185 190

Gly Ser Gly Arg Asp Asn His Ala Val Ser Leu His Ser Ile Tyr Asp
            195                 200                 205

Ile Pro Tyr Ser Ser Ile Gly Pro Ala Leu His Arg Lys Asn Val Arg
210                 215                 220

Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
            245                 250                 255

Asp Asp Val His Phe Leu Phe Ser Glu Ser Thr Leu His Tyr Thr
                260                 265                 270

His Ser Leu Glu Asn Ile Lys Leu Ile Val Met Arg Thr Tyr Phe Pro
            275                 280                 285

Ala Asp Asp Arg Tyr Val Tyr Ile Lys Glu Phe Met Val Lys Arg Val
290                 295                 300

Asp Thr Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
            325                 330                 335

Asn Thr Pro Pro Ile Phe Gln Asp Lys Ala Thr Phe Ser Val Trp Phe
            340                 345                 350

Pro Glu Ala Lys Arg Lys Val Leu Ile Pro Lys Phe Glu Leu Ser Arg
            355                 360                 365

Phe Leu Ser Gly Asn Val Lys Ile Ser Arg Met Leu Val Asp Ala Asp
            370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
            405                 410                 415

Val Ile Val Asn Gly Val Ser Val Lys Ser Glu Trp Asn Val Pro Val
            420                 425                 430

Asp Gln Leu Thr Asp Ile Ser Phe Ser Ile Phe Leu Leu Val Lys Val
            435                 440                 445

Arg Lys Val Gln Ile Glu Leu Met Ser Asp Lys Val Val Ile Glu Ala
450                 455                 460

Arg Gly Leu Leu Arg Arg Phe Ala Asp Ser Leu Lys Ser Ala Val Gly
465                 470                 475                 480

Gly Leu Gly Asp Cys Val Tyr Asp Ala Leu Val Gln Thr Gly Trp Phe
            485                 490                 495

Asp Thr Ser Ser Asp Glu Leu Lys Val Leu Leu Pro Glu Pro Phe Met
            500                 505                 510

Thr Phe Ser Asp Tyr Leu Glu Gly Met Tyr Glu Ala Asp Ala Lys Ile
            515                 520                 525

Glu Arg Glu Ser Val Phe Glu Leu Leu Ala Ser Gly Asp Asp Leu Phe
530                 535                 540

Lys Lys Ile Asp Glu Ile Arg Asn Asn Tyr Ser Gly Val Glu Phe Asp
545                 550                 555                 560

Val Glu Lys Phe Gln Glu Phe Cys Lys Glu Leu Asn Val Asn Pro Met
            565                 570                 575

Leu Ile Gly His Val Ile Glu Ala Ile Phe Ser Gln Lys Ala Gly Val
            580                 585                 590

Thr Val Thr Gly Leu Gly Thr Leu Ser Pro Glu Met Gly Ala Ser Val
            595                 600                 605

Ala Leu Ser Asn Thr Ser Val Asp Thr Cys Glu Asp Met Asp Val Thr

-continued

```
            610                 615                 620
Glu Asp Met Glu Asp Ile Val Leu Met Ala Asp Lys Ser His Ser Tyr
625                 630                 635                 640

Met Ser Pro Glu Met Ala Arg Trp Ala Asp Val Lys Tyr Asp Asn Asn
                    645                 650                 655

Lys Gly Gly Leu Val Glu Tyr Lys Val Gly Thr Ser Met Thr Leu Pro
                660                 665                 670

Ala Thr Trp Ala Glu Lys Gly Lys Ala Val Leu Pro Leu Ser Gly Ile
            675                 680                 685

Cys Val Arg Lys Pro Gln Phe Ser Lys Pro Leu Asp Glu Asp Asp
690                 695                 700

Leu Arg Leu Ser Asn Met Asn Phe Phe Lys Val Ser Asp Leu Lys Leu
705                 710                 715                 720

Lys Lys Thr Ile Thr Pro Val Val Tyr Thr Gly Thr Ile Arg Glu Arg
                    725                 730                 735

Gln Met Lys Asn Tyr Ile Asp Tyr Leu Ser Ala Ser Leu Gly Ser Thr
                740                 745                 750

Leu Gly Asn Leu Glu Arg Ile Val Arg Ser Asp Trp Asn Gly Thr Glu
            755                 760                 765

Glu Ser Met Gln Thr Phe Gly Leu Tyr Asp Cys Glu Lys Cys Lys Trp
770                 775                 780

Leu Leu Leu Pro Ala Glu Lys Lys His Ala Trp Ala Val Val Leu Ala
785                 790                 795                 800

Ser Asp Asp Thr Thr Arg Ile Ile Phe Leu Ser Tyr Asp Glu Ser Gly
                    805                 810                 815

Ser Pro Ile Ile Asp Lys Arg Asn Trp Lys Arg Phe Ala Val Cys Ser
                820                 825                 830

Glu Thr Lys Val Tyr Ser Val Ile Arg Ser Leu Glu Val Leu Asn Lys
            835                 840                 845

Glu Ala Ile Val Asp Pro Gly Val His Ile Thr Leu Val Asp Gly Val
850                 855                 860

Pro Gly Cys Gly Lys Thr Ala Glu Ile Ile Ala Arg Val Asn Trp Lys
865                 870                 875                 880

Thr Asp Leu Val Leu Thr Pro Gly Arg Glu Ala Ala Met Ile Arg
                    885                 890                 895

Arg Arg Ala Cys Ala Leu His Lys Ser Pro Val Ala Thr Ser Asp Asn
                900                 905                 910

Val Arg Thr Phe Asp Ser Phe Val Met Asn Lys Lys Ile Phe Lys Phe
            915                 920                 925

Asp Ala Val Tyr Val Asp Glu Gly Leu Met Val His Thr Gly Leu Leu
930                 935                 940

Asn Phe Ala Leu Lys Ile Ser Gly Cys Lys Lys Ala Phe Val Phe Gly
945                 950                 955                 960

Asp Ala Lys Gln Ile Pro Phe Ile Asn Arg Val Met Asn Phe Asp Tyr
                965                 970                 975

Pro Lys Glu Leu Arg Thr Leu Ile Val Asp Asn Val Glu Arg Arg Tyr
            980                 985                 990

Val Thr His Arg Cys Pro Arg Asp Val Thr Ser Phe Leu Asn Thr Ile
                995                 1000                1005

Tyr Lys Ala Ala Val Ala Thr Thr Ser Pro Val Val His Ser Val
    1010                1015                1020

Lys Ala Ile Lys Val Ser Gly Ala Gly Ile Leu Arg Pro Glu Leu
    1025                1030                1035
```

```
Thr Lys Ile Lys Gly Lys Ile Ile Thr Phe Thr Gln Ser Asp Lys
    1040            1045                1050

Gln Ser Leu Ile Lys Ser Gly Tyr Asn Asp Val Asn Thr Val His
    1055            1060                1065

Glu Ile Gln Gly Glu Thr Phe Glu Glu Thr Ala Val Val Arg Ala
    1070            1075                1080

Thr Pro Thr Pro Ile Gly Leu Ile Ala Arg Asp Ser Pro His Val
    1085            1090                1095

Leu Val Ala Leu Thr Arg His Thr Lys Ala Met Val Tyr Tyr Thr
    1100            1105                1110

Val Val Phe Asp Ala Val Thr Ser Ile Ile Val Asp Val Glu Lys
    1115            1120                1125

Val Asp Gln Ser Ile Leu Thr Met Phe Ala Thr Thr Val Pro Thr
    1130            1135                1140

Lys Xaa Gln Leu Met Gln Asn Ser Leu Tyr Val His Arg Asp Ile
    1145            1150                1155

Phe Leu Pro Val Ser Lys Thr Gly Phe Tyr Thr Asp Met Gln Glu
    1160            1165                1170

Phe Tyr Asp Arg Cys Leu Pro Gly Asn Ser Phe Val Leu Asn Asp
    1175            1180                1185

Phe Asp Ala Val Thr Met Arg Leu Arg Asp Asn Glu Phe Asn Leu
    1190            1195                1200

Gln Pro Cys Arg Leu Thr Leu Ser Asn Leu Asp Pro Val Pro Ala
    1205            1210                1215

Leu Val Lys Ser Glu Ala Gln Asn Phe Leu Ile Pro Val Leu Arg
    1220            1225                1230

Thr Ala Cys Glu Arg Pro Arg Ile Pro Gly Leu Leu Glu Asn Leu
    1235            1240                1245

Val Ala Met Ile Lys Arg Asn Met Asn Thr Pro Asp Leu Ala Gly
    1250            1255                1260

Thr Val Asp Ile Thr Asn Met Ser Ile Ser Ile Val Asp Asn Phe
    1265            1270                1275

Phe Ser Ser Phe Val Arg Asp Glu Val Leu Leu Asp His Leu Asp
    1280            1285                1290

Cys Val Arg Ala Ser Ser Ile Gln Ser Phe Ser Asp Trp Phe Ser
    1295            1300                1305

Cys Gln Pro Thr Ser Ala Val Gly Gln Leu Ala Asn Phe Asn Phe
    1310            1315                1320

Ile Asp Leu Pro Ala Phe Asp Thr Tyr Met His Met Ile Lys Arg
    1325            1330                1335

Gln Pro Lys Ser Arg Leu Asp Thr Ser Ile Gln Ser Glu Tyr Pro
    1340            1345                1350

Ala Leu Gln Thr Ile Val Tyr His Leu Lys Val Val Asn Ala Val
    1355            1360                1365

Phe Gly Pro Val Phe Lys Tyr Leu Thr Thr Lys Phe Leu Ser Met
    1370            1375                1380

Val Asp Ser Ser Lys Phe Phe Phe Tyr Thr Arg Lys Lys Ser Glu
    1385            1390                1395

Asp Leu Gln Glu Phe Phe Ser Asp Leu Ser Ser His Ser Asp Tyr
    1400            1405                1410

Glu Ile Leu Glu Leu Asp Val Ser Lys Tyr Asp Lys Ser Gln Ser
    1415            1420                1425
```

| | | | | | | | | | | |
|---|---|---|---|---|---|---|---|---|---|---|
| Asp | Phe | His | Phe | Ser | Ile | Glu | Met | Ala | Ile | Trp | Glu | Lys | Leu | Gly |
| | | | 1430 | | | | 1435 | | | | 1440 | | | |

Leu Asp Asp Ile Leu Ala Trp Met Trp Ser Met Gly His Lys Arg
　　1445　　　　　　　1450　　　　　　　1455

Thr Ile Leu Gln Asp Phe Gln Ala Gly Ile Lys Thr Leu Ile Tyr
　　1460　　　　　　　1465　　　　　　　1470

Tyr Gln Arg Lys Ser Gly Asp Val Thr Thr Phe Ile Gly Asn Thr
　　1475　　　　　　　1480　　　　　　　1485

Phe Ile Ile Ala Ala Cys Val Ala Ser Met Leu Pro Leu Asp Lys
　　1490　　　　　　　1495　　　　　　　1500

Cys Phe Lys Ala Ser Phe Cys Gly Asp Asp Ser Leu Ile Tyr Leu
　　1505　　　　　　　1510　　　　　　　1515

Pro Lys Gly Leu Glu Tyr Pro Asp Ile Gln Ala Thr Ala Asn Leu
　　1520　　　　　　　1525　　　　　　　1530

Val Trp Asn Phe Glu Ala Lys Leu Phe Arg Lys Lys Tyr Gly Tyr
　　1535　　　　　　　1540　　　　　　　1545

Phe Cys Gly Lys Tyr Ile Ile His His Ala Asn Gly Cys Ile Val
　　1550　　　　　　　1555　　　　　　　1560

Tyr Pro Asp Pro Leu Lys Leu Ile Ser Lys Leu Gly Asn Lys Ser
　　1565　　　　　　　1570　　　　　　　1575

Leu Val Gly Tyr Glu His Val Glu Glu Phe Arg Ile Ser Leu Leu
　　1580　　　　　　　1585　　　　　　　1590

Asp Val Ala His Ser Leu Phe Asn Gly Ala Tyr Phe His Leu Leu
　　1595　　　　　　　1600　　　　　　　1605

Asp Asp Ala Ile His Glu Leu Phe Pro Asn Ala Gly Gly Cys Ser
　　1610　　　　　　　1615　　　　　　　1620

Phe Val Ile Asn Cys Leu Cys Lys Tyr Leu Ser Asp Lys Arg Leu
　　1625　　　　　　　1630　　　　　　　1635

Phe Arg Ser Leu Tyr Ile Asp Val Ser Lys
　　1640　　　　　　　1645

<210> SEQ ID NO 45
<211> LENGTH: 6422
<212> TYPE: DNA
<213> ORGANISM: Cucumber green mottle mosaic virus

<400> SEQUENCE: 45
gttttaattt ttaaaattaa acaaacaaca acaacaacaa caaacaattt aaaacaacaa     60
tggcaaacat taatgaacaa atcaacaacc aacgcgacgc cgcggccagc gggagaaaca    120
atctcgttag ccaattggcg tcaaaaaggg tgtatgacga ggctgttcgc tcgttggatc    180
atcaagacag acgcccaaaa atgaactttt ctcgtgtggt cagcacagag cacaccaggc    240
ttgtaactga tgcgtatccg gagttttcga ttagctttac cgccaccaag aactctgtac    300
actcccttgc gggtagtctg aggctccttg aactggaata tatgatgatg caagtgccct    360
acggctcacc ttgttatgat atcggcggta actatacgca gcacttgttc aaaggtagat    420
catatgtgca ttgctgcaat ccgtgcctgg atcttaaaga tgttgcgagg aacgtgatgt    480
ataacgatat ggtcacacaa catgtacaga ggcacaaggg atctggcggg tgcagacctc    540
ttccaacttt tcagatagat gcattcagga ggtacgataa ttctccctgt gcggtcacct    600
gttcagacgt tttccaagag tgttcctatg attttgggag cggtagggat aatcatgcag    660
tctcgctgca ttcaatctac gatatccctt attcttcgat cggacctgct cttcatagga    720
agaacgtgcg agtttgttat gcagccttc acttctcgga ggcattgctt ttaggttcac    780

```
ctgtaggtaa tttaaatagt attggggctc agtttagggt cgatggtgat gatgtgcatt      840 ttcttttag tgaagagtct actttgcatt atactcatag tttagaaaat atcaaattaa       900
ttgtgatgcg tacttatttt cctgctgatg ataggtacgt gtatattaag gagtttatgg     960
tcaagcgtgt ggatacttc ttctttaggt tggtcagagc agacacacat atgcttcata     1020
aatctgtggg gcactattca aaatcgaaat ctgagtactt tgcgctgaat accctccga     1080 tcttccaaga caaagccacg ttttctgtgt ggtttcctga ggcgaagcgt aaggtgttga    1140
tacccaagtt tgaactttca agattccttt ctgggaatgt gaaaatctct aggatgcttg    1200
tcgatgctga tttcgtccat accattatta atcacattag cacgtatgat aataaggcct    1260
tagtgtggaa gaatgttcag tcctttgtgg aatctatacg ctcaagagta attgtaaacg    1320 gagtttcgt gaaatctgaa tggaacgtac cggttgatca gctcactgat atctcgttct     1380
cgatattcct tctcgtgaag gttaggaagg tacagatcga gttaatgtct gataaagttg    1440
taatcgaggc gaggggcttg ctccggaggt tcgcagacag tcttaaatcc gccgtaggag    1500
gactaggtga ttgcgtctat gatgctctag ttcaaaccgg ctggtttgat acctctagcg    1560
acgaactgaa agttttgcta cctgaaccgt ttatgacctt ttcggattat cttgaaggga    1620
tgtacgaggc agatgcaaag atcgagagag agagtgtctt tgagttgctc gcttccggtg    1680
acgatttgtt caagaaaatc gatgagataa gaaacaatta cagtggagtc gaatttgatg    1740
tagagaaatt ccaggaattt tgcaaggaac tgaatgttaa tcctatgcta attggccatg    1800
ttatcgaagc tattttttcg cagaaagctg gggtgacagt aacgggtctg ggtaccctct    1860
ctcctgagat gggtgcttct gttgcgttat ccaatacctc tgtagataca tgtgaagata    1920
tggatgtaac tgaagatatg gaggatatag tgttgatggc ggacaagagt cattcttaca    1980
tgtccccaga aatggcgaga tgggctgatg taaaatacga caacaataaa gggggcctgg    2040
tcgaatacaa agtcggaacc tcgatgactt tacctgccac ctgggcagag aagggtaagg    2100
ctgtcttacc gttgtcgggg atctgtgtga ggaaaccca ttttcgaag ccgcttgatg       2160 aggaagacga cttgaggtta tcaaacatga atttcttta ggtgagcgat ctgaagttga     2220
agaaaactat cactccagtt gtttacactg ggaccattcg agagaggcaa atgaagaatt    2280
atattgatta cttatcggcc tctcttggtt ctacgctggg taatctggag agaattgtgc    2340
ggagtgattg gaacggtacc gaggagagta tgcaaacgtt cgggttgtat gactgcgaaa    2400
agtgcaagtg gttactgtta ccagccgaaa agaagcacgc atgggctgtg ttctggcaa    2460 gtgatgatac cactcgcata atcttcctct catatgacga atctggttct cccataattg    2520
ataagagaaa ctggaagcga tttgctgttt gctctgagac caaagtctat agcgtaattc    2580
gtagtttaga ggtactaaat aaggaagcaa tagtcgaccc cggggttcat ataacattag    2640
ttgacggagt gccgggttgt ggaaagaccg ccgaaattat agcgagggtc aattggaaaa    2700
ccgatctagt attgactccc gggagggagg cggctgctat gattaggcgg agggcctgcg    2760
ccctgcacaa gtcacctgtg gcaaccagtg acaacgttag aactttcgat tcttttgtga    2820
tgaataagaa aatcttcaag tttgacgctg tctatgttga cgagggtctg atggtccata    2880
cgggtttact taattttgcg ttgaagatct caggttgtaa aaaggccttc gtctttggtg    2940
atgctaagca aatcccgttt ataaacagag tcatgaattt tgattatcct aaggagttaa    3000
gaactttaat agtcgataat gtagagcgta ggtatgttac ccataggtgt cctagagatg    3060
tcactagttt tcttaatact atttacaaag ccgctgtcgc tactactagt ccggttgtac    3120
attctgtgaa ggcgattaaa gtgtcagggg ccggtattct gaggcccgag ttgacgaaga    3180
```

```
tcaaaggaaa gataataacg tttactcaat ctgataagca gtccttgatc aagagtgggt   3240
acaatgacgt gaacactgtg catgaaattc agggagaaac cttgaagag acggcggttg    3300
tgcgtgccac cccgactccg ataggtttaa ttgtccgtga ttcaccacat gtactagtgg   3360
ccttaacgag gcacactaag gcaatggtgt attatactgt tgtgttcgat gcagttacaa   3420
gtataatagt ggatgtggaa aaggtcgacc agtcgatctt gactatgttt gctaccactg   3480
tgcctaccaa atagcaatta atgcagaact cactgtatgt ccatcgtgat attttcctcc   3540
ctgttagtaa aacggggttt tatacagaca tgcaggagtt ctatgataga tgccttcctg   3600
ggaattcctt cgtgctgaat gatttcgatg ccgtaaccat gcggttgagg gacaacgaat   3660
ttaacctaca accttgtagg ctaaccttaa gtaatttaga tccagtaccc gctttggtta   3720
agagtgaagc gcagaatttt ctgattcccg ttttgcgtac ggcctgtgaa aggccgcgca   3780
ttccaggtct ccttgaaaat cttgtagcta tgataaagag gaatatgaat actcctgatc   3840
tagctgggac tgtggatata actaatatgt cgatttctat agtagataac ttcttttctt   3900
cttttgttag agacgaggtt ttgcttgatc atttagattg tgttagggct agttccattc   3960
aaagtttttc tgattggttt tcgtgtcagc caacctcggc ggttggtcaa ttagctaatt   4020
tcaatttcat agatttgcct gcctttgata cttatatgca catgattaag cggcagccca   4080
agagtcggtt ggatacttcg attcagtctg aatatccggc cttgcaaact attgtttatc   4140
accttaaagt ggtaaatgca gttttcggtc cggttttaa gtatttgacc accaagtttc   4200
ttagcatggt agatagttct aagttttct tttacactag gaaaaaatca gaagatctgc    4260
aggaattttt ctcagatctc tcttcccatt ctgattatga gattcttgag ctggatgttt   4320
ctaaatatga caagtcacaa tccgatttcc atttctctat tgagatggca atttgggaaa   4380
aattggggct ggacgatatt ttggcttgga tgtggtctat gggtcacaag agaactatac   4440
tgcaagattt ccaagccggg ataaagacgc tcatttacta tcaacggaag tctggtgatg   4500
taactacttt cataggtaat accttttatta tcgcagcgtg tgtagctagt atgttgccgt   4560
tagacaagtg ttttaaagct agttttttgtg gtgatgattc gctgatctac cttcctaagg   4620
gtttggagta tcctgatata caggctactg ccaacttggt ttggaatttt gaggcgaaac   4680
ttttccgaaa gaagtatggt tacttctgtg ggaagtatat aattcaccat gccaacggct   4740
gtattgttta ccctgaccct ttaaaattaa ttagtaaatt aggtaataag agtcttgtag   4800
ggtatgagca tgttgaggag tttcgtatat ctctcctcga cgtcgctcat agtttgttta   4860
atggtgctta tttccattta ctcgacgatg caatccacga attatttcct aacgctgggg   4920
gttgcagttt tgtaattaat tgtttgtgca agtatttgag tgataagcgc cttttccgta   4980
gtctttatat agatgtctct aagtaaggtg tcggtcgaga actcattgaa acccgagaag   5040
tttgttaaaa tctcttgggt cgataagttg ctccctaact atttttccat tcttaagtat   5100
ttatctataa ctgactttag cgtagttaaa gctcagagct atgaatccct cgtgcctgtc   5160
aagttgttgc gtggtgttga tcttacaaaa cacctttatg tcacattgtt gggcgttgtg   5220
gtttctggtg tatggaacgt accggaatcc tgtaggggtg gtgctactgt tgctctggtt   5280
gacacaagga tgcattctgt tgcagaggga actatatgca aatttcagc tcccgccacc    5340
gtccgcgaat tctctgttag gttcatacct aactattctg tcgtggctgc ggatgccctt   5400
cgcgatcctt ggtcttatt tgtgagactc tctaatgtag ggattaaaga tggtttccat   5460
cctttgacct tagaggtcgc ttgtttagtc gctacaacta actctattat caaaaagggt   5520
```

```
cttagagctt ctgtagtcga gtctgtcgtc tcttccgatc agtccattgt cctagattct    5580
ttatccgaga aagttgaacc tttctttgat aaagttccta tttcggcggc tgtgatggca    5640
agagacccca gttataggtc taggtcgcag tctgtcggtg gtcgtggtaa gcggcattct    5700
aaacctccaa atcggaggtt ggactctgct tctgaagagt ccagttctgt ttctttcgaa    5760
gatggcttac aatccgatca cacctagcaa acttattgcg tttagtgctt cttatgttcc    5820
cgtcaggact ttacttaatt ttctagttgc ttcacaaggt accgccttcc agactcaagc    5880
gggaagagat tctttccgcg agtccctgtc tgcgttaccc tcgtctgtcg tagatattaa    5940
ttctaggttc ccaaatgcgg ttttttacgc tttcctcaac ggtcctgtgt tgaggcctat    6000
cttcgtttcg cttcttagct ctacggatac gcgtaatagg gtcattgagg ttgtagatcc    6060
tagcaatcct acgactgctg agtcgcttaa cgctgtaaag cgtactgatg acgcatctac    6120
ggccgctagg gctgaaatag ataatttaat agagtctatt tctaagggtt ttgatgttta    6180
tgatagggct tcatttgaag ccgcgttttc ggtagtctgg tcagaggtta ccacctcgaa    6240
agcttagctt cgagggtctt ctgatggtgg tgcacaccaa agtgcatagt gctttcccgt    6300
tcacttaaat cgaacggttt gctcattggt ttgcggaaac ctctcacgtg tggcgttgaa    6360
gtttctatgg gcagtaattc tgcaaggggt tcgaatcccc cctttccccg ggtaggggcc    6420
ca                                                                  6422
```

<210> SEQ ID NO 46
<211> LENGTH: 1144
<212> TYPE: PRT
<213> ORGANISM: Cucumber green mottle mosaic virus

<400> SEQUENCE: 46

```
Met Ala Asn Ile Asn Glu Gln Ile Asn Asn Gln Arg Asp Ala Ala Ala
1               5                  10                  15

Ser Gly Arg Asn Asn Leu Val Ser Gln Leu Ala Ser Lys Arg Val Tyr
            20                  25                  30

Asp Glu Ala Val Arg Ser Leu Asp His Gln Asp Arg Arg Pro Lys Met
        35                  40                  45

Asn Phe Ser Arg Val Val Ser Thr Glu His Thr Arg Leu Val Thr Asp
    50                  55                  60

Ala Tyr Pro Glu Phe Ser Ile Ser Phe Thr Ala Thr Lys Asn Ser Val
65                  70                  75                  80

His Ser Leu Ala Gly Ser Leu Arg Leu Leu Glu Leu Glu Tyr Met Met
                85                  90                  95

Met Gln Val Pro Tyr Gly Ser Pro Cys Tyr Asp Ile Gly Gly Asn Tyr
            100                 105                 110

Thr Gln His Leu Phe Lys Gly Arg Ser Tyr Val His Cys Cys Asn Pro
        115                 120                 125

Cys Leu Asp Leu Lys Asp Val Ala Arg Asn Val Met Tyr Asn Asp Met
    130                 135                 140

Val Thr Gln His Val Gln Arg His Lys Gly Ser Gly Gly Cys Arg Pro
145                 150                 155                 160

Leu Pro Thr Phe Gln Ile Asp Ala Phe Arg Arg Tyr Asp Asn Ser Pro
                165                 170                 175

Cys Ala Val Thr Cys Ser Asp Val Phe Gln Glu Cys Ser Tyr Asp Phe
            180                 185                 190

Gly Ser Gly Arg Asp Asn His Ala Val Ser Leu His Ser Ile Tyr Asp
        195                 200                 205
```

```
Ile Pro Tyr Ser Ser Ile Gly Pro Ala Leu His Arg Lys Asn Val Arg
    210                 215                 220

Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
                245                 250                 255

Asp Asp Val His Phe Leu Phe Ser Glu Glu Ser Thr Leu His Tyr Thr
            260                 265                 270

His Ser Leu Glu Asn Ile Lys Leu Ile Val Met Arg Thr Tyr Phe Pro
        275                 280                 285

Ala Asp Asp Arg Tyr Val Tyr Ile Lys Glu Phe Met Val Lys Arg Val
    290                 295                 300

Asp Thr Phe Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
                325                 330                 335

Asn Thr Pro Pro Ile Phe Gln Asp Lys Ala Thr Phe Ser Val Trp Phe
            340                 345                 350

Pro Glu Ala Lys Arg Lys Val Leu Ile Pro Lys Phe Glu Leu Ser Arg
        355                 360                 365

Phe Leu Ser Gly Asn Val Lys Ile Ser Arg Met Leu Val Asp Ala Asp
370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
                405                 410                 415

Val Ile Val Asn Gly Val Ser Val Lys Ser Glu Trp Asn Val Pro Val
            420                 425                 430

Asp Gln Leu Thr Asp Ile Ser Phe Ser Ile Phe Leu Leu Val Lys Val
        435                 440                 445

Arg Lys Val Gln Ile Glu Leu Met Ser Asp Lys Val Val Ile Glu Ala
    450                 455                 460

Arg Gly Leu Leu Arg Arg Phe Ala Asp Ser Leu Lys Ser Ala Val Gly
465                 470                 475                 480

Gly Leu Gly Asp Cys Val Tyr Asp Ala Leu Val Gln Thr Gly Trp Phe
                485                 490                 495

Asp Thr Ser Ser Asp Glu Leu Lys Val Leu Leu Pro Glu Pro Phe Met
            500                 505                 510

Thr Phe Ser Asp Tyr Leu Glu Gly Met Tyr Glu Ala Asp Ala Lys Ile
        515                 520                 525

Glu Arg Glu Ser Val Phe Glu Leu Leu Ala Ser Gly Asp Asp Leu Phe
    530                 535                 540

Lys Lys Ile Asp Glu Ile Arg Asn Asn Tyr Ser Gly Val Glu Phe Asp
545                 550                 555                 560

Val Glu Lys Phe Gln Glu Phe Cys Lys Glu Leu Asn Val Asn Pro Met
                565                 570                 575

Leu Ile Gly His Val Ile Glu Ala Ile Phe Ser Gln Lys Ala Gly Val
            580                 585                 590

Thr Val Thr Gly Leu Gly Thr Leu Ser Pro Glu Met Gly Ala Ser Val
        595                 600                 605

Ala Leu Ser Asn Thr Ser Val Asp Thr Cys Glu Asp Met Asp Val Thr
    610                 615                 620

Glu Asp Met Glu Asp Ile Val Leu Met Ala Asp Lys Ser His Ser Tyr
```

-continued

```
            625                 630                 635                 640
        Met Ser Pro Glu Met Ala Arg Trp Ala Asp Val Lys Tyr Asp Asn Asn
                            645                 650                 655

Lys Gly Gly Leu Val Glu Tyr Lys Val Gly Thr Ser Met Thr Leu Pro
                            660                 665                 670

Ala Thr Trp Ala Glu Lys Gly Lys Ala Val Leu Pro Leu Ser Gly Ile
                            675                 680                 685

Cys Val Arg Lys Pro Gln Phe Ser Lys Pro Leu Asp Glu Glu Asp Asp
                            690                 695                 700

Leu Arg Leu Ser Asn Met Asn Phe Phe Lys Val Ser Asp Leu Lys Leu
        705                 710                 715                 720

Lys Lys Thr Ile Thr Pro Val Val Tyr Thr Gly Thr Ile Arg Glu Arg
                            725                 730                 735

Gln Met Lys Asn Tyr Ile Asp Tyr Leu Ser Ala Ser Leu Gly Ser Thr
                            740                 745                 750

Leu Gly Asn Leu Glu Arg Ile Val Arg Ser Asp Trp Asn Gly Thr Glu
                            755                 760                 765

Glu Ser Met Gln Thr Phe Gly Leu Tyr Asp Cys Glu Lys Cys Lys Trp
                            770                 775                 780

Leu Leu Leu Pro Ala Glu Lys Lys His Ala Trp Ala Val Val Leu Ala
        785                 790                 795                 800

Ser Asp Asp Thr Thr Arg Ile Ile Phe Leu Ser Tyr Asp Glu Ser Gly
                            805                 810                 815

Ser Pro Ile Ile Asp Lys Arg Asn Trp Lys Arg Phe Ala Val Cys Ser
                            820                 825                 830

Glu Thr Lys Val Tyr Ser Val Ile Arg Ser Leu Glu Val Leu Asn Lys
                            835                 840                 845

Glu Ala Ile Val Asp Pro Gly Val His Ile Thr Leu Val Asp Gly Val
                            850                 855                 860

Pro Gly Cys Gly Lys Thr Ala Glu Ile Ile Ala Arg Val Asn Trp Lys
        865                 870                 875                 880

Thr Asp Leu Val Leu Thr Pro Gly Arg Glu Ala Ala Met Ile Arg
                            885                 890                 895

Arg Arg Ala Cys Ala Leu His Lys Ser Pro Val Ala Thr Ser Asp Asn
                            900                 905                 910

Val Arg Thr Phe Asp Ser Phe Val Met Asn Lys Lys Ile Phe Lys Phe
                            915                 920                 925

Asp Ala Val Tyr Val Asp Glu Gly Leu Met Val His Thr Gly Leu Leu
                            930                 935                 940

Asn Phe Ala Leu Lys Ile Ser Gly Cys Lys Lys Ala Phe Val Phe Gly
        945                 950                 955                 960

Asp Ala Lys Gln Ile Pro Phe Ile Asn Arg Val Met Asn Phe Asp Tyr
                            965                 970                 975

Pro Lys Glu Leu Arg Thr Leu Ile Val Asp Asn Val Glu Arg Arg Tyr
                            980                 985                 990

Val Thr His Arg Cys Pro Arg Asp Val Thr Ser Phe Leu Asn Thr Ile
                            995                 1000                1005

Tyr Lys Ala Ala Val Ala Thr Thr Ser Pro Val Val His Ser Val
                            1010                1015                1020

Lys Ala Ile Lys Val Ser Gly Ala Gly Ile Leu Arg Pro Glu Leu
                            1025                1030                1035

Thr Lys Ile Lys Gly Lys Ile Ile Thr Phe Thr Gln Ser Asp Lys
                            1040                1045                1050
```

```
Gln Ser Leu Ile Lys Ser Gly Tyr Asn Asp Val Asn Thr Val His
    1055                1060                1065

Glu Ile Gln Gly Glu Thr Phe Glu Glu Thr Ala Val Val Arg Ala
    1070                1075                1080

Thr Pro Thr Pro Ile Gly Leu Ile Val Arg Asp Ser Pro His Val
    1085                1090                1095

Leu Val Ala Leu Thr Arg His Thr Lys Ala Met Val Tyr Tyr Thr
    1100                1105                1110

Val Val Phe Asp Ala Val Thr Ser Ile Ile Val Asp Val Glu Lys
    1115                1120                1125

Val Asp Gln Ser Ile Leu Thr Met Phe Ala Thr Thr Val Pro Thr
    1130                1135                1140

Lys

<210> SEQ ID NO 47
<211> LENGTH: 1648
<212> TYPE: PRT
<213> ORGANISM: Cucumber green mottle mosaic virus
<220> FEATURE:
<221> NAME/KEY: misc_feature
<222> LOCATION: (1145)..(1145)
<223> OTHER INFORMATION: Xaa can be any naturally occurring amino acid

<400> SEQUENCE: 47

Met Ala Asn Ile Asn Glu Gln Ile Asn Asn Gln Arg Asp Ala Ala
1               5                   10                  15

Ser Gly Arg Asn Asn Leu Val Ser Gln Leu Ala Ser Lys Arg Val Tyr
                20                  25                  30

Asp Glu Ala Val Arg Ser Leu Asp His Gln Asp Arg Arg Pro Lys Met
            35                  40                  45

Asn Phe Ser Arg Val Val Ser Thr Glu His Thr Arg Leu Val Thr Asp
        50                  55                  60

Ala Tyr Pro Glu Phe Ser Ile Ser Phe Thr Ala Thr Lys Asn Ser Val
65                  70                  75                  80

His Ser Leu Ala Gly Ser Leu Arg Leu Leu Glu Leu Glu Tyr Met Met
                85                  90                  95

Met Gln Val Pro Tyr Gly Ser Pro Cys Tyr Asp Ile Gly Gly Asn Tyr
                100                 105                 110

Thr Gln His Leu Phe Lys Gly Arg Ser Tyr Val His Cys Cys Asn Pro
            115                 120                 125

Cys Leu Asp Leu Lys Asp Val Ala Arg Asn Val Met Tyr Asn Asp Met
130                 135                 140

Val Thr Gln His Val Gln Arg His Lys Gly Ser Gly Gly Cys Arg Pro
145                 150                 155                 160

Leu Pro Thr Phe Gln Ile Asp Ala Phe Arg Arg Tyr Asp Asn Ser Pro
                165                 170                 175

Cys Ala Val Thr Cys Ser Asp Val Phe Gln Glu Cys Ser Tyr Asp Phe
            180                 185                 190

Gly Ser Gly Arg Asp Asn His Ala Val Ser Leu His Ser Ile Tyr Asp
        195                 200                 205

Ile Pro Tyr Ser Ser Ile Gly Pro Ala Leu His Arg Lys Asn Val Arg
    210                 215                 220

Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
```

-continued

```
                245                 250                 255
Asp Asp Val His Phe Leu Phe Ser Glu Glu Ser Thr Leu His Tyr Thr
            260                 265                 270
His Ser Leu Glu Asn Ile Lys Leu Ile Val Met Arg Thr Tyr Phe Pro
            275                 280                 285
Ala Asp Asp Arg Tyr Val Tyr Ile Lys Glu Phe Met Val Lys Arg Val
        290                 295                 300
Asp Thr Phe Phe Phe Arg Leu Val Arg Ala Asp Thr His Met Leu His
305                 310                 315                 320
Lys Ser Val Gly His Tyr Ser Lys Ser Lys Ser Glu Tyr Phe Ala Leu
                325                 330                 335
Asn Thr Pro Pro Ile Phe Gln Asp Lys Ala Thr Phe Ser Val Trp Phe
                340                 345                 350
Pro Glu Ala Lys Arg Lys Val Leu Ile Pro Lys Phe Glu Leu Ser Arg
            355                 360                 365
Phe Leu Ser Gly Asn Val Lys Ile Ser Arg Met Leu Val Asp Ala Asp
        370                 375                 380
Phe Val His Thr Ile Ile Asn His Ile Ser Thr Tyr Asp Asn Lys Ala
385                 390                 395                 400
Leu Val Trp Lys Asn Val Gln Ser Phe Val Glu Ser Ile Arg Ser Arg
                405                 410                 415
Val Ile Val Asn Gly Val Ser Val Lys Ser Glu Trp Asn Val Pro Val
                420                 425                 430
Asp Gln Leu Thr Asp Ile Ser Phe Ser Ile Phe Leu Leu Val Lys Val
            435                 440                 445
Arg Lys Val Gln Ile Glu Leu Met Ser Asp Lys Val Val Ile Glu Ala
        450                 455                 460
Arg Gly Leu Leu Arg Arg Phe Ala Asp Ser Leu Lys Ser Ala Val Gly
465                 470                 475                 480
Gly Leu Gly Asp Cys Val Tyr Asp Ala Leu Val Gln Thr Gly Trp Phe
                485                 490                 495
Asp Thr Ser Ser Asp Glu Leu Lys Val Leu Leu Pro Glu Pro Phe Met
                500                 505                 510
Thr Phe Ser Asp Tyr Leu Glu Gly Met Tyr Glu Ala Asp Ala Lys Ile
            515                 520                 525
Glu Arg Glu Ser Val Phe Glu Leu Leu Ala Ser Gly Asp Asp Leu Phe
        530                 535                 540
Lys Lys Ile Asp Glu Ile Arg Asn Asn Tyr Ser Gly Val Glu Phe Asp
545                 550                 555                 560
Val Glu Lys Phe Gln Glu Phe Cys Lys Glu Leu Asn Val Asn Pro Met
                565                 570                 575
Leu Ile Gly His Val Ile Glu Ala Ile Phe Ser Gln Lys Ala Gly Val
                580                 585                 590
Thr Val Thr Gly Leu Gly Thr Leu Ser Pro Glu Met Gly Ala Ser Val
            595                 600                 605
Ala Leu Ser Asn Thr Ser Val Asp Thr Cys Glu Asp Met Asp Val Thr
        610                 615                 620
Glu Asp Met Glu Asp Ile Val Leu Met Ala Asp Lys Ser His Ser Tyr
625                 630                 635                 640
Met Ser Pro Glu Met Ala Arg Trp Ala Asp Val Lys Tyr Asp Asn Asn
                645                 650                 655
Lys Gly Gly Leu Val Glu Tyr Lys Val Gly Thr Ser Met Thr Leu Pro
                660                 665                 670
```

```
Ala Thr Trp Ala Glu Lys Gly Lys Ala Val Leu Pro Leu Ser Gly Ile
            675                 680                 685

Cys Val Arg Lys Pro Gln Phe Ser Lys Pro Leu Asp Glu Glu Asp Asp
        690                 695                 700

Leu Arg Leu Ser Asn Met Asn Phe Phe Lys Val Ser Asp Leu Lys Leu
705                 710                 715                 720

Lys Lys Thr Ile Thr Pro Val Val Tyr Thr Gly Thr Ile Arg Glu Arg
                725                 730                 735

Gln Met Lys Asn Tyr Ile Asp Tyr Leu Ser Ala Ser Leu Gly Ser Thr
                740                 745                 750

Leu Gly Asn Leu Glu Arg Ile Val Arg Ser Asp Trp Asn Gly Thr Glu
            755                 760                 765

Glu Ser Met Gln Thr Phe Gly Leu Tyr Asp Cys Glu Lys Cys Lys Trp
        770                 775                 780

Leu Leu Leu Pro Ala Glu Lys Lys His Ala Trp Ala Val Val Leu Ala
785                 790                 795                 800

Ser Asp Asp Thr Thr Arg Ile Ile Phe Leu Ser Tyr Asp Glu Ser Gly
                805                 810                 815

Ser Pro Ile Ile Asp Lys Arg Asn Trp Lys Arg Phe Ala Val Cys Ser
            820                 825                 830

Glu Thr Lys Val Tyr Ser Val Ile Arg Ser Leu Glu Val Leu Asn Lys
        835                 840                 845

Glu Ala Ile Val Asp Pro Gly Val His Ile Thr Leu Val Asp Gly Val
850                 855                 860

Pro Gly Cys Gly Lys Thr Ala Glu Ile Ile Ala Arg Val Asn Trp Lys
865                 870                 875                 880

Thr Asp Leu Val Leu Thr Pro Gly Arg Glu Ala Ala Ala Met Ile Arg
                885                 890                 895

Arg Arg Ala Cys Ala Leu His Lys Ser Pro Val Ala Thr Ser Asp Asn
                900                 905                 910

Val Arg Thr Phe Asp Ser Phe Val Met Asn Lys Lys Ile Phe Lys Phe
            915                 920                 925

Asp Ala Val Tyr Val Asp Glu Gly Leu Met Val His Thr Gly Leu Leu
        930                 935                 940

Asn Phe Ala Leu Lys Ile Ser Gly Cys Lys Lys Ala Phe Val Phe Gly
945                 950                 955                 960

Asp Ala Lys Gln Ile Pro Phe Ile Asn Arg Val Met Asn Phe Asp Tyr
                965                 970                 975

Pro Lys Glu Leu Arg Thr Leu Ile Val Asp Asn Val Glu Arg Arg Tyr
            980                 985                 990

Val Thr His Arg Cys Pro Arg Asp Val Thr Ser Phe Leu Asn Thr Ile
        995                 1000                1005

Tyr Lys Ala Ala Val Ala Thr Thr Ser Pro Val Val His Ser Val
        1010                1015                1020

Lys Ala Ile Lys Val Ser Gly Ala Gly Ile Leu Arg Pro Glu Leu
        1025                1030                1035

Thr Lys Ile Lys Gly Lys Ile Ile Thr Phe Thr Gln Ser Asp Lys
        1040                1045                1050

Gln Ser Leu Ile Lys Ser Gly Tyr Asn Asp Val Asn Thr Val His
        1055                1060                1065

Glu Ile Gln Gly Glu Thr Phe Glu Glu Thr Ala Val Val Arg Ala
        1070                1075                1080
```

-continued

```
Thr Pro Thr Pro Ile Gly Leu Ile Val Arg Asp Ser Pro His Val
1085             1090             1095

Leu Val Ala Leu Thr Arg His Thr Lys Ala Met Val Tyr Tyr Thr
1100             1105             1110

Val Val Phe Asp Ala Val Thr Ser Ile Ile Val Asp Val Glu Lys
1115             1120             1125

Val Asp Gln Ser Ile Leu Thr Met Phe Ala Thr Thr Val Pro Thr
1130             1135             1140

Lys Xaa Gln Leu Met Gln Asn Ser Leu Tyr Val His Arg Asp Ile
1145             1150             1155

Phe Leu Pro Val Ser Lys Thr Gly Phe Tyr Thr Asp Met Gln Glu
1160             1165             1170

Phe Tyr Asp Arg Cys Leu Pro Gly Asn Ser Phe Val Leu Asn Asp
1175             1180             1185

Phe Asp Ala Val Thr Met Arg Leu Arg Asp Asn Glu Phe Asn Leu
1190             1195             1200

Gln Pro Cys Arg Leu Thr Leu Ser Asn Leu Asp Pro Val Pro Ala
1205             1210             1215

Leu Val Lys Ser Glu Ala Gln Asn Phe Leu Ile Pro Val Leu Arg
1220             1225             1230

Thr Ala Cys Glu Arg Pro Arg Ile Pro Gly Leu Leu Glu Asn Leu
1235             1240             1245

Val Ala Met Ile Lys Arg Asn Met Asn Thr Pro Asp Leu Ala Gly
1250             1255             1260

Thr Val Asp Ile Thr Asn Met Ser Ile Ser Ile Val Asp Asn Phe
1265             1270             1275

Phe Ser Ser Phe Val Arg Asp Glu Val Leu Leu Asp His Leu Asp
1280             1285             1290

Cys Val Arg Ala Ser Ser Ile Gln Ser Phe Ser Asp Trp Phe Ser
1295             1300             1305

Cys Gln Pro Thr Ser Ala Val Gly Gln Leu Ala Asn Phe Asn Phe
1310             1315             1320

Ile Asp Leu Pro Ala Phe Asp Thr Tyr Met His Met Ile Lys Arg
1325             1330             1335

Gln Pro Lys Ser Arg Leu Asp Thr Ser Ile Gln Ser Glu Tyr Pro
1340             1345             1350

Ala Leu Gln Thr Ile Val Tyr His Leu Lys Val Val Asn Ala Val
1355             1360             1365

Phe Gly Pro Val Phe Lys Tyr Leu Thr Thr Lys Phe Leu Ser Met
1370             1375             1380

Val Asp Ser Ser Lys Phe Phe Tyr Thr Arg Lys Lys Ser Glu
1385             1390             1395

Asp Leu Gln Glu Phe Phe Ser Asp Leu Ser Ser His Ser Asp Tyr
1400             1405             1410

Glu Ile Leu Glu Leu Asp Val Ser Lys Tyr Asp Lys Ser Gln Ser
1415             1420             1425

Asp Phe His Phe Ser Ile Glu Met Ala Ile Trp Glu Lys Leu Gly
1430             1435             1440

Leu Asp Asp Ile Leu Ala Trp Met Trp Ser Met Gly His Lys Arg
1445             1450             1455

Thr Ile Leu Gln Asp Phe Gln Ala Gly Ile Lys Thr Leu Ile Tyr
1460             1465             1470

Tyr Gln Arg Lys Ser Gly Asp Val Thr Thr Phe Ile Gly Asn Thr
```

```
                        1475                1480                1485
    Phe Ile Ile Ala Ala Cys Val Ala Ser Met Leu Pro Leu Asp Lys
        1490                1495                1500
    Cys Phe Lys Ala Ser Phe Cys Gly Asp Asp Ser Leu Ile Tyr Leu
        1505                1510                1515
    Pro Lys Gly Leu Glu Tyr Pro Asp Ile Gln Ala Thr Ala Asn Leu
        1520                1525                1530
    Val Trp Asn Phe Glu Ala Lys Leu Phe Arg Lys Lys Tyr Gly Tyr
        1535                1540                1545
    Phe Cys Gly Lys Tyr Ile Ile His His Ala Asn Gly Cys Ile Val
        1550                1555                1560
    Tyr Pro Asp Pro Leu Lys Leu Ile Ser Lys Leu Gly Asn Lys Ser
        1565                1570                1575
    Leu Val Gly Tyr Glu His Val Glu Glu Phe Arg Ile Ser Leu Leu
        1580                1585                1590
    Asp Val Ala His Ser Leu Phe Asn Gly Ala Tyr Phe His Leu Leu
        1595                1600                1605
    Asp Asp Ala Ile His Glu Leu Phe Pro Asn Ala Gly Gly Cys Ser
        1610                1615                1620
    Phe Val Ile Asn Cys Leu Cys Lys Tyr Leu Ser Asp Lys Arg Leu
        1625                1630                1635
    Phe Arg Ser Leu Tyr Ile Asp Val Ser Lys
        1640                1645

<210> SEQ ID NO 48
<211> LENGTH: 6422
<212> TYPE: DNA
<213> ORGANISM: Cucumber green mottle mosaic virus

<400> SEQUENCE: 48
gttttaattt ttaaaattaa acaaacaaca acaacaacaa caaacaattt aaaacaacaa      60
tggcaaacat taatgaacaa atcaacaacc aacgcgacgc cgcggccagc gggagaaaca     120
atctcgttag ccaattggcg tcaaaaaggg tgtatgacga ggctgttcgc tcgttggatc     180
atcaagacag acgcccaaaa atgaactttt ctcgtgtggt cagcacagag cacaccaggc     240
ttgtaactga tgcgtatccg gagttttcga ttagctttac cgccaccaag aactctgtac     300
actcccttgc gggtagtctg aggctccttg aactggaata tatgatgatg caagtgccct     360
acggctcacc ttgttatgat atcggcggta actatacgca gcacttgttc aaaggtagat     420
catatgtgca ttgctgcaat ccgtgcctgg atcttaaaga tgttgcgagg aacgtgatgt     480
ataacgatat ggtcacacaa catgtacaga ggcacaaggg atctggcggg tgcagacctc     540
ttccaacttt tcagatagat gcattcagga ggtacgataa ttctccctgt gcggtcacct     600
gttcagacgt tttccaagag tgttcctatg atttttggga cggtagggat aatcatgcag     660
tctcgctgca ttcaatctac gatatccctt attcttcgat cggacctgct cttcatagga     720
agaacgtgcg agtttgttat gcagcctttc acttctcgga ggcattgctt ttaggttcac     780
ctgtaggtaa tttaaatagt attggggctc agtttagggt cgatggtgat gatgtgcatt     840
ttctttttag tgaagagtct actttgcatt atactcatag tttagaaaat atcaaattaa     900
ttgtgatgcg tacttatttt cctgctgatg ataggtacgt gtatattaag gagtttatgg     960
tcaagcgtgt ggatactttc ttctttaggt tggtcagagc agacacacat atgcttcata    1020
aatctgtggg gcactattca aaatcgaaat ctgagtactt tgcgctgaat acccctccga    1080
```

-continued

| | |
|---|---|
| tcttccaaga caaagccacg tttctgtgt ggtttcctga ggcgaagcgt aaggtgttga | 1140 |
| tacccaagtt tgaactttca agattccttt ctgggaatgt gaaaatctct aggatgcttg | 1200 |
| tcgatgctga tttcgtccat accattatta atcacattag cacgtatgat aataaggcct | 1260 |
| tagtgtggaa gaatgttcag tcctttgtgg aatctatacg ctcaagagta attgtaaacg | 1320 |
| gagtttcggt gaaatctgaa tggaacgtac cggttgatca gctcactgat atctcgttct | 1380 |
| cgatattcct tctcgtgaag gttaggaagg tacagatcga gttaatgtct gataaagttg | 1440 |
| taatcgaggc gaggggcttg ctccggaggt tcgcagacag tcttaaatcc gccgtaggag | 1500 |
| gactaggtga ttgcgtctat gatgctctag ttcaaaccgg ctggtttgat acctctagcg | 1560 |
| acgaactgaa agttttgcta cctgaaccgt ttatgacctt ttcggattat cttgaaggga | 1620 |
| tgtacgaggc agatgcaaag atcgagagag agagtgtctt tgagttgctc gcttccggtg | 1680 |
| acgatttgtt caagaaaatc gatgagataa gaaacaatta cagtggagtc gaatttgatg | 1740 |
| tagagaaatt ccaggaattt tgcaaggaac tgaatgttaa tcctatgcta attggccatg | 1800 |
| ttatcgaagc tatttttcg cagaaagctg gggtgacagt aacgggtctg ggtaccctct | 1860 |
| ctcctgagat gggtgcttct gttgcgttat ccaatacctc tgtagataca tgtgaagata | 1920 |
| tggatgtaac tgaagatatg gaggatatag tgttgatggc ggacaagagt cattcttaca | 1980 |
| tgtccccaga aatggcgaga tgggctgatg taaaatacga caacaataaa ggggggcctgg | 2040 |
| tcgaatacaa agtcggaacc tcgatgactt tacctgccac ctgggcagag aagggtaagg | 2100 |
| ctgtcttacc gttgtcgggg atctgtgtga ggaaacccca atttttcgaag ccgcttgatg | 2160 |
| aggaagacga cttgaggtta tcaaacatga atttctttaa ggtgagcgat ctgaagttga | 2220 |
| agaaaactat cactccagtt gtttacactg ggaccattcg agagaggcaa atgaagaatt | 2280 |
| atattgatta cttatcggcc tctcttggtt ctacgctggg taatctggag agaattgtgc | 2340 |
| ggagtgattg gaacggtacc gaggagagta tgcaaacgtt cgggttgtat gactgcgaaa | 2400 |
| agtgcaagtg gttactgtta ccagccgaaa agaagcacgc atgggctgtg gttctggcaa | 2460 |
| gtgatgatac cactcgcata atcttcctct catatgacga atctggttct cccataattg | 2520 |
| ataagagaaa ctggaagcga tttgctgttt gctctgagac caaagtctat agcgtaattc | 2580 |
| gtagtttaga ggtactaaat aaggaagcaa tagtcgaccc cggggttcat ataacattag | 2640 |
| ttgacggagt gccggttgt ggaaagaccg ccgaaattat agcgagggtc aattggaaaa | 2700 |
| ccgatctagt attgactccc gggagggagg cggctgctat gattaggcgg agggcctgcg | 2760 |
| ccctgcacaa gtcacctgtg gcaaccagtg acaacgttag aactttcgat tcttttgtga | 2820 |
| tgaataagaa aatcttcaag tttgacgctg tctatgttga cgagggtctg atggtccata | 2880 |
| cgggtttact taattttgcg ttgaagatct caggttgtaa aaaggccttc gtctttggtg | 2940 |
| atgctaagca aatcccgttt ataaacagag tcatgaattt tgattatcct aaggagttaa | 3000 |
| gaactttaat agtcgataat gtagagcgta ggtatgttac ccataggtgt cctagagatg | 3060 |
| tcactagttt tcttaatact atttacaaag ccgctgtcgc tactactagt ccggttgtac | 3120 |
| attctgtgaa ggcgattaaa gtgtcagggg ccggtattct gaggcccgag ttgacgaaga | 3180 |
| tcaaaggaaa gataataacg tttactcaat ctgataagca gtccttgatc aagagtgggt | 3240 |
| acaatgacgt gaacactgtg catgaaattc agggagaaac ctttgaagag acggcggttg | 3300 |
| tgcgtgccac cccgactccg ataggtttaa ttgcccgtga ttcaccacat gtactagtgg | 3360 |
| ccttaacgag gcacactaag gcaatggtgt attatactgt tgtgttcgat gcagttacaa | 3420 |
| gtataatagt ggatgtggaa aaggtcgacc agtcgatctt gactatgttt gctaccactg | 3480 |

| | |
|---|---|
| tgcctaccaa atagcaatta atgcagaact cactgtatgt ccatcgtgat attttcctcc | 3540 |
| ctgttagtaa aacggggttt tatacagaca tgcaggagtt ctatgataga tgccttcctg | 3600 |
| ggaattcctt cgtgctgaat gatttcgatg ccgtaaccat gcggttgagg gacaacgaat | 3660 |
| ttaacctaca accttgtagg ctaaccttaa gtaatttaga tccagtaccc gctttggtta | 3720 |
| agagtgaagc gcagaatttt ctgattcccg ttttgcgtac ggcctgtgaa aggccgcgca | 3780 |
| ttccaggtct ccttgaaaat cttgtagcta tgataaagag gaatatgaat actcctgatc | 3840 |
| tagctgggac tgtggatata actaatatgt cgatttctat agtagataac ttcttttctt | 3900 |
| cttttgttag agacgaggtt ttgcttgatc atttagattg tgttagggct agttccattc | 3960 |
| aaagttttc tgattggttt tcgtgtcagc caacctcggc ggttggtcaa ttagctaatt | 4020 |
| tcaatttcat agatttgcct gcctttgata cttatatgca catgattaag cggcagccca | 4080 |
| agagtcggtt ggatacttcg attcagtctg aatatccggc cttgcaaact attgtttatc | 4140 |
| accttaaagt ggtaaatgca gttttcggtc cggttttaa gtatttgacc accaagtttc | 4200 |
| ttagcatggt agatagttct aagttttct tttacactag gaaaaaatca gaagatctgc | 4260 |
| aggaattttt ctcagatctc tcttcccatt ctgattatga gattcttgag ctggatgttt | 4320 |
| ctaaatatga caagtcacaa tccgatttcc atttctctat tgagatggca atttgggaaa | 4380 |
| aattggggct ggacgatatt ttggcttgga tgtggtctat gggtcacaag agaactatac | 4440 |
| tgcaagattt ccaagccggg ataaagacgc tcatttacta tcaacggaag tctggtgatg | 4500 |
| taactacttt cataggtaat accttttatta tcgcagcgtg tgtagctagt atgttgccgt | 4560 |
| tagacaagtg ttttaaagct agtttttgtg gtgatgattc gctgatctac cttcctaagg | 4620 |
| gtttggagta tcctgatata caggctactg ccaacttggt ttggaatttt gaggcgaaac | 4680 |
| ttttccgaaa gaagtatggt tacttctgtg ggaagtatat aattcaccat gccaacggct | 4740 |
| gtattgttta ccctgaccct ttaaaattaa ttagtaaatt aggtaataag agtcttgtag | 4800 |
| ggtatgagca tgttgaggag tttcgtatat ctctcctcga cgtcgctcat agtttgttta | 4860 |
| atggtgctta tttccatttta ctcgacgatg caatccacga attatttcct aacgctgggg | 4920 |
| gttgcagttt tgtaattaat tgtttgtgca agtatttgag tgataagcac cttttccgta | 4980 |
| gtctttatat agatgtctct aagtaaggtg tcggtcgaga actcattgaa acccgagaag | 5040 |
| tttgttaaaa tctcttgggt cgataagttg ctccctaact attttccat tcttaagtat | 5100 |
| ttatctataa ctgactttag cgtagttaaa gctcagagct atgaatccct cgtgcctgtc | 5160 |
| aagttgttgc gtggtgttga tcttacaaaa caccttatg tcacattgtt gggcgttgtg | 5220 |
| gtttctggtg tatggaacgt accggaatcc tgtaggggtg gtgctactgt tgctctggtt | 5280 |
| gacacaagga tgcattctgt tgcagaggga actatatgca aattttcagc tcccgccacc | 5340 |
| gtccgcgaat tctctgttag gttcatacct aactattctg tcgtggctgc ggatgccctt | 5400 |
| cgcgatcctt ggtctttatt tgtgagactc tctaatgtag ggattaaaga tggtttccat | 5460 |
| cctttgacct tagaggtcgc ttgtttagtc gctacaacta actctattat caaaaagggt | 5520 |
| cttagagctt ctgtagtcga gtctgtcgtc tcttccgatc agtccattgt cctagattct | 5580 |
| ttatccgaga aagttgaacc tttctttgat aaagttccta tttcggcggc tgtgatggca | 5640 |
| agagacccca gttataggtc taggtcgcag tctgtcggtg gtcgtggtaa gcggcattct | 5700 |
| aaacctccaa atcggaggtt ggactctgct tctgaagagt ccagttctgt ttctttcgaa | 5760 |
| gatggcttac aatccgatca cacctagcaa acttattgcg tttagtgctt cttatgttcc | 5820 |

```
cgtcaggact ttacttaatt ttctagttgc ttcacaaggt accgccttcc agactcaagc    5880
gggaagagat tctttccgcg agtccctgtc tgcgttaccc tcgtctgtcg tagatattaa    5940
ttctaggttc ccaaatgcgg gttttacgc tttcctcaac ggtcctgtgt tgaggcctat     6000
cttcgtttcg cttcttagct ctacggatac gcgtaatagg gtcattgagg ttgtagatcc    6060
tagcaatcct acgactgctg agtcgcttaa cgctgtaaag cgtactgatg acgcatctac    6120
ggccgctagg gctgaaatag ataatttaat agagtctatt tctaagggtt ttgatgttta    6180
tgatagggct tcatttgaag ccgcgttttc ggtagtctgg tcagaggtta ccacctcgaa    6240
agcttagctt cgagggtctt ctgatggtgg tgcacaccaa agtgcatagt gctttcccgt    6300
tcacttaaat cgaacggttt gctcattggt ttgcggaaac ctctcacgtg tggcgttgaa    6360
gtttctatgg gcagtaattc tgcaaggggt tcgaatcccc cctttccccg ggtaggggcc    6420
ca                                                                  6422
```

<210> SEQ ID NO 49
<211> LENGTH: 1144
<212> TYPE: PRT
<213> ORGANISM: Cucumber green mottle mosaic virus

<400> SEQUENCE: 49

```
Met Ala Asn Ile Asn Glu Gln Ile Asn Asn Gln Arg Asp Ala Ala
1               5                   10                  15

Ser Gly Arg Asn Asn Leu Val Ser Gln Leu Ala Ser Lys Arg Val Tyr
                20                  25                  30

Asp Glu Ala Val Arg Ser Leu Asp His Gln Asp Arg Arg Pro Lys Met
            35                  40                  45

Asn Phe Ser Arg Val Val Ser Thr Glu His Thr Arg Leu Val Thr Asp
        50                  55                  60

Ala Tyr Pro Glu Phe Ser Ile Ser Phe Thr Ala Thr Lys Asn Ser Val
65                  70                  75                  80

His Ser Leu Ala Gly Ser Leu Arg Leu Leu Glu Leu Glu Tyr Met Met
                85                  90                  95

Met Gln Val Pro Tyr Gly Ser Pro Cys Tyr Asp Ile Gly Gly Asn Tyr
            100                 105                 110

Thr Gln His Leu Phe Lys Gly Arg Ser Tyr Val His Cys Cys Asn Pro
        115                 120                 125

Cys Leu Asp Leu Lys Asp Val Ala Arg Asn Val Met Tyr Asn Asp Met
    130                 135                 140

Val Thr Gln His Val Gln Arg His Lys Gly Ser Gly Gly Cys Arg Pro
145                 150                 155                 160

Leu Pro Thr Phe Gln Ile Asp Ala Phe Arg Arg Tyr Asp Asn Ser Pro
                165                 170                 175

Cys Ala Val Thr Cys Ser Asp Val Phe Gln Glu Cys Ser Tyr Asp Phe
            180                 185                 190

Gly Ser Gly Arg Asp Asn His Ala Val Ser Leu His Ser Ile Tyr Asp
        195                 200                 205

Ile Pro Tyr Ser Ser Ile Gly Pro Ala Leu His Arg Lys Asn Val Arg
    210                 215                 220

Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
                245                 250                 255

Asp Asp Val His Phe Leu Phe Ser Glu Glu Ser Thr Leu His Tyr Thr
```

```
                260                 265                 270
His Ser Leu Glu Asn Ile Lys Leu Ile Val Met Arg Thr Tyr Phe Pro
            275                 280                 285
Ala Asp Asp Arg Tyr Val Tyr Ile Lys Glu Phe Met Val Lys Arg Val
            290                 295                 300
Asp Thr Phe Phe Phe Arg Leu Val Arg Ala Asp Thr His Met Leu His
305                 310                 315                 320
Lys Ser Val Gly His Tyr Ser Lys Ser Lys Ser Glu Tyr Phe Ala Leu
                325                 330                 335
Asn Thr Pro Pro Ile Phe Gln Asp Lys Ala Thr Phe Ser Val Trp Phe
            340                 345                 350
Pro Glu Ala Lys Arg Lys Val Leu Ile Pro Lys Phe Glu Leu Ser Arg
            355                 360                 365
Phe Leu Ser Gly Asn Val Lys Ile Ser Arg Met Leu Val Asp Ala Asp
            370                 375                 380
Phe Val His Thr Ile Ile Asn His Ile Ser Thr Tyr Asp Asn Lys Ala
385                 390                 395                 400
Leu Val Trp Lys Asn Val Gln Ser Phe Val Glu Ser Ile Arg Ser Arg
                405                 410                 415
Val Ile Val Asn Gly Val Ser Val Lys Ser Glu Trp Asn Val Pro Val
                420                 425                 430
Asp Gln Leu Thr Asp Ile Ser Phe Ser Ile Phe Leu Leu Val Lys Val
            435                 440                 445
Arg Lys Val Gln Ile Glu Leu Met Ser Asp Lys Val Val Ile Glu Ala
            450                 455                 460
Arg Gly Leu Leu Arg Arg Phe Ala Asp Ser Leu Lys Ser Ala Val Gly
465                 470                 475                 480
Gly Leu Gly Asp Cys Val Tyr Asp Ala Leu Val Gln Thr Gly Trp Phe
                485                 490                 495
Asp Thr Ser Ser Asp Glu Leu Lys Val Leu Leu Pro Glu Pro Phe Met
            500                 505                 510
Thr Phe Ser Asp Tyr Leu Glu Gly Met Tyr Glu Ala Asp Ala Lys Ile
            515                 520                 525
Glu Arg Glu Ser Val Phe Glu Leu Leu Ala Ser Gly Asp Asp Leu Phe
            530                 535                 540
Lys Lys Ile Asp Glu Ile Arg Asn Asn Tyr Ser Gly Val Glu Phe Asp
545                 550                 555                 560
Val Glu Lys Phe Gln Glu Phe Cys Lys Glu Leu Asn Val Asn Pro Met
                565                 570                 575
Leu Ile Gly His Val Ile Glu Ala Ile Phe Ser Gln Lys Ala Gly Val
                580                 585                 590
Thr Val Thr Gly Leu Gly Thr Leu Ser Pro Glu Met Gly Ala Ser Val
            595                 600                 605
Ala Leu Ser Asn Thr Ser Val Asp Thr Cys Gly Asp Met Asp Val Thr
            610                 615                 620
Glu Asp Met Glu Asp Ile Val Leu Met Ala Asp Lys Ser His Ser Tyr
625                 630                 635                 640
Met Ser Pro Glu Met Ala Arg Trp Ala Asp Val Lys Tyr Asp Asn Asn
                645                 650                 655
Lys Gly Gly Leu Val Glu Tyr Lys Val Gly Thr Ser Met Thr Leu Pro
                660                 665                 670
Ala Thr Trp Ala Glu Lys Gly Lys Ala Val Leu Pro Leu Ser Gly Ile
            675                 680                 685
```

-continued

Cys Val Arg Lys Pro Gln Phe Ser Lys Pro Leu Asp Glu Glu Asp
690              695                 700

Leu Arg Leu Ser Asn Met Asn Phe Phe Lys Val Ser Asp Leu Lys Leu
705              710                 715                 720

Lys Lys Thr Ile Thr Pro Val Val Tyr Thr Gly Thr Ile Arg Glu Arg
                725                 730                 735

Gln Met Lys Asn Tyr Ile Asp Tyr Leu Ser Ala Ser Leu Gly Ser Thr
                740                 745                 750

Leu Gly Asn Leu Glu Arg Ile Val Arg Ser Asp Trp Asn Gly Thr Glu
                755                 760                 765

Glu Ser Met Gln Thr Phe Gly Leu Tyr Asp Cys Glu Lys Cys Lys Trp
770              775                 780

Leu Leu Leu Pro Ala Glu Lys Lys His Ala Trp Ala Val Val Leu Ala
785              790                 795                 800

Ser Asp Asp Thr Thr Arg Ile Ile Phe Leu Ser Tyr Asp Glu Ser Gly
                805                 810                 815

Ser Pro Ile Ile Asp Lys Arg Asn Trp Lys Arg Phe Ala Val Cys Ser
                820                 825                 830

Glu Thr Lys Val Tyr Ser Val Ile Arg Ser Leu Glu Val Leu Asn Lys
                835                 840                 845

Glu Ala Ile Val Asp Pro Gly Val His Ile Thr Leu Val Asp Gly Val
850              855                 860

Pro Gly Cys Gly Lys Thr Ala Glu Ile Ile Ala Arg Val Asn Trp Lys
865              870                 875                 880

Thr Asp Leu Val Leu Thr Pro Gly Arg Glu Ala Ala Met Ile Arg
                885                 890                 895

Arg Arg Ala Cys Ala Leu His Lys Ser Pro Val Ala Thr Ser Asp Asn
                900                 905                 910

Val Arg Thr Phe Asp Ser Phe Val Met Asn Lys Lys Ile Phe Lys Phe
                915                 920                 925

Asp Ala Val Tyr Val Asp Glu Gly Leu Met Val His Thr Gly Leu Leu
                930                 935                 940

Asn Phe Ala Leu Lys Ile Ser Gly Cys Lys Lys Ala Phe Val Phe Gly
945              950                 955                 960

Asp Ala Lys Gln Ile Pro Phe Ile Asn Arg Val Met Asn Phe Asp Tyr
                965                 970                 975

Pro Lys Glu Leu Arg Thr Leu Ile Val Asp Asn Val Glu Arg Arg Tyr
                980                 985                 990

Val Thr His Arg Cys Pro Arg Asp Val Thr Ser Phe Leu Asn Thr Ile
                995                 1000                1005

Tyr Lys Ala Ala Val Ala Thr Thr Ser Pro Val Val His Ser Val
   1010             1015                1020

Lys Ala Ile Lys Val Ser Gly Ala Gly Ile Leu Arg Pro Glu Leu
   1025             1030                1035

Thr Lys Ile Lys Gly Lys Ile Ile Thr Phe Thr Gln Ser Asp Lys
   1040             1045                1050

Gln Ser Leu Ile Lys Ser Gly Tyr Asn Asp Val Asn Thr Val His
   1055             1060                1065

Glu Ile Gln Gly Glu Thr Phe Glu Glu Thr Ala Val Val Arg Ala
   1070             1075                1080

Thr Pro Thr Pro Ile Gly Leu Ile Ala Arg Asp Ser Pro His Val
   1085             1090                1095

```
Leu Val Ala Leu Thr Arg His Thr Lys Ala Met Val Tyr Tyr Thr
    1100            1105            1110

Val Val Phe Asp Ala Val Thr Ser Ile Ile Val Asp Val Glu Lys
    1115            1120            1125

Val Asp Gln Ser Ile Leu Thr Met Phe Ala Thr Thr Val Pro Thr
    1130            1135            1140

Lys

<210> SEQ ID NO 50
<211> LENGTH: 1648
<212> TYPE: PRT
<213> ORGANISM: Cucumber green mottle mosaic virus
<220

```
Asp Thr Phe Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
            325                 330                 335

Asn Thr Pro Pro Ile Phe Gln Asp Lys Ala Thr Phe Ser Val Trp Phe
            340                 345                 350

Pro Glu Ala Lys Arg Lys Val Leu Ile Pro Lys Phe Glu Leu Ser Arg
            355                 360                 365

Phe Leu Ser Gly Asn Val Lys Ile Ser Arg Met Leu Val Asp Ala Asp
370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
            405                 410                 415

Val Ile Val Asn Gly Val Ser Val Lys Ser Glu Trp Asn Val Pro Val
            420                 425                 430

Asp Gln Leu Thr Asp Ile Ser Phe Ser Ile Phe Leu Leu Val Lys Val
            435                 440                 445

Arg Lys Val Gln Ile Glu Leu Met Ser Asp Lys Val Val Ile Glu Ala
450                 455                 460

Arg Gly Leu Leu Arg Arg Phe Ala Asp Ser Leu Lys Ser Ala Val Gly
465                 470                 475                 480

Gly Leu Gly Asp Cys Val Tyr Asp Ala Leu Val Gln Thr Gly Trp Phe
            485                 490                 495

Asp Thr Ser Ser Asp Glu Leu Lys Val Leu Leu Pro Glu Pro Phe Met
            500                 505                 510

Thr Phe Ser Asp Tyr Leu Glu Gly Met Tyr Glu Ala Asp Ala Lys Ile
            515                 520                 525

Glu Arg Glu Ser Val Phe Glu Leu Leu Ala Ser Gly Asp Asp Leu Phe
530                 535                 540

Lys Lys Ile Asp Glu Ile Arg Asn Asn Tyr Ser Gly Val Glu Phe Asp
545                 550                 555                 560

Val Glu Lys Phe Gln Glu Phe Cys Lys Glu Leu Asn Val Asn Pro Met
            565                 570                 575

Leu Ile Gly His Val Ile Glu Ala Ile Phe Ser Gln Lys Ala Gly Val
            580                 585                 590

Thr Val Thr Gly Leu Gly Thr Leu Ser Pro Glu Met Gly Ala Ser Val
            595                 600                 605

Ala Leu Ser Asn Thr Ser Val Asp Thr Cys Glu Asp Met Asp Val Thr
            610                 615                 620

Glu Asp Met Glu Asp Ile Val Leu Met Ala Asp Lys Ser His Ser Tyr
625                 630                 635                 640

Met Ser Pro Glu Met Ala Arg Trp Ala Asp Val Lys Tyr Asp Asn Asn
            645                 650                 655

Lys Gly Gly Leu Val Glu Tyr Lys Val Gly Thr Ser Met Thr Leu Pro
            660                 665                 670

Ala Thr Trp Ala Glu Lys Gly Lys Ala Val Leu Pro Leu Ser Gly Ile
            675                 680                 685

Cys Val Arg Lys Pro Gln Phe Ser Lys Pro Leu Asp Glu Glu Asp Asp
            690                 695                 700

Leu Arg Leu Ser Asn Met Asn Phe Phe Lys Val Ser Asp Leu Lys Leu
705                 710                 715                 720
```

```
Lys Lys Thr Ile Thr Pro Val Val Tyr Thr Gly Thr Ile Arg Glu Arg
                725                 730                 735

Gln Met Lys Asn Tyr Ile Asp Tyr Leu Ser Ala Ser Leu Gly Ser Thr
            740                 745                 750

Leu Gly Asn Leu Glu Arg Ile Val Arg Ser Asp Trp Asn Gly Thr Glu
        755                 760                 765

Glu Ser Met Gln Thr Phe Gly Leu Tyr Asp Cys Glu Lys Cys Lys Trp
    770                 775                 780

Leu Leu Leu Pro Ala Glu Lys Lys His Ala Trp Ala Val Val Leu Ala
785                 790                 795                 800

Ser Asp Asp Thr Thr Arg Ile Ile Phe Leu Ser Tyr Asp Glu Ser Gly
                805                 810                 815

Ser Pro Ile Ile Asp Lys Arg Asn Trp Lys Arg Phe Ala Val Cys Ser
            820                 825                 830

Glu Thr Lys Val Tyr Ser Val Ile Arg Ser Leu Glu Val Leu Asn Lys
        835                 840                 845

Glu Ala Ile Val Asp Pro Gly Val His Ile Thr Leu Val Asp Gly Val
    850                 855                 860

Pro Gly Cys Gly Lys Thr Ala Glu Ile Ile Ala Arg Val Asn Trp Lys
865                 870                 875                 880

Thr Asp Leu Val Leu Thr Pro Gly Arg Glu Ala Ala Met Ile Arg
                885                 890                 895

Arg Arg Ala Cys Ala Leu His Lys Ser Pro Val Ala Thr Ser Asp Asn
            900                 905                 910

Val Arg Thr Phe Asp Ser Phe Val Met Asn Lys Lys Ile Phe Lys Phe
        915                 920                 925

Asp Ala Val Tyr Val Asp Glu Gly Leu Met Val His Thr Gly Leu Leu
    930                 935                 940

Asn Phe Ala Leu Lys Ile Ser Gly Cys Lys Lys Ala Phe Val Phe Gly
945                 950                 955                 960

Asp Ala Lys Gln Ile Pro Phe Ile Asn Arg Val Met Asn Phe Asp Tyr
                965                 970                 975

Pro Lys Glu Leu Arg Thr Leu Ile Val Asp Asn Val Glu Arg Arg Tyr
            980                 985                 990

Val Thr His Arg Cys Pro Arg Asp Val Thr Ser Phe Leu Asn Thr Ile
        995                1000                1005

Tyr Lys Ala Ala Val Ala Thr Thr Ser Pro Val His Ser Val
       1010                1015                1020

Lys Ala Ile Lys Val Ser Gly Ala Gly Ile Leu Arg Pro Glu Leu
   1025                1030                1035

Thr Lys Ile Lys Gly Lys Ile Ile Thr Phe Thr Gln Ser Asp Lys
   1040                1045                1050

Gln Ser Leu Ile Lys Ser Gly Tyr Asn Asp Val Asn Thr Val His
   1055                1060                1065

Glu Ile Gln Gly Glu Thr Phe Glu Glu Thr Ala Val Val Arg Ala
   1070                1075                1080

Thr Pro Thr Pro Ile Gly Leu Ile Ala Arg Asp Ser Pro His Val
   1085                1090                1095

Leu Val Ala Leu Thr Arg His Thr Lys Ala Met Val Tyr Tyr Thr
   1100                1105                1110

Val Val Phe Asp Ala Val Thr Ser Ile Ile Val Asp Val Glu Lys
   1115                1120                1125

Val Asp Gln Ser Ile Leu Thr Met Phe Ala Thr Thr Val Pro Thr
```

-continued

```
              1130                1135                1140

Lys Xaa Gln Leu Met Gln Asn Ser Leu Tyr Val His Arg Asp Ile
        1145                1150                1155

Phe Leu Pro Val Ser Lys Thr Gly Phe Tyr Thr Asp Met Gln Glu
        1160                1165                1170

Phe Tyr Asp Arg Cys Leu Pro Gly Asn Ser Phe Val Leu Asn Asp
        1175                1180                1185

Phe Asp Ala Val Thr Met Arg Leu Arg Asp Asn Glu Phe Asn Leu
        1190                1195                1200

Gln Pro Cys Arg Leu Thr Leu Ser Asn Leu Asp Pro Val Pro Ala
        1205                1210                1215

Leu Val Lys Ser Glu Ala Gln Asn Phe Leu Ile Pro Val Leu Arg
        1220                1225                1230

Thr Ala Cys Glu Arg Pro Arg Ile Pro Gly Leu Leu Glu Asn Leu
        1235                1240                1245

Val Ala Met Ile Lys Arg Asn Met Asn Thr Pro Asp Leu Ala Gly
        1250                1255                1260

Thr Val Asp Ile Thr Asn Met Ser Ile Ser Ile Val Asp Asn Phe
        1265                1270                1275

Phe Ser Ser Phe Val Arg Asp Glu Val Leu Leu Asp His Leu Asp
        1280                1285                1290

Cys Val Arg Ala Ser Ser Ile Gln Ser Phe Ser Asp Trp Phe Ser
        1295                1300                1305

Cys Gln Pro Thr Ser Ala Val Gly Gln Leu Ala Asn Phe Asn Phe
        1310                1315                1320

Ile Asp Leu Pro Ala Phe Asp Thr Tyr Met His Met Ile Lys Arg
        1325                1330                1335

Gln Pro Lys Ser Arg Leu Asp Thr Ser Ile Gln Ser Glu Tyr Pro
        1340                1345                1350

Ala Leu Gln Thr Ile Val Tyr His Leu Lys Val Val Asn Ala Val
        1355                1360                1365

Phe Gly Pro Val Phe Lys Tyr Leu Thr Thr Lys Phe Leu Ser Met
        1370                1375                1380

Val Asp Ser Ser Lys Phe Phe Phe Tyr Thr Arg Lys Lys Ser Glu
        1385                1390                1395

Asp Leu Gln Glu Phe Phe Ser Asp Leu Ser Ser His Ser Asp Tyr
        1400                1405                1410

Glu Ile Leu Glu Leu Asp Val Ser Lys Tyr Asp Lys Ser Gln Ser
        1415                1420                1425

Asp Phe His Phe Ser Ile Glu Met Ala Ile Trp Glu Lys Leu Gly
        1430                1435                1440

Leu Asp Asp Ile Leu Ala Trp Met Trp Ser Met Gly His Lys Arg
        1445                1450                1455

Thr Ile Leu Gln Asp Phe Gln Ala Gly Ile Lys Thr Leu Ile Tyr
        1460                1465                1470

Tyr Gln Arg Lys Ser Gly Asp Val Thr Thr Phe Ile Gly Asn Thr
        1475                1480                1485

Phe Ile Ile Ala Ala Cys Val Ala Ser Met Leu Pro Leu Asp Lys
        1490                1495                1500

Cys Phe Lys Ala Ser Phe Cys Gly Asp Asp Ser Leu Ile Tyr Leu
        1505                1510                1515

Pro Lys Gly Leu Glu Tyr Pro Asp Ile Gln Ala Thr Ala Asn Leu
        1520                1525                1530
```

```
Val Trp  Asn Phe Glu Ala Lys  Leu Phe Arg Lys Lys  Tyr Gly Tyr
    1535                 1540                 1545

Phe Cys  Gly Lys Tyr Ile Ile  His His Ala Asn Gly  Cys Ile Val
    1550                 1555                 1560

Tyr Pro  Asp Pro Leu Lys Leu  Ile Ser Lys Leu Gly  Asn Lys Ser
    1565                 1570                 1575

Leu Val  Gly Tyr Glu His Val  Glu Glu Phe Arg Ile  Ser Leu Leu
    1580                 1585                 1590

Asp Val  Ala His Ser Leu Phe  Asn Gly Ala Tyr Phe  His Leu Leu
    1595                 1600                 1605

Asp Asp  Ala Ile His Glu Leu  Phe Pro Asn Ala Gly  Gly Cys Ser
    1610                 1615                 1620

Phe Val  Ile Asn Cys Leu Cys  Lys Tyr Leu Ser Asp  Lys His Leu
    1625                 1630                 1635

Phe Arg  Ser Leu Tyr Ile Asp  Val Ser Lys
    1640                 1645

<210> SEQ ID NO 51
<211> LENGTH: 37
<212> TYPE: DNA
<213> ORGANISM: Artificial Sequence
<220> FEATURE:
<223> OTHER INFORMATION: Primer

<400> SEQUENCE: 51
tgtggtgaat cacggacaat taaacctatc ggagtcg                              37

<210> SEQ ID NO 52
<211> LENGTH: 37
<212> TYPE: DNA
<213> ORGANISM: Artificial Sequence
<220> FEATURE:
<223> OTHER INFORMATION: Primer

<400> SEQUENCE: 52
cgactccgat aggtttaatt gtccgtgatt caccaca                              37

<210> SEQ ID NO 53
<211> LENGTH: 6422
<212> TYPE: DNA
<213> ORGANISM: Cucumber green mottle mosaic virus

<400> SEQUENCE: 53
gttttaattt ttaaaattaa acaaacaaca acaacaacaa caaacaattt aaaacaacaa      60
tggcaaacat taatgaacaa atcaacaacc aacgcgacgc cgcggccagc gggagaaaca     120
atctcgttag ccaattggcg tcaaaaaggg tgtatgacga ggctgttcgc tcgttggatc     180
atcaagacag acgcccaaaa atgaactttt ctcgtgtggt cagcacagag cacaccaggc     240
ttgtaactga tgcgtatccg gagttttcga ttagctttac cgccaccaag aactctgtac     300
actcccttgc gggtggtctg aggctccttg aactggaata tatgatgatg caagtgccct     360
acggctcacc ttgttatgat atcggcggta actatacgca gcacttgttc aaaggtagat     420
catatgtgca ttgctgcaat ccgtgcctgg atcttaaaga tgttgcgagg aacgtgatgt     480
ataacgatat ggtcacacaa catgtacaga ggcacaaggg atctggcggg tgcagacctc     540
ttccaacttt tcagatagat gcattcagga ggtacgataa ttctccctgt gcggtcacct     600
gttcagacgt tttccaagag tgttcctatg attttgggag cggtagggat aatcatgcag     660
```

```
tctcgctgca ttcaatctac gatatccctt attcttcgat cggacctgct cttcatagga     720
agaacgtgcg agtttgttat gcagcctttc acttctcgga ggcattgctt ttaggttcac     780
ctgtaggtaa tttaaatagt attggggctc agtttagggt cgatggtgat gatgtgcatt     840 ttcttttag tgaagagtct actttgcatt atactcatag tttagaaaat atcaaattaa      900
ttgtgatgcg tacttatttt cctgctgatg ataggtacgt gtatattaag gagtttatgg     960
tcaagcgtgt ggatactttc ttctttaggt tggtcagagc agacacacat atgcttcata    1020
aatctgtggg gcactattca aaatcgaaat ctgagtactt tgcgctgaat acccctccga    1080
tcttccaaga caaagccacg ttttctgtgt ggtttcctga ggcgaagcgt aaggtgttga    1140
tacccaagtt tgaactttca agattccttt ctgggaatgt gaaaatctct aggatgcttg    1200
tcgatgctga tttcgtccat accattatta atcacattag cacgtatgat aataaggcct    1260
tagtgtggaa gaatgttcag tcctttgtgg aatctatacg ctcaagagta attgtaaacg    1320
gagtttcggt gaaatctgaa tggaacgtac cggttgatca gctcactgat atctcgttct    1380
cgatattcct tctcgtgaag gttaggaagg tacagatcga gttaatgtct gataaagttg    1440
taatcgaggc gagggggcttg ctccggaggt tcgcagacag tcttaaatcc gccgtagaag    1500
gactaggtga ttgcgtctat gatgctctag ttcaaaccgg ctggtttgat acctctagcg    1560
acgaactgaa agtttgcta cctgaaccgt ttatgacctt ttcggattat cttgaaggga    1620
tgtacgaggc agatgcaaag atcgagagag agagtgtctc tgagttgctc gcttccggtg    1680
acgatttgtt caagaaaatc gatgagataa gaaacaatta cagtggagtc gaatttgatg    1740
tagagaaatt ccaggaattt tgcaaggaac tgaatgttaa tcctatgcta attggccatg    1800
ttatcgaagc tatttttttcg cagaaagctg gggtgacagt aacgggtctg ggtaccctct    1860
ctcctgagat gggtgcttct gttgcgttat ccaatacctc tgtagataca tgtgaagata    1920
tggatgtaac tgaagatatg gaggatatag tgttgatggc ggacaagagt cattcttaca    1980
tgtccccaga aatggcgaga tgggctgatg taaaatacga caacaataaa ggggggcctgg    2040 tcgaatacaa agtcggaacc tcgatgactt tacctgccac ctgggcagag aagggtaagg    2100
ctgtcttacc gttgtcgggg atctgtgtga ggaaaccccca attttcgaag ccgcttgatg    2160
aggaagacga cttgaggtta tcaaacatga atttcttta aggtgagcgat ctgaagttga    2220 agaaaactat cactccagtt gtttacactg ggaccattcg agagaggcaa atgaagaatt    2280
atattgatta cttatcggcc tctcttggtt ctacgctggg taatctggag agaattgtgc    2340
ggagtgattg gaacggtacc gaggagagta tgcaaacgtt cgggttgtat gactgcgaaa    2400
agtgcaagtg gttactgtta ccagccgaaa agaagcacgc atgggctgtg gttctggcaa    2460
gtgatgatac cactcgcata atcttcctct catatgacga atctggttct cccataattg    2520
ataagagaaa ctggaagcga tttgctgttt gctctgagac caaagtctat agcgtaattc    2580
gtagtttaga ggtactaaat aaggaagcaa tagtcgaccc cggggttcat ataacattag    2640
ttgacggagt gccgggttgt ggaaagaccg ccgaaattat agcgagggtc aattggaaaa    2700
ccgatctagt attgactccc gggagggagg cggctgctat gattaggcgg agggcctgcg    2760
ccctgcacaa gtcacctgtg gcaaccagtg acaacgttag aactttcgat tcttttgtga    2820
tgaataagaa aatcttcaag tttgacgctg tctatgttga cgagggtctg atggtccata    2880 cgggttact taattttgcg ttgaagatct caggttgtaa aaaggccttc gtctttggtg    2940
atgctaagca aatcccgttt ataaacagag tcatgaattt tgattatcct aaggagttaa    3000
gaactttaat agtcgataat gtagagcgta ggtatgttac ccataggtgt cctagagatg    3060
```

```
tcactagttt tcttaatact atttacaaag ccgctgtcgc tactactagt ccggttgtac   3120
attctgtgaa ggcgattaaa gtgtcagggg ccggtattct gaggcccgag ttgacgaaga   3180
tcaaaggaaa gataataacg tttactcaat ctgataagca gtccttgatc aagagtgggt   3240
acaatgacgt gaacactgtg catgaaattc agggagaaac ctttgaagag acggcggttg   3300
tgcgtgccac cccgactccg ataggtttaa ttgtccgtga ttcaccacat gtactagtgg   3360
ccttaacgag gcacactaag gcaatggtgt attatactgt tgtgttcgat gcagttacaa   3420
gtataatagc ggatgtggaa aaggtcgacc agtcgatctt gactatgttt gctaccactg   3480
tgcctaccaa atagcaatta atgcagaact cactgtatgt ccatcgtaat attttcctcc   3540
ctgttagtaa aacggggttt tatacagaca tgcaggagtt ctatgataga tgccttcctg   3600
ggaattcctt cgtgctgaat gatttcgatg ccgtaaccat gcggttgagg gacaacgaat   3660
ttaacctaca accttgtagg ctaaccttaa gtaatttaga tccagtaccc gctttggtta   3720
agagtgaagc gcagaatttt ctgattcccg ttttgcgtac ggcctgtgaa aggccgcgca   3780
ttccaggtct ccttgaaaat cttgtagcta tgataaagag gaatatgaat actcctgatc   3840
tagctgggac tgtggatata actaatatgt cgatttctat agtagataac ttcttttctt   3900
cttttgttag agacgaggtt ttgcttgatc atttagattg tgttagggct agttccattc   3960
aaagtttttc tgattggttt tcgtgtcagc caacctcggc ggttggtcaa ttagctaatt   4020
tcaatttcat agatttgcct gcctttgata cttatatgca catgattaag cggcagccca   4080
agagtcggtt ggatacttcg attcagtctg aatatccggc cttgcaaact attgtttatc   4140
accctaaagt ggtaaatgca gttttcggtc cggttttttaa gtatttgacc accaagtttc   4200
ttagcatggt agatagttct aagttttttct tttacactag gaaaaaacca gaagatctgc   4260 aggaatttttt ctcagatctc tcttcccatt ctgattatga gattcttgag ctggatgttt   4320
ctaaatatga caagtcacaa tccgatttcc atttctctat tgagatggca atttgggaaa   4380
aattggggct ggacgatatt ttggcttgga tgtggtctat gggtcacaag agaactatac   4440
tgcaagattt ccaagccggg ataaagacgc tcatttacta tcaacggaag tctggtgatg   4500
taactacttt cataggtaat accttttatta tcgcagcgtg tgtagctagt atgttgccgt   4560
tagacaagtg ttttaaagct agttttttgtg gtgatgattc gctgatctac cttcctaagg   4620
gtttggagta tcctgatata caggctactg ccaacttggt ttggaatttt gaggcgaaac   4680
ttttccgaaa gaagtatggt tacttctgtg ggaagtatat aattcaccat gccaacggct   4740
gtattgttta ccctgacccct ttaaaattaa ttagtaaatt aggtaataag agtcttgtag   4800
ggtatgagca tgttgaggag tttcgtatat ctctcctcga cgtcgctcat agtttgttta   4860
atggtgctta tttccattta ctcgacgatg caatccacga attatttcct aacgctgggg   4920
gttgcagttt tgtaattaat tgtttgtgca agtatttgag tgataagcgc cttttccgta   4980
gtctttatat agatgtctct aagtaaggtg tcggtcgaga actcattgaa acccgagaag   5040
tttgttaaaa tctcttgggt cgataagttg ctccctaact attttccat tcttaagtat   5100 ttatctataa ctgactttag cgtagttaaa gctcagagct atgaatccct cgtgcctgtc   5160
aagttgttgc gtggtgttga tcttacaaaa cacctttatg tcacattgtt gggcgttgtg   5220
gtttctggtg tatggaacgt accggaatcc tgtaggggtg tgctactgt tgctctggtt   5280 gacacaagga tgcattctgt tgcagaggga actatatgca aattttcagc tcccgccacc   5340
gtccgcgaat tctctgttag gttcatacct aactattctg tcgtggctgc ggatgccctt   5400
```

```
cgcgatcctt ggtctttatt tgtgagactc tctaatgtag ggattaaaga tggtttccat    5460
cctttgacct tagaggtcgc ttgtttagtc gctacaacta actctattat caaaaagggt    5520
cttagagctt ctgtagtcga gtctgtcgtc tcttccgatc agtccattgt cctagattct    5580
ttatccgaga aagttgaacc tttctttgat aaagttccta tttcggcggc tgtgatggca    5640
agagacccca gttataggtc taggtcgcag tctgtcggtg gtcgtggtaa gcggcattct    5700
aaacctccaa atcggaggtt ggactctgct tctgaagagt ccagttctgt ttctttcgaa    5760
gatggcttac aatccgatca cacctagcaa acttattgcg tttagtgctt cttatgttcc    5820
cgtcaggact ttacttaatt ttctagttgc ttcacaaggt accgccttcc agactcaagc    5880
gggaagagat tctttccgcg agtccctgtc tgcgttaccc tcgtctgtcg tagatattaa    5940
ttctaggttc ccaaatgcgg ttttttacgc tttcctcaac ggtcctgtgt tgaggcctat    6000
cttcgtttcg cttcttagct ctacggatac gcgtaatagg gtcattgagg ttgtagatcc    6060
tagcaatcct acgactgctg agtcgcttaa cgctgtaaag cgtactgatg acgcatctac    6120
ggccgctagg gctgaaatag ataatttaat agagtctatt tctaagggtt ttgatgttta    6180
tgatagggct tcatttgaag ccgcgttttc ggtagtctgg tcagaggcta ccacctcgaa    6240
agcttagctt cgagggtctt ctgatggtgg tgcacaccaa agtgcatagt gctttcccgt    6300
tcacttaaat cgaacggttt gctcattggt ttgcggaaac ctctcacgtg tggcgttgaa    6360
gtttctatgg gcagtaattc tgcaaggggt tcgaatcccc cctttccccg ggtaggggcc    6420
ca                                                                   6422
```

<210> SEQ ID NO 54
<211> LENGTH: 1144
<212> TYPE: PRT
<213> ORGANISM: Cucumber green mottle mosaic virus

<400> SEQUENCE: 54

Met Ala Asn Ile Asn Glu Gln Ile Asn Gln Arg Asp Ala Ala
1               5                   10                  15

Ser Gly Arg Asn Asn Leu Val Ser Gln Leu Ala Ser Lys Arg Val Tyr
                20                  25                  30

Asp Glu Ala Val Arg Ser Leu Asp His Gln Asp Arg Pro Lys Met
            35                  40                  45

Asn Phe Ser Arg Val Val Ser Thr Glu His Thr Arg Leu Val Thr Asp
50                  55                  60

Ala Tyr Pro Glu Phe Ser Ile Ser Phe Thr Ala Thr Lys Asn Ser Val
65                  70                  75                  80

His Ser Leu Ala Gly Gly Leu Arg Leu Leu Glu Leu Glu Tyr Met Met
                85                  90                  95

Met Gln Val Pro Tyr Gly Ser Pro Cys Tyr Asp Ile Gly Gly Asn Tyr
            100                 105                 110

Thr Gln His Leu Phe Lys Gly Arg Ser Tyr Val His Cys Cys Asn Pro
        115                 120                 125

Cys Leu Asp Leu Lys Asp Val Ala Arg Asn Val Met Tyr Asn Asp Met
130                 135                 140

Val Thr Gln His Val Gln Arg His Lys Gly Ser Gly Gly Cys Arg Pro
145                 150                 155                 160

Leu Pro Thr Phe Gln Ile Asp Ala Phe Arg Arg Tyr Asp Asn Ser Pro
                165                 170                 175

Cys Ala Val Thr Cys Ser Asp Val Phe Gln Glu Cys Ser Tyr Asp Phe
            180                 185                 190

```
Gly Ser Gly Arg Asp Asn His Ala Val Ser Leu His Ser Ile Tyr Asp
            195                 200                 205
Ile Pro Tyr Ser Ser Ile Gly Pro Ala Leu His Arg Lys Asn Val Arg
    210                 215                 220
Val Cys Tyr Ala Ala Phe His Phe Ser Glu Ala Leu Leu Leu Gly Ser
225                 230                 235                 240
Pro Val Gly Asn Leu Asn Ser Ile Gly Ala Gln Phe Arg Val Asp Gly
                245                 250                 255
Asp Asp Val His Phe Leu Phe Ser Glu Ser Thr Leu His Tyr Thr
                260                 265                 270
His Ser Leu Glu Asn Ile Lys Leu Ile Val Met Arg Thr Tyr Phe Pro
            275                 280                 285
Ala Asp Asp Arg Tyr Val Tyr Ile Lys Glu Phe Met Val Lys Arg Val
        290                 295                 300
Asp Thr Phe Phe Phe Arg Leu Val Arg Ala Asp Thr His Met Leu His
305                 310                 315                 320
Lys Ser Val Gly His Tyr Ser Lys Ser Lys Ser Glu Tyr Phe Ala Leu
                325                 330                 335
Asn Thr Pro Pro Ile Phe Gln Asp Lys Ala Thr Phe Ser Val Trp Phe
                340                 345                 350
Pro Glu Ala Lys Arg Lys Val Leu Ile Pro Lys Phe Glu Leu Ser Arg
            355                 360                 365
Phe Leu Ser Gly Asn Val Lys Ile Ser Arg Met Leu Val Asp Ala Asp
        370                 375                 380
Phe Val His Thr Ile Ile Asn His Ile Ser Thr Tyr Asp Asn Lys Ala
385                 390                 395                 400
Leu Val Trp Lys Asn Val Gln Ser Phe Val Glu Ser Ile Arg Ser Arg
                405                 410                 415
Val Ile Val Asn Gly Val Ser Val Lys Ser Glu Trp Asn Val Pro Val
                420                 425                 430
Asp Gln Leu Thr Asp Ile Ser Phe Ser Ile Phe Leu Leu Val Lys Val
            435                 440                 445
Arg Lys Val Gln Ile Glu Leu Met Ser Asp Lys Val Val Ile Glu Ala
        450                 455                 460
Arg Gly Leu Leu Arg Arg Phe Ala Asp Ser Leu Lys Ser Ala Val Glu
465                 470                 475                 480
Gly Leu Gly Asp Cys Val Tyr Asp Ala Leu Val Gln Thr Gly Trp Phe
                485                 490                 495
Asp Thr Ser Ser Asp Glu Leu Lys Val Leu Leu Pro Glu Pro Phe Met
            500                 505                 510
Thr Phe Ser Asp Tyr Leu Glu Gly Met Tyr Glu Ala Asp Ala Lys Ile
        515                 520                 525
Glu Arg Glu Ser Val Ser Glu Leu Leu Ala Ser Gly Asp Asp Leu Phe
530                 535                 540
Lys Lys Ile Asp Glu Ile Arg Asn Asn Tyr Ser Gly Val Glu Phe Asp
545                 550                 555                 560
Val Glu Lys Phe Gln Glu Phe Cys Lys Glu Leu Asn Val Asn Pro Met
                565                 570                 575
Leu Ile Gly His Val Ile Glu Ala Ile Phe Ser Gln Lys Ala Gly Val
                580                 585                 590
Thr Val Thr Gly Leu Gly Thr Leu Ser Pro Glu Met Gly Ala Ser Val
            595                 600                 605
```

```
Ala Leu Ser Asn Thr Ser Val Asp Thr Cys Glu Asp Met Asp Val
610             615             620
Glu Asp Met Glu Asp Ile Val Leu Met Ala Asp Lys Ser His Ser Tyr
625             630             635             640
Met Ser Pro Glu Met Ala Arg Trp Ala Asp Val Lys Tyr Asp Asn Asn
                645             650             655
Lys Gly Gly Leu Val Glu Tyr Lys Val Gly Thr Ser Met Thr Leu Pro
660             665             670
Ala Thr Trp Ala Glu Lys Gly Lys Ala Val Leu Pro Leu Ser Gly Ile
        675             680             685
Cys Val Arg Lys Pro Gln Phe Ser Lys Pro Leu Asp Glu Glu Asp Asp
690             695             700
Leu Arg Leu Ser Asn Met Asn Phe Phe Lys Val Ser Asp Leu Lys Leu
705             710             715             720
Lys Lys Thr Ile Thr Pro Val Val Tyr Thr Gly Thr Ile Arg Glu Arg
                725             730             735
Gln Met Lys Asn Tyr Ile Asp Tyr Leu Ser Ala Ser Leu Gly Ser Thr
        740             745             750
Leu Gly Asn Leu Glu Arg Ile Val Arg Ser Asp Trp Asn Gly Thr Glu
        755             760             765
Glu Ser Met Gln Thr Phe Gly Leu Tyr Asp Cys Glu Lys Cys Lys Trp
770             775             780
Leu Leu Leu Pro Ala Glu Lys Lys His Ala Trp Ala Val Val Leu Ala
785             790             795             800
Ser Asp Asp Thr Thr Arg Ile Ile Phe Leu Ser Tyr Asp Glu Ser Gly
                805             810             815
Ser Pro Ile Ile Asp Lys Arg Asn Trp Lys Arg Phe Ala Val Cys Ser
        820             825             830
Glu Thr Lys Val Tyr Ser Val Ile Arg Ser Leu Glu Val Leu Asn Lys
        835             840             845
Glu Ala Ile Val Asp Pro Gly Val His Ile Thr Leu Val Asp Gly Val
850             855             860
Pro Gly Cys Gly Lys Thr Ala Glu Ile Ile Ala Arg Val Asn Trp Lys
865             870             875             880
Thr Asp Leu Val Leu Thr Pro Gly Arg Glu Ala Ala Met Ile Arg
                885             890             895
Arg Arg Ala Cys Ala Leu His Lys Ser Pro Val Ala Thr Ser Asp Asn
        900             905             910
Val Arg Thr Phe Asp Ser Phe Val Met Asn Lys Lys Ile Phe Lys Phe
        915             920             925
Asp Ala Val Tyr Val Asp Glu Gly Leu Met Val His Thr Gly Leu Leu
930             935             940
Asn Phe Ala Leu Lys Ile Ser Gly Cys Lys Lys Ala Phe Val Phe Gly
945             950             955             960
Asp Ala Lys Gln Ile Pro Phe Ile Asn Arg Val Met Asn Phe Asp Tyr
                965             970             975
Pro Lys Glu Leu Arg Thr Leu Ile Val Asp Asn Val Glu Arg Arg Tyr
        980             985             990
Val Thr His Arg Cys Pro Arg Asp Val Thr Ser Phe Leu Asn Thr Ile
        995             1000            1005
Tyr Lys Ala Ala Val Ala Thr Thr Ser Pro Val Val His Ser Val
        1010            1015            1020
Lys Ala Ile Lys Val Ser Gly Ala Gly Ile Leu Arg Pro Glu Leu
```

-continued

```
            1025                1030                1035

Thr Lys Ile Lys Gly Lys Ile Ile Thr Phe Thr Gln Ser Asp Lys
        1040                1045                1050

Gln Ser Leu Ile Lys Ser Gly Tyr Asn Asp Val Asn Thr Val His
        1055                1060                1065

Glu Ile Gln Gly Glu Thr Phe Glu Glu Thr Ala Val Val Arg Ala
        1070                1075                1080

Thr Pro Thr Pro Ile Gly Leu Ile Val Arg Asp Ser Pro His Val
        1085                1090                1095

Leu Val Ala Leu Thr Arg His Thr Lys Ala Met Val Tyr Tyr Thr
        1100                1105                1110

Val Val Phe Asp Ala Val Thr Ser Ile Ile Ala Asp Val Glu Lys
        1115                1120                1125

Val Asp Gln Ser Ile Leu Thr Met Phe Ala Thr Thr Val Pro Thr
        1130                1135                1140

Lys

<210> SEQ ID NO 55
<211> LENGTH: 1648
<212> TYPE: PRT
<213> ORGANISM: Cucumber green mottle mosaic virus
<220> FEATURE:
<221> NAME/KEY: misc_feature
<222> LOCATION: (1145)..(1145)
<223> OTHER INFORMATION: Xaa can be any naturally occurring amino acid

<400> SEQUENCE: 55

Met Ala Asn Ile Asn Glu Gln Ile Asn Asn Gln Arg Asp Ala Ala Ala
1               5                   10                  15

Ser Gly Arg Asn Asn Leu Val Ser Gln Leu Ala Ser Lys Arg Val Tyr
            20                  25                  30

Asp Glu Ala Val Arg Ser Leu Asp His Gln Asp Arg Arg Pro Lys Met
        35                  40                  45

Asn Phe Ser Arg Val Val Ser Thr Glu His Thr Arg Leu Val Thr Asp
    50                  55                  60

Ala Tyr Pro Glu Phe Ser Ile Ser Phe Thr Ala Thr Lys Asn Ser Val
65                  70                  75                  80

His Ser Leu Ala Gly Gly Leu Arg Leu Leu Glu Leu Glu Tyr Met Met
                85                  90                  95

Met Gln Val Pro Tyr Gly Ser Pro Cys Tyr Asp Ile Gly Gly Asn Tyr
            100                 105                 110

Thr Gln His Leu Phe Lys Gly Arg Ser Tyr Val His Cys Cys Asn Pro
        115                 120                 125

Cys Leu Asp Leu Lys Asp Val Ala Arg Asn Val Met Tyr Asn Asp Met
    130                 135                 140

Val Thr Gln His Val Gln Arg His Lys Gly Ser Gly Gly Cys Arg Pro
145                 150                 155                 160

Leu Pro Thr Phe Gln Ile Asp Ala Phe Arg Arg Tyr Asp Asn Ser Pro
                165                 170                 175

Cys Ala Val Thr Cys Ser Asp Val Phe Gln Glu Cys Ser Tyr Asp Phe
            180                 185                 190

Gly Ser Gly Arg Asp Asn His Ala Val Ser Leu His Ser Ile Tyr Asp
        195                 200                 205

Ile Pro Tyr Ser Ser Ile Gly Pro Ala Leu His Arg Lys Asn Val Arg
    210                 215                 220
```

```
Val Cys Tyr Ala Ala Phe His Phe Ser Glu Ala Leu Leu Gly Ser
225                 230                 235                 240

Pro Val Gly Asn Leu Asn Ser Ile Gly Ala Gln Phe Arg Val Asp Gly
                245                 250                 255

Asp Asp Val His Phe Leu Phe Ser Glu Glu Ser Thr Leu His Tyr Thr
            260                 265                 270

His Ser Leu Glu Asn Ile Lys Leu Ile Val Met Arg Thr Tyr Phe Pro
        275                 280                 285

Ala Asp Asp Arg Tyr Val Tyr Ile Lys Glu Phe Met Val Lys Arg Val
290                 295                 300

Asp Thr Phe Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
                325                 330                 335

Asn Thr Pro Pro Ile Phe Gln Asp Lys Ala Thr Phe Ser Val Trp Phe
                340                 345                 350

Pro Glu Ala Lys Arg Lys Val Leu Ile Pro Lys Phe Glu Leu Ser Arg
            355                 360                 365

Phe Leu Ser Gly Asn Val Lys Ile Ser Arg Met Leu Val Asp Ala Asp
370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
                405                 410                 415

Val Ile Val Asn Gly Val Ser Val Lys Ser Glu Trp Asn Val Pro Val
                420                 425                 430

Asp Gln Leu Thr Asp Ile Ser Phe Ser Ile Phe Leu Leu Val Lys Val
            435                 440                 445

Arg Lys Val Gln Ile Glu Leu Met Ser Asp Lys Val Val Ile Glu Ala
450                 455                 460

Arg Gly Leu Leu Arg Arg Phe Ala Asp Ser Leu Lys Ser Ala Val Glu
465                 470                 475                 480

Gly Leu Gly Asp Cys Val Tyr Asp Ala Leu Val Gln Thr Gly Trp Phe
                485                 490                 495

Asp Thr Ser Ser Asp Glu Leu Lys Val Leu Leu Pro Glu Pro Phe Met
            500                 505                 510

Thr Phe Ser Asp Tyr Leu Glu Gly Met Tyr Glu Ala Asp Ala Lys Ile
        515                 520                 525

Glu Arg Glu Ser Val Ser Glu Leu Leu Ala Ser Gly Asp Asp Leu Phe
530                 535                 540

Lys Lys Ile Asp Glu Ile Arg Asn Asn Tyr Ser Gly Val Glu Phe Asp
545                 550                 555                 560

Val Glu Lys Phe Gln Glu Phe Cys Lys Glu Leu Asn Val Asn Pro Met
                565                 570                 575

Leu Ile Gly His Val Ile Glu Ala Ile Phe Ser Gln Lys Ala Gly Val
                580                 585                 590

Thr Val Thr Gly Leu Gly Thr Leu Ser Pro Glu Met Gly Ala Ser Val
                595                 600                 605

Ala Leu Ser Asn Thr Ser Val Asp Thr Cys Glu Asp Met Asp Val Thr
                610                 615                 620

Glu Asp Met Glu Asp Ile Val Leu Met Ala Asp Lys Ser His Ser Tyr
625                 630                 635                 640

Met Ser Pro Glu Met Ala Arg Trp Ala Asp Val Lys Tyr Asp Asn Asn
```

-continued

```
                645                 650                 655
Lys Gly Gly Leu Val Glu Tyr Lys Val Gly Thr Ser Met Thr Leu Pro
                    660                 665                 670

Ala Thr Trp Ala Glu Lys Gly Lys Ala Val Leu Pro Leu Ser Gly Ile
                675                 680                 685

Cys Val Arg Lys Pro Gln Phe Ser Lys Pro Leu Asp Glu Glu Asp Asp
            690                 695                 700

Leu Arg Leu Ser Asn Met Asn Phe Phe Lys Val Ser Asp Leu Lys Leu
705                 710                 715                 720

Lys Lys Thr Ile Thr Pro Val Val Tyr Thr Gly Thr Ile Arg Glu Arg
                725                 730                 735

Gln Met Lys Asn Tyr Ile Asp Tyr Leu Ser Ala Ser Leu Gly Ser Thr
                740                 745                 750

Leu Gly Asn Leu Glu Arg Ile Val Arg Ser Asp Trp Asn Gly Thr Glu
                755                 760                 765

Glu Ser Met Gln Thr Phe Gly Leu Tyr Asp Cys Glu Lys Cys Lys Trp
770                 775                 780

Leu Leu Leu Pro Ala Glu Lys Lys His Ala Trp Ala Val Val Leu Ala
785                 790                 795                 800

Ser Asp Asp Thr Thr Arg Ile Ile Phe Leu Ser Tyr Asp Glu Ser Gly
                805                 810                 815

Ser Pro Ile Ile Asp Lys Arg Asn Trp Lys Arg Phe Ala Val Cys Ser
                820                 825                 830

Glu Thr Lys Val Tyr Ser Val Ile Arg Ser Leu Glu Val Leu Asn Lys
                835                 840                 845

Glu Ala Ile Val Asp Pro Gly Val His Ile Thr Leu Val Asp Gly Val
850                 855                 860

Pro Gly Cys Gly Lys Thr Ala Glu Ile Ile Ala Arg Val Asn Trp Lys
865                 870                 875                 880

Thr Asp Leu Val Leu Thr Pro Gly Arg Glu Ala Ala Met Ile Arg
                885                 890                 895

Arg Arg Ala Cys Ala Leu His Lys Ser Pro Val Ala Thr Ser Asp Asn
                900                 905                 910

Val Arg Thr Phe Asp Ser Phe Val Met Asn Lys Lys Ile Phe Lys Phe
                915                 920                 925

Asp Ala Val Tyr Val Asp Glu Gly Leu Met Val His Thr Gly Leu Leu
                930                 935                 940

Asn Phe Ala Leu Lys Ile Ser Gly Cys Lys Lys Ala Phe Val Phe Gly
945                 950                 955                 960

Asp Ala Lys Gln Ile Pro Phe Ile Asn Arg Val Met Asn Phe Asp Tyr
                965                 970                 975

Pro Lys Glu Leu Arg Thr Leu Ile Val Asp Asn Val Glu Arg Arg Tyr
                980                 985                 990

Val Thr His Arg Cys Pro Arg Asp Val Thr Ser Phe Leu Asn Thr Ile
                995                 1000                1005

Tyr Lys Ala Ala Val Ala Thr Thr Ser Pro Val Val His Ser Val
            1010                1015                1020

Lys Ala Ile Lys Val Ser Gly Ala Gly Ile Leu Arg Pro Glu Leu
            1025                1030                1035

Thr Lys Ile Lys Gly Lys Ile Ile Thr Phe Thr Gln Ser Asp Lys
            1040                1045                1050

Gln Ser Leu Ile Lys Ser Gly Tyr Asn Asp Val Asn Thr Val His
            1055                1060                1065
```

```
Glu Ile Gln Gly Glu Thr Phe Glu Thr Ala Val Val Arg Ala
    1070                1075                1080

Thr Pro Thr Pro Ile Gly Leu Ile Val Arg Asp Ser Pro His Val
    1085                1090                1095

Leu Val Ala Leu Thr Arg His Thr Lys Ala Met Val Tyr Tyr Thr
    1100                1105                1110

Val Val Phe Asp Ala Val Thr Ser Ile Ile Ala Asp Val Glu Lys
    1115                1120                1125

Val Asp Gln Ser Ile Leu Thr Met Phe Ala Thr Thr Val Pro Thr
    1130                1135                1140

Lys Xaa Gln Leu Met Gln Asn Ser Leu Tyr Val His Arg Asn Ile
    1145                1150                1155

Phe Leu Pro Val Ser Lys Thr Gly Phe Tyr Thr Asp Met Gln Glu
    1160                1165                1170

Phe Tyr Asp Arg Cys Leu Pro Gly Asn Ser Phe Val Leu Asn Asp
    1175                1180                1185

Phe Asp Ala Val Thr Met Arg Leu Arg Asp Asn Glu Phe Asn Leu
    1190                1195                1200

Gln Pro Cys Arg Leu Thr Leu Ser Asn Leu Asp Pro Val Pro Ala
    1205                1210                1215

Leu Val Lys Ser Glu Ala Gln Asn Phe Leu Ile Pro Val Leu Arg
    1220                1225                1230

Thr Ala Cys Glu Arg Pro Arg Ile Pro Gly Leu Leu Glu Asn Leu
    1235                1240                1245

Val Ala Met Ile Lys Arg Asn Met Asn Thr Pro Asp Leu Ala Gly
    1250                1255                1260

Thr Val Asp Ile Thr Asn Met Ser Ile Ser Ile Val Asp Asn Phe
    1265                1270                1275

Phe Ser Ser Phe Val Arg Asp Glu Val Leu Leu Asp His Leu Asp
    1280                1285                1290

Cys Val Arg Ala Ser Ser Ile Gln Ser Phe Ser Asp Trp Phe Ser
    1295                1300                1305

Cys Gln Pro Thr Ser Ala Val Gly Gln Leu Ala Asn Phe Asn Phe
    1310                1315                1320

Ile Asp Leu Pro Ala Phe Asp Thr Tyr Met His Met Ile Lys Arg
    1325                1330                1335

Gln Pro Lys Ser Arg Leu Asp Thr Ser Ile Gln Ser Glu Tyr Pro
    1340                1345                1350

Ala Leu Gln Thr Ile Val Tyr His Pro Lys Val Val Asn Ala Val
    1355                1360                1365

Phe Gly Pro Val Phe Lys Tyr Leu Thr Thr Lys Phe Leu Ser Met
    1370                1375                1380

Val Asp Ser Ser Lys Phe Phe Tyr Thr Arg Lys Lys Pro Glu
    1385                1390                1395

Asp Leu Gln Glu Phe Phe Ser Asp Leu Ser Ser His Ser Asp Tyr
    1400                1405                1410

Glu Ile Leu Glu Leu Asp Val Ser Lys Tyr Asp Lys Ser Gln Ser
    1415                1420                1425

Asp Phe His Phe Ser Ile Glu Met Ala Ile Trp Glu Lys Leu Gly
    1430                1435                1440

Leu Asp Asp Ile Leu Ala Trp Met Trp Ser Met Gly His Lys Arg
    1445                1450                1455
```

| | | | | | | | | | | |
|---|---|---|---|---|---|---|---|---|---|---|
| Thr | Ile | Leu | Gln | Asp | Phe | Gln | Ala | Gly | Ile | Lys | Thr | Leu | Ile | Tyr |
| | 1460 | | | | 1465 | | | | 1470 | |

Thr Ile Leu Gln Asp Phe Gln Ala Gly Ile Lys Thr Leu Ile Tyr
     1460                1465                1470

Tyr Gln Arg Lys Ser Gly Asp Val Thr Thr Phe Ile Gly Asn Thr
     1475                1480                1485

Phe Ile Ile Ala Ala Cys Val Ala Ser Met Leu Pro Leu Asp Lys
     1490                1495                1500

Cys Phe Lys Ala Ser Phe Cys Gly Asp Asp Ser Leu Ile Tyr Leu
     1505                1510                1515

Pro Lys Gly Leu Glu Tyr Pro Asp Ile Gln Ala Thr Ala Asn Leu
     1520                1525                1530

Val Trp Asn Phe Glu Ala Lys Leu Phe Arg Lys Lys Tyr Gly Tyr
     1535                1540                1545

Phe Cys Gly Lys Tyr Ile Ile His His Ala Asn Gly Cys Ile Val
     1550                1555                1560

Tyr Pro Asp Pro Leu Lys Leu Ile Ser Lys Leu Gly Asn Lys Ser
     1565                1570                1575

Leu Val Gly Tyr Glu His Val Glu Glu Phe Arg Ile Ser Leu Leu
     1580                1585                1590

Asp Val Ala His Ser Leu Phe Asn Gly Ala Tyr Phe His Leu Leu
     1595                1600                1605

Asp Asp Ala Ile His Glu Leu Phe Pro Asn Ala Gly Gly Cys Ser
     1610                1615                1620

Phe Val Ile Asn Cys Leu Cys Lys Tyr Leu Ser Asp Lys Arg Leu
     1625                1630                1635

Phe Arg Ser Leu Tyr Ile Asp Val Ser Lys
     1640                1645

<210> SEQ ID NO 56
<211> LENGTH: 47
<212> TYPE: DNA
<213> ORGANISM: Artificial Sequence
<220> FEATURE:
<223> OTHER INFORMATION: Primer

<400> SEQUENCE: 56
ctatataaag actacggaaa aggtgcttat cactcaaata cttgcac         47

<210> SEQ ID NO 57
<211> LENGTH: 47
<212> TYPE: DNA
<213> ORGANISM: Artificial Sequence
<220> FEATURE:
<223> OTHER INFORMATION: Primer

<400> SEQUENCE: 57
gtgcaagtat ttgagtgata agcaccttt ccgtagtctt tatatag           47

<210> SEQ ID NO 58
<211> LENGTH: 6422
<212> TYPE: DNA
<213> ORGANISM: Cucumber green mottle mosaic virus

<400> SEQUENCE: 58 gttttaattt

```
ttgtaactga tgcgtatccg gagttttcga ttagctttac cgccaccaag aactctgtac    300
actcccttgc gggtggtctg aggctccttg aactggaata tatgatgatg caagtgccct    360
acggctcacc ttgttatgat atcggcggta actatacgca gcacttgttc aaaggtagat    420
catatgtgca ttgctgcaat ccgtgcctgg atcttaaaga tgttgcgagg aacgtgatgt    480
ataacgatat ggtcacacaa catgtacaga ggcacaaggg atctggcggg tgcagacctc    540
ttccaacttt tcagatagat gcattcagga ggtacgataa ttctccctgt gcggtcacct    600
gttcagacgt tttccaagag tgttcctatg attttgggag cggtagggat aatcatgcag    660
tctcgctgca ttcaatctac gatatcccct attcttcgat cggacctgct cttcatagga    720
agaacgtgcg agtttgttat gcagcctttc acttctcgga ggcattgctt ttaggttcac    780
ctgtaggtaa tttaaatagt attggggctc agtttagggt cgatggtgat gatgtgcatt    840
ttctttttag tgaagagtct actttgcatt atactcatag tttagaaaat atcaaattaa    900
ttgtgatgcg tacttatttt cctgctgatg ataggtacgt gtatattaag gagtttatgg    960
tcaagcgtgt ggatactttc ttctttaggt tggtcagagc agacacacat atgcttcata   1020
aatctgtggg gcactattca aaatcgaaat ctgagtactt tgcgctgaat accccctccga   1080 tcttccaaga caaagccacg ttttctgtgt ggtttcctga ggcgaagcgt aaggtgttga   1140
tacccaagtt tgaactttca agattccttt ctgggaatgt gaaaatctct aggatgcttg   1200
tcgatgctga tttcgtccat accattatta atcacattag cacgtatgat aataaggcct   1260
tagtgtggaa gaatgttcag tcctttgtgg aatctatacg ctcaagagta attgtaaacg   1320
gagtttcggt gaaatctgaa tggaacgtac cggttgatca gctcactgat atctcgttct   1380
cgatattcct tctcgtgaag gttaggaagg tacagatcga gttaatgtct gataaagttg   1440
taatcgaggc gagggggcttg ctccggaggt tcgcagacag tcttaaatcc gccgtagaag   1500
gactaggtga ttgcgtctat gatgctctag ttcaaaccgg ctggtttgat acctctagcg   1560
acgaactgaa agttttgcta cctgaaccgt ttatgacctt tcggattat cttgaaggga   1620 tgtacgaggc agatgcaaag atcgagagag agagtgtctc tgagttgctc gcttccggtg   1680
acgatttgtt caagaaaatc gatgagataa gaaacaatta cagtggagtc gaatttgatg   1740
tagagaaatt ccaggaattt tgcaaggaac tgaatgttaa tcctatgcta attggccatg   1800
ttatcgaagc tatttttttcg cagaaagctg gggtgacagt aacgggtctg ggtaccctct   1860
ctcctgagat gggtgcttct gttgcgttat ccaataccte tgtagataca tgtgaagata   1920
tggatgtaac tgaagatatg gaggatatag tgttgatggc ggacaagagt cattcttaca   1980
tgtccccaga aatggcgaga tgggctgatg taaaatacga caacaataaa gggggcctgg   2040
tcgaatacaa agtcggaacc tcgatgactt tacctgccac ctgggcagag aagggtaagg   2100
ctgtcttacc gttgtcgggg atctgtgtga ggaaacccca attttcgaag ccgcttgatg   2160
aggaagacga cttgaggtta tcaaacatga atttctttaa ggtgagcgat ctgaagttga   2220
agaaaactat cactccagtt gtttacactg ggaccattcg agagaggcaa atgaagaatt   2280
atattgatta cttatcggcc tctcttggtt ctacgctggg taatctggag agaattgtgc   2340
ggagtgattg gaacggtacc gaggagagta tgcaaacgtt cggttgtat gactgcgaaa   2400 agtgcaagtg gttactgtta ccagccgaaa agaagcacgc atgggctgtg gttctggcaa   2460
gtgatgatac cactcgcata atcttcctct catatgacga atctggttct cccataattg   2520
ataagagaaa ctggaagcga tttgctgttt gctctgagac caaagtctat agcgtaattc   2580
gtagtttaga ggtactaaat aaggaagcaa tagtcgaccc cggggttcat ataacattag   2640
```

```
ttgacggagt gccgggttgt ggaaagaccg ccgaaattat agcgagggtc aattggaaaa    2700
ccgatctagt attgactccc gggagggagg cggctgctat gattaggcgg agggcctgcg    2760
ccctgcacaa gtcacctgtg gcaaccagtg acaacgttag aactttcgat tcttttgtga    2820
tgaataagaa aatcttcaag tttgacgctg tctatgttga cgagggtctg atggtccata    2880
cgggtttact taattttgcg ttgaagatct caggttgtaa aaaggccttc gtctttggtg    2940
atgctaagca aatcccgttt ataaacagag tcatgaattt tgattatcct aaggagttaa    3000
gaactttaat agtcgataat gtagagcgta ggtatgttac ccataggtgt cctagagatg    3060
tcactagttt tcttaatact atttacaaag ccgctgtcgc tactactagt ccggttgtac    3120
attctgtgaa ggcgattaaa gtgtcagggg ccggtattct gaggcccgag ttgacgaaga    3180
tcaaaggaaa gataataacg tttactcaat ctgataagca gtccttgatc aagagtgggt    3240
acaatgacgt gaacactgtg catgaaattc agggagaaac ctttgaagag acggcggttg    3300
tgcgtgccac cccgactccg ataggtttaa ttgcccgtga ttcaccacat gtactagtgg    3360
ccttaacgag gcacactaag gcaatggtgt attatactgt tgtgttcgat gcagttacaa    3420
gtataatagc ggatgtggaa aaggtcgacc agtcgatctt gactatgttt gctaccactg    3480
tgcctaccaa atagcaatta atgcagaact cactgtatgt ccatcgtaat attttcctcc    3540
ctgttagtaa aacgggggttt tatacagaca tgcaggagtt ctatgataga tgccttcctg    3600
ggaattcctt cgtgctgaat gatttcgatg ccgtaaccat gcggttgagg gacaacgaat    3660
ttaacctaca accttgtagg ctaaccttaa gtaatttaga tccagtaccc gctttggtta    3720
agagtgaagc gcagaatttt ctgattcccg ttttgcgtac ggcctgtgaa aggccgcgca    3780
ttccaggtct ccttgaaaat cttgtagcta tgataaagag gaatatgaat actcctgatc    3840
tagctgggac tgtggatata actaatatgt cgatttctat agtagataac ttcttttctt    3900
cttttgttag agacgaggtt ttgcttgatc atttagattg tgttagggct agttccattc    3960
aaagtttttc tgattggttt tcgtgtcagc caacctcggc ggttggtcaa ttagctaatt    4020
tcaatttcat agatttgcct gcctttgata cttatatgca catgattaag cggcagccca    4080
agagtcggtt ggatacttcg attcagtctg aatatccggc cttgcaaact attgtttatc    4140
accctaaagt ggtaaatgca gttttcggtc cggtttttaa gtatttgacc accaagtttc    4200
ttagcatggt agatagttct aagttttttct tttacactag gaaaaaacca gaagatctgc    4260
aggaattttt ctcagatctc tcttcccatt ctgattatga gattcttgag ctggatgttt    4320
ctaaatatga caagtcacaa tccgatttcc atttctctat tgagatggca atttgggaaa    4380
aattggggct ggacgatatt ttggcttgga tgtggtctat gggtcacaag agaactatac    4440
tgcaagattt ccaagccggg ataaagacgc tcatttacta tcaacggaag tctggtgatg    4500
taactacttt cataggtaat acctttatta tcgcagcgtg tgtagctagt atgttgccgt    4560
tagacaagtg ttttaaagct agttttttgtg gtgatgattc gctgatctac cttcctaagg    4620
gtttggagta tcctgatata caggctactg ccaacttggt ttggaatttt gaggcgaaac    4680
ttttccgaaa gaagtatggt tacttctgtg ggaagtatat aattcaccat gccaacggct    4740
gtattgttta ccctgaccct ttaaaattaa ttagtaaatt aggtaataag agtcttgtag    4800
ggtatgagca tgttgaggag tttcgtatat ctctcctcga cgtcgctcat agtttgttta    4860
atggtgctta tttccattta ctcgacgatg caatccacga attatttcct aacgctgggg    4920
gttgcagttt tgtaattaat tgtttgtgca agtatttgag tgataagcac cttttccgta    4980
```

```
gtctttatat agatgtctct aagtaaggtg tcggtcgaga actcattgaa acccgagaag   5040
tttgttaaaa tctcttgggt cgataagttg ctccctaact attttccat tcttaagtat    5100 ttatctataa ctgactttag cgtagttaaa gctcagagct atgaatccct cgtgcctgtc   5160
aagttgttgc gtggtgttga tcttacaaaa cacctttatg tcacattgtt gggcgttgtg   5220
gtttctggtg tatggaacgt accggaatcc tgtaggggtg gtgctactgt tgctctggtt   5280
gacacaagga tgcattctgt tgcagaggga actatatgca aattttcagc tcccgccacc   5340
gtccgcgaat tctctgttag gttcatacct aactattctg tcgtggctgc ggatgccctt   5400
cgcgatcctt ggtctttatt tgtgagactc tctaatgtag ggattaaaga tggtttccat   5460
cctttgacct tagaggtcgc ttgtttagtc gctacaacta actctattat caaaaagggt   5520
cttagagctt ctgtagtcga gtctgtcgtc tcttccgatc agtccattgt cctagattct   5580
ttatccgaga aagttgaacc tttctttgat aaagttccta tttcggcggc tgtgatggca   5640
agagacccca gttataggtc taggtcgcag tctgtcggtg gtcgtggtaa gcggcattct   5700
aaacctccaa atcggaggtt ggactctgct tctgaagagt ccagtctgt ttctttcgaa    5760 gatggcttac aatccgatca cacctagcaa acttattgcg tttagtgctt cttatgttcc   5820
cgtcaggact ttacttaatt ttctagttgc ttcacaaggt accgccttcc agactcaagc   5880
gggaagagat tctttccgcg agtccctgtc tgcgttaccc tcgtctgtcg tagatattaa   5940
ttctaggttc ccaaatgcgg ttttttacgc ttttcctcaac ggtcctgtgt tgaggcctat   6000
cttcgtttcg cttcttagct ctacggatac gcgtaatagg gtcattgagg ttgtagatcc   6060
tagcaatcct acgactgctg agtcgcttaa cgctgtaaag cgtactgatg acgcatctac   6120
ggccgctagg gctgaaatag ataattaat agagtctatt tctaagggtt ttgatgttta   6180
tgatagggct tcatttgaag ccgcgttttc ggtagtctgg tcagaggcta ccacctcgaa   6240
agcttagctt cgagggtctt ctgatggtgg tgcacaccaa agtgcatagt gctttcccgt   6300
tcacttaaat cgaacggttt gctcattggt ttgcggaaac ctctcacgtg tggcgttgaa   6360
gtttctatgg gcagtaattc tgcaaggggt tcgaatcccc cctttccccg ggtaggggcc   6420
ca                                                                  6422
```

<210> SEQ ID NO 59
<211> LENGTH: 1648
<212> TYPE: PRT
<213> ORGANISM: Cucumber green mottle mosaic virus
<220> FEATURE:
<221> NAME/KEY: misc_feature
<222> LOCATION: (1145)..(1145)
<223> OTHER INFORMATION: Xaa can be any naturally occurring amino acid

<400> SEQUENCE: 59

```
Met Ala Asn Ile Asn Glu Gln Ile Asn Asn Gln Arg Asp Ala Ala Ala
1               5                   10                  15

Ser Gly Arg Asn Asn Leu Val Ser Gln Leu Ala Ser Lys Arg Val Tyr
            20                  25                  30

Asp Glu Ala Val Arg Ser Leu Asp His Gln Asp Arg Arg Pro Lys Met
        35                  40                  45

Asn Phe Ser Arg Val Val Ser Thr Glu His Thr Arg Leu Val Thr Asp
    50                  55                  60

Ala Tyr Pro Glu Phe Ser Ile Ser Phe Thr Ala Thr Lys Asn Ser Val
65                  70                  75                  80

His Ser Leu Ala Gly Gly Leu Arg Leu Leu Glu Leu Glu Tyr Met Met
                85                  90                  95
```

```
Met Gln Val Pro Tyr Gly Ser Pro Cys Tyr Asp Ile Gly Gly Asn Tyr
                100                 105                 110

Thr Gln His Leu Phe Lys Gly Arg Ser Tyr Val His Cys Cys Asn Pro
                115                 120                 125

Cys Leu Asp Leu Lys Asp Val Ala Arg Asn Val Met Tyr Asn Asp Met
        130                 135                 140

Val Thr Gln His Val Gln Arg His Lys Gly Ser Gly Gly Cys Arg Pro
145                 150                 155                 160

Leu Pro Thr Phe Gln Ile Asp Ala Phe Arg Arg Tyr Asp Asn Ser Pro
                165                 170                 175

Cys Ala Val Thr Cys Ser Asp Val Phe Gln Glu Cys Ser Tyr Asp Phe
        180                 185                 190

Gly Ser Gly Arg Asp Asn His Ala Val Ser Leu His Ser Ile Tyr Asp
        195                 200                 205

Ile Pro Tyr Ser Ser Ile Gly Pro Ala Leu His Arg Lys Asn Val Arg
        210                 215                 220

Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
                245                 250                 255

Asp Asp Val His Phe Leu Phe Ser Glu Glu Ser Thr Leu His Tyr Thr
            260                 265                 270

His Ser Leu Glu Asn Ile Lys Leu Ile Val Met Arg Thr Tyr Phe Pro
        275                 280                 285

Ala Asp Asp Arg Tyr Val Tyr Ile Lys Glu Phe Met Val Lys Arg Val
        290                 295                 300

Asp Thr Phe Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
                325                 330                 335

Asn Thr Pro Pro Ile Phe Gln Asp Lys Ala Thr Phe Ser Val Trp Phe
            340                 345                 350

Pro Glu Ala Lys Arg Lys Val Leu Ile Pro Lys Phe Glu Leu Ser Arg
        355                 360                 365

Phe Leu Ser Gly Asn Val Lys Ile Ser Arg Met Leu Val Asp Ala Asp
        370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
                405                 410                 415

Val Ile Val Asn Gly Val Ser Val Lys Ser Glu Trp Asn Val Pro Val
            420                 425                 430

Asp Gln Leu Thr Asp Ile Ser Phe Ser Ile Phe Leu Leu Val Lys Val
        435                 440                 445

Arg Lys Val Gln Ile Glu Leu Met Ser Asp Lys Val Val Ile Glu Ala
        450                 455                 460

Arg Gly Leu Leu Arg Arg Phe Ala Asp Ser Leu Lys Ser Ala Val Glu
465                 470                 475                 480

Gly Leu Gly Asp Cys Val Tyr Asp Ala Leu Val Gln Thr Gly Trp Phe
            485                 490                 495

Asp Thr Ser Ser Asp Glu Leu Lys Val Leu Leu Pro Glu Pro Phe Met
        500                 505                 510
```

-continued

```
Thr Phe Ser Asp Tyr Leu Glu Gly Met Tyr Glu Ala Asp Ala Lys Ile
        515                 520                 525

Glu Arg Glu Ser Val Ser Glu Leu Leu Ala Ser Gly Asp Asp Leu Phe
530                 535                 540

Lys Lys Ile Asp Glu Ile Arg Asn Asn Tyr Ser Gly Val Glu Phe Asp
545                 550                 555                 560

Val Glu Lys Phe Gln Glu Phe Cys Lys Glu Leu Asn Val Asn Pro Met
                565                 570                 575

Leu Ile Gly His Val Ile Glu Ala Ile Phe Ser Gln Lys Ala Gly Val
                580                 585                 590

Thr Val Thr Gly Leu Gly Thr Leu Ser Pro Glu Met Gly Ala Ser Val
            595                 600                 605

Ala Leu Ser Asn Thr Ser Val Asp Thr Cys Glu Asp Met Asp Val Thr
        610                 615                 620

Glu Asp Met Glu Asp Ile Val Leu Met Ala Asp Lys Ser His Ser Tyr
625                 630                 635                 640

Met Ser Pro Glu Met Ala Arg Trp Ala Asp Val Lys Tyr Asp Asn Asn
                645                 650                 655

Lys Gly Gly Leu Val Glu Tyr Lys Val Gly Thr Ser Met Thr Leu Pro
                660                 665                 670

Ala Thr Trp Ala Glu Lys Gly Lys Ala Val Leu Pro Leu Ser Gly Ile
            675                 680                 685

Cys Val Arg Lys Pro Gln Phe Ser Lys Pro Leu Asp Glu Glu Asp Asp
        690                 695                 700

Leu Arg Leu Ser Asn Met Asn Phe Phe Lys Val Ser Asp Leu Lys Leu
705                 710                 715                 720

Lys Lys Thr Ile Thr Pro Val Val Tyr Thr Gly Thr Ile Arg Glu Arg
                725                 730                 735

Gln Met Lys Asn Tyr Ile Asp Tyr Leu Ser Ala Ser Leu Gly Ser Thr
                740                 745                 750

Leu Gly Asn Leu Glu Arg Ile Val Arg Ser Asp Trp Asn Gly Thr Glu
            755                 760                 765

Glu Ser Met Gln Thr Phe Gly Leu Tyr Asp Cys Glu Lys Cys Lys Trp
770                 775                 780

Leu Leu Leu Pro Ala Glu Lys Lys His Ala Trp Ala Val Val Leu Ala
785                 790                 795                 800

Ser Asp Asp Thr Thr Arg Ile Ile Phe Leu Ser Tyr Asp Glu Ser Gly
                805                 810                 815

Ser Pro Ile Ile Asp Lys Arg Asn Trp Lys Arg Phe Ala Val Cys Ser
            820                 825                 830

Glu Thr Lys Val Tyr Ser Val Ile Arg Ser Leu Glu Val Leu Asn Lys
        835                 840                 845

Glu Ala Ile Val Asp Pro Gly Val His Ile Thr Leu Val Asp Gly Val
850                 855                 860

Pro Gly Cys Gly Lys Thr Ala Glu Ile Ile Ala Arg Val Asn Trp Lys
865                 870                 875                 880

Thr Asp Leu Val Leu Thr Pro Gly Arg Glu Ala Ala Ala Met Ile Arg
                885                 890                 895

Arg Arg Ala Cys Ala Leu His Lys Ser Pro Val Ala Thr Ser Asp Asn
                900                 905                 910

Val Arg Thr Phe Asp Ser Phe Val Met Asn Lys Lys Ile Phe Lys Phe
            915                 920                 925

Asp Ala Val Tyr Val Asp Glu Gly Leu Met Val His Thr Gly Leu Leu
```

```
                 930                 935                 940
Asn Phe Ala Leu Lys Ile Ser Gly Cys Lys Lys Ala Phe Val Phe Gly
945                 950                 955                 960

Asp Ala Lys Gln Ile Pro Phe Ile Asn Arg Val Met Asn Phe Asp Tyr
                965                 970                 975

Pro Lys Glu Leu Arg Thr Leu Ile Val Asp Asn Val Glu Arg Arg Tyr
                980                 985                 990

Val Thr His Arg Cys Pro Arg Asp Val Thr Ser Phe Leu Asn Thr Ile
                995                1000                1005

Tyr Lys Ala Ala Val Ala Thr Thr Ser Pro Val Val His Ser Val
       1010                1015                1020

Lys Ala Ile Lys Val Ser Gly Ala Gly Ile Leu Arg Pro Glu Leu
       1025                1030                1035

Thr Lys Ile Lys Gly Lys Ile Ile Thr Phe Thr Gln Ser Asp Lys
       1040                1045                1050

Gln Ser Leu Ile Lys Ser Gly Tyr Asn Asp Val Asn Thr Val His
       1055                1060                1065

Glu Ile Gln Gly Glu Thr Phe Glu Glu Thr Ala Val Val Arg Ala
       1070                1075                1080

Thr Pro Thr Pro Ile Gly Leu Ile Ala Arg Asp Ser Pro His Val
       1085                1090                1095

Leu Val Ala Leu Thr Arg His Thr Lys Ala Met Val Tyr Tyr Thr
       1100                1105                1110

Val Val Phe Asp Ala Val Thr Ser Ile Ile Ala Asp Val Glu Lys
       1115                1120                1125

Val Asp Gln Ser Ile Leu Thr Met Phe Ala Thr Thr Val Pro Thr
       1130                1135                1140

Lys Xaa Gln Leu Met Gln Asn Ser Leu Tyr Val His Arg Asn Ile
       1145                1150                1155

Phe Leu Pro Val Ser Lys Thr Gly Phe Tyr Thr Asp Met Gln Glu
       1160                1165                1170

Phe Tyr Asp Arg Cys Leu Pro Gly Asn Ser Phe Val Leu Asn Asp
       1175                1180                1185

Phe Asp Ala Val Thr Met Arg Leu Arg Asp Asn Glu Phe Asn Leu
       1190                1195                1200

Gln Pro Cys Arg Leu Thr Leu Ser Asn Leu Asp Pro Val Pro Ala
       1205                1210                1215

Leu Val Lys Ser Glu Ala Gln Asn Phe Leu Ile Pro Val Leu Arg
       1220                1225                1230

Thr Ala Cys Glu Arg Pro Arg Ile Pro Gly Leu Leu Glu Asn Leu
       1235                1240                1245

Val Ala Met Ile Lys Arg Asn Met Asn Thr Pro Asp Leu Ala Gly
       1250                1255                1260

Thr Val Asp Ile Thr Asn Met Ser Ile Ser Ile Val Asp Asn Phe
       1265                1270                1275

Phe Ser Ser Phe Val Arg Asp Glu Val Leu Leu Asp His Leu Asp
       1280                1285                1290

Cys Val Arg Ala Ser Ser Ile Gln Ser Phe Ser Asp Trp Phe Ser
       1295                1300                1305

Cys Gln Pro Thr Ser Ala Val Gly Gln Leu Ala Asn Phe Asn Phe
       1310                1315                1320

Ile Asp Leu Pro Ala Phe Asp Thr Tyr Met His Met Ile Lys Arg
       1325                1330                1335
```

Gln Pro Lys Ser Arg Leu Asp Thr Ser Ile Gln Ser Glu Tyr Pro
1340                1345                1350

Ala Leu Gln Thr Ile Val Tyr His Pro Lys Val Val Asn Ala Val
1355                1360                1365

Phe Gly Pro Val Phe Lys Tyr Leu Thr Thr Lys Phe Leu Ser Met
1370                1375                1380

Val Asp Ser Ser Lys Phe Phe Phe Tyr Thr Arg Lys Lys Pro Glu
1385                1390                1395

Asp Leu Gln Glu Phe Phe Ser Asp Leu Ser Ser His Ser Asp Tyr
1400                1405                1410

Glu Ile Leu Glu Leu Asp Val Ser Lys Tyr Asp Lys Ser Gln Ser
1415                1420                1425

Asp Phe His Phe Ser Ile Glu Met Ala Ile Trp Glu Lys Leu Gly
1430                1435                1440

Leu Asp Asp Ile Leu Ala Trp Met Trp Ser Met Gly His Lys Arg
1445                1450                1455

Thr Ile Leu Gln Asp Phe Gln Ala Gly Ile Lys Thr Leu Ile Tyr
1460                1465                1470

Tyr Gln Arg Lys Ser Gly Asp Val Thr Thr Phe Ile Gly Asn Thr
1475                1480                1485

Phe Ile Ile Ala Ala Cys Val Ala Ser Met Leu Pro Leu Asp Lys
1490                1495                1500

Cys Phe Lys Ala Ser Phe Cys Gly Asp Asp Ser Leu Ile Tyr Leu
1505                1510                1515

Pro Lys Gly Leu Glu Tyr Pro Asp Ile Gln Ala Thr Ala Asn Leu
1520                1525                1530

Val Trp Asn Phe Glu Ala Lys Leu Phe Arg Lys Lys Tyr Gly Tyr
1535                1540                1545

Phe Cys Gly Lys Tyr Ile Ile His His Ala Asn Gly Cys Ile Val
1550                1555                1560

Tyr Pro Asp Pro Leu Lys Leu Ile Ser Lys Leu Gly Asn Lys Ser
1565                1570                1575

Leu Val Gly Tyr Glu His Val Glu Glu Phe Arg Ile Ser Leu Leu
1580                1585                1590

Asp Val Ala His Ser Leu Phe Asn Gly Ala Tyr Phe His Leu Leu
1595                1600                1605

Asp Asp Ala Ile His Glu Leu Phe Pro Asn Ala Gly Gly Cys Ser
1610                1615                1620

Phe Val Ile Asn Cys Leu Cys Lys Tyr Leu Ser Asp Lys His Leu
1625                1630                1635

Phe Arg Ser Leu Tyr Ile Asp Val Ser Lys
1640                1645

<210> SEQ ID NO 60
<211> LENGTH: 6422
<212> TYPE: DNA
<213> ORGANISM: Cucumber green mottle mosaic virus

<400> SEQUENCE: 60
gttttaattt ttaaaattaa acaaacaaca acaacaacaa caaacaattt aaaacaacaa      60
tggcaaacat taatgaacaa atcaacaacc aacgcgacgc cgcggccagc gggagaaaca     120
atctcgttag ccaattggcg tcaaaaaggg tgtatgacga ggctgttcgc tcgttggatc     180
atcaagacag acgcccaaaa atgaactttt ctcgtgtggt cagcacagag cacaccaggc     240

```
ttgtaactga tgcgtatccg gagttttcga ttagctttac cgccaccaag aactctgtac      300
actcccttgc gggtagtctg aggctccttg aactggaata tatgatgatg caagtgccct      360
acggctcacc ttgttatgat atcggcggta actatacgca gcacttgttc aaaggtagat      420
catatgtgca ttgctgcaat ccgtgcctgg atcttaaaga tgttgcgagg aacgtgatgt      480
ataacgatat ggtcacacaa catgtacaga ggcacaaggg atctggcggg tgcagacctc      540
ttccaacttt tcagatagat gcattcagga ggtacgataa ttctccctgt gcggtcacct      600
gttcagacgt tttccaagag tgttcctatg attttgggag cggtagggat aatcatgcag      660
tctcgctgca ttcaatctac gatatccctt attcttcgat cggacctgct cttcatagga      720
agaacgtgcg agtttgttat gcagcctttc acttctcgga ggcattgctt ttaggttcac      780
ctgtaggtaa tttaaatagt attggggctc agtttagggt cgatggtgat gatgtgcatt      840 ttcttttttag tgaagagtct actttgcatt atactcatag tttagaaaat atcaaattaa      900
ttgtgatgcg tacttatttt cctgctgatg ataggtacgt gtatattaag gagtttatgg      960
tcaagcgtgt ggatactttc ttctttaggt tggtcagagc agacacacat atgcttcata     1020
aatctgtggg gcactattca aaatcgaaat ctgagtactt tgcgctgaat acccctccga     1080
tcttccaaga caaagccacg ttttctgtgt ggtttcctga ggcgaagcgt aaggtgttga     1140
tacccaagtt tgaactttca agattccttt ctgggaatgt gaaaatctct aggatgcttg     1200
tcgatgctga tttcgtccat accattatta atcacattag cacgtatgat aataaggcct     1260
tagtgtggaa gaatgttcag tcctttgtgg aatctatacg ctcaagagta attgtaaacg     1320
gagtttcggt gaaatctgaa tggaacgtac cggttgatca gctcactgat atctcgttct     1380
cgatattcct tctcgtgaag gttaggaagg tacagatcga gttaatgtct gataaagttg     1440
taatcgaggc gagggggcttg ctccggaggt tcgcagacag tcttaaatcc gccgtaggag     1500
gactaggtga ttgcgtctat gatgctctag ttcaaaccgg ctggtttgat acctctagcg     1560
acgaactgaa agttttgcta cctgaaccgt ttatgacctt tcggattat cttgaaggga     1620 tgtacgaggc agatgcaaag atcgagagag agagtgtctt tgagttgctc gcttccggtg     1680
acgatttgtt caagaaaatc gatgagataa gaaacaatta cagtggagtc gaatttgatg     1740
tagagaaatt ccaggaattt tgcaaggaac tgaatgttaa tcctatgcta attggccatg     1800
ttatcgaagc tattttttcg cagaaagctg gggtgacagt aacgggtctg ggtaccctct     1860
ctcctgagat gggtgcttct gttgcgttat ccaatacctc tgtagataca tgtgaagata     1920
tggatgtaac tgaagatatg gaggatatag tgttgatggc ggacaagagt cattcttaca     1980
tgtccccaga aatggcgaga tgggctgatg taaaatacga caacaataaa ggggggctgg     2040
tcgaatacaa agtcggaacc tcgatgactt tacctgccac ctgggcagag aagggtaagg     2100
ctgtcttacc gttgtcgggg atctgtgtga ggaaacccca atttttcgaag ccgcttgatg     2160 aggaagacga cttgaggtta tcaaacatga atttctttaa ggtgagcgat ctgaagttga     2220
agaaaactat cactccagtt gtttacactg ggaccattcg agagaggcaa atgaagaatt     2280
atattgatta cttatcggcc tctcttggtt ctacgctggg taatctggag agaattgtgc     2340
ggagtgattg gaacggtacc gaggagagta tgcaaacgtt cggggttgtat gactgcgaaa     2400 agtgcaagtg gttactgtta ccagccgaaa agaagcacgc atgggctgtg ttctggcaa      2460 gtgatgatac cactcgcata atcttcctct catatgacga atctggttct cccataattg      2520
ataagagaaa ctggaagcga tttgctgttt gctctgagac caaagtctat agcgtaattc     2580
```

```
gtagtttaga ggtactaaat aaggaagcaa tagtcgaccc cggggttcat ataacattag    2640
ttgacggagt gccgggttgt ggaaagaccg ccgaaattat agcgagggtc aattggaaaa    2700
ccgatctagt attgactccc gggagggagg cggctgctat gattaggcgg agggcctgcg    2760
ccctgcacaa gtcacctgtg gcaaccagtg acaacgttag aactttcgat tcttttgtga    2820
tgaataagaa aatcttcaag tttgacgctg tctatgttga cgagggtctg atggtccata    2880
cgggtttact taattttgcg ttgaagatct caggttgtaa aaaggccttc gtctttggtg    2940
atgctaagca aatcccgttt ataaacagag tcatgaattt tgattatcct aaggagttaa    3000
gaactttaat agtcgataat gtagagcgta ggtatgttac ccataggtgt cctagagatg    3060
tcactagttt tcttaatact atttacaaag ccgctgtcgc tactactagt ccggttgtac    3120
attctgtgaa ggcgattaaa gtgtcagggg ccggtattct gaggcccgag ttgacgaaga    3180
tcaaaggaaa gataataacg tttactcaat ctgataagca gtccttgatc aagagtgggt    3240
acaatgacgt gaacactgtg catgaaattc agggagaaac ctttgaagag acggcggttg    3300
tgcgtgccac cccgactccg ataggtttaa ttgtccgtga ttcaccacat gtactagtgg    3360
ccttaacgag gcacactaag gcaatggtgt attatactgt tgtgttcgat gcagttacaa    3420
gtataatagt ggatgtggaa aaggtcgacc agtcgatctt gactatgttt gctaccactg    3480
tgcctaccaa atagcaatta atgcagaact cactgtatgt ccatcgtgat attttcctcc    3540
ctgttagtaa aacggggttt tatacagaca tgcaggagtt ctatgataga tgccttcctg    3600
ggaattcctt cgtgctgaat gatttcgatg ccgtaaccat gcggttgagg gacaacgaat    3660
ttaacctaca accttgtagg ctaaccttaa gtaatttaga tccagtaccc gctttggtta    3720
agagtgaagc gcagaatttt ctgattcccg ttttgcgtac ggcctgtgaa aggccgcgca    3780
ttccaggtct ccttgaaaat cttgtagcta tgataaagag gaatatgaat actcctgatc    3840
tagctgggac tgtggatata actaatatgt cgatttctat agtagataac ttcttttctt    3900
cttttgttag agacgaggtt ttgcttgatc atttagattg tgttagggct agttccattc    3960 aaagttttc tgattggttt tcgtgtcagc caacctcggc ggttggtcaa ttagctaatt    4020
tcaatttcat agatttgcct gccttttgata cttatatgca catgattaag cggcagccca    4080
agagtcggtt ggatacttcg attcagtctg aatatccggc cttgcaaact attgtttatc    4140 acctaaagt ggtaaatgca gttttcggtc cggttttaa gtatttgacc accaagtttc    4200
ttagcatggt agatagttct aagttttct tttacactag gaaaaaatca gaagatctgc    4260 aggaatttt ctcagatctc tcttcccatt ctgattatga gattcttgag ctggatgttt    4320
ctaaatatga caagtcacaa tccgatttcc atttctctat tgagatggca atttgggaaa    4380
aattggggct ggacgatatt ttggcttgga tgtggtctat gggtcacaag agaactatac    4440
tgcaagattt ccaagccggg ataaagacgc tcatttacta tcaacggaag tctggtgatg    4500
taactacttt cataggtaat acctttatta tcgcagcgtg tgtagctagt atgttgccgt    4560
tagacaagtg ttttaaagct agttttgtg gtgatgattc gctgatctac cttcctaagg    4620
gtttggagta tcctgatata caggctactg ccaacttggt ttggaatttt gaggcgaaac    4680
ttttccgaaa gaagtatggt tacttctgtg ggaagtatat aattcaccat gccaacggct    4740
gtattgttta ccctgaccct ttaaaattaa ttagtaaatt aggtaataag agtcttgtag    4800
ggtatgagca tgttgaggag tttcgtatat ctctcctcga cgtcgctcat agtttgttta    4860
atggtgctta tttccatta ctcgacgatg caatccacga attatttcct aacgctgggg    4920
gttgcagttt tgtaattaat tgtttgtgca agtatttgag tgataagcac cttttccgta    4980
```

-continued

```
gtctttatat agatgtctct aagtaaggtg tcggtcgaga actcattgaa acccgagaag   5040
tttgttaaaa tctcttgggt cgataagttg ctccctaact attttccat  tcttaagtat   5100 ttatctataa ctgactttag cgtagttaaa gctcagagct atgaatccct cgtgcctgtc   5160
aagttgttgc gtggtgttga tcttacaaaa caccttatg  tcacattgtt gggcgttgtg   5220
gtttctggtg tatggaacgt accggaatcc tgtaggggtg gtgctactgt tgctctggtt   5280
gacacaagga tgcattctgt tgcagaggga actatatgca aattttcagc tcccgccacc   5340
gtccgcgaat tctctgttag gttcatacct aactattctg tcgtggctgc ggatgccctt   5400
cgcgatcctt ggtctttatt tgtgagactc tctaatgtag ggattaaaga tggtttccat   5460
cctttgacct tagaggtcgc ttgtttagtc gctacaacta actctattat caaaaagggt   5520
cttagagctt ctgtagtcga gtctgtcgtc tcttccgatc agtccattgt cctagattct   5580
ttatccgaga aagttgaacc tttctttgat aaagttccta tttcggcggc tgtgatggca   5640
agagacccca gttataggtc taggtcgcag tctgtcggtg gtcgtggtaa gcggcattct   5700
aaacctccaa atcggaggtt ggactctgct tctgaagagt ccagttctgt ttctttcgaa   5760
gatggcttac aatccgatca cacctagcaa acttattgcg tttagtgctt cttatgttcc   5820
cgtcaggact ttacttaatt ttctagttgc ttcacaaggt accgccttcc agactcaagc   5880
gggaagagat tctttccgcg agtccctgtc tgcgttaccc tcgtctgtcg tagatattaa   5940
ttctaggttc ccaaatgcgg gttttttacgc tttcctcaac ggtcctgtgt tgaggcctat   6000
cttcgtttcg cttcttagct ctacggatac gcgtaatagg gtcattgagg ttgtagatcc   6060
tagcaatcct acgactgctg agtcgcttaa cgctgtaaag cgtactgatg acgcatctac   6120
ggccgctagg gctgaaatag ataatttaat agagtctatt tctaagggtt ttgatgttta   6180 tgataggget tcatttgaag ccgcgttttc ggtagtctgg tcagaggtta ccacctcgaa   6240
agcttagctt cgagggtctt ctgatggtgg tgcacaccaa agtgcatagt gctttcccgt   6300
tcacttaaat cgaacggttt gctcattggt ttgcggaaac ctctcacgtg tggcgttgaa   6360
gtttctatgg gcagtaattc tgcaaggggt tcgaatcccc cctttccccg ggtaggggcc   6420
ca                                                                 6422
```

<210> SEQ ID NO 61
<211> LENGTH: 1144
<212> TYPE: PRT
<213> ORGANISM: Cucumber green mottle mosaic virus

<400> SEQUENCE: 61

```
Met Ala Asn Ile Asn Glu Gln Ile Asn Asn Gln Arg Asp Ala Ala
1               5                   10                  15

Ser Gly Arg Asn Asn Leu Val Ser Gln Leu Ala Ser Lys Arg Val Tyr
            20                  25                  30

Asp Glu Ala Val Arg Ser Leu Asp His Gln Asp Arg Arg Pro Lys Met
        35                  40                  45

Asn Phe Ser Arg Val Val Ser Thr Glu His Thr Arg Leu Val Thr Asp
    50                  55                  60

Ala Tyr Pro Glu Phe Ser Ile Ser Phe Thr Ala Thr Lys Asn Ser Val
65                  70                  75                  80

His Ser Leu Ala Gly Ser Leu Arg Leu Leu Glu Leu Glu Tyr Met Met
                85                  90                  95

Met Gln Val Pro Tyr Gly Ser Pro Cys Tyr Asp Ile Gly Gly Asn Tyr
            100                 105                 110
```

```
Thr Gln His Leu Phe Lys Gly Arg Ser Tyr Val His Cys Cys Asn Pro
        115                 120                 125
Cys Leu Asp Leu Lys Asp Val Ala Arg Asn Val Met Tyr Asn Asp Met
    130                 135                 140
Val Thr Gln His Val Gln Arg His Lys Gly Ser Gly Gly Cys Arg Pro
145                 150                 155                 160
Leu Pro Thr Phe Gln Ile Asp Ala Phe Arg Arg Tyr Asp Asn Ser Pro
                165                 170                 175
Cys Ala Val Thr Cys Ser Asp Val Phe Gln Glu Cys Ser Tyr Asp Phe
            180                 185                 190
Gly Ser Gly Arg Asp Asn His Ala Val Ser Leu His Ser Ile Tyr Asp
        195                 200                 205
Ile Pro Tyr Ser Ser Ile Gly Pro Ala Leu His Arg Lys Asn Val Arg
    210                 215                 220
Val Cys Tyr Ala Ala Phe His Phe Ser Glu Ala Leu Leu Leu Gly Ser
225                 230                 235                 240
Pro Val Gly Asn Leu Asn Ser Ile Gly Ala Gln Phe Arg Val Asp Gly
                245                 250                 255
Asp Asp Val His Phe Leu Phe Ser Glu Glu Ser Thr Leu His Tyr Thr
            260                 265                 270
His Ser Leu Glu Asn Ile Lys Leu Ile Val Met Arg Thr Tyr Phe Pro
        275                 280                 285
Ala Asp Asp Arg Tyr Val Tyr Ile Lys Glu Phe Met Val Lys Arg Val
    290                 295                 300
Asp Thr Phe Phe Phe Arg Leu Val Arg Ala Asp Thr His Met Leu His
305                 310                 315                 320
Lys Ser Val Gly His Tyr Ser Lys Ser Lys Ser Glu Tyr Phe Ala Leu
                325                 330                 335
Asn Thr Pro Pro Ile Phe Gln Asp Lys Ala Thr Phe Ser Val Trp Phe
            340                 345                 350
Pro Glu Ala Lys Arg Lys Val Leu Ile Pro Lys Phe Glu Leu Ser Arg
        355                 360                 365
Phe Leu Ser Gly Asn Val Lys Ile Ser Arg Met Leu Val Asp Ala Asp
    370                 375                 380
Phe Val His Thr Ile Ile Asn His Ile Ser Thr Tyr Asp Asn Lys Ala
385                 390                 395                 400
Leu Val Trp Lys Asn Val Gln Ser Phe Val Glu Ser Ile Arg Ser Arg
                405                 410                 415
Val Ile Val Asn Gly Val Ser Val Lys Ser Glu Trp Asn Val Pro Val
            420                 425                 430
Asp Gln Leu Thr Asp Ile Ser Phe Ser Ile Phe Leu Leu Val Lys Val
        435                 440                 445
Arg Lys Val Gln Ile Glu Leu Met Ser Asp Lys Val Val Ile Glu Ala
    450                 455                 460
Arg Gly Leu Leu Arg Arg Phe Ala Asp Ser Leu Lys Ser Ala Val Gly
465                 470                 475                 480
Gly Leu Gly Asp Cys Val Tyr Asp Ala Leu Val Gln Thr Gly Trp Phe
                485                 490                 495
Asp Thr Ser Ser Asp Glu Leu Lys Val Leu Leu Pro Glu Pro Phe Met
            500                 505                 510
Thr Phe Ser Asp Tyr Leu Glu Gly Met Tyr Glu Ala Asp Ala Lys Ile
        515                 520                 525
```

```
Glu Arg Glu Ser Val Phe Glu Leu Leu Ala Ser Gly Asp Asp Leu Phe
530                 535                 540

Lys Lys Ile Asp Glu Ile Arg Asn Asn Tyr Ser Gly Val Glu Phe Asp
545                 550                 555                 560

Val Glu Lys Phe Gln Glu Phe Cys Lys Glu Leu Asn Val Asn Pro Met
                565                 570                 575

Leu Ile Gly His Val Ile Glu Ala Ile Phe Ser Gln Lys Ala Gly Val
                580                 585                 590

Thr Val Thr Gly Leu Gly Thr Leu Ser Pro Glu Met Gly Ala Ser Val
            595                 600                 605

Ala Leu Ser Asn Thr Ser Val Asp Thr Cys Gly Asp Met Asp Val Thr
        610                 615                 620

Glu Asp Met Glu Asp Ile Val Leu Met Ala Asp Lys Ser His Ser Tyr
625                 630                 635                 640

Met Ser Pro Glu Met Ala Arg Trp Ala Asp Val Lys Tyr Asp Asn Asn
                645                 650                 655

Lys Gly Gly Leu Val Glu Tyr Lys Val Gly Thr Ser Met Thr Leu Pro
                660                 665                 670

Ala Thr Trp Ala Glu Lys Gly Lys Ala Val Leu Pro Leu Ser Gly Ile
            675                 680                 685

Cys Val Arg Lys Pro Gln Phe Ser Lys Pro Leu Asp Glu Glu Asp Asp
690                 695                 700

Leu Arg Leu Ser Asn Met Asn Phe Phe Lys Val Ser Asp Leu Lys Leu
705                 710                 715                 720

Lys Lys Thr Ile Thr Pro Val Val Tyr Thr Gly Thr Ile Arg Glu Arg
                725                 730                 735

Gln Met Lys Asn Tyr Ile Asp Tyr Leu Ser Ala Ser Leu Gly Ser Thr
                740                 745                 750

Leu Gly Asn Leu Glu Arg Ile Val Arg Ser Asp Trp Asn Gly Thr Glu
            755                 760                 765

Glu Ser Met Gln Thr Phe Gly Leu Tyr Asp Cys Glu Lys Cys Lys Trp
        770                 775                 780

Leu Leu Leu Pro Ala Glu Lys Lys His Ala Trp Ala Val Val Leu Ala
785                 790                 795                 800

Ser Asp Asp Thr Thr Arg Ile Ile Phe Leu Ser Tyr Asp Glu Ser Gly
                805                 810                 815

Ser Pro Ile Ile Asp Lys Arg Asn Trp Lys Arg Phe Ala Val Cys Ser
                820                 825                 830

Glu Thr Lys Val Tyr Ser Val Ile Arg Ser Leu Glu Val Leu Asn Lys
            835                 840                 845

Glu Ala Ile Val Asp Pro Gly Val His Ile Thr Leu Val Asp Gly Val
850                 855                 860

Pro Gly Cys Gly Lys Thr Ala Glu Ile Ile Ala Arg Val Asn Trp Lys
865                 870                 875                 880

Thr Asp Leu Val Leu Thr Pro Gly Arg Glu Ala Ala Met Ile Arg
                885                 890                 895

Arg Arg Ala Cys Ala Leu His Lys Ser Pro Val Ala Thr Ser Asp Asn
                900                 905                 910

Val Arg Thr Phe Asp Ser Phe Val Met Asn Lys Lys Ile Phe Lys Phe
            915                 920                 925

Asp Ala Val Tyr Val Asp Glu Gly Leu Met Val His Thr Gly Leu Leu
930                 935                 940

Asn Phe Ala Leu Lys Ile Ser Gly Cys Lys Lys Ala Phe Val Phe Gly
```

```
                945                 950                 955                 960
Asp Ala Lys Gln Ile Pro Phe Ile Asn Arg Val Met Asn Phe Asp Tyr
                    965                 970                 975
Pro Lys Glu Leu Arg Thr Leu Ile Val Asp Asn Val Glu Arg Arg Tyr
                    980                 985                 990
Val Thr His Arg Cys Pro Arg Asp Val Thr Ser Phe Leu Asn Thr Ile
                    995                 1000                1005
Tyr Lys Ala Ala Val Ala Thr Thr Ser Pro Val Val His Ser Val
            1010                1015                1020
Lys Ala Ile Lys Val Ser Gly Ala Gly Ile Leu Arg Pro Glu Leu
            1025                1030                1035
Thr Lys Ile Lys Gly Lys Ile Ile Thr Phe Thr Gln Ser Asp Lys
            1040                1045                1050
Gln Ser Leu Ile Lys Ser Gly Tyr Asn Asp Val Asn Thr Val His
            1055                1060                1065
Glu Ile Gln Gly Glu Thr Phe Glu Glu Thr Ala Val Val Arg Ala
            1070                1075                1080
Thr Pro Thr Pro Ile Gly Leu Ile Val Arg Asp Ser Pro His Val
            1085                1090                1095
Leu Val Ala Leu Thr Arg His Thr Lys Ala Met Val Tyr Tyr Thr
            1100                1105                1110
Val Val Phe Asp Ala Val Thr Ser Ile Ile Val Asp Val Glu Lys
            1115                1120                1125
Val Asp Gln Ser Ile Leu Thr Met Phe Ala Thr Thr Val Pro Thr
            1130                1135                1140
Lys

<210> SEQ ID NO 62
<211> LENGTH: 1648
<212> TYPE: PRT
<213> ORGANISM: Cucumber green mottle mosaic virus
<220> FEATURE:
<221> NAME/KEY: misc_feature
<222> LOCATION: (1145)..(1145)
<223> OTHER INFORMATION: Xaa can be any naturally occurring amino acid

<400> SEQUENCE: 62

Met Ala Asn Ile Asn Glu Gln Ile Asn Gln Arg Asp Ala Ala
1               5                   10                  15

Ser Gly Arg Asn Asn Leu Val Ser Gln Leu Ala Ser Lys Arg Val Tyr
                20                  25                  30

Asp Glu Ala Val Arg Ser Leu Asp His Gln Asp Arg Arg Pro Lys Met
            35                  40                  45

Asn Phe Ser Arg Val Val Ser Thr Glu His Thr Arg Leu Val Thr Asp
50                  55                  60

Ala Tyr Pro Glu Phe Ser Ile Ser Phe Thr Ala Thr Lys Asn Ser Val
65                  70                  75                  80

His Ser Leu Ala Gly Ser Leu Arg Leu Leu Glu Leu Glu Tyr Met Met
                85                  90                  95

Met Gln Val Pro Tyr Gly Ser Pro Cys Tyr Asp Ile Gly Gly Asn Tyr
                100                 105                 110

Thr Gln His Leu Phe Lys Gly Arg Ser Tyr Val His Cys Cys Asn Pro
            115                 120                 125

Cys Leu Asp Leu Lys Asp Val Ala Arg Asn Val Met Tyr Asn Asp Met
            130                 135                 140
```

-continued

Val Thr Gln His Val Gln Arg His Lys Gly Ser Gly Gly Cys Arg Pro
145                 150                 155                 160

Leu Pro Thr Phe Gln Ile Asp Ala Phe Arg Arg Tyr Asp Asn Ser Pro
            165                 170                 175

Cys Ala Val Thr Cys Ser Asp Val Phe Gln Glu Cys Ser Tyr Asp Phe
                180                 185                 190

Gly Ser Gly Arg Asp Asn His Ala Val Ser Leu His Ser Ile Tyr Asp
            195                 200                 205

Ile Pro Tyr Ser Ser Ile Gly Pro Ala Leu His Arg Lys Asn Val Arg
    210                 215                 220

Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
                245                 250                 255

Asp Asp Val His Phe Leu Phe Ser Glu Ser Thr Leu His Tyr Thr
                260                 265                 270

His Ser Leu Glu Asn Ile Lys Leu Ile Val Met Arg Thr Tyr Phe Pro
        275                 280                 285

Ala Asp Asp Arg Tyr Val Tyr Ile Lys Glu Phe Met Val Lys Arg Val
    290                 295                 300

Asp Thr Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
                325                 330                 335

Asn Thr Pro Pro Ile Phe Gln Asp Lys Ala Thr Phe Ser Val Trp Phe
            340                 345                 350

Pro Glu Ala Lys Arg Lys Val Leu Ile Pro Lys Phe Glu Leu Ser Arg
        355                 360                 365

Phe Leu Ser Gly Asn Val Lys Ile Ser Arg Met Leu Val Asp Ala Asp
370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
            405                 410                 415

Val Ile Val Asn Gly Val Ser Val Lys Ser Glu Trp Asn Val Pro Val
            420                 425                 430

Asp Gln Leu Thr Asp Ile Ser Phe Ser Ile Phe Leu Leu Val Lys Val
        435                 440                 445

Arg Lys Val Gln Ile Glu Leu Met Ser Asp Lys Val Val Ile Glu Ala
450                 455                 460

Arg Gly Leu Leu Arg Arg Phe Ala Asp Ser Leu Lys Ser Ala Val Gly
465                 470                 475                 480

Gly Leu Gly Asp Cys Val Tyr Asp Ala Leu Val Gln Thr Gly Trp Phe
            485                 490                 495

Asp Thr Ser Ser Asp Glu Leu Lys Val Leu Pro Glu Pro Phe Met
        500                 505                 510

Thr Phe Ser Asp Tyr Leu Glu Gly Met Tyr Glu Ala Asp Ala Lys Ile
            515                 520                 525

Glu Arg Glu Ser Val Phe Glu Leu Leu Ala Ser Gly Asp Asp Leu Phe
        530                 535                 540

Lys Lys Ile Asp Glu Ile Arg Asn Asn Tyr Ser Gly Val Glu Phe Asp
545                 550                 555                 560

Val Glu Lys Phe Gln Glu Phe Cys Lys Glu Leu Asn Val Asn Pro Met

```
                565                 570                 575
Leu Ile Gly His Val Ile Glu Ala Ile Phe Ser Gln Lys Ala Gly Val
            580                 585                 590
Thr Val Thr Gly Leu Gly Thr Leu Ser Pro Glu Met Gly Ala Ser Val
            595                 600                 605
Ala Leu Ser Asn Thr Ser Val Asp Thr Cys Glu Asp Met Asp Val Thr
            610                 615                 620
Glu Asp Met Glu Asp Ile Val Leu Met Ala Asp Lys Ser His Ser Tyr
625                 630                 635                 640
Met Ser Pro Glu Met Ala Arg Trp Ala Asp Val Lys Tyr Asp Asn Asn
                645                 650                 655
Lys Gly Gly Leu Val Glu Tyr Lys Val Gly Thr Ser Met Thr Leu Pro
                660                 665                 670
Ala Thr Trp Ala Glu Lys Gly Lys Ala Val Leu Pro Leu Ser Gly Ile
                675                 680                 685
Cys Val Arg Lys Pro Gln Phe Ser Lys Pro Leu Asp Glu Glu Asp Asp
            690                 695                 700
Leu Arg Leu Ser Asn Met Asn Phe Phe Lys Val Ser Asp Leu Lys Leu
705                 710                 715                 720
Lys Lys Thr Ile Thr Pro Val Val Tyr Thr Gly Thr Ile Arg Glu Arg
                725                 730                 735
Gln Met Lys Asn Tyr Ile Asp Tyr Leu Ser Ala Ser Leu Gly Ser Thr
                740                 745                 750
Leu Gly Asn Leu Glu Arg Ile Val Arg Ser Asp Trp Asn Gly Thr Glu
            755                 760                 765
Glu Ser Met Gln Thr Phe Gly Leu Tyr Asp Cys Glu Lys Cys Lys Trp
            770                 775                 780
Leu Leu Leu Pro Ala Glu Lys Lys His Ala Trp Ala Val Val Leu Ala
785                 790                 795                 800
Ser Asp Asp Thr Thr Arg Ile Ile Phe Leu Ser Tyr Asp Glu Ser Gly
                805                 810                 815
Ser Pro Ile Ile Asp Lys Arg Asn Trp Lys Arg Phe Ala Val Cys Ser
            820                 825                 830
Glu Thr Lys Val Tyr Ser Val Ile Arg Ser Leu Glu Val Leu Asn Lys
            835                 840                 845
Glu Ala Ile Val Asp Pro Gly Val His Ile Thr Leu Val Asp Gly Val
            850                 855                 860
Pro Gly Cys Gly Lys Thr Ala Glu Ile Ile Ala Arg Val Asn Trp Lys
865                 870                 875                 880
Thr Asp Leu Val Leu Thr Pro Gly Arg Glu Ala Ala Met Ile Arg
            885                 890                 895
Arg Arg Ala Cys Ala Leu His Lys Ser Pro Val Ala Thr Ser Asp Asn
                900                 905                 910
Val Arg Thr Phe Asp Ser Phe Val Met Asn Lys Lys Ile Phe Lys Phe
            915                 920                 925
Asp Ala Val Tyr Val Asp Glu Gly Leu Met Val His Thr Gly Leu Leu
            930                 935                 940
Asn Phe Ala Leu Lys Ile Ser Gly Cys Lys Lys Ala Phe Val Phe Gly
945                 950                 955                 960
Asp Ala Lys Gln Ile Pro Phe Ile Asn Arg Val Met Asn Phe Asp Tyr
                965                 970                 975
Pro Lys Glu Leu Arg Thr Leu Ile Val Asp Asn Val Glu Arg Arg Tyr
            980                 985                 990
```

```
Val Thr His Arg Cys Pro Arg Asp  Val Thr Ser Phe Leu  Asn Thr Ile
        995                 1000                1005

Tyr Lys  Ala Ala Val Ala Thr   Thr Ser Pro Val  His Ser Val
    1010             1015                1020

Lys Ala  Ile Lys Val Ser Gly   Ala Gly Ile Leu  Arg Pro Glu Leu
    1025             1030                1035

Thr Lys  Ile Lys Gly Lys Ile   Ile Thr Phe Thr  Gln Ser Asp Lys
    1040             1045                1050

Gln Ser  Leu Ile Lys Ser Gly   Tyr Asn Asp Val  Asn Thr Val His
    1055             1060                1065

Glu Ile  Gln Gly Glu Thr Phe   Glu Glu Thr Ala  Val Val Arg Ala
    1070             1075                1080

Thr Pro  Thr Pro Ile Gly Leu   Ile Val Arg Asp  Ser Pro His Val
    1085             1090                1095

Leu Val  Ala Leu Thr Arg His   Thr Lys Ala Met  Val Tyr Tyr Thr
    1100             1105                1110

Val Val  Phe Asp Ala Val Thr   Ser Ile Ile Val  Asp Val Glu Lys
    1115             1120                1125

Val Asp  Gln Ser Ile Leu Thr   Met Phe Ala Thr  Thr Val Pro Thr
    1130             1135                1140

Lys Xaa  Gln Leu Met Gln Asn   Ser Leu Tyr Val  His Arg Asp Ile
    1145             1150                1155

Phe Leu  Pro Val Ser Lys Thr   Gly Phe Tyr Thr  Asp Met Gln Glu
    1160             1165                1170

Phe Tyr  Asp Arg Cys Leu Pro   Gly Asn Ser Phe  Val Leu Asn Asp
    1175             1180                1185

Phe Asp  Ala Val Thr Met Arg   Leu Arg Asp Asn  Glu Phe Asn Leu
    1190             1195                1200

Gln Pro  Cys Arg Leu Thr Leu   Ser Asn Leu Asp  Pro Val Pro Ala
    1205             1210                1215

Leu Val  Lys Ser Glu Ala Gln   Asn Phe Leu Ile  Pro Val Leu Arg
    1220             1225                1230

Thr Ala  Cys Glu Arg Pro Arg   Ile Pro Gly Leu  Leu Glu Asn Leu
    1235             1240                1245

Val Ala  Met Ile Lys Arg Asn   Met Asn Thr Pro  Asp Leu Ala Gly
    1250             1255                1260

Thr Val  Asp Ile Thr Asn Met   Ser Ile Ser Ile  Val Asp Asn Phe
    1265             1270                1275

Phe Ser  Ser Phe Val Arg Asp   Glu Val Leu Leu  Asp His Leu Asp
    1280             1285                1290

Cys Val  Arg Ala Ser Ser Ile   Gln Ser Phe Ser  Asp Trp Phe Ser
    1295             1300                1305

Cys Gln  Pro Thr Ser Ala Val   Gly Gln Leu Ala  Asn Phe Asn Phe
    1310             1315                1320

Ile Asp  Leu Pro Ala Phe Asp   Thr Tyr Met His  Met Ile Lys Arg
    1325             1330                1335

Gln Pro  Lys Ser Arg Leu Asp   Thr Ser Ile Gln  Ser Glu Tyr Pro
    1340             1345                1350

Ala Leu  Gln Thr Ile Val Tyr   His Leu Lys Val  Val Asn Ala Val
    1355             1360                1365

Phe Gly  Pro Val Phe Lys Tyr   Leu Thr Thr Lys  Phe Leu Ser Met
    1370             1375                1380
```

```
Val Asp Ser Ser Lys Phe Phe Phe Tyr Thr Arg Lys Lys Ser Glu
    1385                1390                1395

Asp Leu Gln Glu Phe Phe Ser Asp Leu Ser Ser His Ser Asp Tyr
    1400                1405                1410

Glu Ile Leu Glu Leu Asp Val Ser Lys Tyr Asp Lys Ser Gln Ser
    1415                1420                1425

Asp Phe His Phe Ser Ile Glu Met Ala Ile Trp Glu Lys Leu Gly
    1430                1435                1440

Leu Asp Asp Ile Leu Ala Trp Met Trp Ser Met Gly His Lys Arg
    1445                1450                1455

Thr Ile Leu Gln Asp Phe Gln Ala Gly Ile Lys Thr Leu Ile Tyr
    1460                1465                1470

Tyr Gln Arg Lys Ser Gly Asp Val Thr Thr Phe Ile Gly Asn Thr
    1475                1480                1485

Phe Ile Ile Ala Ala Cys Val Ala Ser Met Leu Pro Leu Asp Lys
    1490                1495                1500

Cys Phe Lys Ala Ser Phe Cys Gly Asp Asp Ser Leu Ile Tyr Leu
    1505                1510                1515

Pro Lys Gly Leu Glu Tyr Pro Asp Ile Gln Ala Thr Ala Asn Leu
    1520                1525                1530

Val Trp Asn Phe Glu Ala Lys Leu Phe Arg Lys Lys Tyr Gly Tyr
    1535                1540                1545

Phe Cys Gly Lys Tyr Ile Ile His His Ala Asn Gly Cys Ile Val
    1550                1555                1560

Tyr Pro Asp Pro Leu Lys Leu Ile Ser Lys Leu Gly Asn Lys Ser
    1565                1570                1575

Leu Val Gly Tyr Glu His Val Glu Glu Phe Arg Ile Ser Leu Leu
    1580                1585                1590

Asp Val Ala His Ser Leu Phe Asn Gly Ala Tyr Phe His Leu Leu
    1595                1600                1605

Asp Asp Ala Ile His Glu Leu Phe Pro Asn Ala Gly Gly Cys Ser
    1610                1615                1620

Phe Val Ile Asn Cys Leu Cys Lys Tyr Leu Ser Asp Lys His Leu
    1625                1630                1635

Phe Arg Ser Leu Tyr Ile Asp Val Ser Lys
    1640                1645

<210> SEQ ID NO 63
<211> LENGTH: 1144
<212> TYPE: PRT
<213> ORGANISM: Cucumber green mottle mosaic virus

<400> SEQUENCE: 63

Met Ala Asn Ile Asn Glu Gln Ile Asn Asn Gln Arg Asp Ala Ala Ala
1               5                   10                  15

Ser Gly Arg Asn Asn Leu Val Ser Gln Leu Ala Ser Lys Arg Val Tyr
                20                  25                  30

Asp Glu Ala Val Arg Ser Leu Asp His Gln Asp Arg Arg Pro Lys Met
            35                  40                  45

Asn Phe Ser Arg Val Val Ser Thr Glu His Thr Arg Leu Val Thr Asp
        50                  55                  60

Ala Tyr Pro Glu Phe Ser Ile Ser Phe Thr Ala Thr Lys Asn Ser Val
65                  70                  75                  80

His Ser Leu Ala Gly Gly Leu Arg Leu Leu Glu Leu Glu Tyr Met Met
                85                  90                  95
```

```
Met Gln Val Pro Tyr Gly Ser Pro Cys Tyr Asp Ile Gly Gly Asn Tyr
            100                 105                 110

Thr Gln His Leu Phe Lys Gly Arg Ser Tyr Val His Cys Cys Asn Pro
            115                 120                 125

Cys Leu Asp Leu Lys Asp Val Ala Arg Asn Val Met Tyr Asn Asp Met
130                 135                 140

Val Thr Gln His Val Gln Arg His Lys Gly Ser Gly Gly Cys Arg Pro
145                 150                 155                 160

Leu Pro Thr Phe Gln Ile Asp Ala Phe Arg Arg Tyr Asp Asn Ser Pro
            165                 170                 175

Cys Ala Val Thr Cys Ser Asp Val Phe Gln Glu Cys Ser Tyr Asp Phe
            180                 185                 190

Gly Ser Gly Arg Asp Asn His Ala Val Ser Leu His Ser Ile Tyr Asp
            195                 200                 205

Ile Pro Tyr Ser Ser Ile Gly Pro Ala Leu His Arg Lys Asn Val Arg
            210                 215                 220

Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
            245                 250                 255

Asp Asp Val His Phe Leu Phe Ser Glu Glu Ser Thr Leu His Tyr Thr
            260                 265                 270

His Ser Leu Glu Asn Ile Lys Leu Ile Val Met Arg Thr Tyr Phe Pro
            275                 280                 285

Ala Asp Asp Arg Tyr Val Tyr Ile Lys Glu Phe Met Val Lys Arg Val
            290                 295                 300

Asp Thr Phe Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
            325                 330                 335

Asn Thr Pro Pro Ile Phe Gln Asp Lys Ala Thr Phe Ser Val Trp Phe
            340                 345                 350

Pro Glu Ala Lys Arg Lys Val Leu Ile Pro Lys Phe Glu Leu Ser Arg
            355                 360                 365

Phe Leu Ser Gly Asn Val Lys Ile Ser Arg Met Leu Val Asp Ala Asp
370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
            405                 410                 415

Val Ile Val Asn Gly Val Ser Val Lys Ser Glu Trp Asn Val Pro Val
            420                 425                 430

Asp Gln Leu Thr Asp Ile Ser Phe Ser Ile Phe Leu Leu Val Lys Val
            435                 440                 445

Arg Lys Val Gln Ile Glu Leu Met Ser Asp Lys Val Val Ile Glu Ala
            450                 455                 460

Arg Gly Leu Leu Arg Arg Phe Ala Asp Ser Leu Lys Ser Ala Val Glu
465                 470                 475                 480

Gly Leu Gly Asp Cys Val Tyr Asp Ala Leu Val Gln Thr Gly Trp Phe
            485                 490                 495

Asp Thr Ser Ser Asp Glu Leu Lys Val Leu Leu Pro Glu Pro Phe Met
            500                 505                 510
```

```
Thr Phe Ser Asp Tyr Leu Glu Gly Met Tyr Glu Ala Asp Ala Lys Ile
            515                 520                 525

Glu Arg Glu Ser Val Ser Glu Leu Leu Ala Ser Gly Asp Asp Leu Phe
530                 535                 540

Lys Lys Ile Asp Glu Ile Arg Asn Asn Tyr Ser Gly Val Glu Phe Asp
545                 550                 555                 560

Val Glu Lys Phe Gln Glu Phe Cys Lys Glu Leu Asn Val Asn Pro Met
                565                 570                 575

Leu Ile Gly His Val Ile Glu Ala Ile Phe Ser Gln Lys Ala Gly Val
                580                 585                 590

Thr Val Thr Gly Leu Gly Thr Leu Ser Pro Glu Met Gly Ala Ser Val
            595                 600                 605

Ala Leu Ser Asn Thr Ser Val Asp Thr Cys Glu Asp Met Asp Val Thr
            610                 615                 620

Glu Asp Met Glu Asp Ile Val Leu Met Ala Asp Lys Ser His Ser Tyr
625                 630                 635                 640

Met Ser Pro Glu Met Ala Arg Trp Ala Asp Val Lys Tyr Asp Asn Asn
                645                 650                 655

Lys Gly Gly Leu Val Glu Tyr Lys Val Gly Thr Ser Met Thr Leu Pro
                660                 665                 670

Ala Thr Trp Ala Glu Lys Gly Lys Ala Val Leu Pro Leu Ser Gly Ile
            675                 680                 685

Cys Val Arg Lys Pro Gln Phe Ser Lys Pro Leu Asp Glu Glu Asp Asp
            690                 695                 700

Leu Arg Leu Ser Asn Met Asn Phe Phe Lys Val Ser Asp Leu Lys Leu
705                 710                 715                 720

Lys Lys Thr Ile Thr Pro Val Val Tyr Thr Gly Thr Ile Arg Glu Arg
                725                 730                 735

Gln Met Lys Asn Tyr Ile Asp Tyr Leu Ser Ala Ser Leu Gly Ser Thr
                740                 745                 750

Leu Gly Asn Leu Glu Arg Ile Val Arg Ser Asp Trp Asn Gly Thr Glu
            755                 760                 765

Glu Ser Met Gln Thr Phe Gly Leu Tyr Asp Cys Glu Lys Cys Lys Trp
            770                 775                 780

Leu Leu Leu Pro Ala Glu Lys Lys His Ala Trp Ala Val Val Leu Ala
785                 790                 795                 800

Ser Asp Asp Thr Thr Arg Ile Ile Phe Leu Ser Tyr Asp Glu Ser Gly
                805                 810                 815

Ser Pro Ile Ile Asp Lys Arg Asn Trp Lys Arg Phe Ala Val Cys Ser
                820                 825                 830

Glu Thr Lys Val Tyr Ser Val Ile Arg Ser Leu Glu Val Leu Asn Lys
            835                 840                 845

Glu Ala Ile Val Asp Pro Gly Val His Ile Thr Leu Val Asp Gly Val
850                 855                 860

Pro Gly Cys Gly Lys Thr Ala Glu Ile Ile Ala Arg Val Asn Trp Lys
865                 870                 875                 880

Thr Asp Leu Val Leu Thr Pro Gly Arg Glu Ala Ala Met Ile Arg
                885                 890                 895

Arg Arg Ala Cys Ala Leu His Lys Ser Pro Val Ala Thr Ser Asp Asn
                900                 905                 910

Val Arg Thr Phe Asp Ser Phe Val Met Asn Lys Lys Ile Phe Lys Phe
            915                 920                 925

Asp Ala Val Tyr Val Asp Glu Gly Leu Met Val His Thr Gly Leu Leu
```

```
                930             935             940
Asn Phe Ala Leu Lys Ile Ser Gly Cys Lys Lys Ala Phe Val Phe Gly
945                 950                 955                 960

Asp Ala Lys Gln Ile Pro Phe Ile Asn Arg Val Met Asn Phe Asp Tyr
                965                 970                 975

Pro Lys Glu Leu Arg Thr Leu Ile Val Asp Asn Val Glu Arg Arg Tyr
            980                 985                 990

Val Thr His Arg Cys Pro Arg Asp Val Thr Ser Phe Leu Asn Thr Ile
        995                 1000                1005

Tyr Lys Ala Ala Val Ala Thr Thr Ser Pro Val Val His Ser Val
    1010                1015                1020

Lys Ala Ile Lys Val Ser Gly Ala Gly Ile Leu Arg Pro Glu Leu
    1025                1030                1035

Thr Lys Ile Lys Gly Lys Ile Ile Thr Phe Thr Gln Ser Asp Lys
    1040                1045                1050

Gln Ser Leu Ile Lys Ser Gly Tyr Asn Asp Val Asn Thr Val His
    1055                1060                1065

Glu Ile Gln Gly Glu Thr Phe Glu Glu Thr Ala Val Val Arg Ala
    1070                1075                1080

Thr Pro Thr Pro Ile Gly Leu Ile Ala Arg Asp Ser Pro His Val
    1085                1090                1095

Leu Val Ala Leu Thr Arg His Thr Lys Ala Met Val Tyr Tyr Thr
    1100                1105                1110

Val Val Phe Asp Ala Val Thr Ser Ile Ile Ala Asp Val Glu Lys
    1115                1120                1125

Val Asp Gln Ser Ile Leu Thr Met Phe Ala Thr Thr Val Pro Thr
    1130                1135                1140

Lys

<210> SEQ ID NO 64
<211> LENGTH: 1648
<212> TYPE: PRT
<213> ORGANISM: Cucumber green mottle mosaic virus
<220> FEATURE:
<221> NAME/KEY: misc_feature
<222> LOCATION: (1145)..(1145)
<223> OTHER INFORMATION: Xaa can be any naturally occurring amino acid

<400> SEQUENCE: 64

Met Ala Asn Ile Asn Glu Gln Ile Asn Asn Gln Arg Asp Ala Ala Ala
1               5                   10                  15

Ser Gly Arg Asn Asn Leu Val Ser Gln Leu Ala Ser Lys Arg Val Tyr
            20                  25                  30

Asp Glu Ala Val Arg Ser Leu Asp His Gln Asp Arg Arg Pro Lys Met
        35                  40                  45

Asn Phe Ser Arg Val Val Ser Thr Glu His Thr Arg Leu Val Thr Asp
    50                  55                  60

Ala Tyr Pro Glu Phe Ser Ile Ser Phe Thr Ala Thr Lys Asn Ser Val
65                  70                  75                  80

His Ser Leu Ala Gly Gly Leu Arg Leu Leu Glu Leu Glu Tyr Met Met
                85                  90                  95

Met Gln Val Pro Tyr Gly Ser Pro Cys Tyr Asp Ile Gly Gly Asn Tyr
            100                 105                 110

Thr Gln His Leu Phe Lys Gly Arg Ser Tyr Val His Cys Cys Asn Pro
        115                 120                 125
```

```
Cys Leu Asp Leu Lys Asp Val Ala Arg Asn Val Met Tyr Asn Asp Met
130                 135                 140

Val Thr Gln His Val Gln Arg His Lys Gly Ser Gly Gly Cys Arg Pro
145                 150                 155                 160

Leu Pro Thr Phe Gln Ile Asp Ala Phe Arg Arg Tyr Asp Asn Ser Pro
                165                 170                 175

Cys Ala Val Thr Cys Ser Asp Val Phe Gln Glu Cys Ser Tyr Asp Phe
                180                 185                 190

Gly Ser Gly Arg Asp Asn His Ala Val Ser Leu His Ser Ile Tyr Asp
            195                 200                 205

Ile Pro Tyr Ser Ser Ile Gly Pro Ala Leu His Arg Lys Asn Val Arg
210                 215                 220

Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
                245                 250                 255

Asp Asp Val His Phe Leu Phe Ser Glu Glu Ser Thr Leu His Tyr Thr
                260                 265                 270

His Ser Leu Glu Asn Ile Lys Leu Ile Val Met Arg Thr Tyr Phe Pro
            275                 280                 285

Ala Asp Asp Arg Tyr Val Tyr Ile Lys Glu Phe Met Val Lys Arg Val
290                 295                 300

Asp Thr Phe Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
                325                 330                 335

Asn Thr Pro Pro Ile Phe Gln Asp Lys Ala Thr Phe Ser Val Trp Phe
                340                 345                 350

Pro Glu Ala Lys Arg Lys Val Leu Ile Pro Lys Phe Glu Leu Ser Arg
            355                 360                 365

Phe Leu Ser Gly Asn Val Lys Ile Ser Arg Met Leu Val Asp Ala Asp
370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
                405                 410                 415

Val Ile Val Asn Gly Val Ser Val Lys Ser Glu Trp Asn Val Pro Val
                420                 425                 430

Asp Gln Leu Thr Asp Ile Ser Phe Ser Ile Phe Leu Leu Val Lys Val
            435                 440                 445

Arg Lys Val Gln Ile Glu Leu Met Ser Asp Lys Val Val Ile Glu Ala
450                 455                 460

Arg Gly Leu Leu Arg Arg Phe Ala Asp Ser Leu Lys Ser Ala Val Glu
465                 470                 475                 480

Gly Leu Gly Asp Cys Val Tyr Asp Ala Leu Val Gln Thr Gly Trp Phe
                485                 490                 495

Asp Thr Ser Ser Asp Glu Leu Lys Val Leu Leu Pro Glu Pro Phe Met
                500                 505                 510

Thr Phe Ser Asp Tyr Leu Glu Gly Met Tyr Glu Ala Asp Ala Lys Ile
            515                 520                 525

Glu Arg Glu Ser Val Ser Glu Leu Leu Ala Ser Gly Asp Asp Leu Phe
530                 535                 540

Lys Lys Ile Asp Glu Ile Arg Asn Asn Tyr Ser Gly Val Glu Phe Asp
```

```
                545                 550                 555                 560
Val Glu Lys Phe Gln Glu Phe Cys Lys Glu Leu Asn Val Asn Pro Met
                    565                 570                 575
Leu Ile Gly His Val Ile Glu Ala Ile Phe Ser Gln Lys Ala Gly Val
                    580                 585                 590
Thr Val Thr Gly Leu Gly Thr Leu Ser Pro Glu Met Gly Ala Ser Val
                    595                 600                 605
Ala Leu Ser Asn Thr Ser Val Asp Thr Cys Gly Asp Met Asp Val Thr
                    610                 615                 620
Glu Asp Met Glu Asp Ile Val Leu Met Ala Asp Lys Ser His Ser Tyr
                625                 630                 635                 640
Met Ser Pro Glu Met Ala Arg Trp Ala Asp Val Lys Tyr Asp Asn Asn
                    645                 650                 655
Lys Gly Gly Leu Val Glu Tyr Lys Val Gly Thr Ser Met Thr Leu Pro
                    660                 665                 670
Ala Thr Trp Ala Glu Lys Gly Lys Ala Val Leu Pro Leu Ser Gly Ile
                    675                 680                 685
Cys Val Arg Lys Pro Gln Phe Ser Lys Pro Leu Asp Glu Glu Asp Asp
                    690                 695                 700
Leu Arg Leu Ser Asn Met Asn Phe Phe Lys Val Ser Asp Leu Lys Leu
                705                 710                 715                 720
Lys Lys Thr Ile Thr Pro Val Val Tyr Thr Gly Thr Ile Arg Glu Arg
                    725                 730                 735
Gln Met Lys Asn Tyr Ile Asp Tyr Leu Ser Ala Ser Leu Gly Ser Thr
                    740                 745                 750
Leu Gly Asn Leu Glu Arg Ile Val Arg Ser Asp Trp Asn Gly Thr Glu
                755                 760                 765
Glu Ser Met Gln Thr Phe Gly Leu Tyr Asp Cys Glu Lys Cys Lys Trp
                770                 775                 780
Leu Leu Leu Pro Ala Glu Lys Lys His Ala Trp Ala Val Val Leu Ala
                785                 790                 795                 800
Ser Asp Asp Thr Thr Arg Ile Ile Phe Leu Ser Tyr Asp Glu Ser Gly
                    805                 810                 815
Ser Pro Ile Ile Asp Lys Arg Asn Trp Lys Arg Phe Ala Val Cys Ser
                    820                 825                 830
Glu Thr Lys Val Tyr Ser Val Ile Arg Ser Leu Glu Val Leu Asn Lys
                    835                 840                 845
Glu Ala Ile Val Asp Pro Gly Val His Ile Thr Leu Val Asp Gly Val
                    850                 855                 860
Pro Gly Cys Gly Lys Thr Ala Glu Ile Ile Ala Arg Val Asn Trp Lys
                865                 870                 875                 880
Thr Asp Leu Val Leu Thr Pro Gly Arg Glu Ala Ala Met Ile Arg
                    885                 890                 895
Arg Arg Ala Cys Ala Leu His Lys Ser Pro Val Ala Thr Ser Asp Asn
                    900                 905                 910
Val Arg Thr Phe Asp Ser Phe Val Met Asn Lys Lys Ile Phe Lys Phe
                    915                 920                 925
Asp Ala Val Tyr Val Asp Glu Gly Leu Met Val His Thr Gly Leu Leu
                    930                 935                 940
Asn Phe Ala Leu Lys Ile Ser Gly Cys Lys Lys Ala Phe Val Phe Gly
                945                 950                 955                 960
Asp Ala Lys Gln Ile Pro Phe Ile Asn Arg Val Met Asn Phe Asp Tyr
                    965                 970                 975
```

```
Pro Lys Glu Leu Arg Thr Leu Ile Val Asp Asn Val Glu Arg Arg Tyr
            980                 985                 990

Val Thr His Arg Cys Pro Arg Asp Val Thr Ser Phe Leu Asn Thr Ile
            995                 1000                1005

Tyr Lys Ala Ala Val Ala Thr Thr Ser Pro Val Val His Ser Val
        1010                1015                1020

Lys Ala Ile Lys Val Ser Gly Ala Gly Ile Leu Arg Pro Glu Leu
        1025                1030                1035

Thr Lys Ile Lys Gly Lys Ile Ile Thr Phe Thr Gln Ser Asp Lys
        1040                1045                1050

Gln Ser Leu Ile Lys Ser Gly Tyr Asn Asp Val Asn Thr Val His
        1055                1060                1065

Glu Ile Gln Gly Glu Thr Phe Glu Glu Thr Ala Val Val Arg Ala
        1070                1075                1080

Thr Pro Thr Pro Ile Gly Leu Ile Ala Arg Asp Ser Pro His Val
        1085                1090                1095

Leu Val Ala Leu Thr Arg His Thr Lys Ala Met Val Tyr Tyr Thr
        1100                1105                1110

Val Val Phe Asp Ala Val Thr Ser Ile Ile Ala Asp Val Glu Lys
        1115                1120                1125

Val Asp Gln Ser Ile Leu Thr Met Phe Ala Thr Thr Val Pro Thr
        1130                1135                1140

Lys Xaa Gln Leu Met Gln Asn Ser Leu Tyr Val His Arg Asn Ile
        1145                1150                1155

Phe Leu Pro Val Ser Lys Thr Gly Phe Tyr Thr Asp Met Gln Glu
        1160                1165                1170

Phe Tyr Asp Arg Cys Leu Pro Gly Asn Ser Phe Val Leu Asn Asp
        1175                1180                1185

Phe Asp Ala Val Thr Met Arg Leu Arg Asp Asn Glu Phe Asn Leu
        1190                1195                1200

Gln Pro Cys Arg Leu Thr Leu Ser Asn Leu Asp Pro Val Pro Ala
        1205                1210                1215

Leu Val Lys Ser Glu Ala Gln Asn Phe Leu Ile Pro Val Leu Arg
        1220                1225                1230

Thr Ala Cys Glu Arg Pro Arg Ile Pro Gly Leu Leu Glu Asn Leu
        1235                1240                1245

Val Ala Met Ile Lys Arg Asn Met Asn Thr Pro Asp Leu Ala Gly
        1250                1255                1260

Thr Val Asp Ile Thr Asn Met Ser Ile Ser Ile Val Asp Asn Phe
        1265                1270                1275

Phe Ser Ser Phe Val Arg Asp Glu Val Leu Leu Asp His Leu Asp
        1280                1285                1290

Cys Val Arg Ala Ser Ser Ile Gln Ser Phe Ser Asp Trp Phe Ser
        1295                1300                1305

Cys Gln Pro Thr Ser Ala Val Gly Gln Leu Ala Asn Phe Asn Phe
        1310                1315                1320

Ile Asp Leu Pro Ala Phe Asp Thr Tyr Met His Met Ile Lys Arg
        1325                1330                1335

Gln Pro Lys Ser Arg Leu Asp Thr Ser Ile Gln Ser Glu Tyr Pro
        1340                1345                1350

Ala Leu Gln Thr Ile Val Tyr His Pro Lys Val Val Asn Ala Val
        1355                1360                1365
```

Phe Gly Pro Val Phe Lys Tyr Leu Thr Thr Lys Phe Leu Ser Met
1370            1375              1380

Val Asp Ser Ser Lys Phe Phe Tyr Thr Arg Lys Lys Pro Glu
1385            1390              1395

Asp Leu Gln Glu Phe Phe Ser Asp Leu Ser Ser His Ser Asp Tyr
1400            1405              1410

Glu Ile Leu Glu Leu Asp Val Ser Lys Tyr Asp Lys Ser Gln Ser
1415            1420              1425

Asp Phe His Phe Ser Ile Glu Met Ala Ile Trp Glu Lys Leu Gly
1430            1435              1440

Leu Asp Asp Ile Leu Ala Trp Met Trp Ser Met Gly His Lys Arg
1445            1450              1455

Thr Ile Leu Gln Asp Phe Gln Ala Gly Ile Lys Thr Leu Ile Tyr
1460            1465              1470

Tyr Gln Arg Lys Ser Gly Asp Val Thr Thr Phe Ile Gly Asn Thr
1475            1480              1485

Phe Ile Ile Ala Ala Cys Val Ala Ser Met Leu Pro Leu Asp Lys
1490            1495              1500

Cys Phe Lys Ala Ser Phe Cys Gly Asp Asp Ser Leu Ile Tyr Leu
1505            1510              1515

Pro Lys Gly Leu Glu Tyr Pro Asp Ile Gln Ala Thr Ala Asn Leu
1520            1525              1530

Val Trp Asn Phe Glu Ala Lys Leu Phe Arg Lys Lys Tyr Gly Tyr
1535            1540              1545

Phe Cys Gly Lys Tyr Ile Ile His His Ala Asn Gly Cys Ile Val
1550            1555              1560

Tyr Pro Asp Pro Leu Lys Leu Ile Ser Lys Leu Gly Asn Lys Ser
1565            1570              1575

Leu Val Gly Tyr Glu His Val Glu Glu Phe Arg Ile Ser Leu Leu
1580            1585              1590

Asp Val Ala His Ser Leu Phe Asn Gly Ala Tyr Phe His Leu Leu
1595            1600              1605

Asp Asp Ala Ile His Glu Leu Phe Pro Asn Ala Gly Gly Cys Ser
1610            1615              1620

Phe Val Ile Asn Cys Leu Cys Lys Tyr Leu Ser Asp Lys Arg Leu
1625            1630              1635

Phe Arg Ser Leu Tyr Ile Asp Val Ser Lys
1640            1645

<210> SEQ ID NO 65
<211> LENGTH: 161
<212> TYPE: PRT
<213> ORGANISM: Cucumber green mottle mosaic virus

<400> SEQUENCE: 65

Met Ala Tyr Asn Pro Ile Thr Pro Ser Lys Leu Ile Ala Phe Ser Ala
1               5                   10                  15

Ser Tyr Val Pro Val Arg Thr Leu Leu Asn Phe Leu Val Ala Ser Gln
                20                  25                  30

Gly Thr Ala Phe Gln Thr Gln Ala Gly Arg Asp Ser Phe Arg Glu Ser
            35                  40                  45

Leu Ser Ala Leu Pro Ser Ser Val Val Asp Ile Asn Ser Arg Phe Pro
        50                  55                  60

Asn Ala Gly Phe Tyr Ala Phe Leu Asn Gly Pro Val Leu Arg Pro Ile
65                  70                  75                  80

```
Phe Val Ser Leu Leu Ser Ser Thr Asp Thr Arg Asn Arg Val Ile Glu
                85              90                  95

Val Val Asp Pro Ser Asn Pro Thr Thr Ala Glu Ser Leu Asn Ala Val
            100             105                 110

Lys Arg Thr Asp Asp Ala Ser Thr Ala Ala Arg Ala Glu Ile Asp Asn
        115                 120                 125

Leu Ile Glu Ser Ile Ser Lys Gly Phe Asp Val Tyr Asp Arg Ala Ser
    130             135                 140

Phe Glu Ala Ala Phe Ser Val Val Trp Ser Glu Ala Thr Thr Ser Lys
145             150                 155                 160

Ala
```